US007968574B2

(12) United States Patent
Hangauer, Jr.

(10) Patent No.: US 7,968,574 B2
(45) Date of Patent: Jun. 28, 2011

(54) BIARYL COMPOSITIONS AND METHODS FOR MODULATING A KINASE CASCADE

(75) Inventor: David G. Hangauer, Jr., East Amherst, NY (US)

(73) Assignee: Kinex Pharmaceuticals, LLC, Buffalo, NY (US)

( * ) Notice: Subject to any disclaimer, the term of this patent is extended or adjusted under 35 U.S.C. 154(b) by 943 days.

(21) Appl. No.: 11/480,174

(22) Filed: Jun. 29, 2006

(65) Prior Publication Data

US 2007/0015752 A1    Jan. 18, 2007

Related U.S. Application Data

(63) Continuation-in-part of application No. 11/321,419, filed on Dec. 28, 2005, now Pat. No. 7,300,931.

(60) Provisional application No. 60/639,834, filed on Dec. 28, 2004, provisional application No. 60/704,551, filed on Aug. 1, 2005, provisional application No. 60/727,341, filed on Oct. 17, 2005.

(51) Int. Cl.
C07D 413/10    (2006.01)
C07D 401/12    (2006.01)
C07D 213/56    (2006.01)
A61K 31/5377   (2006.01)
A61K 31/4439   (2006.01)
A61K 31/4418   (2006.01)

(52) U.S. Cl. .............. 514/357; 514/235.5; 514/340; 546/268.4; 546/337; 544/131

(58) Field of Classification Search .......... 546/323, 546/268.4, 337; 514/357, 235.5, 340; 544/131
See application file for complete search history.

(56) References Cited

U.S. PATENT DOCUMENTS

| | | | |
|---|---|---|---|
| 3,868,380 A | 2/1975 | Molteni et al. | 260/295 |
| 4,010,279 A | 3/1977 | Griss et al. | 424/309 |
| 6,538,960 B1 | 3/2003 | Sabi et al. | 369/13.38 |
| 6,624,180 B2 * | 9/2003 | South et al. | 514/352 |
| 6,844,367 B1 | 1/2005 | Zhu et al. | 514/620 |
| 6,969,726 B2 * | 11/2005 | Lou et al. | 514/376 |
| 2004/0242572 A1 | 12/2004 | Stenkamp et al. | 514/227.2 |
| 2005/0043317 A1 * | 2/2005 | Zhou et al. | 514/252.05 |
| 2005/0059713 A1 | 3/2005 | Mjalli et al. | 514/357 |
| 2006/0100245 A1 * | 5/2006 | Bakthavatchalam et al. | 514/332 |
| 2006/0160800 A1 | 7/2006 | Hangauer, Jr. | 514/235.2 |

FOREIGN PATENT DOCUMENTS

| | | |
|---|---|---|
| EP | 0 463 638 A1 | 1/1992 |
| WO | WO 9219208 A1 * | 11/1992 |
| WO | WO 96/12473 | 5/1996 |
| WO | WO 99/01127 | 1/1999 |
| WO | WO 01/19788 A2 | 3/2001 |
| WO | WO 01/85726 A1 | 11/2001 |
| WO | WO 02/079197 A1 | 10/2002 |
| WO | WO 03/059903 A2 | 7/2003 |
| WO | WO 03/078404 A1 | 9/2003 |
| WO | WO 03/087057 A1 | 10/2003 |
| WO | WO 03/093248 A1 | 11/2003 |
| WO | WO 03/093297 A2 | 11/2003 |
| WO | WO 2004/011427 A2 | 2/2004 |
| WO | WO 2004/056774 A2 | 7/2004 |
| WO | WO 2004056774 A2 * | 7/2004 |
| WO | WO 2005/013914 A2 | 2/2005 |
| WO | WO 2005/032493 A2 | 4/2005 |
| WO | WO 2006/071960 A2 | 7/2006 |
| WO | WO 2007/026920 A2 | 3/2007 |
| WO | WO 2007/095383 A2 | 8/2007 |

OTHER PUBLICATIONS

Homma et al. J. Med. Chem. 1983, 26, 1499-1504.*
Davidson et al., "Discovery and characterization of a substrate selective p38α inhibitor", *Biochemistry*, 43:11658-11671 (2004).
Cain et al., "Potential Antitumor Agents. IX. Bisquaternary Salts", *J. Med. Chem.*,11(5):963-966 (1968).
Liechti et al., "Salicylanilides as inhibitors of the protein tyrosine kinase epidermal growth factor receptor", *Eur. J. Med. Chem.*, 39(1):11-26 (2004).
Million et al., "Inhibition of the EGF-stimulated cellular proliferation of ER 22 cells by hydroxybiphenyl derivatives", *J. Med. Chem.*, 38(23):4693-4703 (1995).
Zhng et al., "Design, synthesis, and SAR of anthranilamide-based factor Xa inhibitors incorporating substituted biphenyl P4 motifs", *Bioorg. Med. Chem. Lett.*, 14(4):983-987 (2004).
Duong et al., "Inhibition of osteoclast function by adenovirus expressing Antisense protein-tyrosine kinase 2", *J. Biol. Chem.*, 276(10):7484-7492 (2001).
Frame, M.C., "Src in cancer:deregulation and consequences for cell behaviour", *Biochem. Biophys. Acta*, 1602:114-130 (2002).
Guo et al., "Tyrosine phosphorylation of the NR2B subunit of the NMDA receptor in the spinal cord during the development and maintenance of inflammatory hyperalgesia", *J. Neurosci.*, 22(14):6208-6217 (2002).

(Continued)

*Primary Examiner* — Joseph R Kosack
*Assistant Examiner* — Matthew P Coughlin
(74) *Attorney, Agent, or Firm* — Mintz, Kevin, Cohn, Ferris, Glovsky, and Popeo, P.C.; Ivor R. Elrifi, Esq.; Heidi A. Erlacher

(57) ABSTRACT

The invention relates to compounds and methods for modulating one or more components of a kinase cascade. The invention relates to compounds of the formula I:

(I)

[Chemical structure showing biaryl compound with substituents $R_6$, $R_5$, $R_4$, $X_a$, $X_b$, $X_z$, $X_d$, $X_c$, $X_e$, $X_y$, and linker T]

or a pharmaceutically acceptable salt thereof. The compounds of the invention are useful for methods of protecting against or treating hearing loss, osteoporosis, cell proliferative disorders, obesity, diabetes, eye disease, stroke, atherosclerosis, neuropathic pain or hepatitis B.

24 Claims, 23 Drawing Sheets

OTHER PUBLICATIONS

Hadjeri et al., "Antimitotic activity of 5-hydroxy-7-methoxy-2-phenyl-4-quinolones". *J. Med. Chem.*, 47:4964-4970 (2004).

Miyazaki et al., "Src kinase activity is essential for osteoclast function", *J. Biol. Chem.*, 279(17):17660-17666 (2004).

Parang et al., "Recent advances in the discovery of Src kinase inhibitors", *Expert Opin. Ther. Patents*, 15(9):1183-1207 (2005).

Paul et al., "Src deficiency or blockade of Src activity in mice provides cerebral protection following stroke", *Nat. Med.*, 7(2):222-227 (2001).

Yu et al., "Src, a molecular switch governing gain control of synaptic transmission mediated by N-methyl-D-aspartate receptors", *Proc. Natl. Acad. Sci. USA*, 96:7697-7704 (1999).

\* cited by examiner

Figure 8
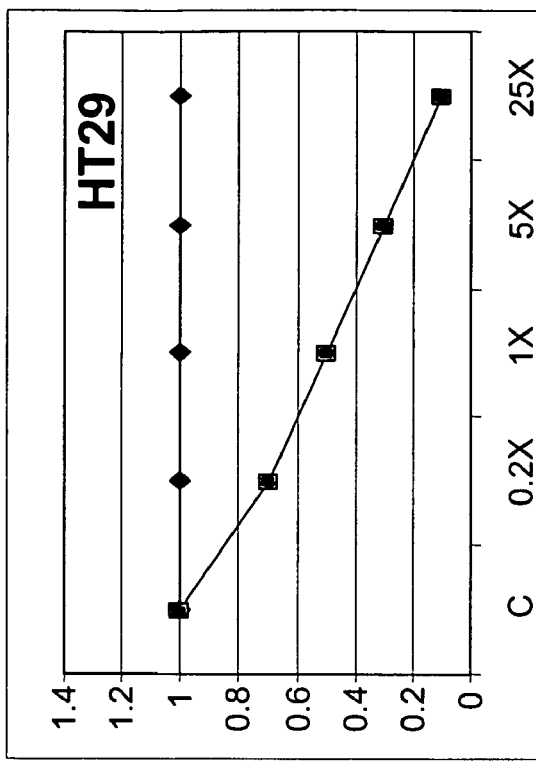
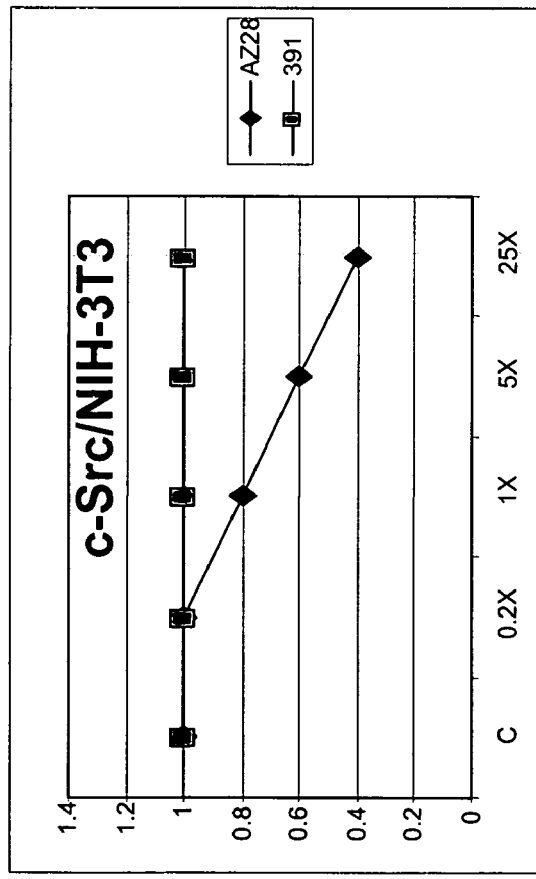

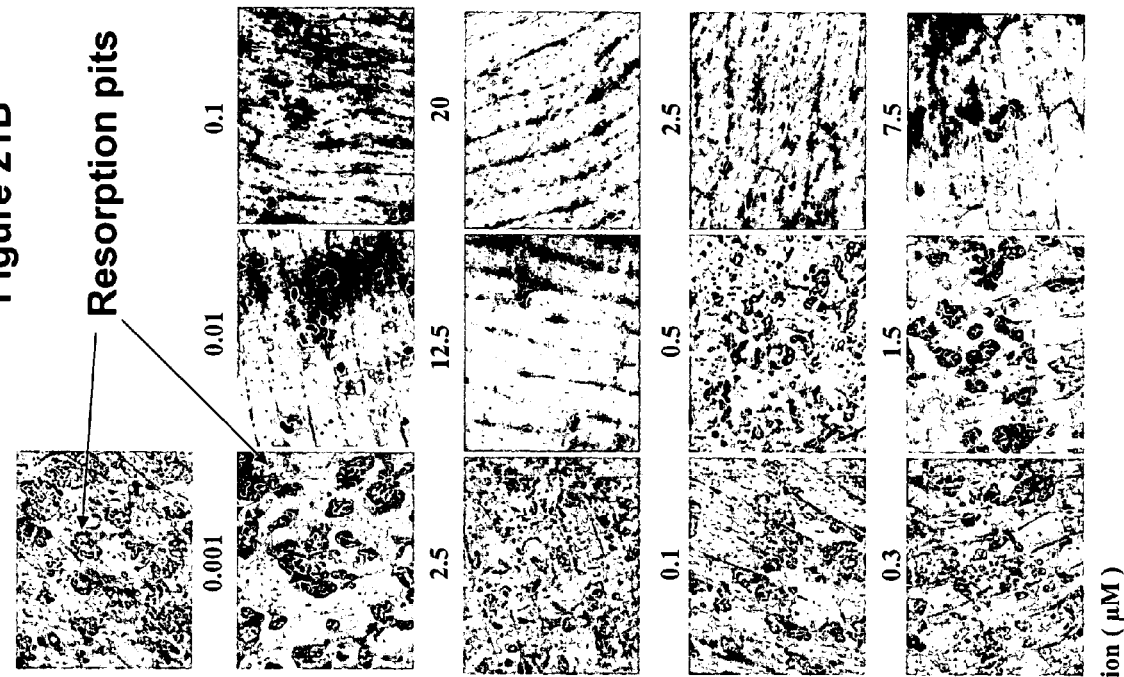
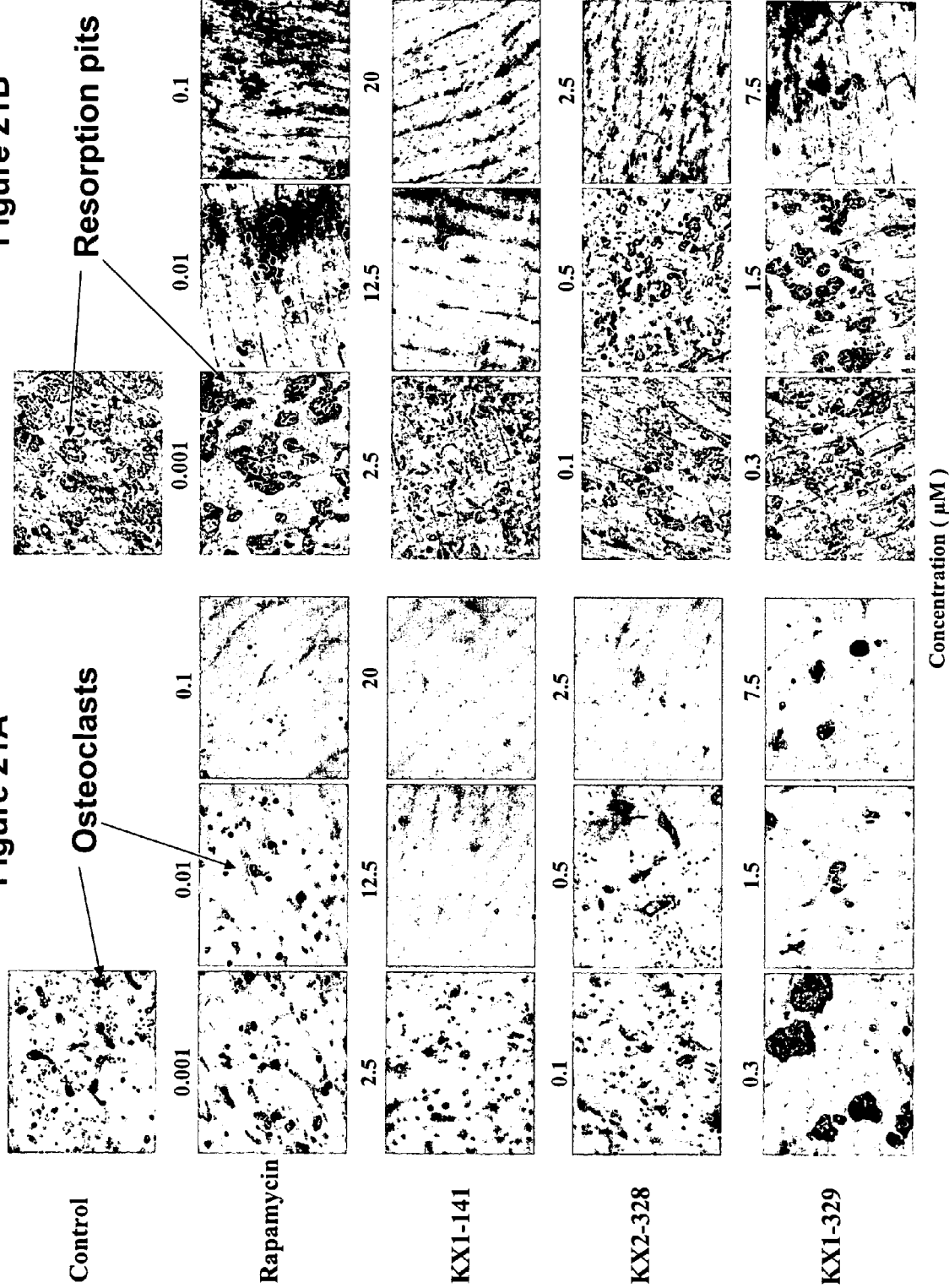

BIARYL COMPOSITIONS AND METHODS FOR MODULATING A KINASE CASCADE

RELATED APPLICATIONS

This application is a continuation in part of U.S. Ser. No. 11/321,419, filed Dec. 28, 2005 now U.S. Pat. No. 7,300,931 which claims priority to provisional patent applications U.S. Ser. No. 60/639,834, filed on Dec. 28, 2004, U.S. Ser. No. 60/704,551, filed on Aug. 1, 2005, and U.S. Ser. No. 60/727,341, filed on Oct. 17, 2005, each of which is incorporated herein by reference in its entirety.

BACKGROUND OF THE INVENTION

Signal transduction is any process by which a cell converts one kind of signal or stimulus into another. Processes referred to as signal transduction often involve a sequence of biochemical reactions inside the cell, which are carried out by enzymes and linked through second messengers. In many transduction processes, an increasing number of enzymes and other molecules become engaged in the events that proceed from the initial stimulus. In such cases the chain of steps is referred to as a "signaling cascade" or a "second messenger pathway" and often results in a small stimulus eliciting a large response. One class of molecules involved in signal transduction is the kinase family of enzymes. The largest group of kinases are protein kinases, which act on and modify the activity of specific proteins. These are used extensively to transmit signals and control complex processes in cells.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate, ATP, in a highly conserved pocket. Protein phosphatases catalyze the transfer of phosphate in the opposite direction.

A tyrosine kinase is an enzyme that can transfer a phosphate group from ATP to a tyrosine residue in a protein. Phosphorylation of proteins by kinases is an important mechanism in signal transduction for regulation of enzyme activity. The tyrosine kinases are divided into two groups; those that are cytoplasmic proteins and the transmembrane receptor-linked kinases. In humans, there are 32 cytoplasmic protein tyrosine kinases and 58 receptor-linked protein-tyrosine kinases. The hormones and growth factors that act on cell surface tyrosine kinase-linked receptors are generally growth-promoting and function to stimulate cell division (e.g., insulin, insulin-like growth factor 1, epidermal growth factor).

Inhibitors of various known protein kinases or protein phosphatases have a variety of therapeutic applications. One promising potential therapeutic use for protein kinase or protein phosphatase inhibitors is as anti-cancer agents. About 50% of the known oncogene products are protein tyrosine kinases (PTKs) and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products). There are at least 9 members of the Src family of non-receptor PTK's with pp60$^{c-src}$ (hereafter referred to simply as "Src") being the prototype PTK of the family wherein the approximately 300 amino acid catalytic domains are highly conserved. The hyperactivation of Src has been reported in a number of human cancers, including those of the colon, breast, lung, bladder, and skin, as well as in gastric cancer, hairy cell leukemia, and neuroblastoma. Overstimulated cell proliferation signals from transmembrane receptors (e.g. EGFR and p185HER2/Neu) to the cell interior also appear to pass through Src. Consequently, it has recently been proposed that Src is a universal target for cancer therapy, because hyperactivation (without mutation) is involved in tumor initiation, progression, and metastasis for many important human tumor types.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders.

SUMMARY OF THE INVENTION

Compounds of the invention are useful in modulation a component of the kinase signaling cascade. Some compounds may be useful in modulation of more than one component of a kinase signaling cascade. The compounds of the present invention are useful as pharmaceutical agents. The compounds of the invention may be useful for modulating regulation of a kinase which may be involved in a normal cellular signal transduction pathway (e.g., cell growth, differentiation, survival, adhesion, migration, etc.), or a kinase involved in a disease or disorder. Such diseases and disorders include, without limitation, cancers, osteoporosis, cardiovascular disorders, immune system dysfunction, type II diabetes, obesity, and transplant rejection.

The compounds of the invention are useful in treating diseases and disorders that are modulated by tyrosine kinase inhibition. For example, the compounds of the invention are useful in treating diseases and disorders that are modulated by Src kinase. The compounds of the invention may also be useful in treating diseases and disorders that are modulated by focal adhesion kinase (FAK).

For example the compounds may be useful as anti-proliferative agents, for treating mammals, such as for treating humans and animals. The compounds may be used without limitation, for example, as anti-cancer, anti-angiogenesis, anti-metastatic, anti-microbial, anti-bacterial, anti-fungal, anti-parasitic and/or anti-viral agents. The compounds of the invention are useful, for example, in treating lung cancer. The compounds of the invention are also useful, for example, in treating colon cancer. The compounds of the invention are also useful, for example, in treating breast cancer.

Compounds of the invention include compounds of Formula I, and salts, solvates, hydrates, or prodrugs thereof:

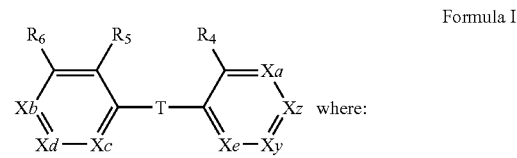

Formula I where:

T is absent (i.e., the rings are connected by a bond), $CR_{12}R_{13}$, $C(O)$, O, S, $S(O)$, $S(O)_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl, or

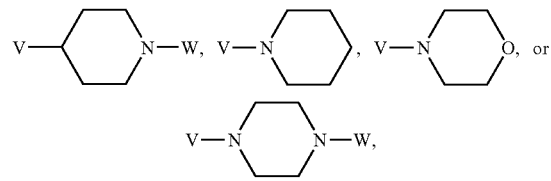

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $OPO_3H_2$, $OPO_3H_2$, $NH_2$, $NHR_{19}$, $NHR_{20}R_{21}$,

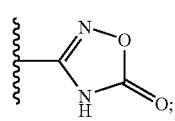

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

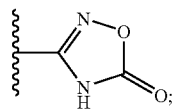

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

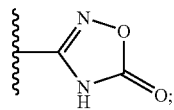

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

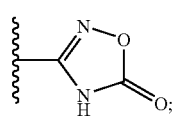

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or $R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl;

Z is $(CHR_1)_n$—$C(O)$—$NR_2(CHR_3)_m$—Ar, where Ar is a substituted or unsubstituted aryl or nitrogen-containing heteroaryl group, such as benzene, pyridine, or pyrimidine. For example, Z is;

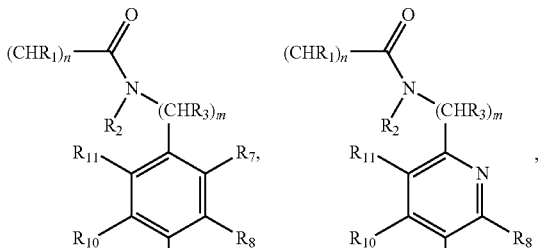

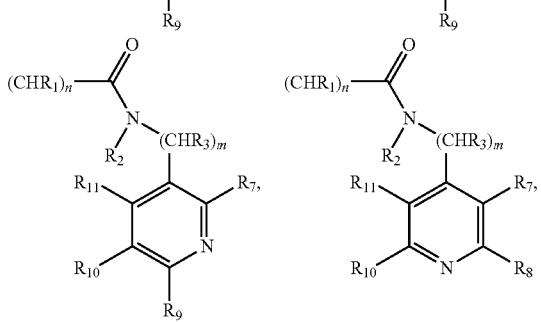

-continued

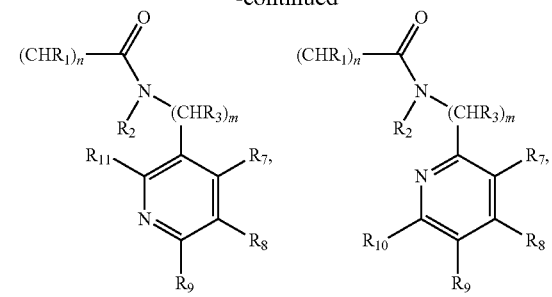

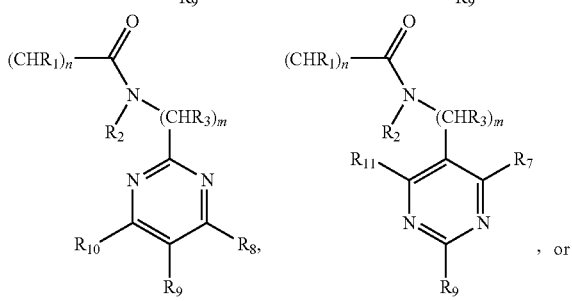

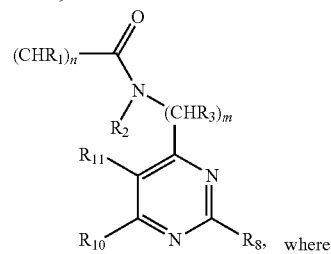

where $R_1$, $R_2$, and $R_3$ are independently H or $C_1$, $C_2$, $C_3$, $C_4$, $C_5$, or $C_6$ alkyl;

n and m are, independently 0, 1, or 2;

$R_7$, $R_8$, $R_9$, $R_{10}$, and $R_{11}$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

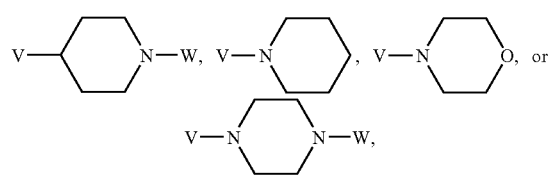

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $OPO_3H_2$, $OPO_3H_2$, $NH_2$, $NHR_{19}$, $NHR_{20}R_{21}$,

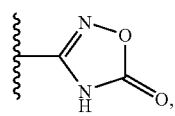

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

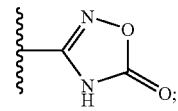

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

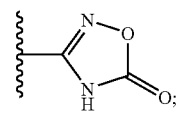

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

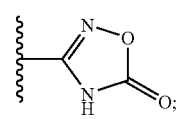

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

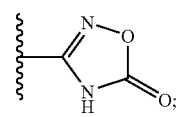

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, $-CH_2-$, $-CH_2CH_2-$, $-CH_2CH_2CH_2-$, $-O-CH_2-$, $-OCH_2CH_2-$, or $-OCH_2CH_2CH_2-$ In certain compounds of the invention, Z is

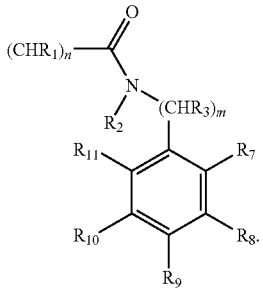

Certain compounds of the invention are selected from Compounds 1-136 and 137. For example, the compound of the invention is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 93, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137.

Compounds of the invention include Compounds 33, 38, 40, 76, 133, 134, 136 and 137.

Certain compounds of the invention are selected from Compounds 138-246 and 247. For example, the compound of the invention is Compound 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, or 247.

Compounds of the invention include Compounds 146 and 147.

Certain compounds of the invention are selected from Compounds 248-273 and 274. For example, the compound of the invention is Compound 248, 249, 250, 251, 252, 253, 254, 255, 256, 257, 258, 259, 260, 261, 262, 263, 264, 265, 266, 267, 268, 269, 270, 271, 272, 273, or 274.

In certain Compounds of Formula I, at least one of $X_a$, $X_b$, $X_c$, $X_d$ and $X_e$ is N.

For example, in the compound of Formula I, $X_a$ is N and each of $X_b$, $X_c$, $X_d$ and $X_e$ is CR.

In certain compounds of Formula I, $X_y$ is CY, and $X_z$ is CZ.

For example, in certain compounds of Formula I, Y is hydrogen.

In certain compounds of Formula I, $R_b$ is $C_1$, $C_2$, $C_3$, $C_4$, $C_5$, or $C_6$ alkoxy. For example, $R_b$ is methoxy or ethoxy. In certain compounds of Formula I, $R_b$ is hydrogen. In other compounds of Formula I, $R_b$ is selected from F, Cl, Br, and I.

In other compounds of Formula I, $R_b$ is

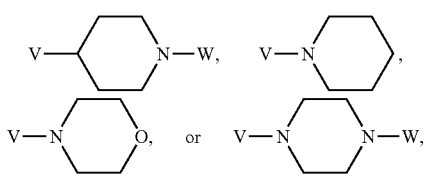

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—. For example, V is a bond. In certain compounds of Formula I, W is hydrogen. In other compounds of Formula I, W is $C_1$, $C_2$, $C_3$, $C_4$, $C_5$, or $C_6$ alkyl.

In certain compounds of Formula I, $R_c$ is $C_1$, $C_2$, $C_3$, $C_4$, $C_5$, or $C_6$ alkoxy. For example, $R_c$ is methoxy or ethoxy. In other compounds of Formula I, $R_c$ is hydrogen, F, Cl, Br, or I.

In other compounds of Formula I, $R_c$ is

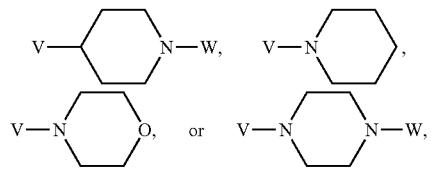

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—.

For example, V is a bond. In certain compounds of Formula I, W is hydrogen. In other compounds of Formula I, W is $C_1$, $C_2$, $C_3$, $C_4$, $C_5$, or $C_6$ alkyl.

In certain compounds of Formula I, Rd is $C_1$, $C_2$, $C_3$, $C_4$, $C_5$, or $C_6$ alkoxy. For example, $R_d$ is methoxy or ethoxy. In other compounds of Formula I, Rd is hydrogen, F, Cl, Br, or I.

In other compounds of Formula I, $R_d$ is

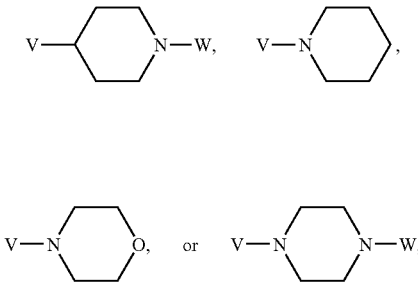

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—.

For example, V is a bond. In certain compounds of Formula I, W is hydrogen. In other compounds of Formula I, W is $C_1$, $C_2$, $C_3$, $C_4$, $C_5$, or $C_6$ alkyl.

The invention includes a solvate of a compound according to Formula I.

The invention also includes a hydrate of a compound according to Formula I.

The invention also includes an acid addition salt of a compound according to Formula I. For example, a hydrochloride salt.

The invention also includes a prodrug of a compound according to Formula I.

The invention also includes a pharmaceutically acceptable salt of a compound of Formula I.

The invention also includes a composition of a compound according to Formula I and at least one pharmaceutically acceptable excipient.

The invention relates to a compound of Formula I, having a structure according to one of Formulae II, III, IV, V, VI, VII, VIII, IX, X, XI, XII, and XIII:

Formula II:
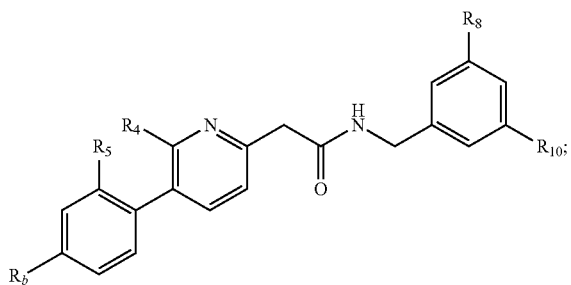
Formula III:
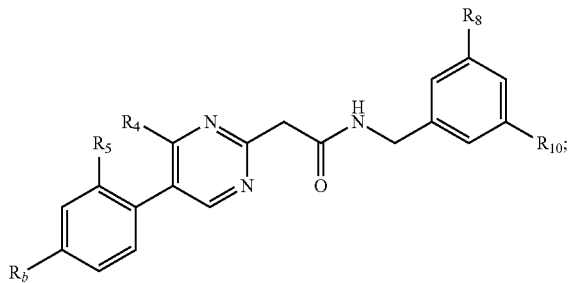
Formula IV:
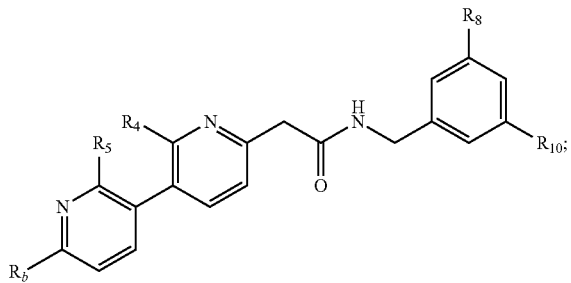
Formula V:
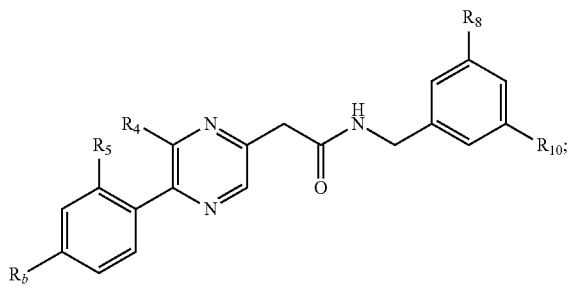
Formula VI:
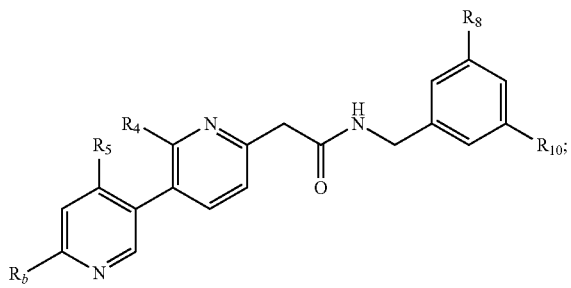
Formula VII:
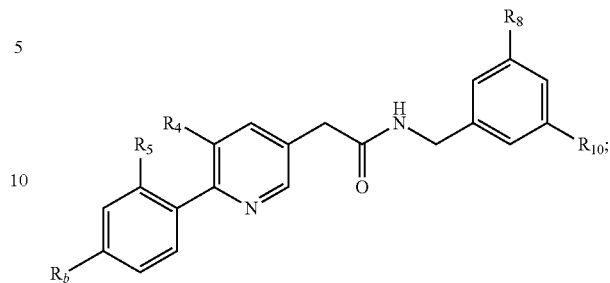
Formula VIII:
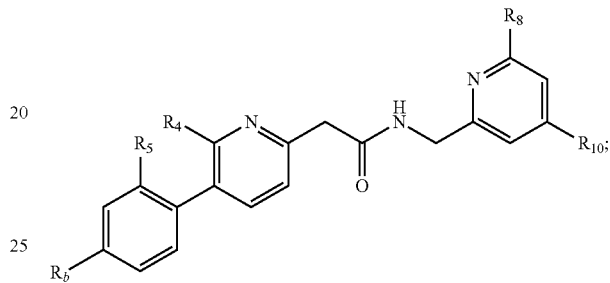
Formula IX:
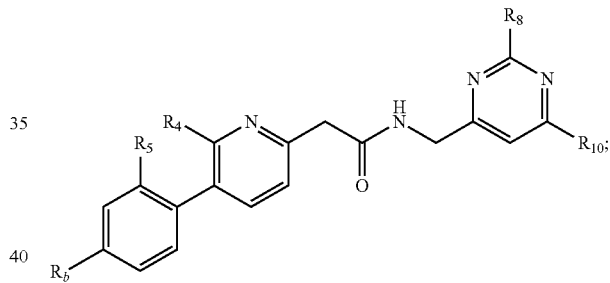
Formula X:
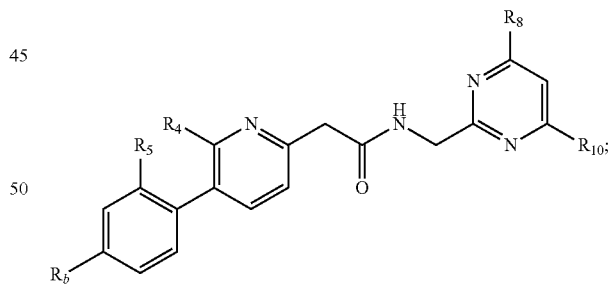
Formula XI:
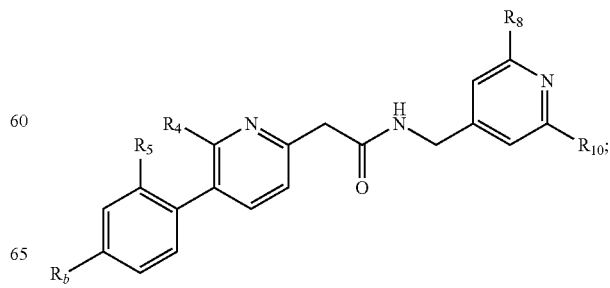

Formula XII:

[chemical structure]

Formula XIII:

[chemical structure]

or a salt, solvate, hydrate, or prodrug thereof, where: $R_b$, $R_4$, $R_5$, $R_8$, and $R_{10}$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

[chemical structures: V—piperidine-N—W, V—N-piperidine, V—N-morpholine-O, or V—N-piperazine-N—W]

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, 3H, H, $OPO_3H_2$, $OPO_3H_2$, $NH_2$, $NHR_{19}$, $NHR_{20}R_{21}$,

[chemical structure: oxadiazolone]

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

[chemical structure: oxadiazolone]

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

[chemical structure: oxadiazolone]

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

[chemical structure: oxadiazolone]

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

[chemical structure: oxadiazolone]

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring; and V is a bond, $-CH_2-$, $-CH_2CH_2-$, $-CH_2CH_2CH_2-$, $-O-CH_2-$, $-OCH_2CH_2-$ or $-OCH_2CH_2CH_2-$.

For example, in the compound of Formula II, III, IV, V, VI, VII, VIII, IX, X, XI, XII, and XIII, $R_8$ is hydrogen, F, Cl, Br, or I. For example, $R_8$ is F. In certain compounds, $R_8$ is H.

In certain compounds of Formula II, III, IV, V, VI, VII, VIII, IX, X, XI, XII, and XIII, $R_b$ is $C_1$, $C_2$, $C_3$, $C_4$, $C_5$, or $C_6$ alkoxy. For example, $R_b$ is methoxy or ethoxy.

In certain compounds of Formula II, III, IV, V, VI, VII, VIII, IX, X, XI, XII, and XIII, $R_b$ is hydrogen, Cl, Br, or I. In other compounds, in the compound of Formula II, III, IV, V, VI, VII, VIII, IX, X, XI, XII, and XIII, $R_b$ is

[chemical structures: V—piperidine-N—W, V—N-piperidine, V—N-morpholine-O, or V—N-piperazine-N—W]

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, $-CH_2-$, $-CH_2CH_2-$, $-CH_2CH_2CH_2-$, $-O-CH_2-$, $-OCH_2CH_2-$ or $-OCH_2CH_2CH_2-$.

In certain compounds of Formula II, III, IV, V, VI, VII, VIII, IX, X, XI, XII, and XIII, $R_4$ is hydrogen, $C_1$, $C_2$, $C_3$, $C_4$, $C_5$, or $C_6$ alkoxy, F, Cl, Br, or I. In other compounds, in the compound of Formula II, III, IV, V, VI, VII, VIII, IX, X, XI, XII, and XIII, $R_4$ is

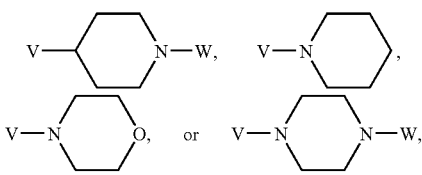

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

In certain compounds of Formula II, III, IV, V, VI, VII, VIII, IX, X, XI, XII, and XIII, $R_5$ is hydrogen, $C_1$, $C_2$, $C_3$, $C_4$, $C_5$, or $C_6$ alkoxy, F, Cl, Br, or I. In other compounds, in the compound of Formula II, III, IV, V, VI, VII, VIII, IX, X, XI, XII, and XIII, $R_5$ is

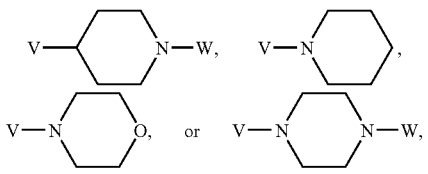

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

In certain compounds of Formula II, III, IV, V, VI, VII, VIII, IX, X, XI, XII, and XIII, $R_{10}$ is hydrogen, $C_1$, $C_2$, $C_3$, $C_4$, $C_5$, or $C_6$ alkoxy, F, Cl, Br, or I. For example, $R_{10}$ is methoxy, ethoxy or isobutoxy.

In other compounds of Formula II, III, IV, V, VI, VII, VIII, IX, X, XI, XII, and XIII, $R_{10}$ is

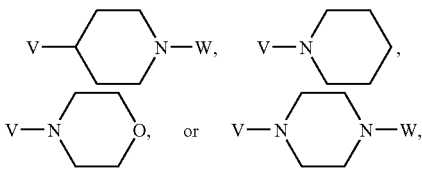

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

For example, in the compound of Formula II, III, IV, V, VI, VII, VIII, IX, X, XI, XII, and XIII, W is hydrogen, or $C_1$, $C_2$, $C_3$, $C_4$, $C_5$, or $C_6$ alkyl.

Certain compounds of the invention include compounds according to Formula II.

The invention relates to a solvate of a compound according to one of Formulae II, III, IV, V, VI, VII, VIII, IX, X, XI, XII, and XIII. The invention also relates to a hydrate of a compound according to one of Formulae II, III, IV, V, VI, VII, VIII, IX, X, XI, XII, and XIII.

The invention also relates to an acid addition salt of a compound according to one of Formulae II, III, IV, V, VI, VII, VIII, IX, X, XI, XII, and XIII. For example, a hydrochloride salt.

Further, the invention relates to a prodrug of a compound according to one of Formulae II, III, IV, V, VI, VII, VIII, IX, X, XI, XII, and XIII.

The invention also relates to a pharmaceutically acceptable salt of a compound of one of Formulae II, III, IV, V, VI, VII, VIII, IX, X, XI, XII, and XIIII.

The invention includes compositions comprising a compound according to one of Formulae I, II, III, IV, V, VI, VII, VIII, IX, X, XI, XII, and XIII and at least one pharmaceutically acceptable excipient.

The invention relates to compounds and methods of using the compounds to modulate a component of the kinase signaling cascade. Some compounds may be useful in modulation of more than one component of a kinase signaling cascade. The compounds of the present invention are useful as pharmaceutical agents.

Certain compounds of the invention are non-ATP competitive kinase inhibitors.

The invention relates to compounds and methods of using the compounds to treat cell proliferation disorders.

The invention also includes a method of preventing or treating a cell proliferation disorder by administering a pharmaceutical composition that includes a compound according to one of Formulae I, II, III, IV, V, VI, VII, VIII, IX, X, XI, XII, and XIII, or a salt, solvate, hydrate, or prodrug thereof, and at least one pharmaceutically acceptable excipient to a subject in need thereof.

For example, the cell proliferation disorder is pre-cancer or cancer. The cell proliferation disorder treated or prevented by the compounds of the invention may be a cancer, such as, for example, colon cancer or lung cancer.

The cell proliferation disorder treated or prevented by the compounds of the invention may be a hyperproliferative disorder The cell proliferation disorder treated or prevented by the compounds of the invention may be psoriases.

For example, the treatment or prevention of the proliferative disorder may occur through the inhibition of a tyrosine kinase. For example, the tyrosine kinase can be a Src kinase or focal adhesion kinase (FAK).

The invention relates to a method of treating or preventing a disease or disorder that is modulated by tyrosine kinase inhibition, by administering a pharmaceutical composition that includes a compound according to Formula I or one of Formulae II, III, IV, V, VI, VII, VIII, IX, X, XI, XII, and XIII, or a salt, solvate, hydrate, or prodrug thereof, and at least one pharmaceutically acceptable excipient. For example, the disease or disorder that is modulated by tyrosine kinase inhibition is cancer, pre-cancer, a hyperproliferative disorder, or a microbial infection. For example, the compound is a compound according to Formula I or II.

The pharmaceutical composition of the invention may modulate a kinase pathway. For example, the kinase pathway is a Src kinase pathway, or a focal adhesion kinase pathway.

The pharmaceutical composition of the invention may modulate a kinase directly. For example, the kinase is Src kinase, or focal adhesion kinase.

Certain pharmaceutical compositions of the invention are non-ATP competitive kinase inhibitors.

The compounds of the invention are also useful to treat or prevent a microbial infection, such as a bacterial, fungal, parasitic or viral infection.

Certain pharmaceutical compositions of the invention include a compound selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 93, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, and 137. For example, the pharmaceutical composition includes Compound 33, 38, 40, 76, 133, 134, 136 or 137.

Certain pharmaceutical compositions of the invention include a compound selected from Compound 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, and 247. For example, the pharmaceutical composition includes Compound 146 or 147.

Certain compounds of the invention are selected from Compounds 248-274. For example, the compound of the invention is Compound 248, 249, 250, 251, 252, 253, 254, 255, 256, 257, 258, 259, 260, 261, 262, 263, 264, 265, 266, 267, 268, 269, 270, 271, 272, 273, or 274.

A compound of the invention may be used as a pharmaceutical agent. For example, a compound of the invention is used as an anti-proliferative agent, for treating humans and/or animals, such as for treating humans and/or other mammals. The compounds may be used without limitation, for example, as anti-cancer, anti-angiogenesis, anti-microbial, anti-bacterial, anti-fungal, anti-parasitic and/or anti-viral agents. Additionally, the compounds may be used for other cell proliferation-related disorders such as diabetic retinopathy, macular degeneration and psoriases. Anti-cancer agents include antimetastatic agents.

The compound of the invention used as a pharmaceutical agent includes a compound selected from Compounds 1-136 and 137. For example, the compound of the invention used as a pharmaceutical agent is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 93, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137. For example, the compound of the invention used as a pharmaceutical agent is selected from Compounds 33, 38, 40, 76, 133, 134, 136 and 137.

Certain pharmaceutical agents include a compound selected from the compounds listed in Table 2. For example, the compound of the invention used as a pharmaceutical agent is Compound 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, or 247. For example, the compound of the invention used as a pharmaceutical agent is 146 or 147.

Certain pharmaceutical agents include a compound selected from the compounds listed in Table 3. For example, the compound of the invention used as a pharmaceutical agent is Compound 248, 249, 250, 251, 252, 253, 254, 255, 256, 257, 258, 259, 260, 261, 262, 263, 264, 265, 266, 267, 268, 269, 270, 271, 272, 273, or 274.

In one aspect of the invention, a compound of the invention, for example, a compound of Formula I or one of Formulae II, III, IV, V, VI, VII, VIII, IX, X, XI, XII, and XIII, is used to modulate a kinase cascade. For example, the compound is used to modulate a component of a kinase cascase which is responsible for the manifestation of a disease or disorder.

Such diseases and disorders include cancers, osteoporosis, cardiovascular disorders, immune system dysfunction, type II diabetes, obesity, and transplant rejection.

For example, a compound of the invention may be used to treat or prevent a cell proliferation disorder in an subject. In one aspect of the embodiment, the cell proliferation disorder is pre-cancer or cancer. In another aspect of the embodiment, the cell proliferation disorder is a hyperproliferative disorder. In another embodiment, prevention or treatment of the cell proliferation disorder, cancer or hyperproliferative disorder occurs through the inhibition of a kinase. In another embodiment, prevention or treatment of the cell proliferation disorder, cancer or hyperproliferative disorder occurs through the inhibition of a tyrosine kinase. In another embodiment, prevention or treatment of the cell proliferation disorder, cancer or hyperproliferative disorder occurs through the inhibition of Src kinase or focal adhesion kinase (FAK). In another embodiment, the subject is a mammal. In one embodiment, the subject is human.

The invention is also drawn to a method of treating or preventing cancer or a proliferation disorder in a subject, comprising administering an effective amount of a compound of the invention, for example, a compound of Formula I or one of Formulae II, III, IV, V, VI, VII, VIII, IX, X, XI, XII, and XIII. For example, the compound of the invention may be a kinase inhibitor. The compound of the invention may be a non-ATP competitive kinase inhibitor. The compound of the invention may inhibit a kinase directly, or it may affect the kinase pathway.

Another aspect of the invention includes compounds of Formula IA, and salts, solvates, hydrates, or prodrugs thereof:

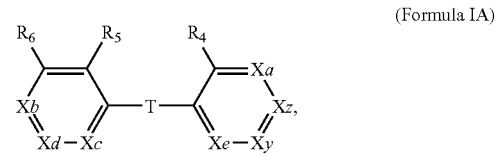

(Formula IA)

wherein: T is absent (i.e., the rings are connected by a bond), $CR_{12}R_{13}$, C(O), O, S, S(O), S(O)$_2$, NR$_{14}$, C(R$_{15}$R$_{16}$)C(R$_{17}$R$_{18}$), CH$_2$O, or OCH$_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower (C$_1$, C$_2$, C$_3$, C$_4$, C$_5$, or C$_6$) alkyl, C$_1$, C$_2$, C$_3$, C$_4$, C$_5$, or C$_6$ alkoxy, O-lower (C$_1$, C$_2$, C$_3$, C$_4$, C$_5$, or C$_6$) alkyl-aryl, and O-benzyl;

$X_a$ is CR$_a$ or N, or N—O;

$X_b$ is $CR_b$, N, or N—O;
$X_c$ is $CR_c$ or N, or N—O;
$X_d$ is $CR_d$ or N, or N—O;
$X_e$ is $CR_e$, N, or N—O;
$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

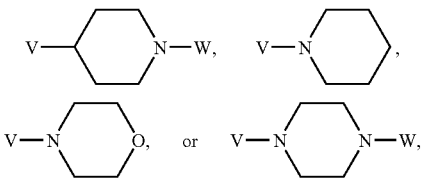

wherein W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $OPO_3H_2$, $OPO_3H_2$, $NH_2$, $NHR_{19}$, $NHR_{20}R_{21}$,

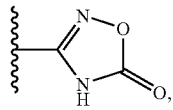

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

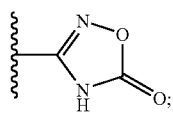

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

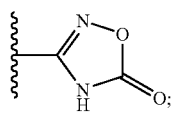

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

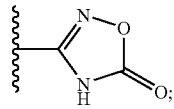

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

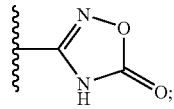

$R_{19}$, $R_{20}$ and $R_2$, are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl; and Z is $(CHR_1)_n$—C(O)—$NR_2(CHR_3)_m$—Ar, where Ar is a substituted or unsubstituted aryl or nitrogen-containing heteroaryl group, $R_1$, $R_2$, and $R_3$ are independently H or $C_1$, $C_2$, $C_3$, $C_4$, $C_5$, or $C_6$ alkyl; and n and m are, independently 0, 1, or 2;

provided that at least one of $R_a$, $R_b$, $R_c$, $R_d$, $R_e$, $R_4$, $R_5$, and $R_6$ is P.

In one embodiment of the invention, at least one of $X_a$, $X_b$, $X_c$, $X_d$, $X_e$, $X_y$, and $X_z$ is N. In another embodiment, at least two of $X_a$, $X_b$, $X_c$, $X_d$, $X_e$, $X_y$, and $X_z$ are N. In another embodiment, at least one of $X_a$ and $X_y$ is N. For example, both $X_a$ and $X_y$ are N. In another embodiment, $X_a$, $X_b$, $X_c$, $X_d$, and $X_e$ are not each N or N—O. In another embodiment, $X_c$, $X_d$, and $X_e$ are not each N or N—O.

In one embodiment, T is absent. In another embodiment, $X_b$ is $CR_b$. In another embodiment, $R_b$ is P. For example, in one embodiment, P is O-lower ($C_1$, $C_2$, $C_3$, $C_4$, $C_5$, or $C_6$) alkyl-K. In one embodiment, lower ($C_1$, $C_2$, $C_3$, $C_4$, $C_5$, or $C_6$) alkyl is $CH_2CH_2CH_2$. In one embodiment, lower ($C_1$, $C_2$, $C_3$, $C_4$, $C_5$, or $C_6$) alkyl is branched alkyl. For example, branched alkyl is

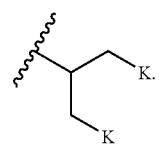

In another embodiment, K, L, M, N, or Q, if present, is lower $C_1$, $C_2$, $C_3$, $C_4$, $C_5$ or $C_6$ alkoxy. For example, K is methoxy. In one embodiment, branched alkyl is

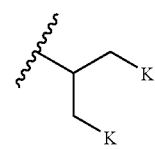

and K is methoxy. In another embodiment, K, L, M, N, or Q, if present, is COOH. For example, in one embodiment, K is COOH. In another embodiment, K, L, M, N, or Q, if present, is aryl. For example, aryl is tetrazole.

In one embodiment, $R_b$ is

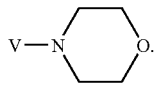

In another embodiment, $R_b$ is

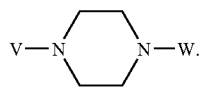

In one embodiment, V is —OCH$_2$CH$_2$. In another embodiment, V is a bond. In one embodiment, W is $C_1$, $C_2$, $C_3$, $C_4$, $C_5$, or $C_6$ alkyl. For example, W is methyl or ethyl.

In one embodiment, $X_z$ is CZ, further wherein Z is

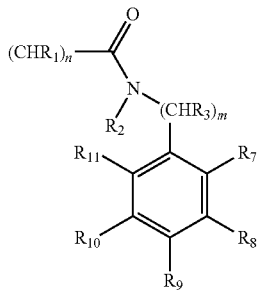

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

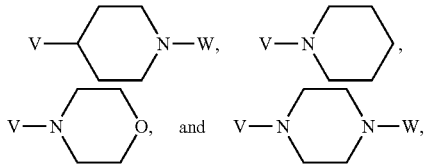

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl. In another embodiment, at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl. In another embodiment, at least one of $R_8$ or $R_{10}$ is halogen. For example, halogen is fluorine. In another embodiment, at least one of $R_7$ or $R_{11}$ is $C_1$, $C_2$, $C_3$, $C_4$, $C_5$, or $C_6$ alkoxy or O-benzyl. For example, at least one of $R_7$ or $R_{11}$ is ethoxy or at least one of $R_7$ or $R_{11}$ is O-benzyl. In one embodiment, $R_1$ is H. In one embodiment, n is 1. In one embodiment, $R_2$ is H. In one embodiment, $R_3$ is H. In one embodiment, m is 1. In another embodiment, m and n are each 1 and $R_2$ and $R_3$ are each H.

In one embodiment, $R_4$ and $R_6$ are each H. In another embodiment $R_5$ is selected from halogen and $C_1$, $C_2$, $C_3$, $C_4$, $C_5$, or $C_6$ alkyl. In one embodiment, $R_5$ is halogen. For example, $R_5$ is Cl or F. In another embodiment, $R_5$ is $C_1$, $C_2$, $C_3$, $C_4$, $C_5$, or $C_6$ alkyl. For example, $R_5$ is methyl or ethyl.

The invention includes a solvate of a compound according to Formula IA. The invention includes a hydrate of compound according to Formula IA. The invention includes an acid addition salt of a compound according to Formula IA. For example, a hydrochloride salt. In another embodiment, the invention includes a pharmaceutically acceptable salt. The invention includes a composition comprising a compound of Formula IA and at least one pharmaceutically acceptable excipient.

Certain compounds of the invention include compounds selected from Compound 248, 249, 250, 251, 252, 253, 254, 255, 256, 257, 258, 259, 260, 261, 262, 263, 264, 265, 266, 267, 268, 269, 270, 271, 272, 273, and 274.

Another aspect of the invention includes a method of protecting against or treating hearing loss in a subject comprising administering a compound having the Formulae I, IA, II, III, IV, V, VI, VII, VIII, IX, X, XI, XII, and XIII. In one embodiment, the compound inhibits one or more components of a kinase signaling cascade. In one embodiment, the compound is an allosteric inhibitor. In one embodiment, the compound is a peptide substrate inhibitor. In one embodiment, the compound does not inhibit ATP binding to the protein kinase. In one embodiment, the compound inhibits a Src family protein kinase. In one embodiment, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically e.g., by administering drops into the ear, intraarterially, intralesionally, by metering pump, or by application to mucous membranes. In another embodiment, the compound is administered with a pharmaceutically acceptable carrier.

In one embodiment, the compound is administered before initiation of hearing loss. In another embodiment, the compound is administered after initiation of hearing loss.

In one embodiment, the compound is administered in combination with a drug that causes hearing loss e.g., cis platinum or an aminoglycoside antibiotic. In another embodiment, the compound is administred in combination with a drug that targets hairy cells.

In one embodiment, at least one of $X_a$, $X_b$, $X_c$, $X_d$, $X_e$, $X_y$ and $X_z$ is N. In another embodiment, T is absent. In another embodiment, $X_z$ is CZ and Z is

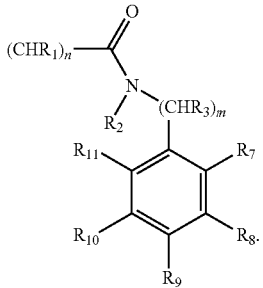

In one embodiment, m and n are each 1 and $R_2$ and $R_3$ are each H. In another embodiment, at least one of $R_7$, $R_8$, $R_9$, $R_{10}$ and $R_{11}$ is halogen, $C_1$, $C_2$, $C_3$, $C_4$, $C_5$, or $C_6$ alkyl, or O-benzyl. In one embodiment, the compound is

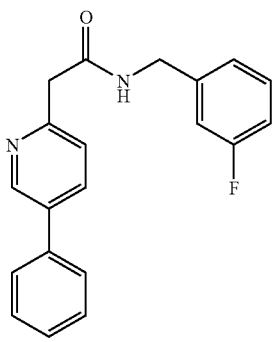

Another aspect of the invention includes a method of protecting against or treating osteoporosis in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, at least one of $X_a$, $X_b$, $X_c$, $X_d$, $X_e$, $X_y$, and $X_z$ is N. In another embodiment, T is absent. In another embodiment, $X_z$ is CZ and Z is

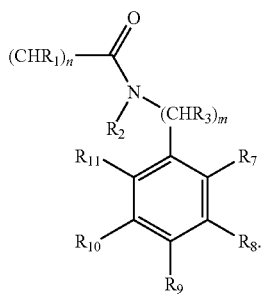

In one embodiment, m and n are each 1 and $R_2$ and $R_3$ are each H. In another embodiment, at least one of $R_7$, $R_8$, $R_9$, $R_{10}$ and $R_{11}$ is halogen, $C_1$, $C_2$, $C_3$, $C_4$, $C_5$, or $C_6$ alkyl, or O-benzyl. In one embodiment, the compound is Compound 25 (KX1-329), Compound 38 (KX2-377), Compound 76 (KX2-361), Compound 133 (KX2-392), Compound 134 (KX2-391), or Compound 137 (KX2-394).

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before initiation of osteoporosis. In another embodiment, the compound is administered after initiation of osteoporosis.

Another aspect of the invention includes a method of protecting against or treating ophthalmic diseases e.g., macular degeneration, retinopathy, macular edema, etc. in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase. In another embodiment, the compound inhibits one or more components in the VEGF pathway.

In one embodiment, the administration of the compound is carried out orally, parentally, subcutaneously, intravenously, intramuscularly, intraperitoneally, by intranasal instillation, by intracavitary or intravesical instillation, topically (e.g., by administering drops to the eye), intraarterially, intralesionally, by metering pump, or by application to mucous membranes. In one embodiment, the compound is administered with a pharmaceutically acceptable carrier. In one embodiment, the compound is administered before initiation of the ophthalmic disease. In another embodiment, the compound is administered after initiation of ophthalmic disease.

Another aspect of the invention includes a method of protecting against or treating diabetes in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of diabetes. In another embodiment, the compound is administered after the onset of diabetes.

Another aspect of the invention includes a method of protecting against or treating obesity in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the subject is obese. In another embodiment, the compound is administered after the subject is obese.

Another aspect of the invention includes a method of protecting against or treating stroke in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before a stroke has occurred. In another embodiment, the compound is administered after a stroke has occurred.

Another aspect of the invention includes a method of protecting against or treating athrosclerosis in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is $pp60^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of regulating immune system activity in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is $pp60^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of protecting against or treating chronic neuropathic pain in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is $pp60^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of chronic neuropathic pain. In another embodiment, the compound is administered after the onset of chronic neuropathic pain.

Another aspect of the invention includes a method of protecting against or treating hepatitis B in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is $pp60^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of hepatitis B. In another embodiment, the compound is administered after the onset of hepatitis B.

Another aspect of the invention is a method of preventing or treating a cell proliferation disorder comprising administering to a subject in need thereof a compound having the Formula IA. In one embodiment, the compound inhibits one or more components of a protein kinase signaling cascade. In another embodiment, the compound is an allosteric inhibitor. In another embodiment, the compound is a peptide substrate inhibitor. In another embodiment, the compound does not inhibit ATP binding to a protein kinase. In one embodiment, the compound inhibits a Src family protein kinase. In another embodiment, the Src family protein kinase is $pp60^{c-src}$ tyrosine kinase.

In one embodiment, at least one of $X_a$, $X_b$, $X_c$, $X_d$, $X_e$, $X_y$, and $X_z$ is N. In another embodiment, $X_z$ is CZ, further wherein Z is

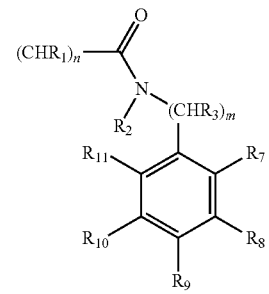

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

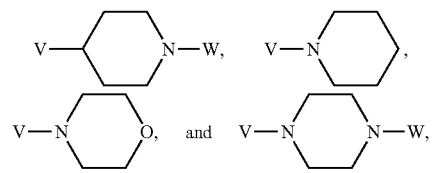

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl. In one embodiment, at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl. In another embodiment, m and n are each 1 and $R_2$ and $R_3$ are each H. In one embodiment, $R_4$ and $R_6$ are each H. In one embodiment of the invention, a compound is selected from 248, 249, 250, 251, 252, 253, 254, 255, 256, 257, 258, 259, 260, 261, 262, 263, 264, 265, 266, 267, 268, 269, 270, 271, 272, 273, or 274.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

BRIEF DESCRIPTION OF THE DRAWINGS

FIG. 8A is a graph indicating the effect of AZ28 and KX2-391 on autophosphorylation of FAK in c-Src/NIH-3T3 cells; FIG. 8B is a graph indicating the effect of AZ28 and KX2-391 on autophosphorylation of FAK in HT-29 cells.

FIG. 21A is a series of illustrations depicting the effect of compounds on osteoclast formation on bone slices.

FIG. 21B is a series of illustrations demonstrating the effect of compounds on the formation of resorption pits on bone slices.

DETAILED DESCRIPTION OF THE INVENTION

Figure 1:
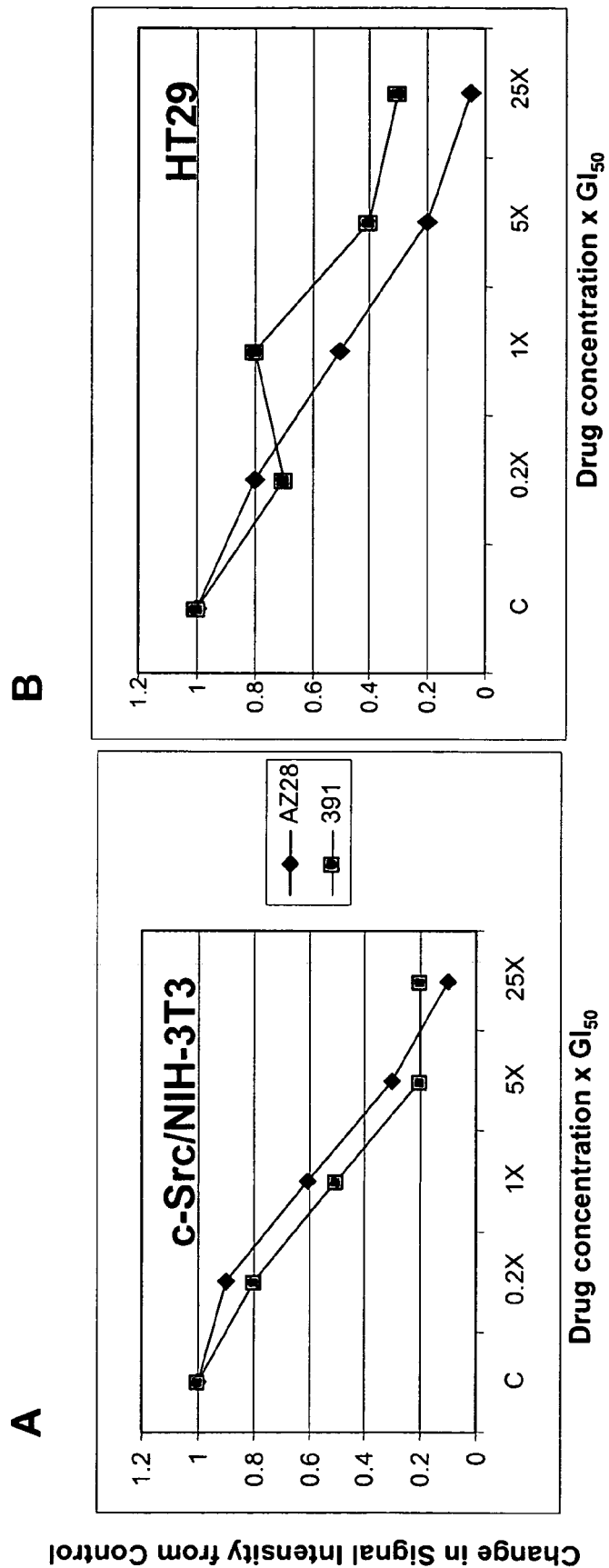
FIG. 1A is a graph indicating the effect of AZ28 and KX2-391 on Src autophosphorylation in c-Src/NIH-3T3 cells.
FIG. 1B is a graph indicating the effect of AZ28 and KX2-391 on Src autophosphorylation in HT-29 cells.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders. Such diseases and disorders include, for example, cancers, osteoporosis, cardiovascular disorders, immune system dysfunction, type II diabetes, obesity, and transplant rejection.

Compounds of the invention are useful in modulation a component of the kinase signaling cascade. Some compounds may be useful in modulation of more than one component of a kinase signaling cascade. The phrase "modulates one or more components of a protein kinase signaling cascade" means that one or more components of the kinase signaling cascade are affected such that the functioning of a cell changes. Components of a protein kinase signaling cascade include any proteins involved directly or indirectly in the kinase signaling pathway including second messengers and upstream and downstream targets.

A number of protein kinases and phosphatases are known, and are targets for the development of therapeutics. See, e.g., Hidaka and Kobayashi, Annu. Rev. Pharmacol. Toxicol, 1992, 32:377-397; Davies et al., Biochem. J., 2000, 351:95-105, each of which is incorporated by reference herein.

One family of kinases, the protein tyrosine kinases are divided into two large families: receptor tyrosine kinases, or RTKs (e.g., insulin receptor kinase (IRK), epidermal growth factor receptor (EGFR), basic fibroblast growth factor receptor (FGFR), platelet-derived growth factor receptor (PDGFR), vascular endothelial growth factor receptor (VEGFR-2 or Flk1/KDR), and nerve growth factor receptor (NGFR)) and nonreceptor tyrosine kinases, or NRTKs (e.g., the Src family (Src, Fyn, Yes, Blk, Yrk, Fgr, Hck, Lck, and Lyn), Fak, Jak, Abl and Zap70). See, for example, Parang and Sun, Expert Opin. Ther. Patents, 2005, 15:1183-1207, incorporated by reference herein.

Because of the role of Src kinases in a variety of cancers, these kinases are the subject of a number of studies relating to the development of Src inhibitors as cancer therapeutics, including highly metastatic cancer cell growth. Src inhibitors are sought as therapeutics for a variety of cancers, including, for example, colon cancer, precancerous colon lesions, ovarian cancer, breast cancer, epithelial cancers, esophageal cancer, non-small cell lung cancer, pancreatic cancer, and others. See, e.g., Frame, Biochim. Biophys. Acta, 2002, 1602:114-130 and Parang and Sun, Expert Opin. Ther. Patents, 2005, 15:1183-1207.

Inhibition of other kinases may be useful in the treatment and modulation of other types of diseases and disorders. For example, various eye diseases may be inhibited or prevented by administration of VEGF receptor tyrosine kinase inhibitors. Inhibitors of the tyrosine phosphatase PTP-1B and/or glycogen phosphorylase may provide treatments for Type II diabetes or obesity. Inhibitors of p56lck may be useful in treating immune system disorders. Other targets include HIV reverse transcriptase, thromboxane synthase, EGFRTK, p55 fyn, etc.

Compounds of the invention may be Src signaling inhibitors that bind in the Src peptide substrate site. The activity of various compounds of the invention has been studied in c-Src (527F, constitutively active and transforming) transformed NIH3T3 cells and in human colon cancer cells (HT29). For example, in these cell lines, KX2-391 was shown to reduce the phosphorylation level of known Src protein substrates in a dose-dependent fashion and in good correlation with growth inhibitory effects. Thus, in some embodiments, compounds of the invention may directly inhibit Src, and may do so by binding in the peptide binding site (as opposed to binding at an allosteric site).

Molecular modeling experiments have been performed which show that compounds of the invention fit into the model Src substrate site (See, e.g., U.S. Pat. Nos. 7,005,445 and 7,070,936). Modeling is also used to retool the Src kinase inhibitor scaffolds in order to target other kinases, simply by using a different set of side chains present on the molecules and/or modifying the scaffold itself.

Without wishing to be bound by theory, it is believed that the conformation of some kinases (e.g., Src) outside cells relative to the conformation inside cells is markedly different, because inside cells, many kinases are is embedded in multi-protein signaling complexes. Thus, because the peptide substrate binding site is not well formed in an isolated kinase (as shown by Src x-ray structures), it is believed that the activity against isolated kinase for a peptide substrate binding inhibitor would be weak. Binding to this site in an isolated kinase assay requires the inhibitor to capture the very small percentage of total protein in an isolated enzyme assay that is in the same conformation that exists inside cells. This requires a large excess of the inhibitor to drain significant amounts of the enzyme from the catalytic cycle in the assay in order to be detectable.

However, for cell-based assays, a large inhibitor excess is not needed because the peptide binding site is expected to be formed. In cell-based Src assays, SH2 & SH3 domain binding proteins have already shifted the Src conformation so that the peptide substrate binding site is fully formed. Thus, low concentrations of the inhibitor can remove the enzyme from the catalytic cycle since all of the enzyme is in the tight binding conformation.

The vast majority of known kinase inhibitors are ATP competitive and show poor selectivity in a panel of isolated kinase assays. However, many of the compounds of the invention are thought to be peptide substrate binding inhibitors. Thus, traditional high throughput screening of compounds against isolated enzymes, such as Src, would not result in the discovery of compounds of the invention.

There is considerable recent literature support for targeting pp60c-src (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al. (1999) Oncogene 18(33): 4654-4662). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hisano, et al., Proc. Annu. Meet. Am. Assoc. Cancer Res. 38:A1925 (1997)). Additionally, reduced VEGF mRNA expression was noted upon Src inhibition and tumors derived from these Src-inhibited cell lines showed reduced angiogenic development (Ellis et al., Journal of Biological Chemistry 273 (2):1052-1057 (1998)).

For example, a knock-out of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., (1997) Genes & Development 11: 2835-2844). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Src has been proposed to be a "universal" target for cancer therapy since it has been found to be overactivated in a growing number of human tumors (Levitzki, Current Opinion in Cell Biology, 8, 239-244 (1996); Levitzki, Anti-Cancer Drug Design, 11, 175-182 (1996)). The potential benefits of Src inhibition for cancer therapy appear to be four-fold inhibition of uncontrolled cell growth caused by autocrine growth factor loop effects, inhibition of metastasis due to triggering apoptosis upon breaking free from the cell matrix, inhibition of tumor angiogenesis via reduced VEGF levels, low toxicity.

Prostate cancer cells have been reported to have both an over expression of paxillin and p130cas and are hyperphosphorylated (Tremblay et al., Int. J. Cancer, 68, 164-171, 1996) and may thus be a prime target for Src inhibitors.

Thus, the invention relates to compounds and methods of using compounds to treat cell proliferation disorders.

The compounds of the present invention are useful as pharmaceutical agents, for example, as therapeutic agents for treating humans and animals. The compounds may be used without limitation, for example, as anti-cancer, anti-angiogenesis, anti-metastatic, anti-microbial, anti-bacterial, anti-fungal, anti-parasitic and/or anti-viral agents. The compounds may be used for other cell proliferation-related disorders such as psoriases.

As described herein, a compound of the invention may be used to protect against or prevent hearing loss in a subject. In order to protect against hearing loss, the compound may be administered prior to noise exposure or exposure to a drug which induces hearing loss. Such drugs may include chemotherapeutic drugs (e.g., platinum-based drugs which target hair cells) and aminoglycoside antibiotics. A compound of the invention may provide a synergistic effect with certain cancer drugs. For example, promising inhibitors can be screened in primary human tumor tissue assays, particularly to look for synergy with other known anti-cancer drugs. In addition, the protein kinase inhibitors may reduce toxicity of certain cancer drugs (e.g., platinum-based drugs which are toxic to the cochlea and kidney), thereby allowing increased dosage.

Alternatively, a compound of the invention may be used to treat hearing loss in a subject. In this embodiment, the compound is administered to the subject subsequent to the initiation of hearing loss to reduce the level of hearing loss. A compound of the invention may be involved in modulating a kinase cascade, e.g. a kinase inhibitor, a non-ATP competitive inhibitor, a tyrosine kinase inhibitor, a Src inhibitor or a focal adhesion kinase (FAK) modulator. Although not wishing to be bound by theory, it is believed that the administration of kinase inhibitors prevents apoptosis of cochlear hair cells, thereby preventing hearing loss. In one embodiment, administration of a compound of the invention is administered to a subject suffering from hearing loss in order to prevent further hearing loss. In another embodiment, administration of a compound of the invention is administered to a subject suffering from hearing loss in order to restore lost hearing. In particular, following noise exposure, the tight cell junctures between the cochlear hair cells, as well as the cell-extracellular matrix interaction, are torn and stressed. The stressing of these tight cell junctures initiates apoptosis in the cells through a complex signaling pathway in which tyrosine kinases act as molecular switches, interacting with focal adhesion kinase to transduce signals of cell-matrix disruptions to the nucleus. It is believed that the administration of kinase inhibitors prevents the initiation of apoptosis in this cascade.

The identification of apoptosis in the noise-exposed cochlea has generated a number of new possibilities for the prevention of noise-induced hearing loss (NIHL) (Hu, et al.; 2000, *Acta. Otolaryngol.*, 120, 19-24). For example, the ear can be protected from NIHL by administration of antioxidant drugs to the round window of the ear (Hight, et al.; 2003, *Hear. Res.*, 179, 21-32; Hu, et al.; *Hear. Res.* 113, 198-206). Specifically, NIHL has been reduced by the administration of FDA-approved antioxidant compounds (N-L-acetylcysteine (L-NAC) and salicylate) in the chinchilla (Kopke, et al.; 2000, *Hear. Res.*, 149, 138-146). Moreover, Harris et al. have recently described prevention of NIHL with Src-PTK inhibitors (Harris, et al.; 2005, *Hear. Res.*, 208, 14-25). Thus, it is hypothesized that the administration of a compound of the instant invention which modulates the activity of kinases, is useful for treating hearing loss.

Changes in cell attachment or cell stress can activate a variety of signals through the activation of integrins and through the phosphorylation of PTKs, including the Src family of tyrosine kinases. Src interactions have been linked to signaling pathways that modify the cytoskeleton and activate a variety of protein kinase cascades that regulate cell survival and gene transcription (reviewed in Giancotti and Ruoslahti; 1999, *Science*, 285, 1028-1032). In fact, recent results have indicated that outer hair cells (OHC), which had detached at the cell base following an intense noise exposure, underwent apoptotic cell death. Specifically, the Src PTK signaling cascade is thought to be involved in both metabolic- and mechanically-induced initiation of apoptosis in sensory cells of the cochlea. In a recent study, Src inhibitors provided protection from a 4 hour, 4 kHz octave band noise at 106 dB, indicating that Src-PTKs might be activated in outer hair cells following noise exposure (Harris, et al.; 2005, *Hear. Res.*, 208, 14-25). Thus, compounds of the instant invention that modulate the activity of Src, are useful in treating hearing loss.

The present invention relates to a method for protecting against or treating osteoporosis in a subject. This method involves administering an effective amount of a compound of the invention to the subject to protect against or to treat osteoporosis. In order to protect against osteoporosis, the compound may be administered prior to the development of osteoporosis. Alternatively, the compound may be used to treat osteoporosis in a subject. In this embodiment, the compound is administered to the subject subsequent to the initiation of osteoporosis to reduce the level of osteoporosis.

A compound of the invention can be, e.g. a non-ATP competitive inhibitor. The compound of the invention can modulate a kinase signaling cascade, depending upon the particular side chains and scaffold modifications selected. The compound of the invention can be a kinase inhibitor. For example, the compound can be a protein tyrosine kinase (PTK) inhibitor. The proline-rich tyrosine kinase (PYK2; also known as cell adhesion kinase β, related adhesion focal tyrosine kinase, or calcium-dependent tyrosine kinase) and focal adhesion kinase (FAK) are members of a distinct family of non receptor protein-tyrosine kinases that are regulated by a variety of extracellular stimuli (Avraham, et al.; 2000, *Cell Signal.*, 12, 123-133; Schlaepfer, et al.; 1999, *Prog. Biophys. Mol. Biol.*, 71, 435-478). The compound of the invention can be a Src inhibitor. It has been shown that Src deficiency is associated with osteoporosis in mice, because of loss of osteoclast function (Soriano, et al.; 1991, *Cell*, 64, 693-702). Alternatively, the compound of the invention can modulate the expression of interleukin-1 receptor associated kinase M (IRAK-M). Mice that lack IRAK-M develop severe osteoporosis, which is associated with the accelerated differentiation of osteoclasts, an increase in the half-life of osteoclasts, and their activation (Hongmei, et al.; 2005, *J. Exp. Med.*, 201, 1169-1177).

Multinucleated osteoclasts originate from the fusion of mononuclear phagocytes and play a major role in bone development and remodeling via the resorption of bone. Osteoclasts are multinucleated, terminally differentiated cells that degrade mineralized matrix. In normal bone tissue, there is a balance between bone formation by osteoblasts and bone resorption by osteoclasts. When the balance of this dynamic and highly regulated process is disrupted, bone resorption can exceed bone formation resulting in quantitative bone loss. Because osteoclasts are essential for the development and remodeling of bone, increases in their number and/or activity lead to diseases that are associated with generalized bone loss (e.g., osteoporosis) and others with localized bone loss (e.g., rheumatoid arthritis, periodontal disease).

Osteoclasts and osteoblasts both command a multitude of cellular signaling pathways involving protein kinases. Osteoclast activation is initiated by adhesion to bone, cytoskeletal rearrangement, formation of the sealing zone, and formation of the polarized ruffled membrane. It is believed that protein-tyrosine kinase 2 (PYK2) participates in the transfer of signals from the cell surface to the cytoskeleton, as it is tyrosine phosphorylated and activated by adhesion-initiated signaling in osteoclasts (Duong, et al.; 1998, *J. Clin. Invest.*, 102, 881-892). Recent evidence has indicated that the reduction of PYK2 protein levels results in the inhibition of osteoclast formation and bone resorption in vitro (Duong, et al.; 2001, *J. Bio. Chem.*, 276, 7484-7492). Therefore, the inhibition of PYK2 or other protein tyrosine kinases might reduce the level of osteoporosis by decreasing osteoclast formation and bone resorption. Thus, without wishing to be bound by theory, it is hypothesized that the administration of a compound of the instant invention will modulate kinase (e.g. PTK) activity and therefore result in the inhibition of osteoclast formation and/or bone resorption, thereby treating osteoporosis.

Src tyrosine kinase stands out as a promising therapeutic target for bone disease as validated by Src knockout mouse studies and in vitro cellular experiments, suggesting a regulatory role for Src in both osteoclasts (positive) and osteoblasts (negative). In osteoclasts, Src plays key roles in motility, polarization, survival, activation (ruffled border formation) and adhesion, by mediating various signal transduction pathways, especially in cytokine and integrin signaling (Parang and Sun; 2005, *Expert Opin. Ther. Patents*, 15, 1183-1207). Moreover, targeted disruption of the src gene in mice induces osteopetrosis, a disorder characterized by decreased bone resorption, without showing any obvious morphological or functional abnormalities in other tissues or cells (Soriano, et al.; 1991, *Cell*, 64, 693-702). The osteopetrotic phenotype of $src^{-/-}$ mice is cell-autonomous and results from defects in mature osteoclasts, which normally express high levels of Src protein (Horne, et al.; 1991, *Cell*, 119, 1003-1013). By limiting the effectiveness of Src tyrosine kinase, which triggers osteoclast activity and inhibits osteoblasts, Src inhibitors are thought to lessen bone break down and encourage bone formation. Because osteoclasts normally express high levels of Src, inhibition of Src kinase activity might be useful in the treatment of osteoporosis (Missbach, et al.; 1999, *Bone*, 24, 437-449). Thus, the PTK inhibitors of the instant invention that modulate the activity of Src, are useful in treating osteoporosis.

As described herein, a compound of the invention may be used to protect against or prevent obesity in a subject. In order to protect against obesity, the compound may be administered prior to the development of obesity in a subject. Alternatively, the compound may be used to treat obesity in a subject. A compound of the instant invention may be involved in modulating a kinase signaling cascade, e.g., a kinase inhibitor, a non-ATP competitive inhibitor, a tyrosine kinase inhibitor, a protein tyrosine phosphatase inhibitor, or a protein-tyrosine phosphatase 1B inhibitor.

Obesity is associated with diabetes and increased insulin resistance in insulin responsive tissues, such as skeletal muscle, liver, and white adipose tissue (Klaman, et al.; 2000, *Mol. Cell. Biol.*, 20, 5479-5489). Insulin plays a critical role in the regulation of glucose homeostasis, lipid metabolism, and energy balance. Insulin signaling is initiated by binding of insulin to the insulin receptor (IR), a receptor tyrosine kinase. Insulin binding evokes a cascade of phosphorylation events, beginning with the autophosphorylation of the IR on multiple tyrosyl residues. Autophosphorylation enhances IR kinase activity and triggers downstream signaling events. The stimulatory effects of protein tyrosine kinases and the inhibitory effects of protein tyrosine phosphatases largely define the action of insulin. Appropriate insulin signaling minimizes large fluctuations in blood glucose concentrations and ensures adequate delivery of glucose to cells. Since insulin stimulation leads to multiple tyrosyl phosphorylation events, enhanced activity of one or more protein-tyrosine phosphatases (PTPs) could lead to insulin resistance, which may lead to obesity. Indeed, increased PTP activity has been reported in several insulin-resistant states, including obesity (Ahmad, et al.; 1997, *Metabolism*, 46, 1140-1145). Thus, without wishing to be bound by theory, the administration of a compound of the instant invention modulates kinase (e.g., PTP) activity, thereby treating obesity in a subject.

Insulin signaling begins with the activation of the IR via tyrosine phosphorylation and culminates in the uptake of glucose into cells by the glucose transporter, GLUT4 (Saltiel and Kahn; 2001, *Nature*, 414, 799-806). The activated IR must then be deactivated and returned to a basal state, a process that is believed to involve protein-tyrosine phosphatase-1B (PTP-1B) (Ahmad, et al; 1997, *J. Biol. Chem.*, 270, 20503-20508). Disruption of the gene that codes for PTP-1B in mice results in sensitivity to insulin and increased resistance to diet-induced obesity (Elchebly, et al.; 1999, *Science*, 283, 1544-1548; Klaman, et al.; 2000, *Mol. Cell. Biol.*, 20, 5479-5489). The decreased adiposity in PTP-1B deficient mice was due to a marked reduction in fat cell mass without a decrease in adipocyte number (Klaman, et al.; 2000, *Mol. Cell. Biol.*, 20, 5479-5489). Moreover, leanness in PTP-1B-deficient mice was accompanied by increased basal metabolic rate and total energy expenditure, without marked alteration of uncoupling protein mRNA expression. The disruption of the PTP-1B gene demonstrated that altering the activity of PTP-1B can modulate insulin signaling and dietary-induced obesity in vivo. Thus, without wishing to be bound by theory, the administration of a compound of the instant invention that modulates insulin signaling (e.g., PTP-1B activity), is useful in treating obesity in a subject.

As described herein, a compound of the invention may be used to protect against or prevent diabetes in a subject. In order to protect against diabetes, the compound may be administered prior to the development of diabetes in a subject. Alternatively, the compound may be used to treat diabetes in a subject. The compound of the instant invention may be involved in modulating a kinase signaling cascade, e.g. a kinase inhibitor, a non-ATP competitive inhibitor, a tyrosine kinase inhibitor, a phosphatase and tension homologue on chromosome 10 (PTEN) inhibitor, or a sequence homology 2-containing inositol 5'-phosphatase 2 (SHIP2) inhibitor.

Type 2 diabetes mellitus (T2DM) is a disorder of dysregulated energy metabolism. Energy metabolism is largely controlled by the hormone insulin, a potent anabolic agent that promotes the synthesis and storage of proteins, carbohydrates and lipids, and inhibits their breakdown and release back into the circulation. Insulin action is initiated by binding to its tyrosine kinase receptor, which results in autophosphorylation and increased catalytic activity of the kinase (Patti, et al.; 1998, *J. Basic Clin. Physiol. Pharmacol.* 9, 89-109). Tyrosine phosphorylation causes insulin receptor substrate (IRS) proteins to interact with the p85 regulatory subunit of phosphatidylinositol 3-kinase (PI3K), leading to the activation of the enzyme and its targeting to a specific subcellular location, depending on the cell type. The enzyme generates the lipid product phosphatidylinositol-3,4,5-trisphosphate (PtdIns(3,4,5)P$_3$), which regulates the localization and activity of numerous proteins (Kido, et al.; 2001, *J. Clin. Endocrinol. Metab.*, 86, 972-979). PI3K has an essential role in insulin-stimulated glucose uptake and storage, inhibition of lipolysis and regulation of hepatic gene expression (Saltiel, et al.; 2001, *Nature*, 414, 799-806). Overexpression of dominant-interfering forms of PI3K can block glucose uptake and translocation of glutamate transporter four, GLUT4, to the plasma membrane (Quon, et al.; 1995, *Mol. Cell. Biol.*, 15, 5403-5411). Thus, the administration of a compound of the instant invention that modulates kinase (e.g. PI3K) activity, and therefore results in increased glucose uptake, is useful in treating diabetes.

PTEN is a major regulator of PI3K signaling in may cell types, and functions as a tumor suppressor due to antagonism of the anti-apoptotic, proliferative and hypertrophic activities of the PI3K pathway (Goberdhan, et al.; 2003, *Hum. Mol. Genet.*, 12, R239-R248; Leslie, et al.; 2004, *J. Biochem.*, 382, 1-11). Although not wishing to be bound by theory, it is believed that PTEN attenuates the PI3K pathway by dephosphorylation of the PtdIns(3,4,5)P$_3$ molecule, degrading this important lipid second messenger to PtdIns(4,5)P$_2$. In a recent study, reduction of endogenous PTEN protein by 50% using small interfering RNA (siRNA) enhanced insulin-dependent increases in PtdIns(3,4,5)P$_3$ levels, and glucose uptake (Tang, et al.; 2005, *J. Biol. Chem.*, 280, 22523-22529). Thus, without wishing to be bound by theory, it is hypothesized that the administration of a compound of the instant invention that modulates PTEN activity, and therefore results in increased glucose uptake, is useful for treating diabetes.

PtdIns(3,4,5)P$_3$ levels are also controlled by the family of SRC homology 2 (SH2)-containing inositol 5'-phosphatase (SHIP) proteins, SHIP1 and SHIP2 (Lazar and Saltiel; 2006, *Nature Reviews*, 5, 333-342). SHIP2, expressed in skeletal muscle, among other insulin-sensitive tissues, catalyzes the conversion of PtdIns(3,4,5)P$_3$ into PtdIns(3,4)P$_2$ (Pesesse, et al.; 1997; *Biochem Biophys. Res. Commun.*, 239, 697-700; Backers, et al.; 2003, *Adv. Enzyme Regul.*, 43, 15-28; Chi, et al.; 2004, *J. Biol. Chem.*, 279, 44987-44995; Sleeman, et al.; 2005, *Nature Med.*, 11, 199-205). Overexpression of SHIP2 markedly reduced insulin-stimulated PtdIns(3,4,5)P$_3$ levels, consistent with the proposed capacity of SHIP2 to attenuate the activation of downstream effectors of PI3K (Ishihara, et al.; 1999, *Biochem. Biophys. Res. Commun.*, 260, 265-272). Thus, without wishing to be bound by theory, it is hypothesized that the administration of a compound of the instant invention which modulates SHIP2 activity, and therefore results in increased glucose uptake, is useful for treating diabetes.

As described herein, a compound of the invention may be used to protect against or prevent eye disease in a subject. In order to protect against eye disease, the compound may be administered prior to the development of eye disease in a subject. Alternatively, the compound may be used to treat eye disease in a subject, e.g. macular degeneration, retinopathy, and macular edema. The compound of the instant invention may be involved in modulating a kinase cascade, e.g. a kinase inhibitor, a non-ATP competitive inhibitor, a tyrosine kinase inhibitor, e.g. a vascular endothelial growth factor (VEGF) receptor tyrosine kinase inhibitor.

Vision-threatening neovascularization of the physiologically avascular cornea can occur. The proliferative retinopathies, principally diabetic retinopathy and age-related macular degeneration, are characterized by increased vascular permeability, leading to retinal edema and subretinal fluid accumulation, and the proliferation of new vessels that are prone to hemorrhage. Angiogenesis, the formation of new blood vessels from preexisting capillaries, is an integral part of both normal development and numerous pathological processes. VEGF, a central mediator of the complex cascade of angiogenesis and a potent permeability factor, is an attractive target for novel therapeutics. VEGF is the ligand for two membrane-bound tyrosine kinase receptors, VEGFR-1 and VEGFR-2. Ligand binding triggers VEGFR dimerization and transphosphorylation with subsequent activation of an intracellular tyrosine kinase domain. The ensuing intracellular signaling axis results in vascular endothelial cell proliferation, migration, and survival. Thus, without wishing to be bound by theory, it is hypothesized that the administration of a compound of the instant invention which modulates kinase activity, e.g. tyrosine kinase activity, and results in the inhibition of angiogenesis and/or neovascularization, is useful for treating an eye disease, e.g. macular degeneration, retinopathy and/or macular edema.

Macular degeneration is characterized by VEGF-mediated retinal leakage (an increase in vascular permeability) and by the abnormal growth of small blood vessels in the back of the eye (angiogenesis). VEGF has been identified in neovascular membranes in both diabetic retinopathy and age-related macular degeneration, and intraocular levels of the factor correlate with the severity of neovascularization in diabetic retinopathy (Kvanta, et al.; 1996, *Invest. Ophthal. Vis. Sci.*, 37, 1929-1934; Aiello, et al.; 1994, *N. Engl. J. Med.*, 331, 1480-1487). Therapeutic antagonism of VEGF in these models results in significant inhibition of both retinal and choroidal neovascularization, as well as a reduction in vascular permeability (Aiello, et al.; 1995, *Proc. Natl. Acad. Sci. USA.*, 92, 10457-10461; Krzystolik, et al.; 2002, *Arch. Ophthal.*, 120, 338-346; Qaum, et al.; 2001, *Invest. Ophthal. Vis. Sci.*, 42, 2408-2413). Thus, without wishing to be bound by theory, it is hypothesized that the administration of a compound of the instant invention which modulates VEGF activity, and results in the inhibition of angiogenesis and/or neovascularization, is useful for treating an eye disease, e.g. macular degeneration, retinopathy and/or macular edema.

The compounds of the invention are used in methods of treating, preventing, ameliorating a stroke in a subject who is at risk of suffering a stroke, is suffering from a stroke or has suffered a stroke. The compounds of the invention are useful in methods of treating patients who are undergoing post-stroke rehabilitation.

A stroke, also known as a cerebrovascular accident (CVA), is an acute neurological injury whereby the blood supply to a part of the brain is interrupted due to either blockage of an artery or rupture of a blood vessel. The part of the brain in which blood supply is interrupted no longer receives oxygen and/or nutrients carried by the blood. The brain cells become damaged or necrotic, thereby impairing function in or from that part of the brain. Brain tissue ceases to function if deprived of oxygen for more than 60 to 90 seconds and after a few minutes will suffer irreversible injury possibly leading to a death of the tissue, i.e., infarction.

Strokes are classified into two major types: ischemic, i.e., blockage of a blood vessel supplying the brain, and hemorrhagic, i.e., bleeding into or around the brain. The majority of all strokes are ischemic strokes. Ischemic stroke is commonly divided into thrombotic stroke, embolic stroke, systemic hypoperfusion (Watershed stroke), or venous thrombosis. In thrombotic stroke, a thrombus-forming process develops in the affected artery, the thrombus, i.e., blood clot, gradually narrows the lumen of the artery, thereby impeding blood flow to distal tissue. These clots usually form around atherosclerotic plaques. There are two types of thrombotic strokes, which are categorized based on the type of vessel on which the thrombus is formed. Large vessel thrombotic stroke involves the common and internal carotids, vertebral, and the Circle of Willis. Small vessel thrombotic stroke involves the intracerebral arteries, branches of the Circle of Willis, middle cerebral artery stem, and arteries arising from the distal vertebral and basilar artery.

A thrombus, even if non-occluding, can lead to an embolic stroke if the thrombus breaks off, at which point it becomes an embolus. An embolus refers to a traveling particle or debris in the arterial bloodstream originating from elsewhere. Embolic stroke refers to the blockage of arterial access to a part of the brain by an embolus. An embolus is frequently a blood clot, but it can also be a plaque that has broken off from an atherosclerotic blood vessel or a number of other substances including fat, air, and even cancerous cells. Because an embolus arises from elsewhere, local therapy only solves the problem temporarily. Thus, the source of the embolus must be identified. There are four categories of embolic stroke: those with a known cardiac source; those with a potential cardiac or aortic source (from trans-thoracic or trans-esophageal echocardiogram); those with an arterial source; and those with unknown source.

Systemic hypoperfusion is the reduction of blood flow to all parts of the body. It is most commonly due to cardiac pump failure from cardiac arrest or arrhythmias, or from reduced cardiac output as a result of myocardial infarction, pulmonary embolism, pericardial effusion, or bleeding. Hypoxemia (i.e., low blood oxygen content) may precipitate the hypoperfusion. Because the reduction in blood flow is global, all parts of the brain may be affected, especially the "watershed" areas which are border zone regions supplied by the major cerebral arteries. Blood flow to these area has not necessary stopped, but instead may have lessened to the point where brain damage occurs.

Veins in the brain function to drain the blood back to the body. When veins are occluded due to thrombosis, the draining of blood is blocked and the blood backs up, causing cerebral edema. This cerebral edema can result in both ischemic and hemorrhagic strokes. This commonly occurs in the rare disease sinus vein thrombosis.

Stroke is diagnosed in a subject or patient using one or more of a variety of techniques known in the art, such as, for example, neurological examination, blood tests, CT scans (without contrast enhancements), MRI scans, Doppler ultrasound, and arteriography (i.e., roentgenography of arteries after injection of radiopacque material into the blood stream). If a stroke is confirmed on imaging, various other studies are performed to determine whether there is a peripheral source of emboli. These studies include, e.g., an ultrasound/doppler study of the carotid arteries (to detect carotid stenosis); an electrocardiogram (ECG) and echocardiogram (to identify arrhythmias and resultant clots in the heart which may spread to the brain vessels through the bloodstream); a Holter monitor study to identify intermittent arrhythmias and an angiogram of the cerebral vasculature (if a bleed is thought to have originated from an aneurysm or arteriovenous malformation).

Compounds useful in these methods of treating, preventing or ameliorating stroke or a symptom associated with stroke are compounds that modulate kinase signaling cascade preceding, during or after a stroke. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating stroke or a symptom associated with stroke described herein is an allosteric inhibitor of kinase signaling cascade preceding, during or after a stroke. Preferably, the compound used in the methods of treating, preventing or ameliorating stroke or a symptom associated with stroke described herein is a non-ATP competitive inhibitor of kinase signaling cascade preceding, during or after a stroke.

Inhibition of Src activity has been shown to provide cerebral protection during stroke. (See Paul et al., Nature Medicine, vol. 7(2):222-227 (2001), which is hereby incorporated by reference in its entirety). Vascular endothelia growth factor (VEGF), which is produced in response to the ischemic injury, has been shown to promote vascular permeability. Studies have shown that the Src kinase regulates VEGF-mediated VP in the brain following stroke, and administration of an Src inhibitor before and after stroke reduced edema, improved cerebral perfusion and decreased infarct volume after injury occurred. (Paul et al., 2001). Thus, Src inhibition may be useful in the prevention, treatment or amelioration of secondary damage following a stroke.

The compounds of the invention prevent, treat or ameliorate stroke or a symptom associated with stroke. Symptoms of a stroke include sudden numbness or weakness, especially on one side of the body; sudden confusion or trouble speaking or understanding speech; sudden trouble seeing in one or both eyes; sudden trouble with walking, dizziness, or loss of balance or coordination; or sudden severe headache with no known cause.

Generally there are three treatment stages for stroke: prevention, therapy immediately after the stroke, and post-stroke rehabilitation. Therapies to prevent a first or recurrent stroke are based on treating the underlying risk factors for stroke, such as, e.g., hypertension, high cholesterol, atrial fibrillation, and diabetes. Acute stroke therapies try to stop a stroke while it is happening by quickly dissolving the blood clot causing an ischemic stroke or by stopping the bleeding of a hemorrhagic stroke. Post-stroke rehabilitation helps individuals overcome disabilities that result from stroke damage. Medication or drug therapy is the most common treatment for stroke. The most popular classes of drugs used to prevent or treat stroke are anti-thrombotics (e.g., anti-platelet agents and anticoagulants) and thrombolytics. The compounds are administered to a patient who is at risk of suffering a stroke, is suffering from a stroke or has suffered a stroke at a time before, during, after, or any combination thereof, the occurrence of a stroke. The compounds of the invention are administered alone, in pharmaceutical compositions, or in combination with any of a variety of known treatments, such as, for example, an anti-platelet medication (e.g., aspirin, clopidogrel, dipyridamole), an anti-coagulant (e.g., warfarin), or a thrombolytic medication (e.g., tissue plasminogen activator (t-PA), reteplase, Urokinase, streptokinase, tenectaplase, lanoteplase, or anistreplase.

The compounds of the invention are used in methods of treating, preventing, ameliorating atherosclerosis or a symptom thereof in a subject who is at risk for or suffering from atherosclerosis.

Atherosclerosis is a disease affecting the arterial blood vessel and is commonly referred to as a "hardening" of the arteries. It is caused by the formation of multiple plaques within the arteries. Atherosclerotic plaques, though compensated for by artery enlargement, eventually lead to plaque ruptures and stenosis (i.e., narrowing) of the artery, which, in turn, leads to an insufficient blood supply to the organ it feeds. Alternatively, if the compensating artery enlargement process is excessive, a net aneurysm results. These complications are chronic, slowly progressing and cumulative. Most commonly, soft plaque suddenly ruptures, causing the formation of a blood clot (i.e., thrombus) that rapidly slows or stops blood flow, which, in turn, leads to death of the tissues fed by the artery. This catastrophic event is called an infarction. For example, coronary thrombosis of a coronary artery causes a myocardial infarction, commonly known as a heart attack. A myocardial infarction occurs when an atherosclerotic plaque slowly builds up in the inner lining of a coronary artery and then suddenly ruptures, totally occluding the artery and preventing blood flow downstream.

Atherosclerosis and acute myocardial infarction are diagnosed in a patient using any of a variety of clinical and/or laboratory tests such as, physical examination, radiologic or ultrasound examination and blood analysis. For example, a doctor or clinical can listen to a subject's arteries to detect an abnormal whooshing sound, called a bruit. A bruit can be heard with a stethoscope when placed over the affected artery. Alternatively, or in addition, the clinician or physician can check pulses, e.g., in the leg or foot, for abnormalities such as weakness or absence. The physician or clinical may perform blood work to check for cholesterol levels or to check the levels of cardiac enzymes, such as creatine kinase, troponin and lactate dehydrogenase, to detect abnormalities. For example, troponin sub-units I or T, which are very specific for the myocardium, rise before permanent injury develops. A positive troponin in the setting of chest pain may accurately predict a high likelihood of a myocardial infarction in the near future. Other tests to diagnose atherosclerosis and/or myocardial infarction include, for example, EKG (electrocardiogram) to measure the rate and regularity of a subject's heartbeat; chest X-ray, measuring ankle/brachial index, which compares the blood pressure in the ankle with the blood pressure in the arm; ultrasound analysis of arteries; CT scan of areas of interest; angiography; an exercise stress test, nuclear heart scanning; and magnetic resonance imaging (MRI) and positron emission tomography (PET) scanning of the heart.

Compounds useful in these methods of treating, preventing or ameliorating atherosclerosis or a symptom thereof are compounds that modulate kinase signaling cascade in a patient at risk for or suffering from atherosclerosis. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating atherosclerosis or a symptom thereof described herein is an allosteric inhibitor of kinase signaling cascade involved in atherosclerosis. Preferably, the compound used in the methods of treating, preventing or ameliorating atherosclerosis or a symptom associated with atherosclerosis described herein is a non-ATP competitive inhibitor of kinase signaling cascade involved in atherosclerosis.

Cellular signal transduction by Src is believed to play a key role in increased permeability of vessels, known as vascular permeability (VP). Vascular endothelia growth factor (VEGF), which is produced in response to the ischemic injury, including, e.g., myocardial infarction, has been shown to promote vascular permeability. Studies have shown that the inhibition of Src kinase decreases VEGF-mediated VP. (See Parang and Sun, Expert Opin. Ther. Patents, vol. 15(9): 1183-1206 (2005), which is hereby incorporated by reference in its entirety). Mice treated with an Src inhibitor demonstrated reduced tissue damage associated with trauma or injury to blood vessels after myocardial infarction, as compared to untreated mice. (See e.g., U.S. Patent Publication Nos. 20040214836 and 20030130209 by Cheresh et al., the contents of which are hereby incorporated by reference in their entirety). Thus, Src inhibition may be useful in the prevention, treatment or amelioration of secondary damage following injury due to atherosclerosis, such as, for example, myocardial infarction.

The compounds of the invention prevent, treat or ameliorate stroke or a symptom associated with atherosclerosis. Atherosclerosis generally does not produce symptoms until it severely narrows the artery and restricts blood flow, or until it causes a sudden obstruction. Symptoms depend on where the plaques and narrowing develop, e.g., in the heart, brain, other vital organs and legs or almost anywhere in the body. The initial symptoms of atherosclerosis may be pain or cramps when the body requires more oxygen, for example during exercise, when a person may feel chest pain (angina) because of lack of oxygen to the heart or leg cramps because of lack of oxygen to the legs. Narrowing of the arteries supplying blood to the brain may cause dizziness or transient ischaemic attacks (TIA's) where the symptoms and signs of a stroke last less than 24 hours. Typically, these symptoms develop gradually.

Symptoms of myocardial infarction are characterized by varying degrees of chest pain, discomfort, sweating, weakness, nausea, vomiting, and arrhythmias, sometimes causing loss of consciousness. Chest pain is the most common symptom of acute myocardial infarction and is often described as a tightness, pressure, or squeezing sensation. Pain may radiate to the jaw, neck, arms, back, and epigastrium, most often to the left arm or neck. Chest pain is more likely caused by myocardial infarction when it lasts for more than 30 minutes. Patients suffering from a myocardial infarction may exhibit shortness of breath (dyspnea) especially if the decrease in myocardial contractility due to the infarct is sufficient to cause left ventricular failure with pulmonary congestion or even pulmonary edema.

The compounds of the invention are administered alone, in pharmaceutical compositions, or in combination with any of a variety of known treatments for atherosclerosis, such as, for example, cholesterol-lowering drugs (e.g., statins), anti-platelet medications, or anticoagulants.

The compounds of the invention are used in methods of treating, preventing, ameliorating neuropathic pain, such as chronic neuropathic pain, or a symptom thereof in a subject who is at risk of suffering from, is suffering from, or has suffered neuropathic pain.

Neuropathic pain, also known as neuralgia, is qualitatively different from ordinary nociceptive pain. Neuropathic pain usually presents as a steady burning and/or "pins and needles" and/or "electric shock" sensations. The difference between nociceptive pain and neuropathic pain is due to the fact that "ordinary", nociceptive pain stimulates only pain nerves, while a neuropathy often results in the stimulation of both pain and non-pain sensory nerves (e.g., nerves that respond to touch, warmth, cool) in the same area, thereby producing signals that the spinal cord and brain do not normally expect to receive.

Neuropathic pain is a complex, chronic pain state that usually is accompanied by tissue injury. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury.

Neuropathic pain is diagnosed in a subject or patient using one or more of a variety of laboratory and/or clinical techniques known in the art, such as, for example, physical examination.

Compounds useful in these methods of treating, preventing or ameliorating neuropathic pain, such as chronic neuropathic pain, or a symptom associated with neuropathic pain are compounds that modulate kinase signaling cascade involved in neuropathic pain. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating neuropathic pain or a symptom thereof is an allosteric inhibitor of kinase signaling cascade involved in neuropathic pain. Preferably, the compound used in the methods of treating, preventing or ameliorating neuropathic pain or a symptom thereof is a non-ATP competitive inhibitor of kinase signaling cascade involved in neuropathic pain.

c-Src has been shown to regulate the activity of N-methyl-D-aspartate (NMDA) receptors. (See Yu et al., Proc. Natl. Acad. Sci. USA, vol. 96:7697-7704 (1999), which is hereby incorporated by reference in its entirety). Studies have shown that PP2, a low molecular weight Src kinase inhibitor, decreases phosphorylation of the NMDA receptor NM2 subunit. (See Guo et al., J. Neuro., vol. 22:6208-6217 (2002), which is hereby incorporated by reference in its entirety). Thus, Src inhibition, which in turn, inhibits the activity NMDA receptors, may be useful in the prevention, treatment or amelioration of neuropathic pain, such as chronic neuropathic pain.

The compounds of the invention prevent, treat or ameliorate neuropathic pain, such as chronic neuropathic pain, or a symptom associated with neuropathic pain. Symptoms of neuropathic pain include shooting and burning pain, tingling and numbness.

The compounds of the invention are administered alone, in pharmaceutical compositions, or in combination with any of a variety of known treatments, such as, for example, analgesics, opioids, tricyclic antidepressants, anticonvulsants and serotonin norepinephrine reuptake inhibitors The compounds of the invention are used in methods of treating, preventing, ameliorating hepatitis B or a symptom thereof in a subject who is at risk for or suffering from hepatitis B.

The hepatitis B virus, a member of the Hepadnavirus family, consists of a proteinaceous core particle containing the viral genome in the form of double stranded DNA with single-stranded regions and an outer lipid-based envelope with embedded proteins. The envelope proteins are involved in viral binding and release into susceptible cells. The inner capsid relocates the DNA genome to the cell's nucleus where viral mRNAs are transcribed. Three subgenomic transcripts encoding the envelope proteins are made, along with a transcript encoding the X protein. A fourth pre-genomic RNA is transcribed, which is exported to the cytosol and translates the viral polymerase and core proteins. Polymerase and pre-genomic RNA are encapsidated in assembling core particles, where reverse transcription of the pre-genomic RNA to genomic DNA occurs by the polymerase protein. The mature core particle then exits the cell via normal secretory pathways, acquiring an envelope along the way.

Hepatitis B is one of a few known non-retroviral viruses that employ reverse transcription as part of the replication process. Other viruses which use reverse transcription include, e.g., HTLV or HIV.

During HBV infection, the host immune response is responsible for both hepatocellular damage and viral clearance. While the innate immune response does not play a significant role in these processes, the adaptive immune response, particularly virus-specific cytotoxic T lymphocytes (CTLs), contributes to nearly all of the liver injury associated with HBV infection. By killing infected cells and by producing antiviral cytokines capable of purging HBV from viable hepatocytes, CTLs also eliminate the virus. Although liver damage is initiated and mediated by the CTLs, antigen-nonspecific inflammatory cells can worsen CTL-induced immunopathology and platelets may facilitate the accumulation of CTLs into the liver.

Hepatitis B is diagnosed in a patient using any of a variety of clinical and/or laboratory tests such as, physical examination, and blood or serum analysis. For example, blood or serum is assayed for the presence of viral antigens and/or antibodies produced by the host. In a common test for Hepatitis B, detection of hepatitis B surface antigen (HBsAg) is used to screen for the presence of infection. It is the first detectable viral antigen to appear during infection with this virus; however, early in an infection, this antigen may not be present and it may be undetectable later in the infection as it is being cleared by the host. During this 'window' in which the host remains infected but is successfully clearing the virus, IgM antibodies to the hepatitis B core antigen (anti-HBc IGM) may be the only serologic evidence of disease.

Shortly after the appearance of the HBsAg, another antigen named as the hepatitis B e antigen (HBeAg) will appear. Traditionally, the presence of HBeAg in a host's serum is associated with much higher rates of viral replication; however, some variants of the hepatitis B virus do not produce the "e" antigen at all. During the natural course of an infection, the HBeAg may be cleared, and antibodies to the "e" antigen (anti-HBe) will arise immediately afterward. This conversion is usually associated with a dramatic decline in viral replication. If the host is able to clear the infection, eventually the HBsAg will become undetectable and will be followed by antibodies to the hepatitis B surface antigen (anti-HBs). A person negative for HBsAg but positive for anti-HBs has either cleared an infection or has been vaccinated previously. A number of people who are positive for HBsAg may have very little viral multiplication, and hence may be at little risk of long-term complications or of transmitting infection to others.

Compounds useful in these methods of treating, preventing or ameliorating hepatitis B or a symptom thereof are compounds that modulate kinase signaling cascade in a patient at risk for or suffering from hepatitis B. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating hepatitis B or a symptom thereof described herein is an allosteric inhibitor of kinase signaling cascade involved in hepatitis B. Preferably, the compound used in the methods of treating, preventing or ameliorating hepatitis B or a symptom associated with hepatitis B described herein is a non-ATP competitive inhibitor of kinase signaling cascade involved in hepatitis B.

Src plays a role in the replication of the hepatitis B virus. The virally encoded transcription factor HBx activates Src in a step that is required from propagation of the HBV virus. (See e.g., Klein et al., EMBO J., vol. 18:5019-5027 (1999); Klein et al., Mol. Cell. Biol., vol. 17:6427-6436 (1997), each of which is hereby incorporated by reference in its entirety). Thus, Src inhibition, which in turn, inhibits Src-mediated propagation of the HBV virus, may be useful in the prevention, treatment or amelioration of hepatitis B or a symptom thereof.

The compounds of the invention prevent, treat or ameliorate hepatitis B or a symptom associated with hepatitis B. Symptoms of hepatitis B typically develop within 30-180 days of exposure to the virus. However, up to half of all people infected with the hepatitis B virus have no symptoms. The symptoms of hepatitis B are often compared to flu, and include, e.g., appetite loss; fatigue; nausea and vomiting, itching all over the body; pain over the liver (e.g., on the right side of the abdomen, under the lower rib cage), jaundice, and changes in excretory functions.

The compounds of the invention are administered alone, in pharmaceutical compositions, or in combination with any of a variety of known treatments for hepatitis B, such as, for example, interferon alpha, lamivudine (Epivir-HBV) and baraclude (entecavir).

As described herein, the compounds of the invention may be used to regulate immune system activity in a subject, thereby protecting against or preventing autoimmune disease, e.g., rheumatoid arthritis, multiple sclerosis, sepsis and lupus as well as transplant rejection and allergic diseases. Alternatively, the compound may be used to treat autoimmune disease in a subject. For example, the compound may result in reduction in the severity of symptoms or halt impending progression of the autoimmune disease in a subject. The compound of the invention may be involved in modulating a kinase signaling cascade, e.g., a kinase inhibitor, a non-ATP competitive inhibitor, a tyrosine kinase inhibitor, e.g., a Src inhibitor, a p59fyn (Fyn) inhibitor or a p56lck (Lck) inhibitor.

Autoimmune diseases are diseases caused by a breakdown of self-tolerance such that the adaptive immune system responds to self antigens and mediates cell and tissue damage. Autoimmune diseases can be organ specific (e.g., thyroiditis or diabetes) or systemic (e.g., systemic lupus erythematosus). T cells modulate the cell-mediated immune response in the adaptive immune system. Under normal conditions, T cells express antigen receptors (T cell receptors) that recognize peptide fragments of foreign proteins bound to self major histocompatibility complex molecules. Among the earliest recognizable events after T cell receptor (TCR) stimulation are the activation of Lck and Fyn, resulting in TCR phosphorylation on tyrosine residues within immunoreceptor tyrosine-based activation motifs (Zamoyska, et al.; 2003, *Immunol. Rev.*, 191, 107-118). Tyrosine kinases, such as Lck (which is a member of the Src family of protein tyrosine kinases) play an essential role in the regulation of cell signaling and cell proliferation by phosphorylating tyrosine residues of peptides and proteins (Levitzki; 2001, *Top. Curr. Chem.*, 211, 1-15; Longati, et al.; 2001, *Curr. Drug Targets*, 2, 41-55; Qian, and Weiss; 1997, *Curr. Opin. Cell Biol.*, 9, 205-211). Thus, although not wishing to be bound by theory, it is hypothesized that the administration of a compound of the instant invention which modulates tyrosine kinase (e.g., Src) activity is useful in the treatment of autoimmune disease.

The tyrosine kinases lck and fyn are both activated in the TCR pathway; thus, inhibitors of lck and/or fyn have potential utility as autoimmune agents (Palacios and Weiss; 2004, *Oncogene*, 23, 7990-8000). Lck and Fyn are predominantly expressed by T cells through most of their lifespan. The roles of Lck and Fyn in T cell development, homeostasis and activation have been demonstrated by animal and cell line studies (Parang and Sun; 2005, *Expert Opin. The. Patents*, 15, 1183-1207). Lck activation is involved in autoimmune diseases and transplant rejection (Kamens, et al.; 2001, *Curr. Opin. Investig. Drugs*, 2, 1213-1219). Results have shown that the lck (−) Jurkat cell lines are unable to proliferate, produce cytokines, and generate increases in intracellular calcium, inositol phosphate, and tyrosine phosphorylation in response to T cell receptor stimulation (Straus and Weiss; 1992, *Cell.*, 70, 585-593; Yamasaki, et al.; 1996, *Mol. Cell. Biol.*, 16, 7151-7160). Therefore, an agent inhibiting lck would effectively block T cell function, act as an immunosuppressive agent, and have potential utility in autoimmune diseases, such as rheumatoid arthritis, multiple sclerosis, and lupus, as well as in the area of transplant rejection and allergic diseases (Hanke and Pollok; 1995, *Inflammation Res.*, 44, 357-371). Thus, although not wishing to be bound by theory, it is hypothesized that the administration of a compound of the instant invention which modulates one or more members of the Src family of protein tyrosine kinases (e.g., lck and/or fyn) is useful in the treatment of autoimmune disease.

Compounds of the invention include compunds with water solubilizing groups appended on the compound (Wermuth, C. G., *The Practice of Medicinal Chemistry* 2003, p. 617). e.g., $SO_3H$, $OSO_3H$, $OPO_3H_2$, $OPO_3H_2$, amines,

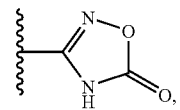

tetrazole, etc.

Compounds of the invention include compounds of Formula I, and salts thereof:

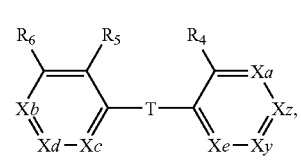

(Formula I)

where:

T is absent (i.e., the rings are connected by a bond), $CR_{12}R_{13}$, $C(O)$, O, S, $S(O)$, $S(O)_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$ or N, or N—O;

$X_b$ is $CR_b$, N, or N—O;

$X_c$ is $CR_c$ or N, or N—O;

$X_d$ is $CR_d$ or N, or N—O;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

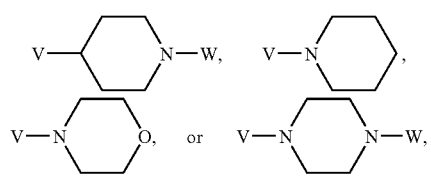

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $OPO_3H_2$, $OPO_3H_2$, $NH_2$, $NHR_{19}$, $NHR_{20}R_{21}$,

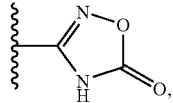

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

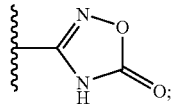

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

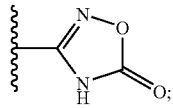

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

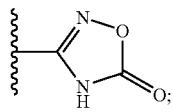

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

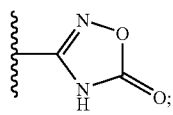

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl;

Z is $(CHR_1)_n$—C(O)—$NR_2(CHR_3)_m$—Ar, where Ar is a substituted or unsubstituted aryl or nitrogen-containing heteroaryl group, such as benzene, pyridine, or pyrimidine. For example, Z is:

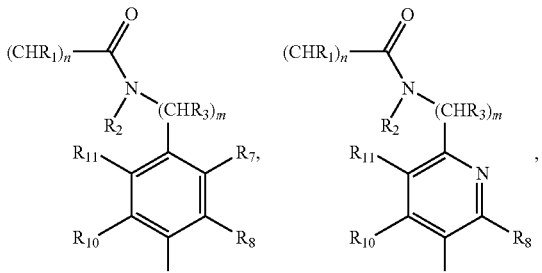

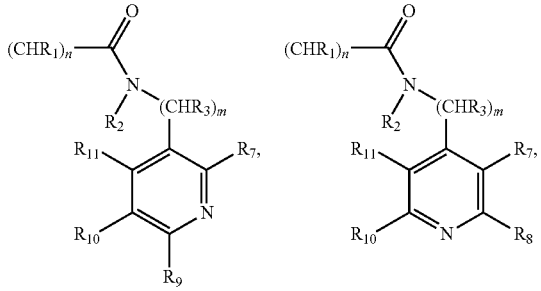

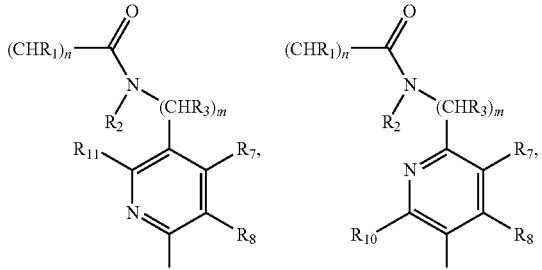

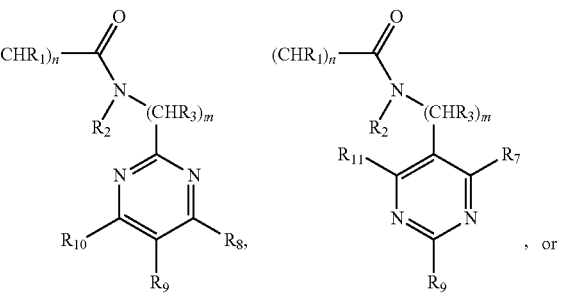

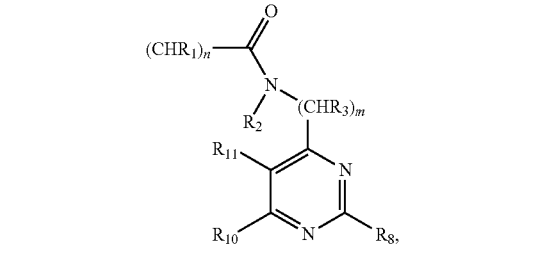

where $R_1$, $R_2$, and $R_3$ are independently H or $C_1$, $C_2$, $C_3$, $C_4$, $C_5$, or $C_6$ alkyl;

n and m are, independently 0, 1, or 2; $R_7$, $R_8$, $R_9$, $R_{10}$, and $R_{11}$ are, independently, hydrogen, hydroxyl, halogen, P, $C_1$, $C_2$, $C_3$, $C_4$, $C_5$, or $C_6$ alkyl, C, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2H$-lower ($C_1$, $C_2$, $C_3$, $C_4$, $C_5$, or $C_6$) alkyl,

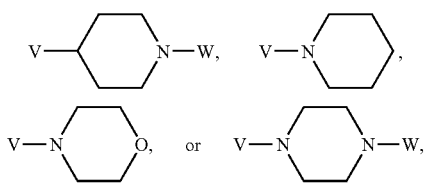

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $OPO_3H_2$, $OPO_3H_2$, $NH_2$, $NHR_{19}$, $NHR_{20}R_{21}$,

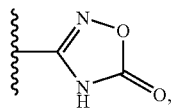

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

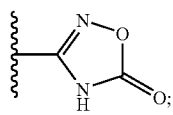

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

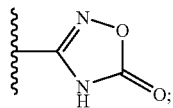

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

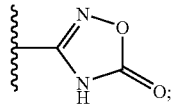

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

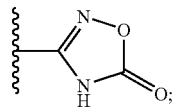

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, —$CH_2$—, —$CH_2CH_2$—, —$CH_2CH_2CH_2$—, —O—$CH_2$—, —$OCH_2CH_2$—, or —$OCH_2CH_2CH_2$—.

In certain compounds of the invention, Z is

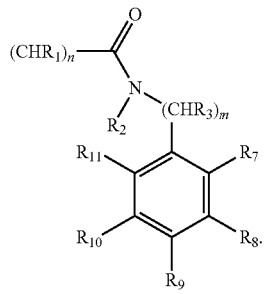

Certain compounds of the invention are selected from Compounds 1-136 and 137. For example, the compound of the invention is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 93, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137.

Compounds of the invention include Compounds 33, 38, 40, 76, 133, 134, 136 and 137.

Certain compounds of the invention are selected from Compounds 138-246 and 247. For example, the compound of the invention is Compound 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, or 247.

Compounds of the invention include Compounds 146 and 147.

Certain compounds of the invention are selected from Compounds 248-273 and 274. For example, the compound of the invention is Compound 248, 249, 250, 251, 252, 253, 254, 255, 256, 257, 258, 259, 260, 261, 262, 263, 264, 265, 266, 267, 268, 269, 270, 271, 272, 273, or 274.

In certain Compounds of Formula I, at least one of $X_a$, $X_b$, $X_c$, $X_d$ and $X_e$ is N.

For example, in the compound of Formula I, $X_a$ is N and each of $X_b$, $X_c$, $X_d$ and $X_e$ is CR.

In certain compounds of Formula I, $X_y$ is CY, and $X_z$ is CZ.

For example, in certain compounds of Formula I, Y is hydrogen.

The compounds of the invention can tolerate a wide variety of functional groups, so various substituted starting materials can be used to synthesize them. The syntheses described herein generally provide the desired final bi-aryl compound at or near the end of the overall process, although it may be desirable in certain instances to further convert the compound to a pharmaceutically acceptable salt, ester, or prodrug thereof.

In certain compounds of Formula I, $R_b$ is $C_1$, $C_2$, $C_3$, $C_4$, $C_5$, or $C_6$ alkoxy. For example, $R_b$ is methoxy or ethoxy. In certain compounds of Formula I, $R_b$ is hydrogen. In other compounds of Formula I, $R_b$ is selected from F, Cl, Br, and I. For example, $R_b$ is F.

In other compounds of Formula I, $R_b$ is

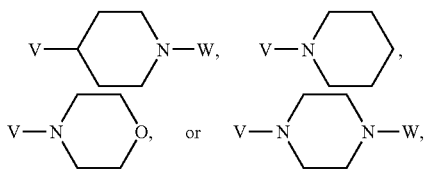

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—. For example, V is a bond. In certain compounds of Formula I, V is —CH$_2$—, —CH$_2$CH$_2$— or —CH$_2$CH$_2$CH$_2$—. In other compounds, V is —O—CH$_2$—, —OCH$_2$CH$_2$— or —OCH$_2$CH$_2$CH$_2$—.

In certain compounds of Formula I, W is hydrogen. In other compounds, W is $C_1$, $C_2$, $C_3$, $C_4$, $C_5$, or $C_6$ alkyl. In some compounds, W is methyl.

In certain compounds of Formula I, $R_c$ is halogen, for example, $R_c$, is F, Cl, Br, or I. In some compounds, $R_c$ is F. In other compounds, $R_c$ is Cl.

In some compounds, $R_c$ is $C_1$, $C_2$, $C_3$, $C_4$, $C_5$, or $C_6$ alkoxy. In some compounds, $R_c$ is methoxy or ethoxy. In some embodiments, $R_c$ is ethoxy.

In other compounds of Formula I, $R_c$ is hydrogen.
In other compounds of Formula I, $R_c$ is

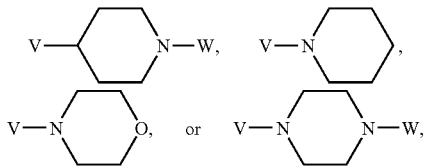

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—. In some compounds, V is a bond. In other compounds, V is —CH$_2$—, —CH$_2$CH$_2$— or —CH$_2$CH$_2$CH$_2$—. In other compounds, V is —O—CH$_2$—, —OCH$_2$CH$_2$— or —OCH$_2$CH$_2$CH$_2$—.

In some compounds of Formula I, W is hydrogen. In other compounds, W is $C_1$, $C_2$, $C_3$, $C_4$, $C_5$, or $C_6$ alkyl. In certain compounds, W is methyl.

In certain compounds of Formula I, $R_b$ is $C_1$, $C_2$, $C_3$, $C_4$, $C_5$, or $C_6$ alkoxy. For example, $R_b$ is methoxy or ethoxy. In certain compounds of Formula I, $R_b$ is hydrogen. In other compounds of Formula I, $R_b$ is selected from F, Cl, Br, and I. For example, $R_b$ is F.

In other compounds of Formula I, $R_b$ is

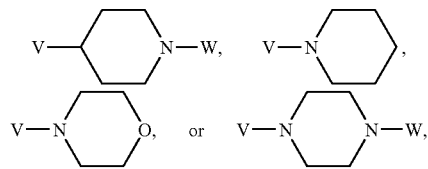

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—. For example, V is a bond. In certain compounds of Formula I, V is —CH$_2$—, —CH$_2$CH$_2$— or —CH$_2$CH$_2$CH$_2$—. In other compounds, V is —O—CH$_2$—, —OCH$_2$CH$_2$— or —OCH$_2$CH$_2$CH$_2$—.

In certain compounds of Formula I, W is hydrogen. In other compounds, W is $C_1$, $C_2$, $C_3$, $C_4$, $C_5$, or $C_6$ alkyl. In some compounds, W is methyl.

In certain compounds of Formula I, $R_d$ is halogen, for example, $R_d$ is F, Cl, Br, or I. In some compounds, $R_d$ is F. In other compounds, $R_d$ is Cl.

In some compounds, $R_d$ is $C_1$, $C_2$, $C_3$, $C_4$, $C_5$, or $C_6$ alkoxy. In some compounds, $R_d$ is methoxy or ethoxy. In some embodiments, $R_d$ is ethoxy.

In other compounds of Formula I, $R_d$ is hydrogen.
In other compounds of Formula I, $R_d$ is

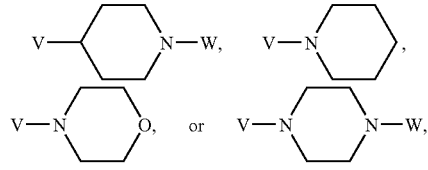

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—. In some compounds, V is a bond. In other compounds, V is —CH$_2$—, —CH$_2$CH$_2$— or —CH$_2$CH$_2$CH$_2$—. In other compounds, V is —O—CH$_2$—, —OCH$_2$CH$_2$— or —OCH$_2$CH$_2$CH$_2$—.

In some compounds of Formula I, W is hydrogen. In other compounds, W is $C_1$, $C_2$, $C_3$, $C_4$, $C_5$, or $C_6$ alkyl. In certain compounds, W is methyl.

The invention relates to a compound of Formula I, having a structure according to one of Formulae II, III, IV, V, VI, VII, VIII, IX, X, XI, XII, and XIII:

Formula II:

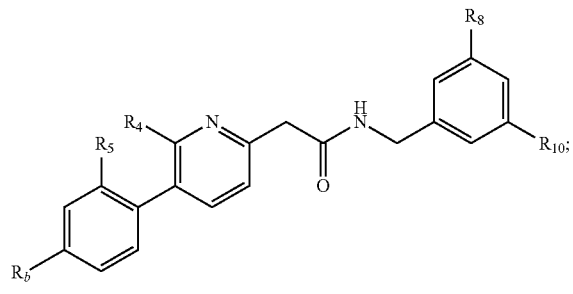

Formula III:
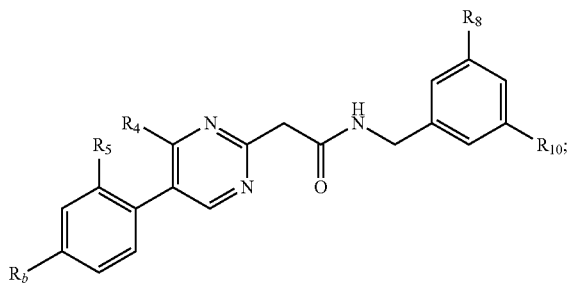
Formula IV:
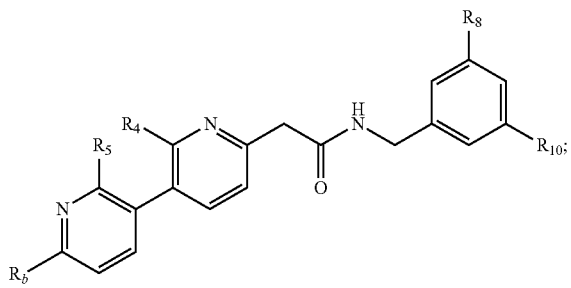
Formula V:
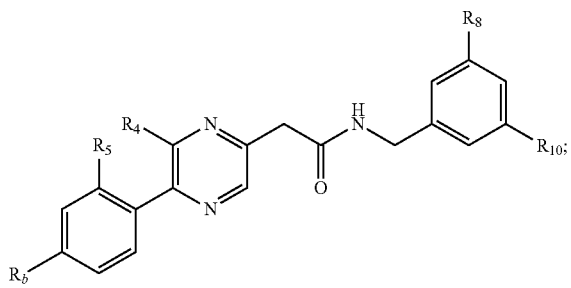
Formula VI:
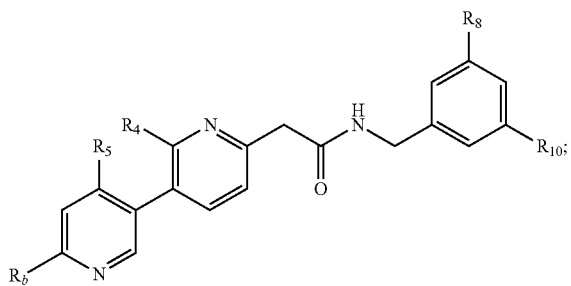
Formula VII:
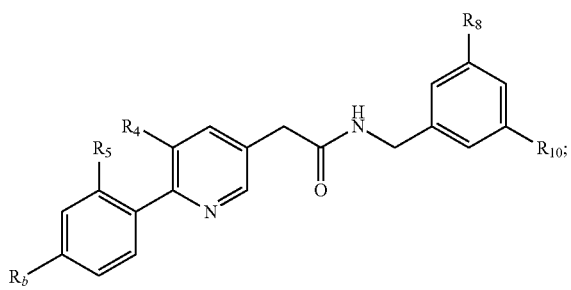
Formula VIII:
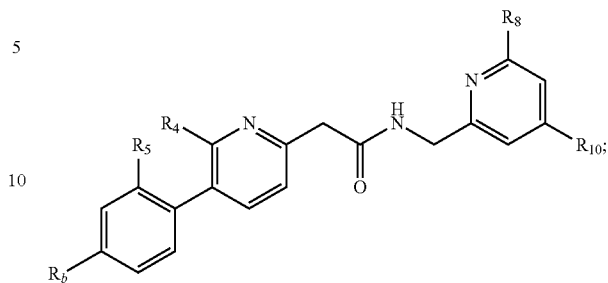
Formula IX:
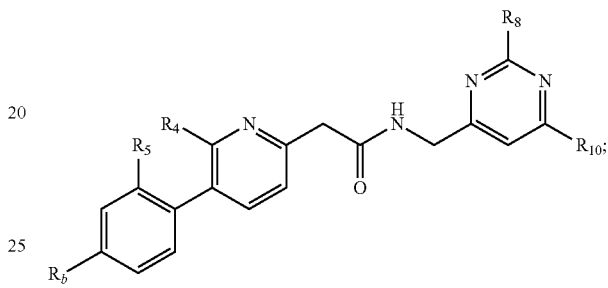
Formula X:
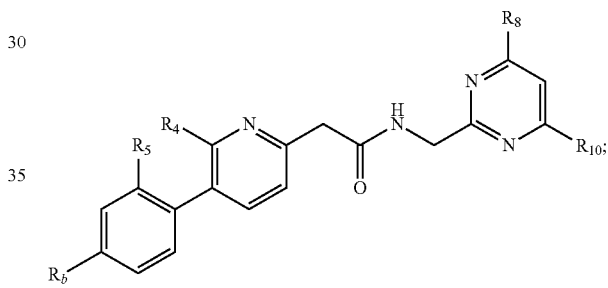
Formula XI:
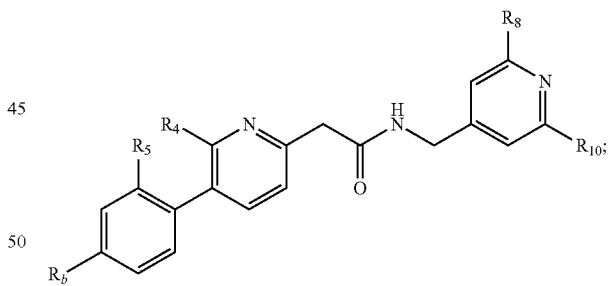
Formula XII:
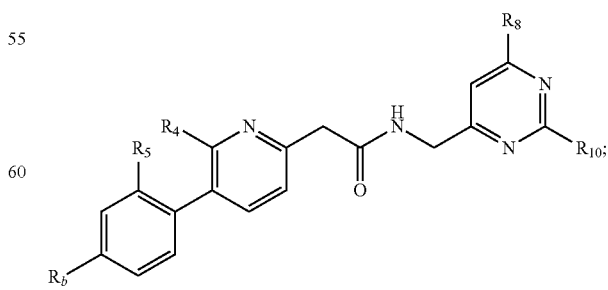

-continued

Formula XIII:

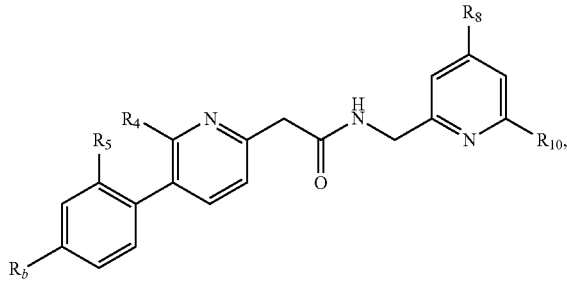

or a salt, solvate, hydrate, or prodrug thereof, where:

$R_b$, $R_4$, $R_5$, $R_8$, and $R_{10}$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O-lower ($C_1$, $C_2$, $C_3$, $C_4$, $C_5$, or $C_6$) alkyl, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

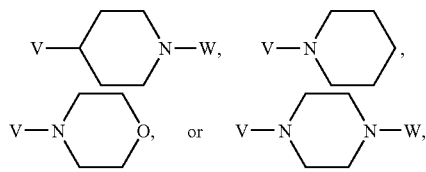

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, $-CH_2-$, $-CH_2CH_2-$, $-CH_2CH_2CH_2-$, $-O-CH_2-$, $-OCH_2CH_2-$ or $-OCH_2CH_2CH_2-$.

For example, in the compound of Formula II, III, IV, V, VI, VII, VIII, IX, X, XI, XII, and XIII, $R_8$ is hydrogen, F, Cl, Br, or I. For example, $R_8$ is F. In certain compounds, $R_8$ is H.

In certain compounds of Formula II, III, IV, V, VI, VII, VIII, IX, X, XI, XII, and XIII, $R_b$ is $C_1$, $C_2$, $C_3$, $C_4$, $C_5$, or $C_6$ alkoxy. For example, $R_b$ is methoxy or ethoxy. In certain compounds, $R_b$ is ethoxy. In certain compounds, $R_b$ is hydrogen.

In certain compounds of Formula II, III, IV, V, VI, VII, VIII, IX, X, XI, XII, and XIII, $R_b$ is Cl, Br, or I. For example, $R_b$ is F or Cl. In other compounds, in the compound of Formula II, III, IV, V, VI, VII, VIII, IX, X, XI, XII, and XIII, $R_b$ is

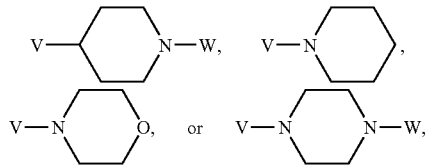

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, $-CH_2-$, $-CH_2CH_2-$, $-CH_2CH_2CH_2-$, $-O-CH_2-$, $-OCH_2CH_2-$ or $-OCH_2CH_2CH_2-$. In some compounds, V is $-O-CH_2-$, $-OCH_2CH_2-$ or $-OCH_2CH_2CH_2-$. In certain compounds W is H. In other compounds, W is $C_1$, $C_2$, $C_3$, $C_4$, $C_5$, or $C_6$ alkyl. For example, W is methyl.

In certain compounds of Formula II, III, IV, V, VI, VII, VIII, IX, X, XI, XII, and XIII, $R_4$ is hydrogen, $C_1$, $C_2$, $C_3$, $C_4$, $C_5$, or $C_6$ alkoxy, F, Cl, Br, or I. In some compounds, $R_4$ is $C_1$, $C_2$, $C_3$, $C_4$, $C_5$, or $C_6$ alkoxy. For example, $R_4$ is methoxy or ethoxy. In other compounds, in the compound of Formula II, III, IV, V, VI, VII, VIII, IX, X, XI, XII, and XIII, $R_4$ is

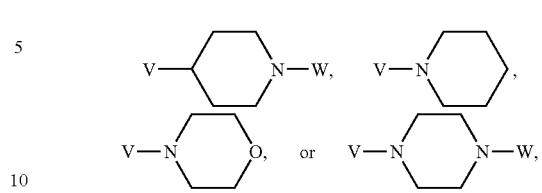

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $-CH_2-$, $-CH_2CH_2-$, $-CH_2CH_2CH_2-$, $-O-CH_2-$, $-OCH_2CH_2-$ or $-OCH_2CH_2CH_2-$. In certain compounds, V is a bond. In other compounds, V is $-CH_2-$, $-CH_2CH_2-$ or $-CH_2CH_2CH_2-$. In other compounds, V is $-O-CH_2-$, $-OCH_2CH_2-$ or $-OCH_2CH_2CH_2-$.

In certain compounds of Formula II, III, IV, V, VI, VII, VIII, IX, X, XI, XII, and XIII, $R_5$ is hydrogen, $C_1$, $C_2$, $C_3$, $C_4$, $C_5$, or $C_6$ alkoxy, F, Cl, Br, or I. For example, $R_5$ is hydrogen. In some compounds, $R_5$ is ethoxy. In certain compounds $R_5$ is F. In other compounds, in the compound of Formula II, III, IV, V, VI, VII, VIII, IX, X, XI, XII, and XIII, $R_5$ is

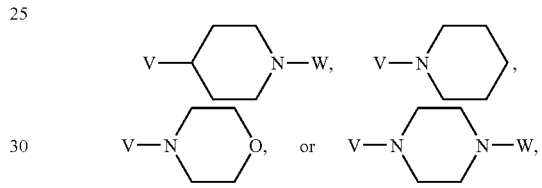

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $-CH_2-$, $-CH_2CH_2-$, $-CH_2CH_2CH_2-$, $-O-CH_2-$, $-OCH_2CH_2-$ or $-OCH_2CH_2CH_2-$. In certain compounds, V is a bond. In other compounds, V is $-CH_2-$, $-CH_2CH_2-$ or $-CH_2CH_2CH_2-$. In other compounds, V is $-O-CH_2-$, $-OCH_2CH_2-$ or $-OCH_2CH_2CH_2-$.

In certain compounds of Formula II, III, IV, V, VI, VII, VIII, IX, X, XI, XII, and XIII, $R_{10}$ is hydrogen, $C_1$, $C_2$, $C_3$, $C_4$, $C_5$, or $C_6$ alkoxy, F, Cl, Br, or I. In some compounds $R_{10}$ is $C_1$, $C_2$, $C_3$, $C_4$, $C_5$, or $C_6$ alkoxy. For example, $R_{10}$ is methoxy or ethoxy. In some compounds, $R_{10}$ is isobutoxy. In some compounds, $R_{10}$ is hydrogen. In certain compounds, $R_{10}$ is halogen. For example, $R_{10}$ is F or Cl.

In other compounds of Formula II, III, IV, V, VI, VII, VIII, IX, X, XI, XII, and XIII, $R_{10}$ is

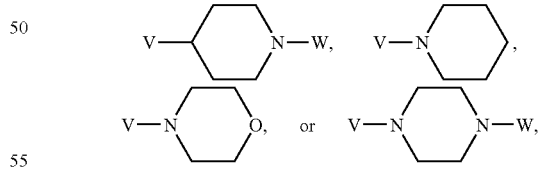

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $-CH_2-$, $-CH_2CH_2-$, $-CH_2CH_2CH_2-$, $-O-CH_2-$, $-OCH_2CH_2-$ or $-OCH_2CH_2CH_2-$. In certain compounds, V is a bond. In other compounds, V is $-CH_2-$, $-CH_2CH_2-$ or $-CH_2CH_2CH_2-$. In other compounds, V is $-O-CH_2-$, $-OCH_2CH_2-$ or $-OCH_2CH_2CH_2$.

For example, in the compound of Formula II, III, IV, V, VI, VII, VIII, IX, X, XI, XII, and XIII, W is hydrogen, or $C_1$, $C_2$, $C_3$, $C_4$, $C_5$, or $C_6$ alkyl. In some compounds, W is methyl.

Certain compounds of the invention include compounds according to Formula II.

Compounds of the invention include those listed in Table 1:

TABLE 1

| Compound # | KX # | Compound |
|---|---|---|
| 1 | 1-136 | biphenyl-CH$_2$-C(=O)-NH-CH$_2$-(3-hydroxyphenyl) |
| 2 | 1-305 | biphenyl-CH$_2$-C(=O)-NH-CH$_2$-(3-fluorophenyl) |
| 3 | 1-306 | biphenyl-CH$_2$-C(=O)-NH-CH$_2$-(3-OBn-5-OH-phenyl) |
| 4 | 1-307 | 3-phenylphenyl-CH$_2$-C(=O)-NH-CH$_2$-(3-fluorophenyl) |
| 5 | 1-308 | biphenyl-CH$_2$-C(=O)-NH-(3-fluorophenyl) |
| 6 | 1-309 | (2'-fluorobiphenyl-4-yl)-CH$_2$-C(=O)-NH-CH$_2$-(3-fluorophenyl) |

TABLE 1-continued
| Compound # | KX # | Compound |
|---|---|---|
| 7 | 1-310 | 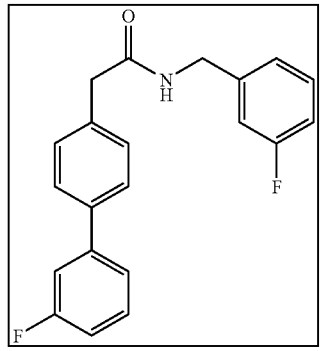 |
| 8 | 1-311 | 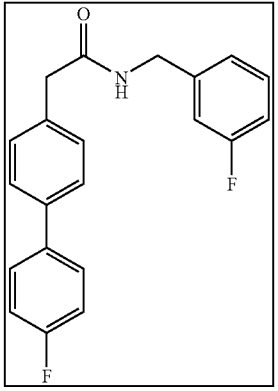 |
| 9 | 1-312 | 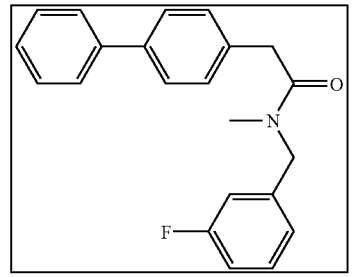 |
| 10 | 1-313 | 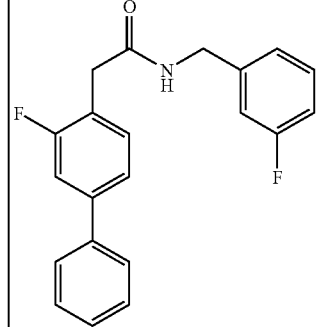 |

TABLE 1-continued
| Compound # | KX # | Compound |
|---|---|---|
| 11 | 1-314 | 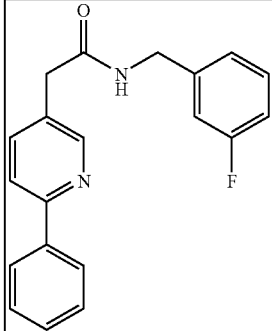 |
| 12 | 1-315 | 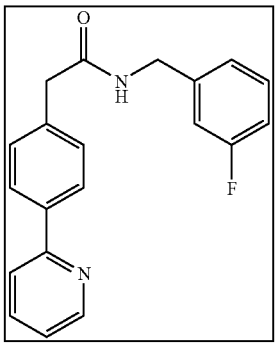 |
| 13 | 1-316 | 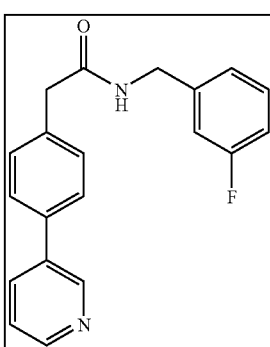 |
| 14 | 1-317 | 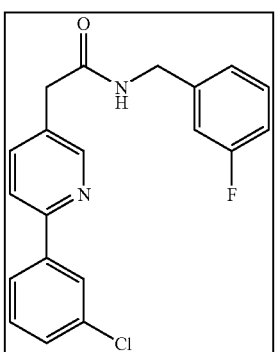 |

TABLE 1-continued
| Compound # | KX # | Compound |
|---|---|---|
| 15 | 1-318 | 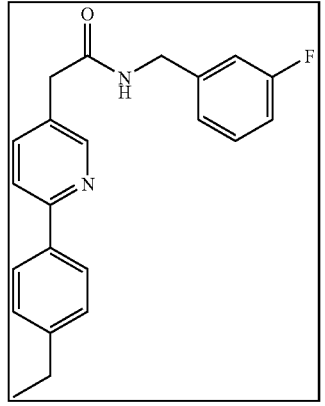 |
| 16 | 1-319 | 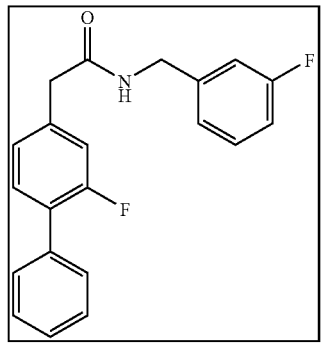 |
| 17 | 1-320 | 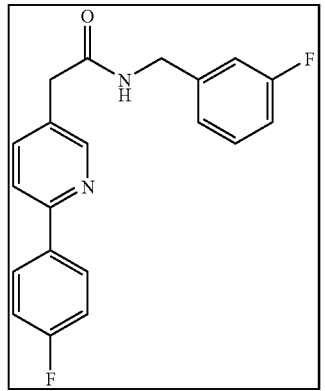 |
| 18 | 1-321 | 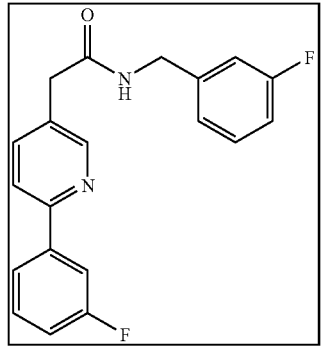 |

TABLE 1-continued

| Compound # | KX # | Compound |
|---|---|---|
| 19 | 1-322 | 2-[6-(3-ethoxyphenyl)pyridin-3-yl]-N-(3-fluorobenzyl)acetamide |
| 20 | 1-323 | 4-{5-[2-(3-fluorobenzylamino)-2-oxoethyl]pyridin-2-yl}benzoic acid |
| 21 | 1-324 | 2-[6-(2-ethoxyphenyl)pyridin-3-yl]-N-(3-fluorobenzyl)acetamide |
| 22 | 1-325 | 2-[6-(4-ethoxyphenyl)pyridin-3-yl]-N-(3-fluorobenzyl)acetamide |

TABLE 1-continued
| Compound # | KX # | Compound |
|---|---|---|
| 23 | 1-326 | 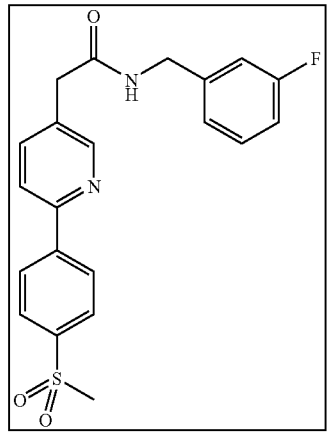 |
| 24 | 1-327 | 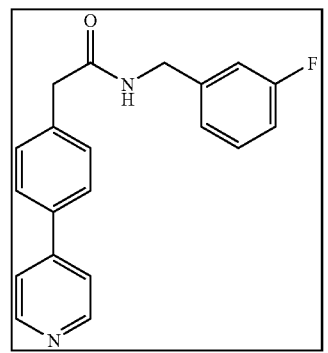 |
| 25 | 1-329 | 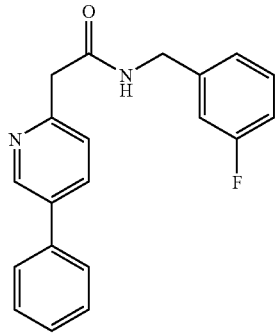 |
| 26 | 1-357 | 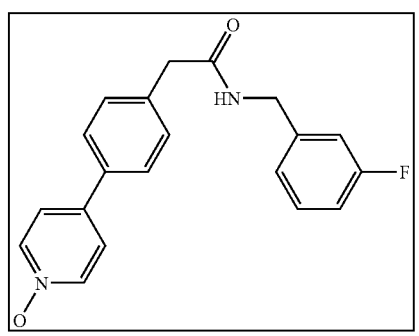 |

TABLE 1-continued
| Compound # | KX # | Compound |
|---|---|---|
| 27 | 1-358 | 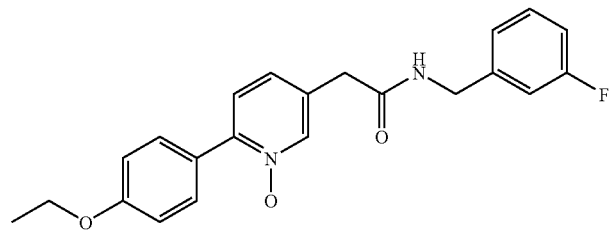 |
| 28 | 2-359 | 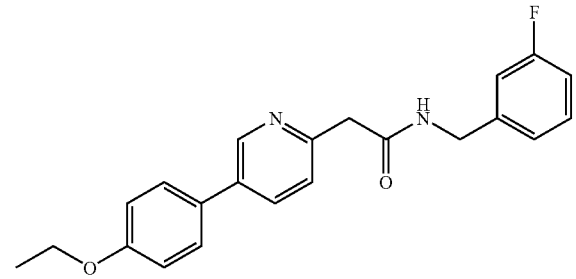 |
| 29 | 2-368 | 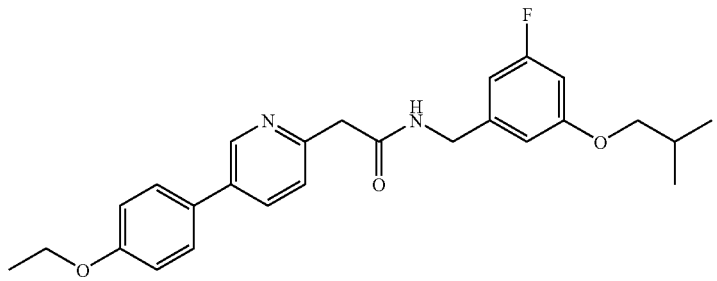 |
| 30 | 2-380 | 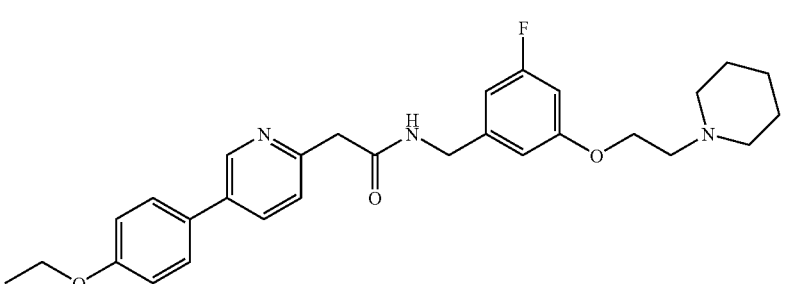 |
| 31 | 2-378 | 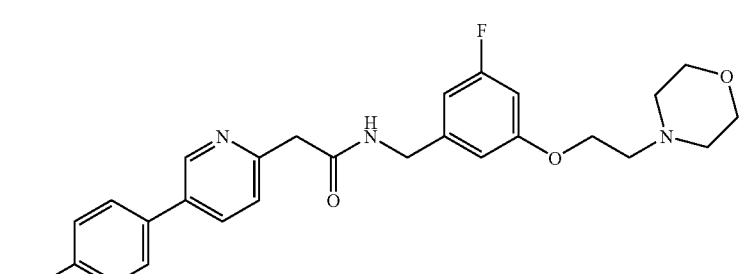 |

TABLE 1-continued
| Compound # | KX # | Compound |
|---|---|---|
| 32 | | 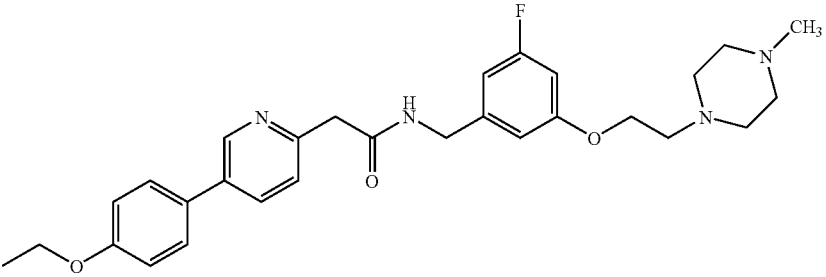 |
| 33 | 2-381 | 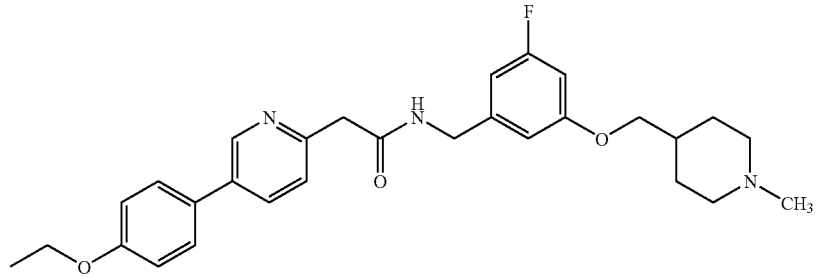 |
| 34 | | 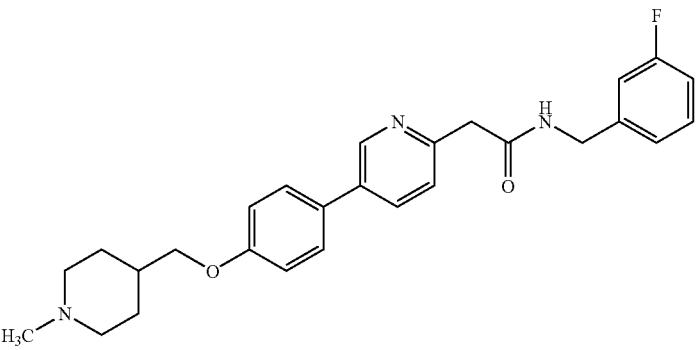 |
| 35 | | 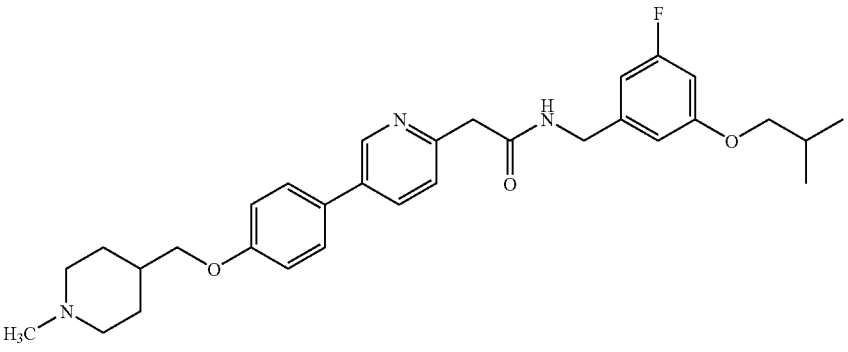 |
| 36 | 2-375 | 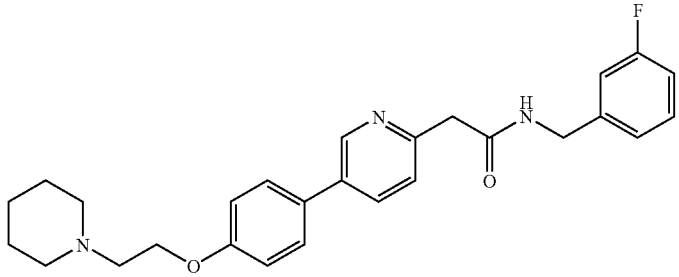 |

TABLE 1-continued

| Compound # | KX # | Compound |
|---|---|---|
| 37 | 2-386 | |
| 38 | 2-377 | |
| 39 | 2-387 | |
| 40 | 2-365 | |
| 41 | 2-367 | |

TABLE 1-continued

| Compound # | KX # | Compound |
|---|---|---|
| 42 | | (structure) |
| 43 | | (structure) |
| 44 | | (structure) |
| 45 | | (structure) |
| 46 | | (structure) |

TABLE 1-continued

| Compound # | KX # | Compound |
|---|---|---|
| 47 | | |
| 48 | | |
| 49 | | |
| 50 | | |
| 51 | | |

TABLE 1-continued
| Compound # | KX # | Compound |
|---|---|---|
| 52 | | 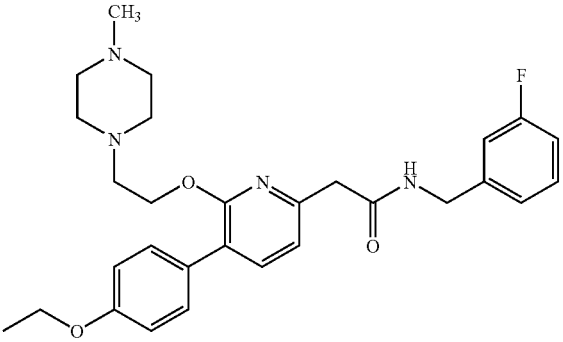 |
| 53 | | 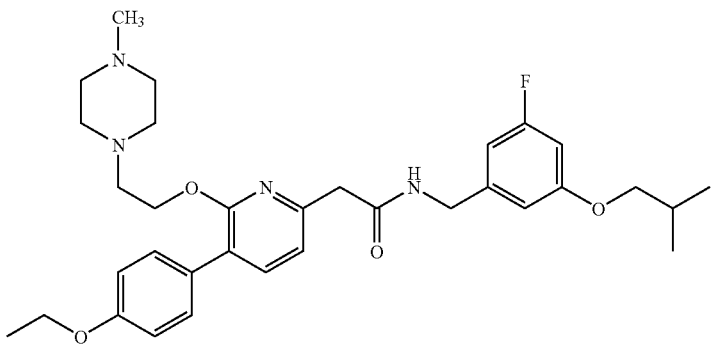 |
| 54 | 2-360 | 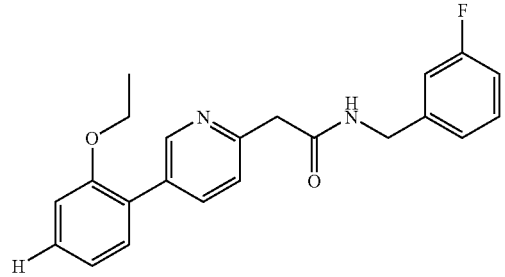 |
| 55 | 2-369 | 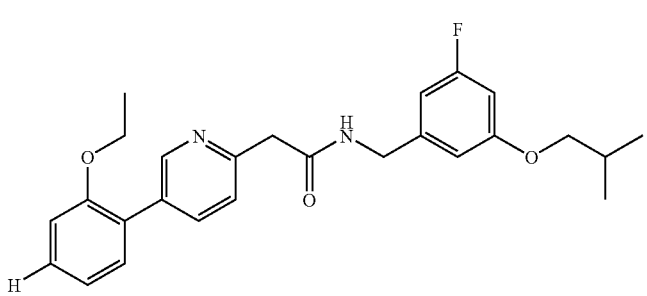 |
| 56 | | 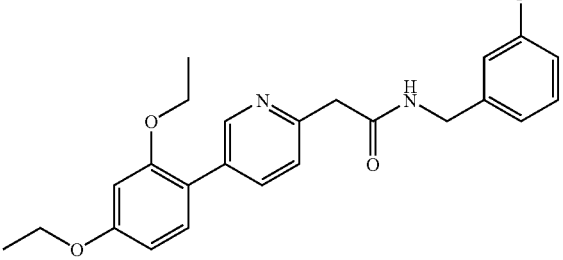 |

TABLE 1-continued

| Compound # | KX # | Compound |
|---|---|---|
| 57 | | |
| 58 | | |
| 59 | | |
| 60 | 2-389 | |
| 61 | | |

TABLE 1-continued

| Compound # | KX # | Compound |
|---|---|---|
| 62 | | |
| 63 | | |
| 64 | 2-384 | |
| 65 | | |
| 66 | 2-388 | |

TABLE 1-continued
| Compound # | KX # | Compound |
|---|---|---|
| 67 | | 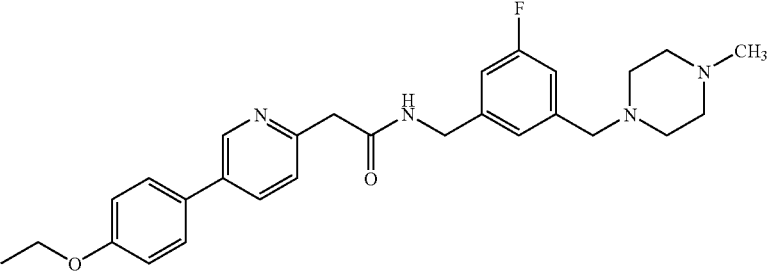 |
| 68 | 2-382 | 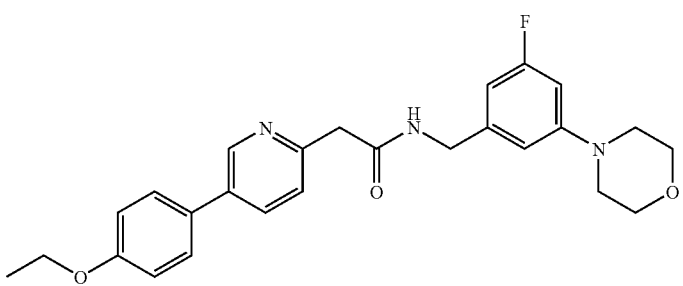 |
| 69 | | 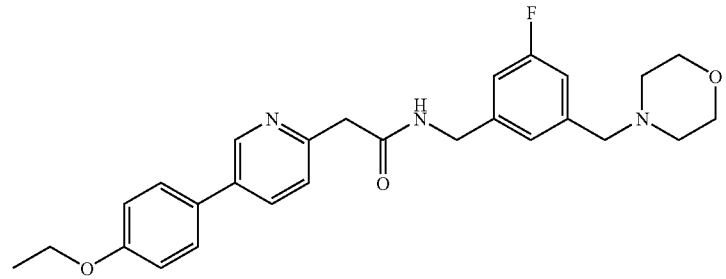 |
| 70 | 2-379 | 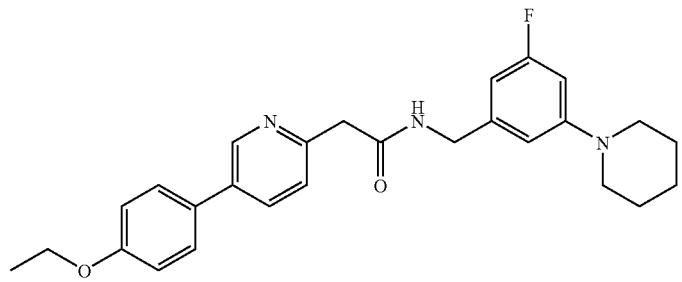 |
| 71 | | 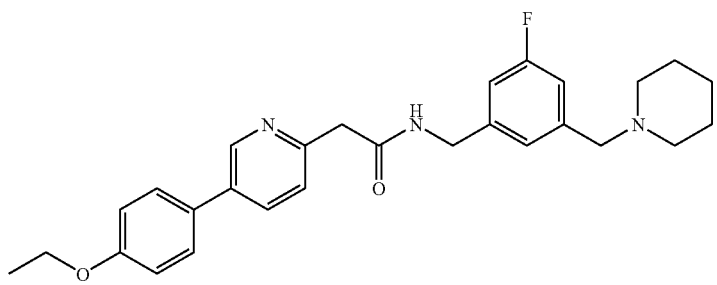 |

TABLE 1-continued

| Compound # | KX # | Compound |
|---|---|---|
| 72 | 2-373 | |
| 73 | | |
| 74 | 2-376 | |
| 75 | 2-366 | |

TABLE 1-continued
| Compound # | KX # | Compound |
|---|---|---|
| 76 | 2-361 | 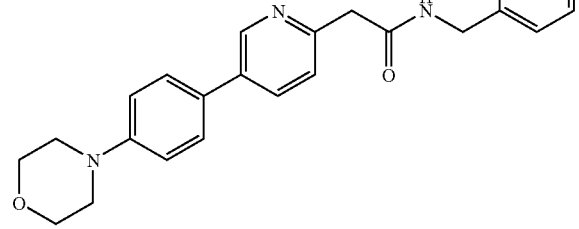 |
| 77 | 2-370 | 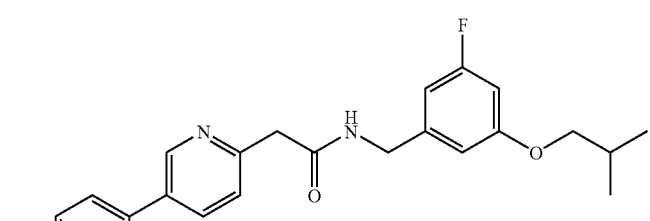 |
| 78 | 2-362 |  |
| 79 | 2-363 | 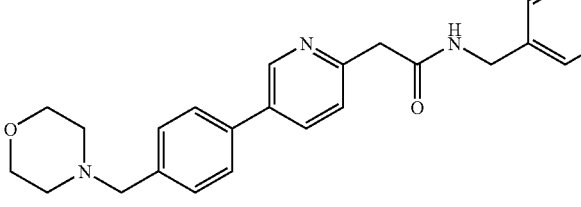 |
| 80 | 2-372 | 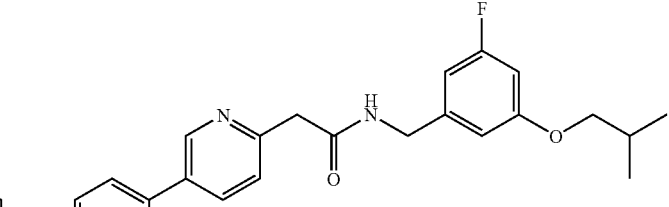 |

TABLE 1-continued

| Compound # | KX # | Compound |
|---|---|---|
| 81 | 2-371 | |
| 82 | 2-364 | |
| 83 | 2-385 | |
| 84 | | |
| 85 | | |

TABLE 1-continued
| Compound # | KX # | Compound |
|---|---|---|
| 86 | | 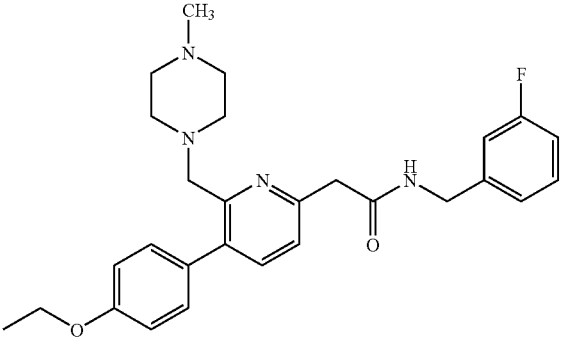 |
| 87 | | 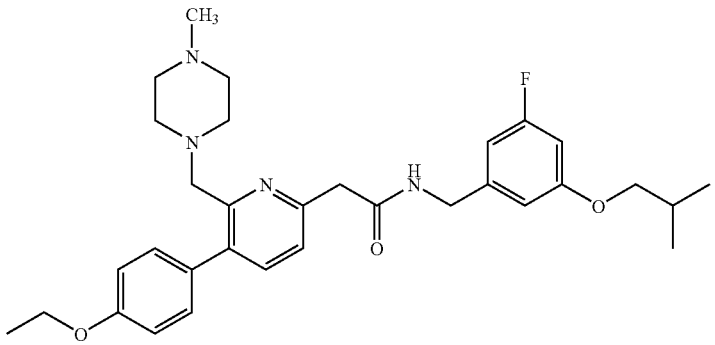 |
| 88 | | 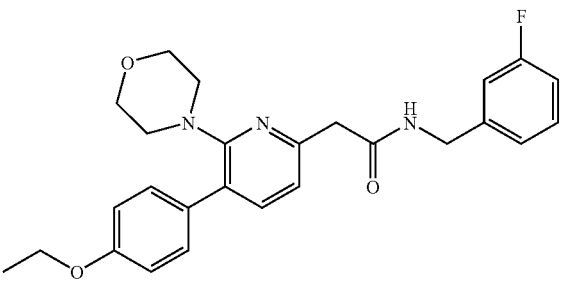 |
| 89 | | 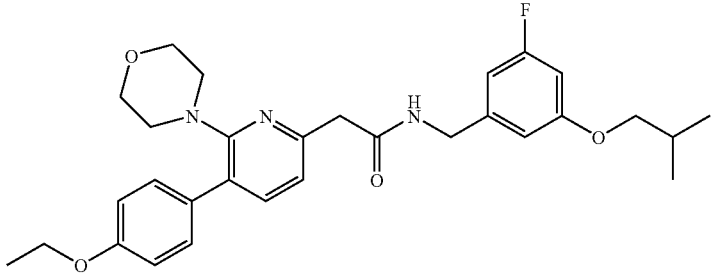 |
| 90 | | 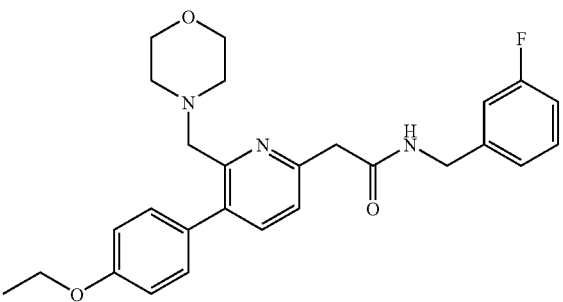 |

TABLE 1-continued
| Compound # | KX # | Compound |
|---|---|---|
| 91 | | 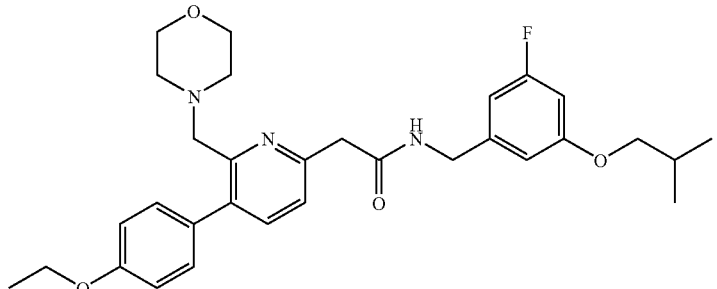 |
| 92 | | 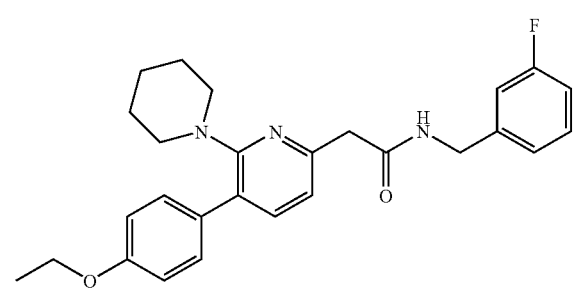 |
| 93 | | 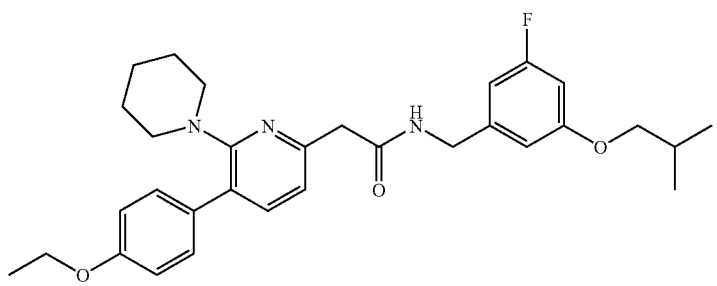 |
| 94 | | 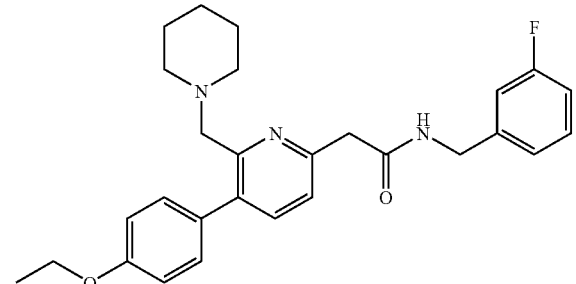 |
| 95 | | 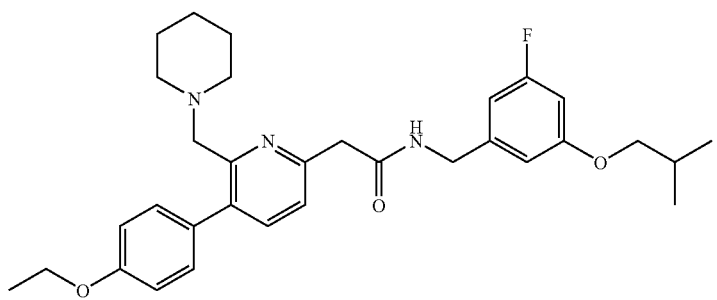 |

TABLE 1-continued
| Compound # | KX # | Compound |
|---|---|---|
| 96 | | 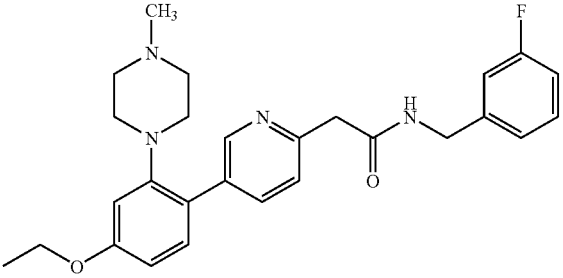 |
| 97 | | 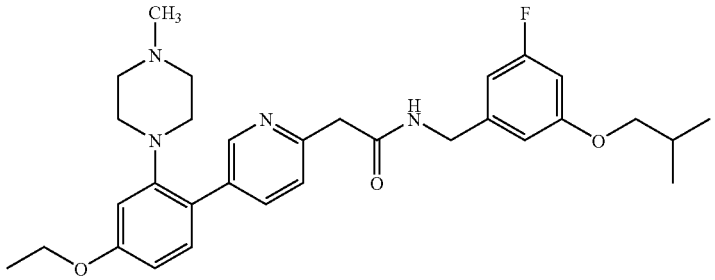 |
| 98 | | 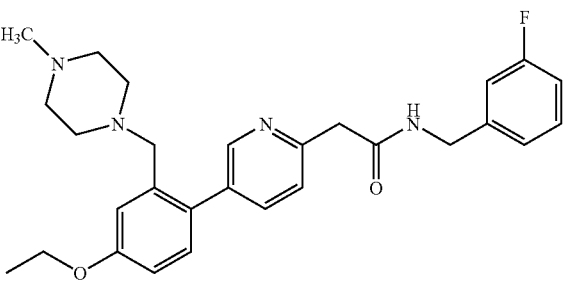 |
| 99 | | 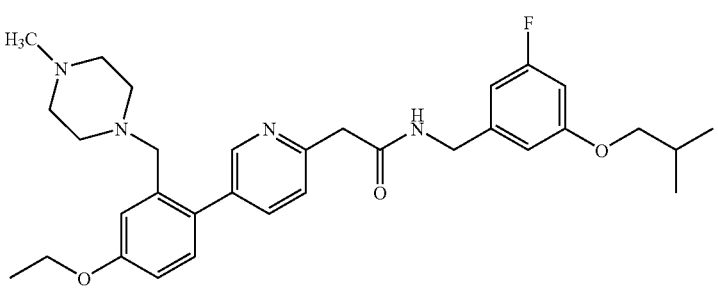 |
| 100 | | 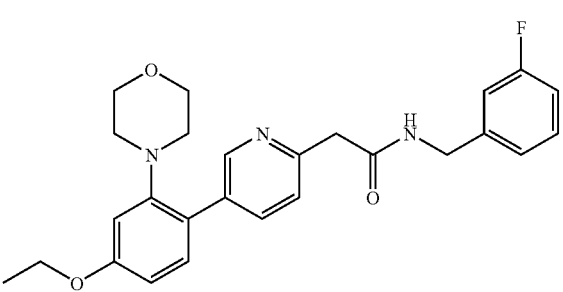 |

TABLE 1-continued
| Compound # | KX # | Compound |
|---|---|---|
| 101 | | 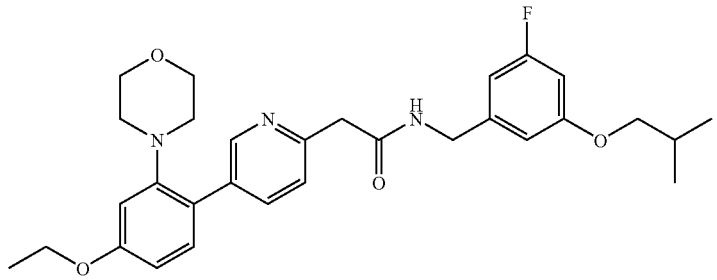 |
| 102 | | 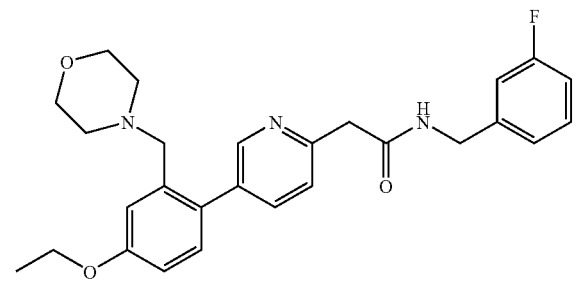 |
| 103 | | 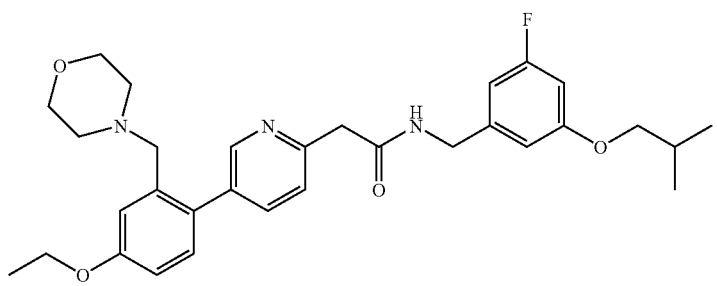 |
| 104 | | 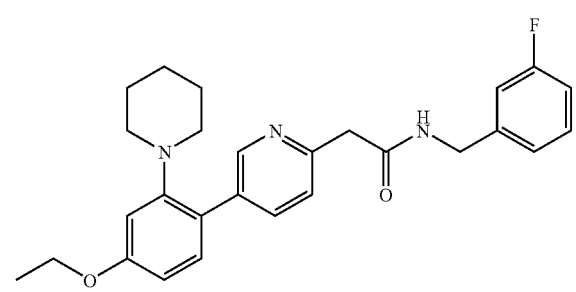 |
| 105 | | 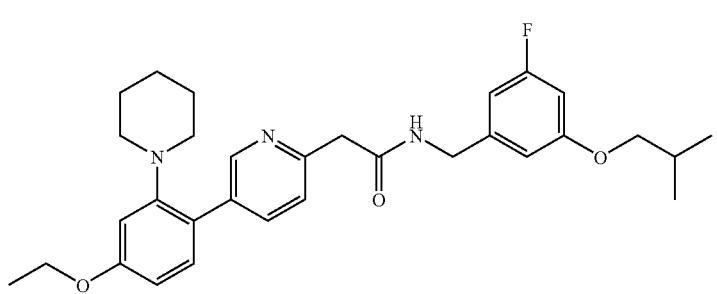 |

TABLE 1-continued

| Compound # | KX # | Compound |
|---|---|---|
| 106 | | |
| 107 | | |
| 108A | 1-072 (Chiral Center) | |
| 108B | 1-121 (Opposite Enantiomer Of 108A) | |
| 109 | 1-75 | |
| 110 | 1-62 | |

TABLE 1-continued

| Compound # | KX # | Compound |
|---|---|---|
| 111 | 1-64 | |
| 112 | 1-117 | |
| 113 | | |
| 114 | 2-390 | |
| 115 | 2-374 | |

TABLE 1-continued
| Compound # | KX # | Compound |
|---|---|---|
| 116 | 2-383 | 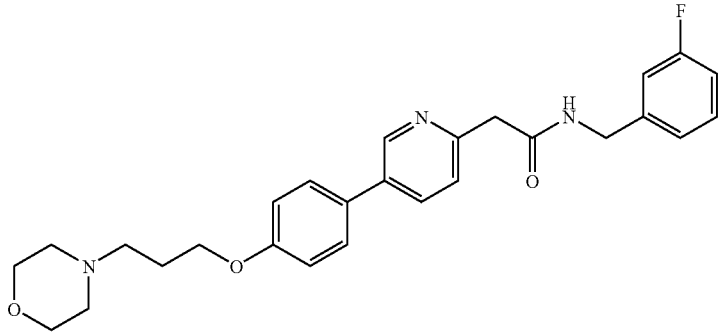 |
| 117 | | 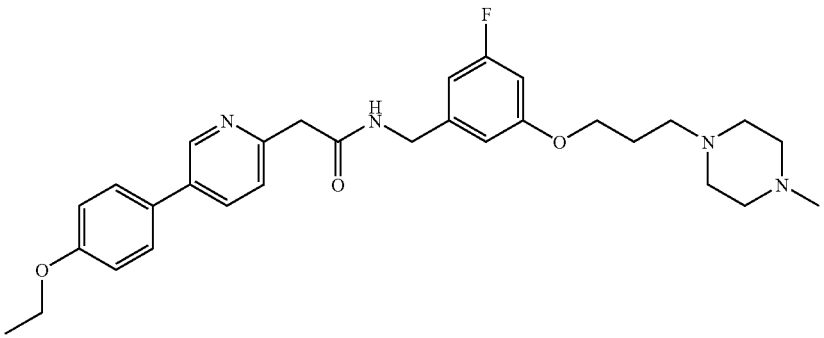 |
| 118 | | 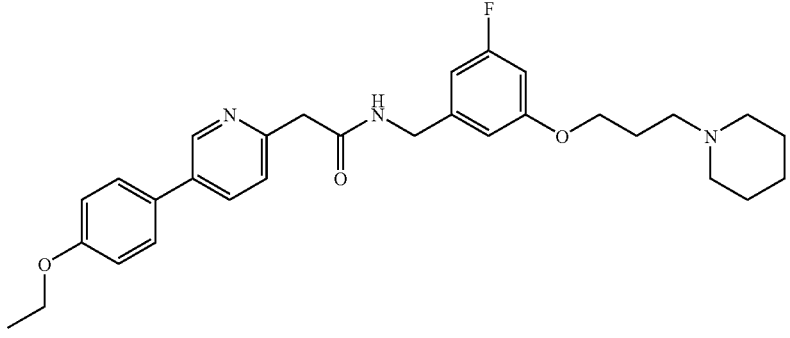 |
| 119 | | 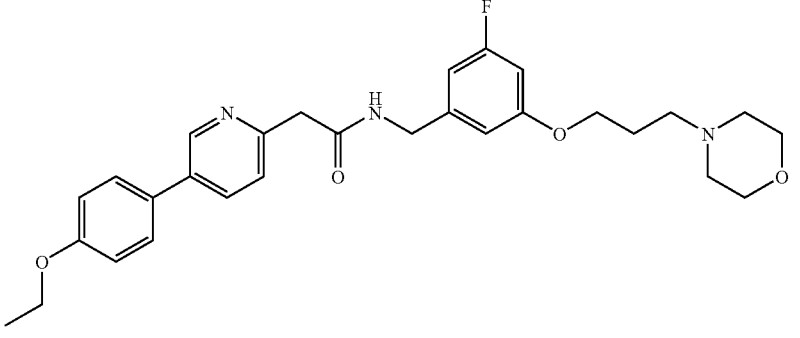 |

TABLE 1-continued

| Compound # | KX # | Compound |
|---|---|---|
| 120 | | |
| 121 | | |
| 122 | | |
| 123 | | |
| 124 | | |

TABLE 1-continued

| Compound # | KX # | Compound |
|---|---|---|
| 125 | | 2-(5-(4-fluorophenyl)pyridin-2-yl)-N-(3-fluoro-5-(3-morpholinopropoxy)benzyl)acetamide |
| 126 | | 2-(5-(4-chlorophenyl)pyridin-2-yl)-N-(3-fluoro-5-(3-morpholinopropoxy)benzyl)acetamide |
| 127 | | 2-(5-(4-fluorophenyl)pyridin-2-yl)-N-(3-fluoro-5-(2-(4-methylpiperazin-1-yl)ethoxy)benzyl)acetamide |
| 128 | | 2-(5-(4-chlorophenyl)pyridin-2-yl)-N-(3-fluoro-5-(2-(4-methylpiperazin-1-yl)ethoxy)benzyl)acetamide |
| 129 | | 2-(5-(4-fluorophenyl)pyridin-2-yl)-N-(3-fluoro-5-(2-(piperidin-1-yl)ethoxy)benzyl)acetamide |

TABLE 1-continued

| Compound # | KX # | Compound |
|---|---|---|
| 130 | | |
| 131 | | |
| 132 | | |
| 133 | 2-392 | |
| 134 | 2-391 | |

TABLE 1-continued

| Compound # | KX # | Compound |
|---|---|---|
| 135 | 329-N oxide | |
| 136 | 2-393 | |
| 137 | 2-394 | |

Other Compounds are listed in Table 2.

TABLE 2

| | | |
|---|---|---|
| 138 | | |
| 139 | | |

TABLE 2-continued
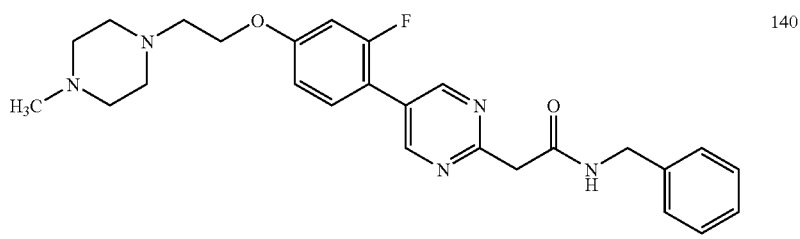
140
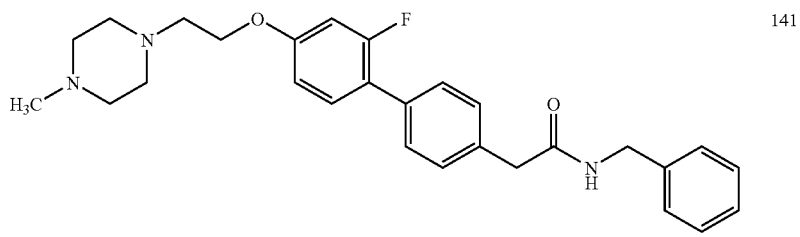
141
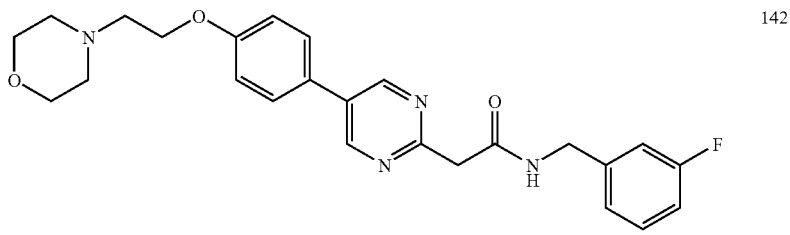
142
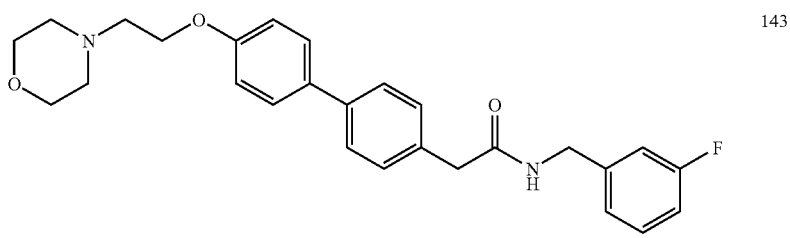
143
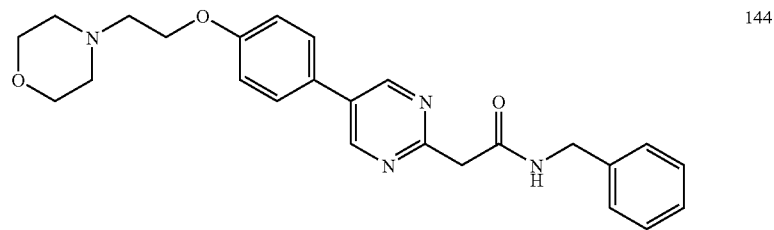
144
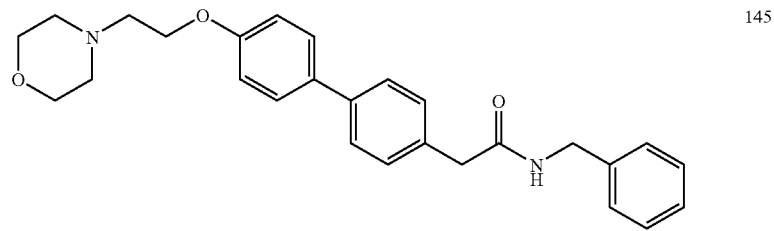
145

TABLE 2-continued
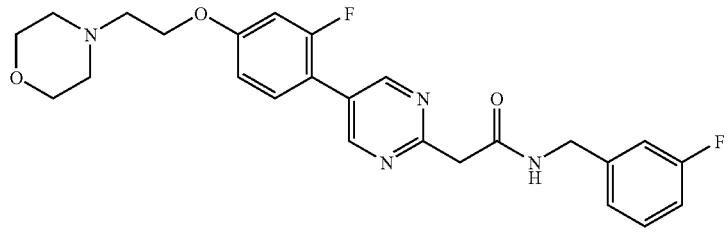
146
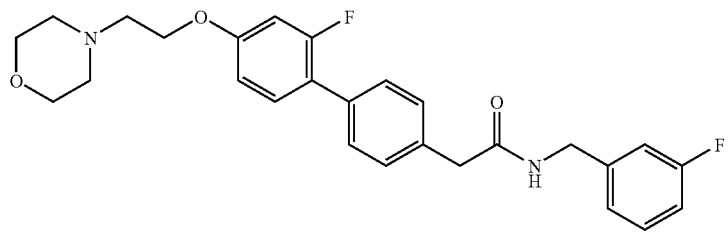
147
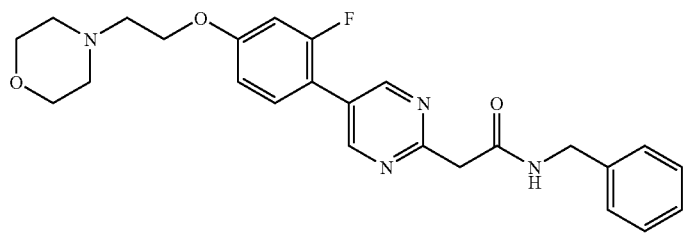
148
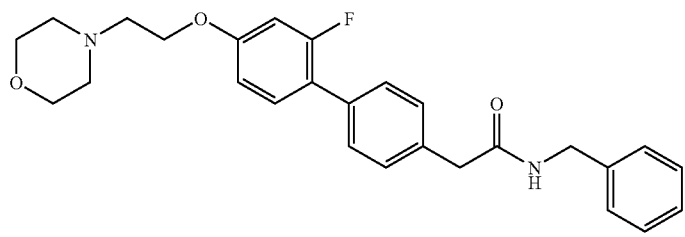
149
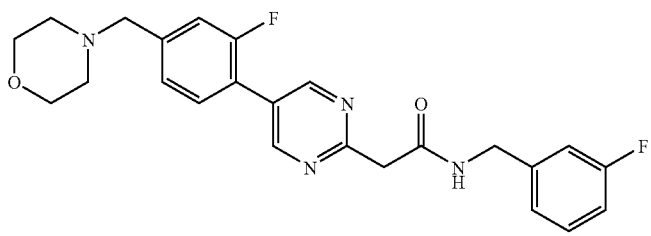
150
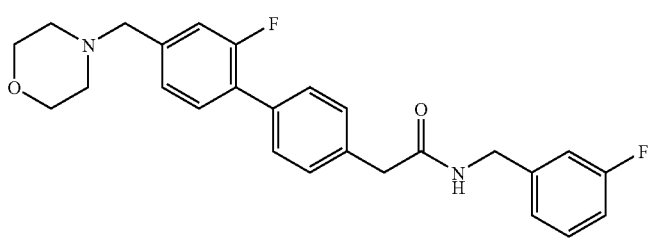
151

TABLE 2-continued
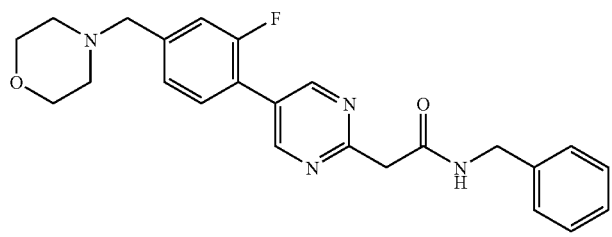 152
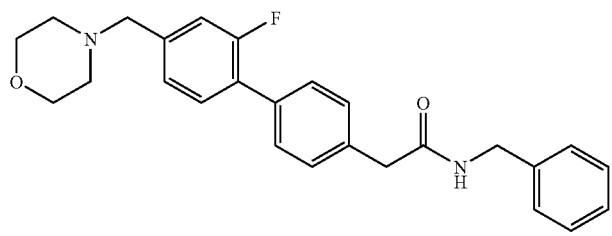 153
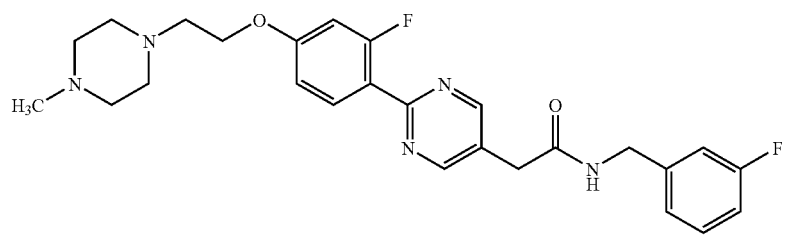 154
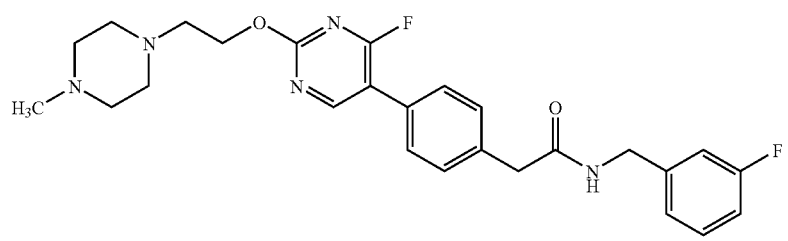 155
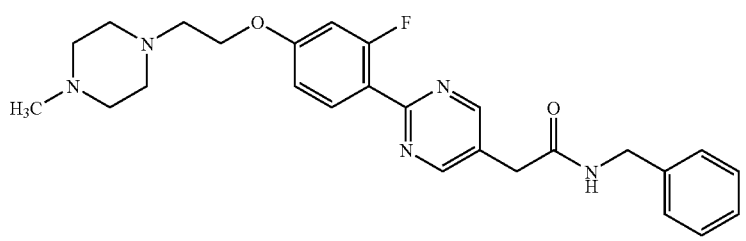 156
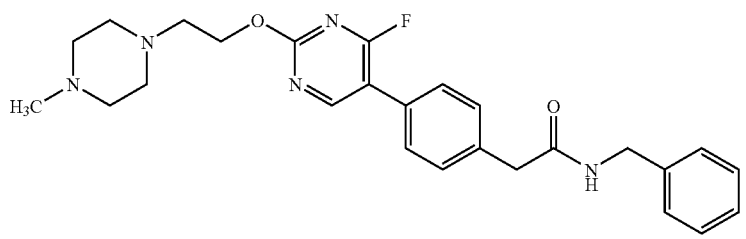 157

TABLE 2-continued
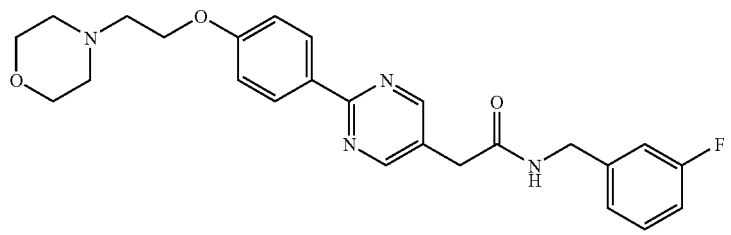
158
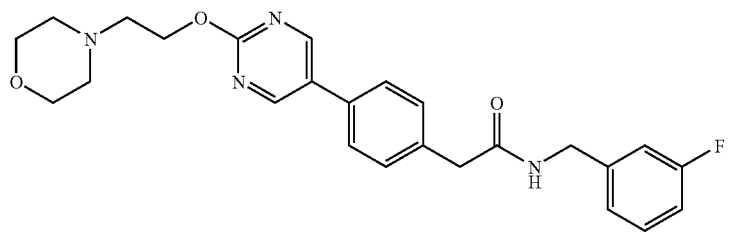
159
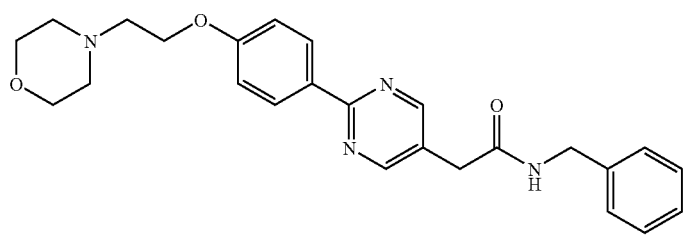
160
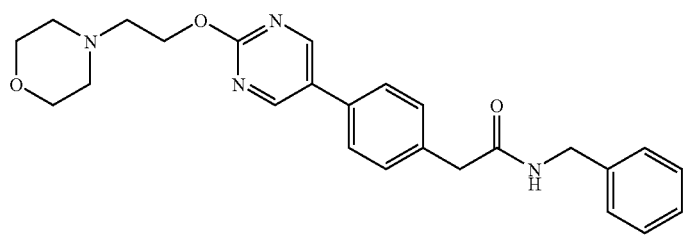
161
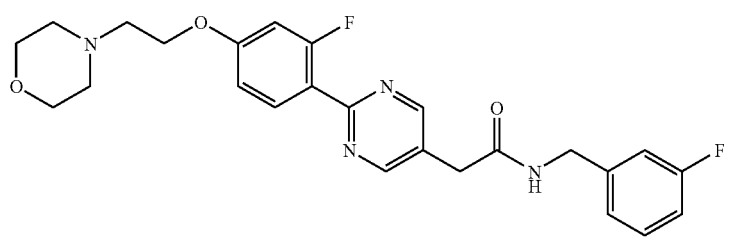
162
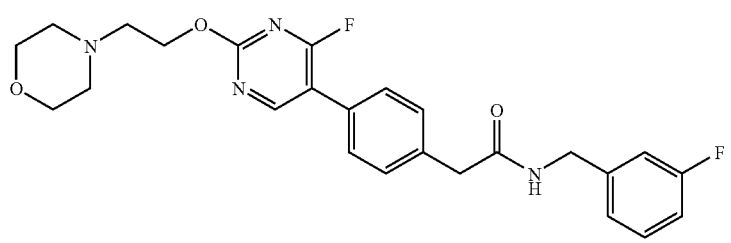
163

TABLE 2-continued
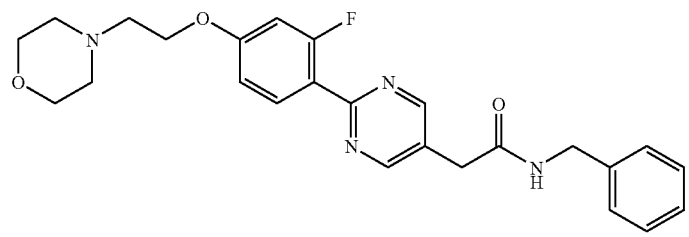
164
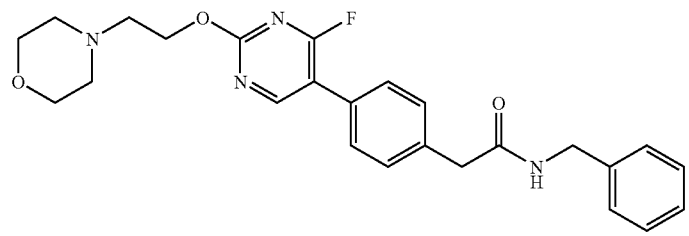
165
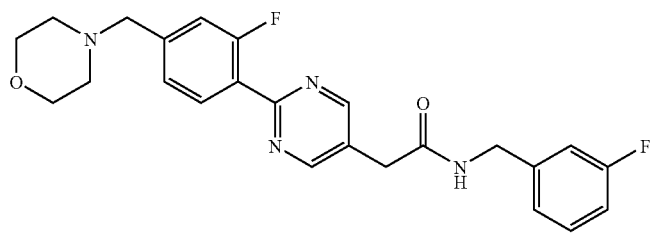
166
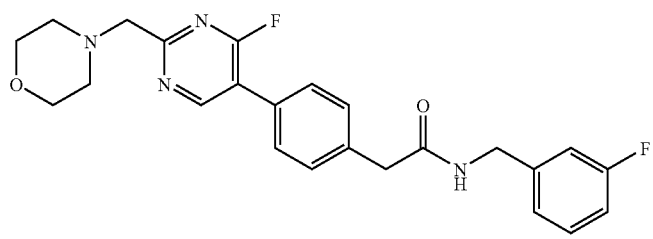
167
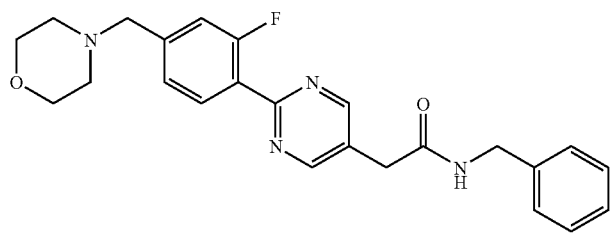
168
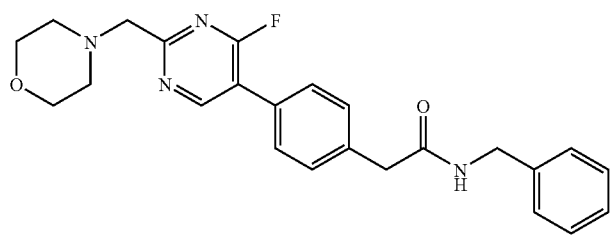
169

TABLE 2-continued
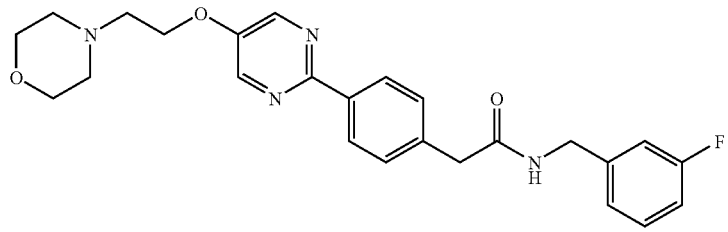 170
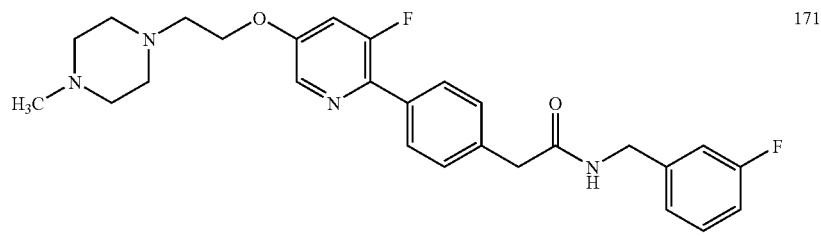 171
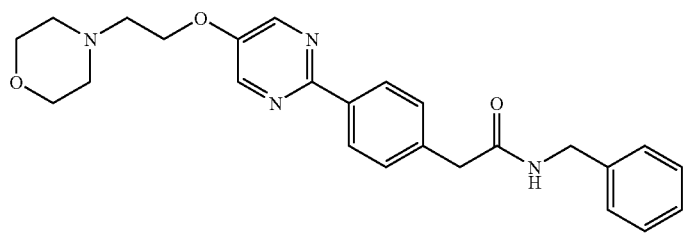 172
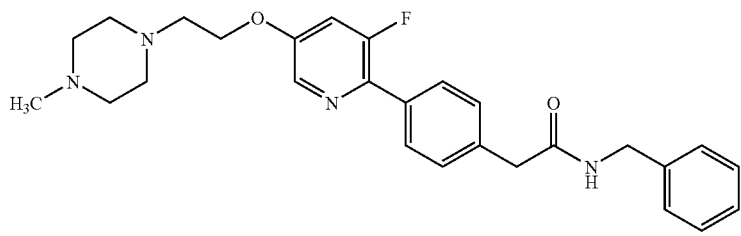 173
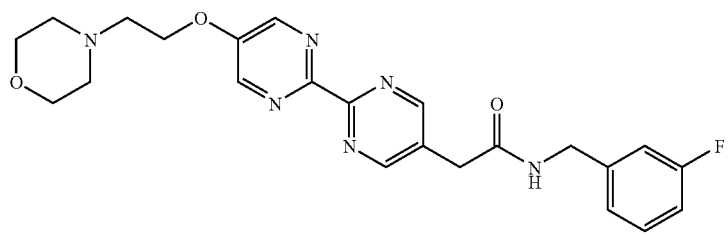 174
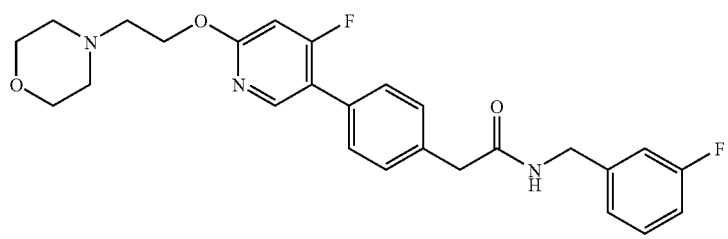 175

TABLE 2-continued
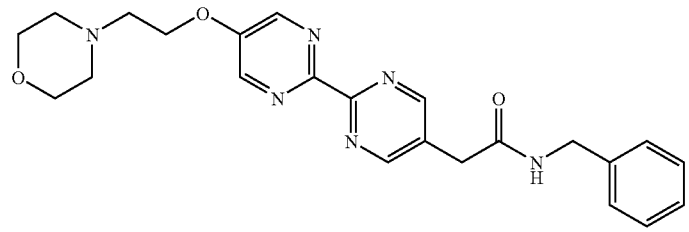
176
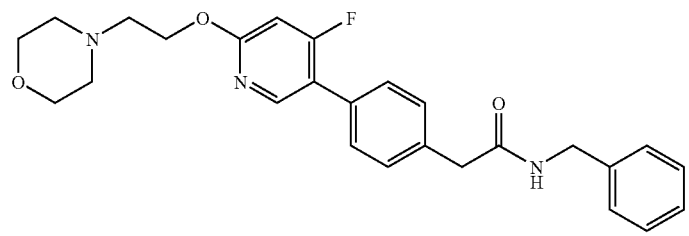
177
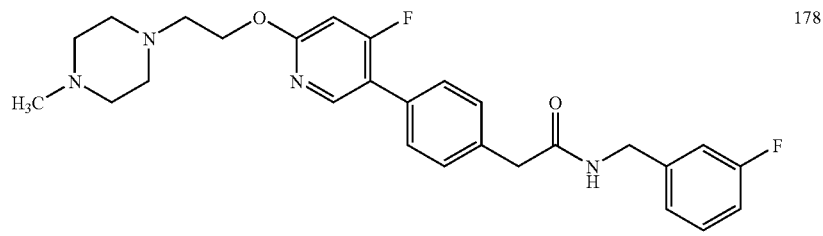
178
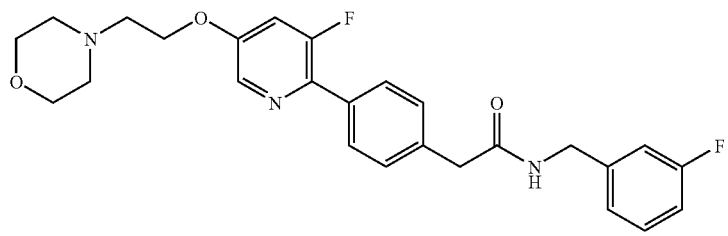
179
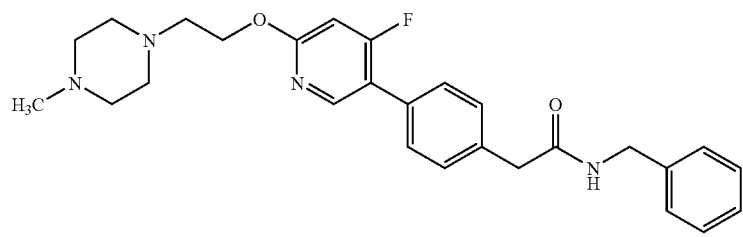
180
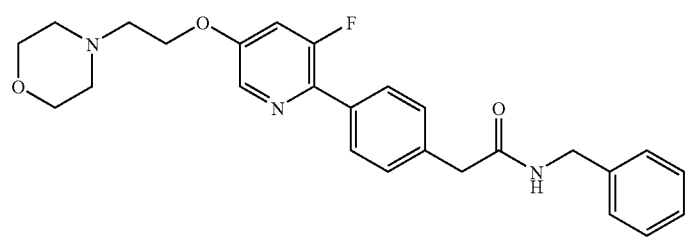
181

TABLE 2-continued
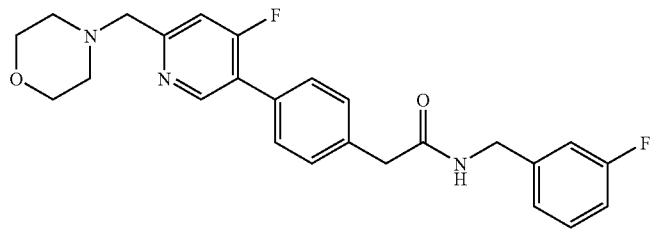 182
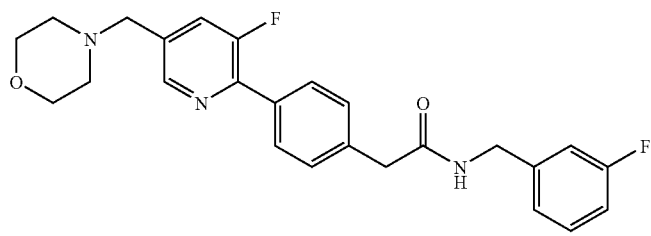 183
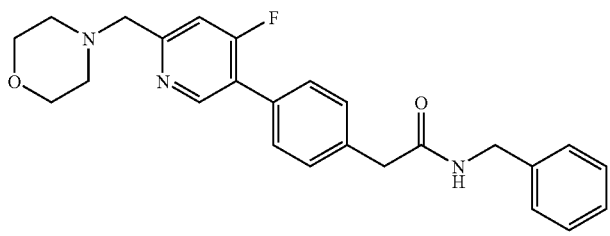 184
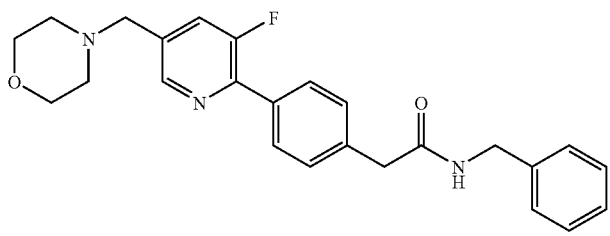 185
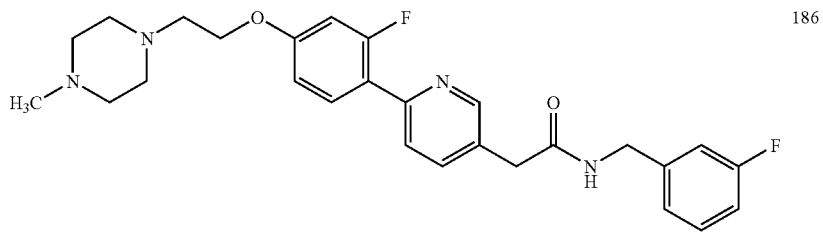 186
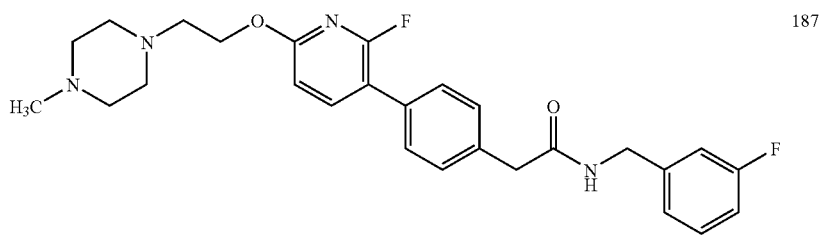 187

TABLE 2-continued
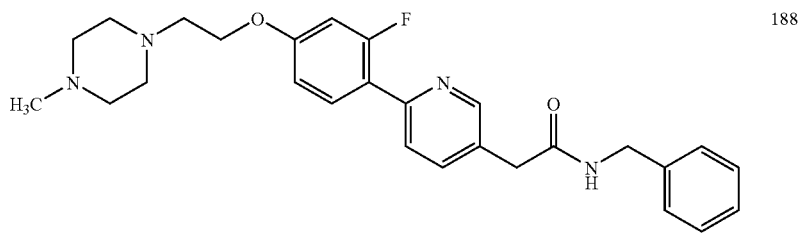
188
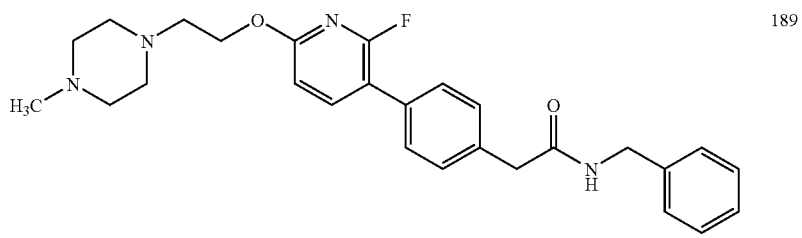
189
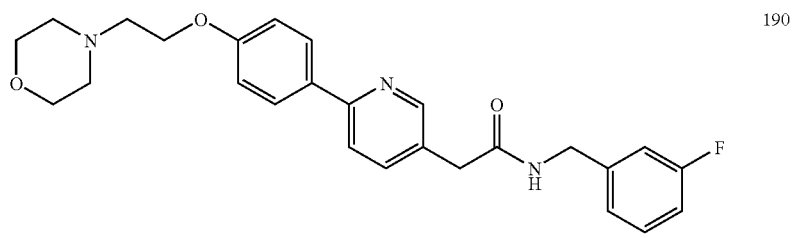
190
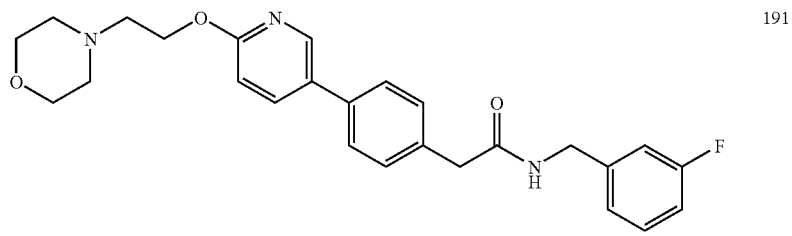
191
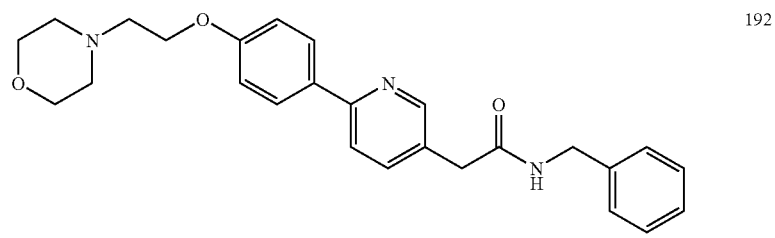
192
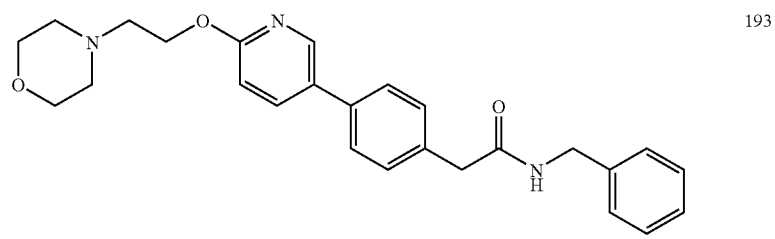
193

TABLE 2-continued
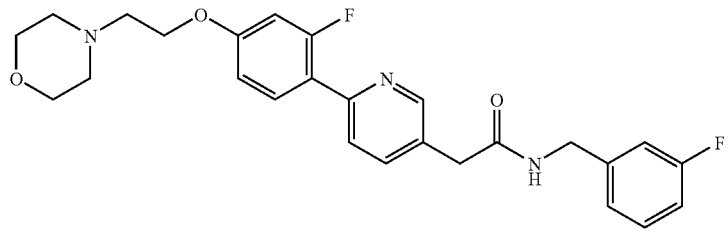
194
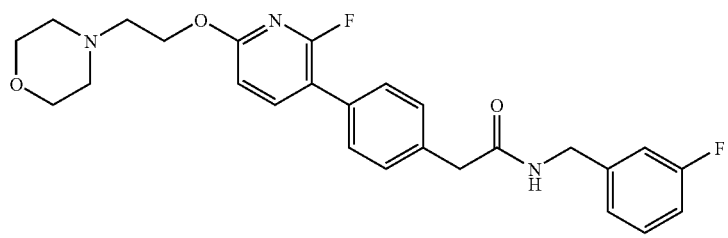
195
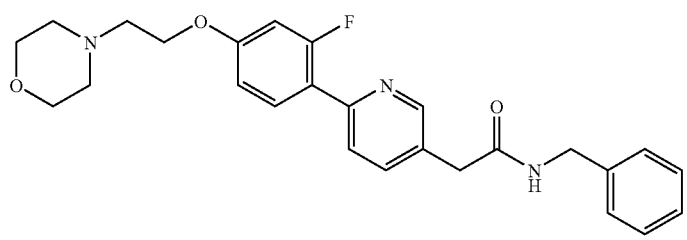
196
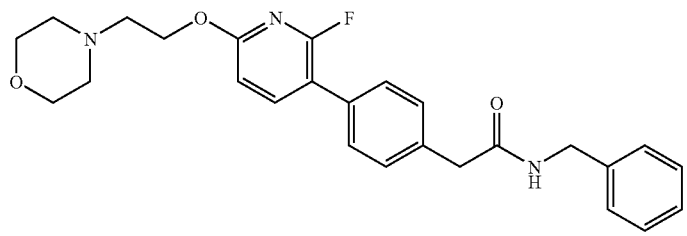
197
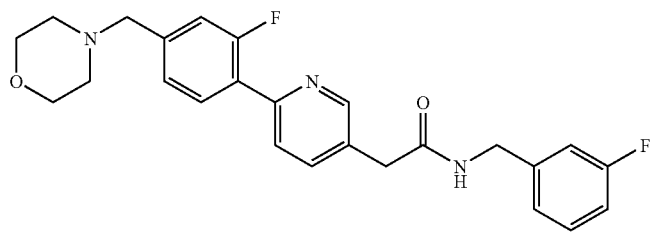
198
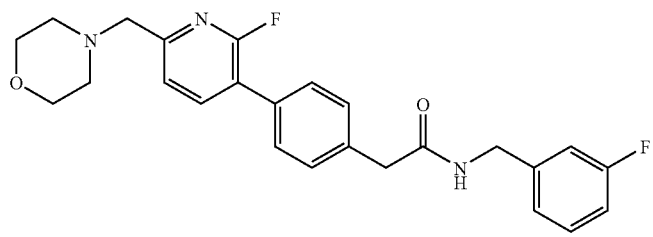
199

TABLE 2-continued
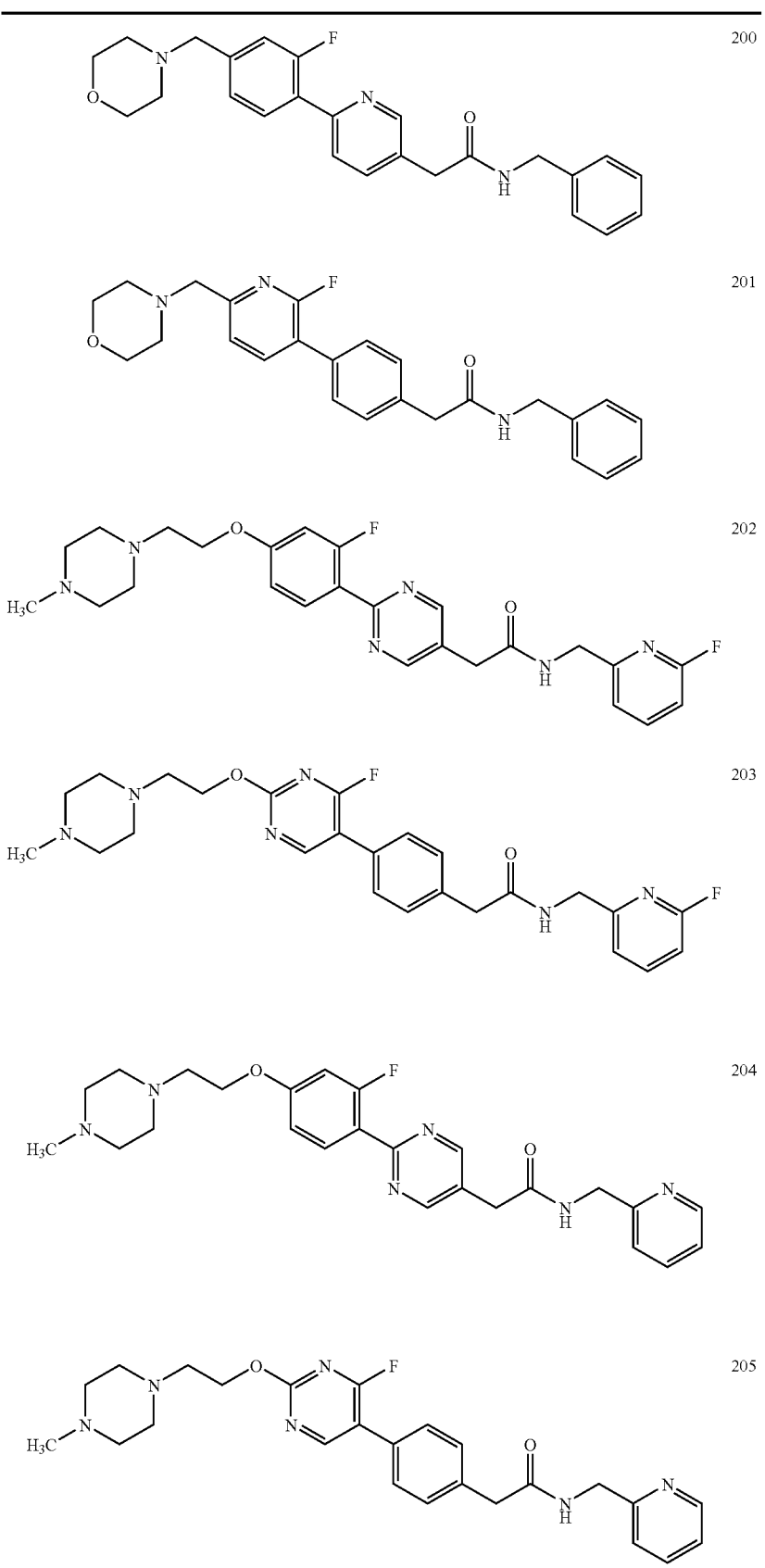

TABLE 2-continued
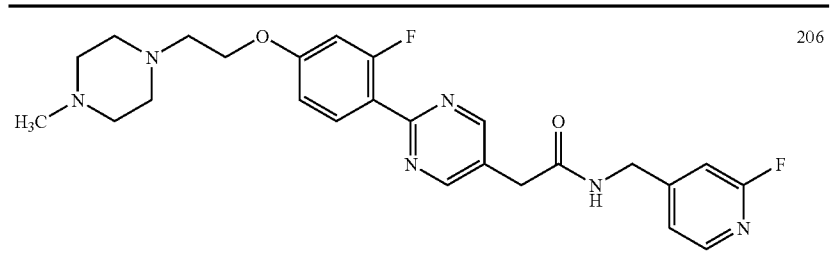 206
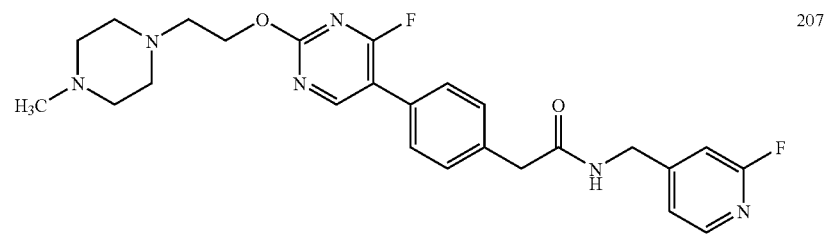 207
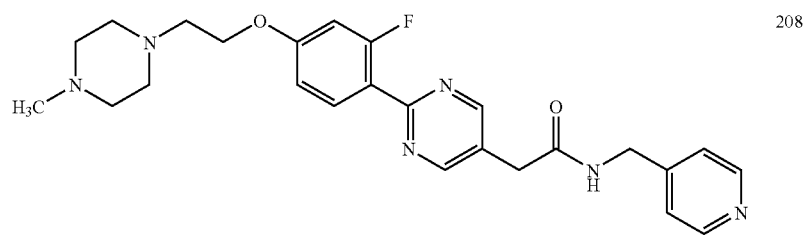 208
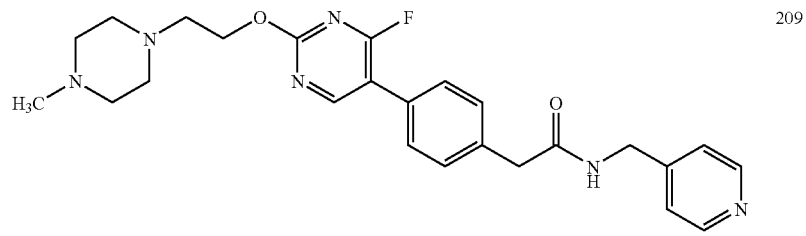 209
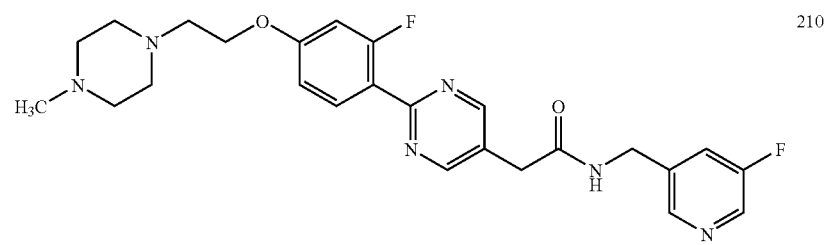 210
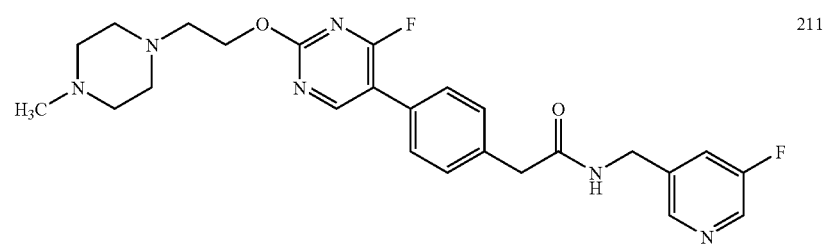 211

TABLE 2-continued
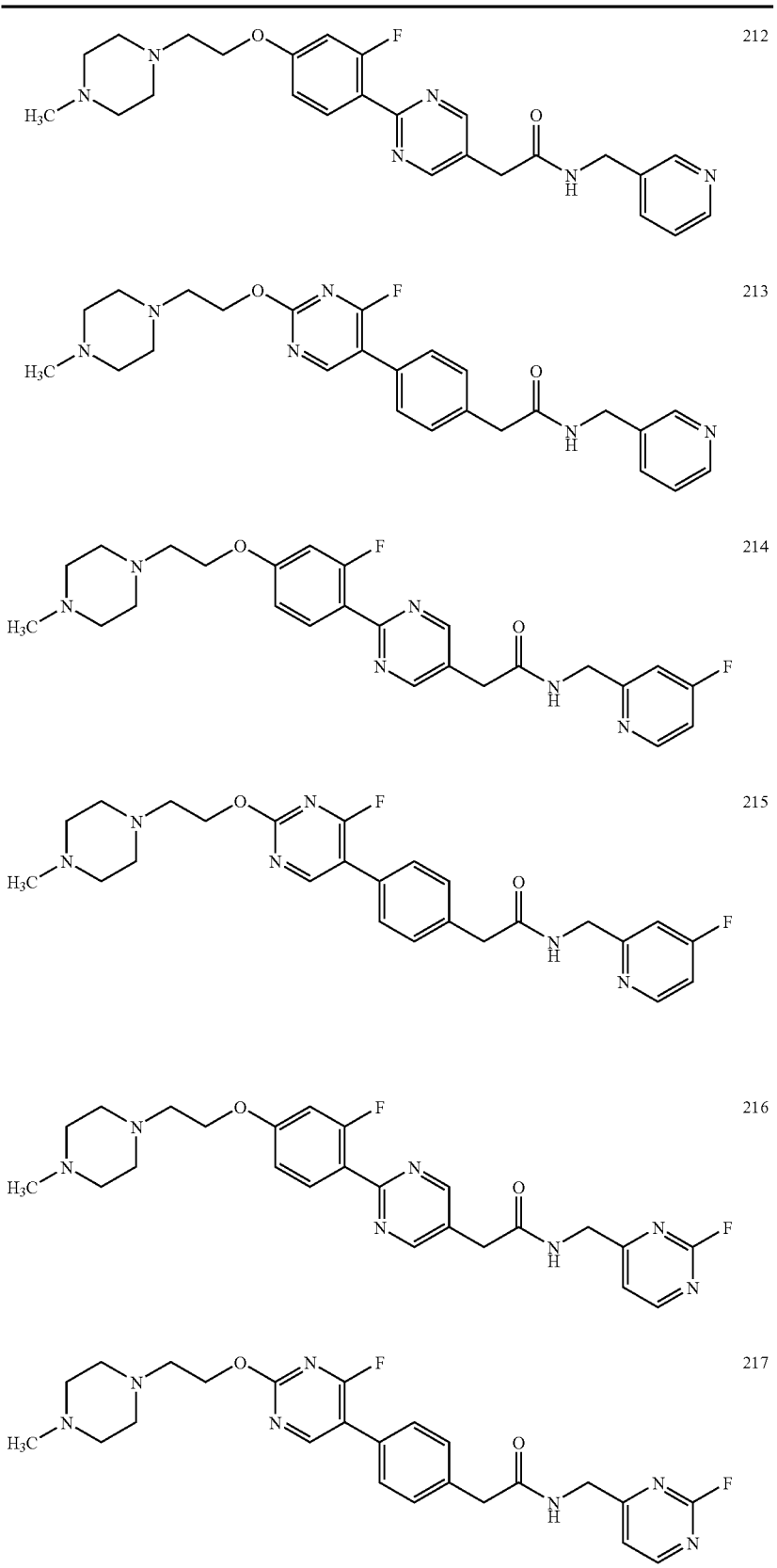

TABLE 2-continued
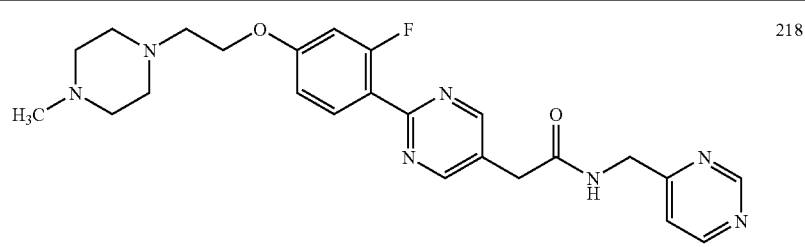 218
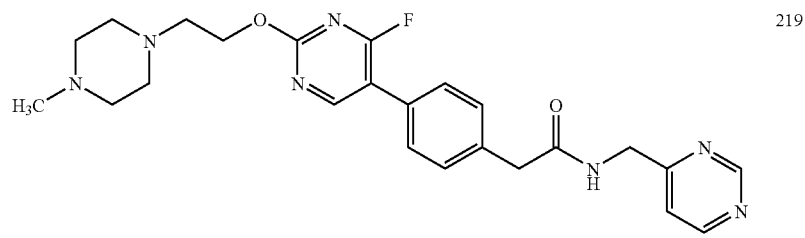 219
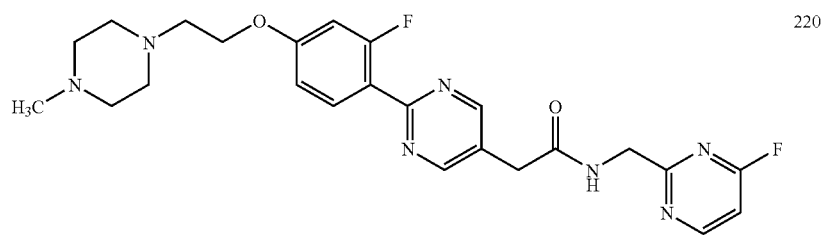 220
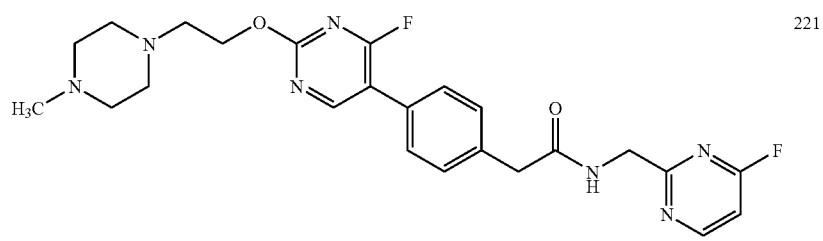 221
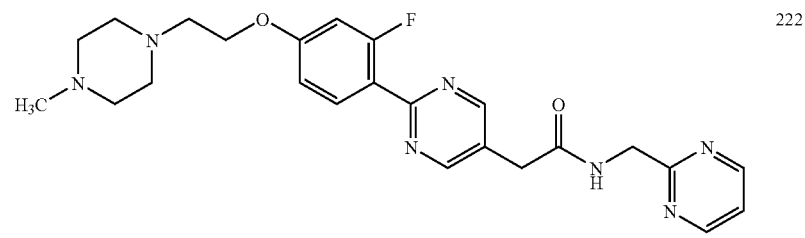 222
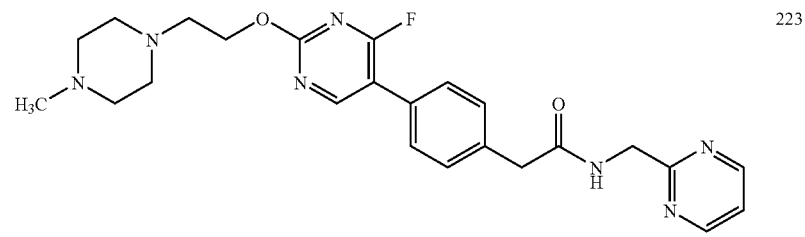 223

TABLE 2-continued
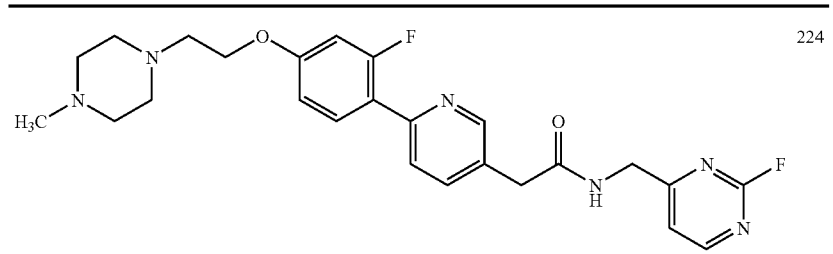
224
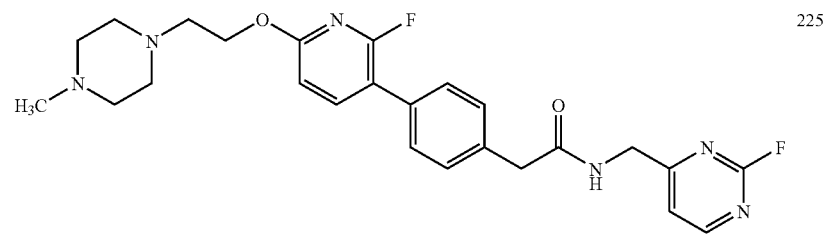
225
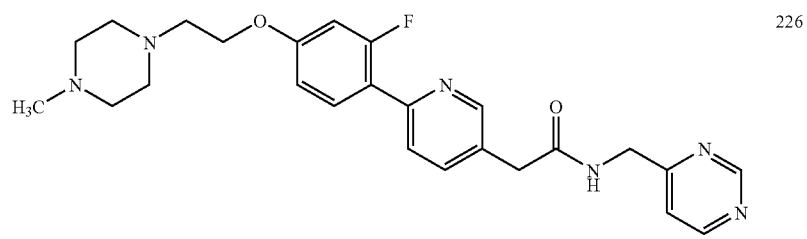
226
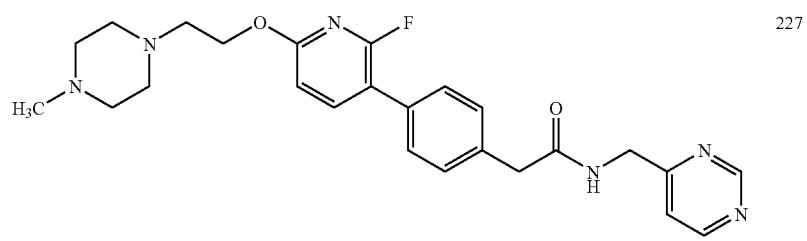
227
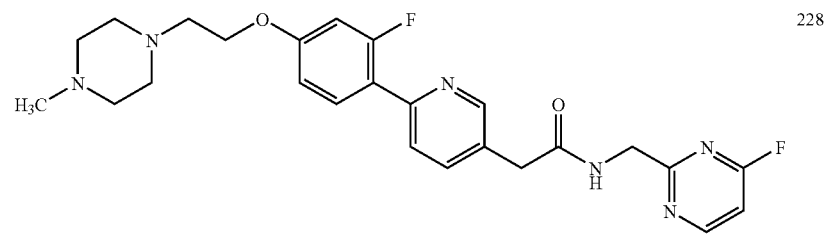
228
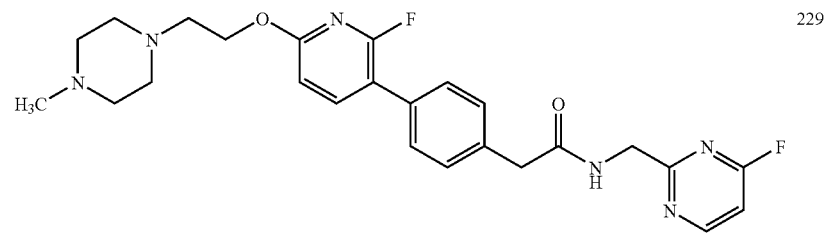
229

TABLE 2-continued
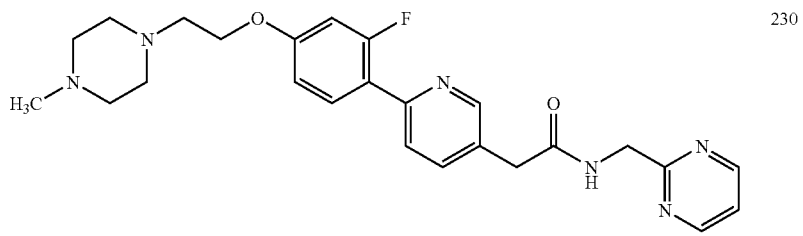
230
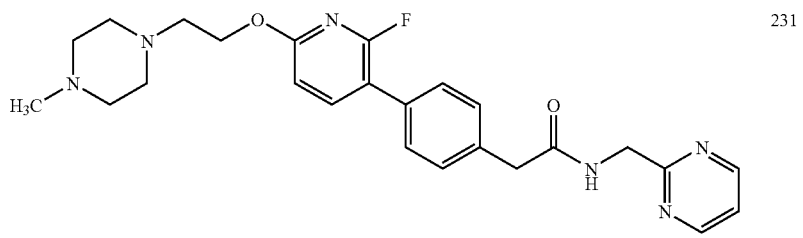
231
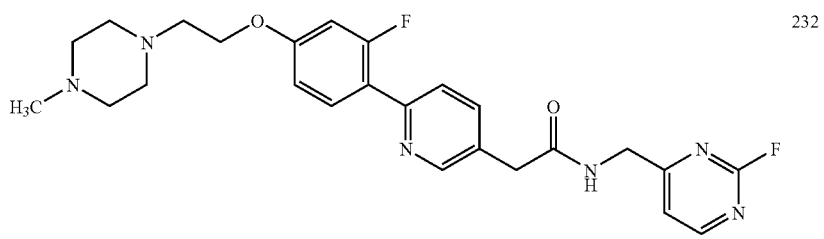
232
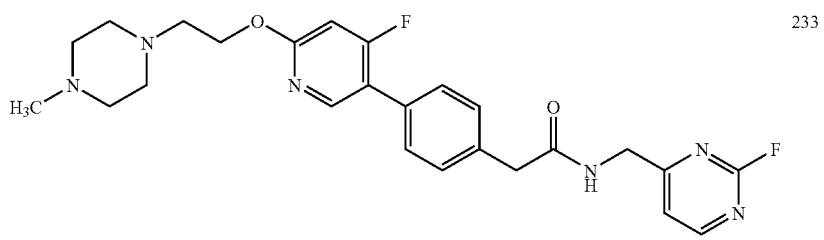
233
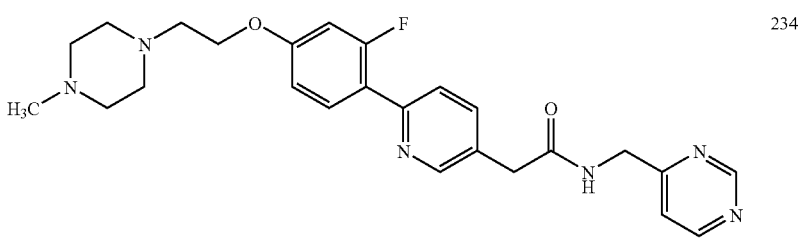
234
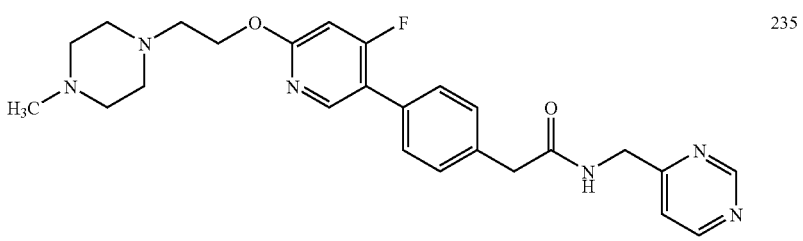
235

TABLE 2-continued
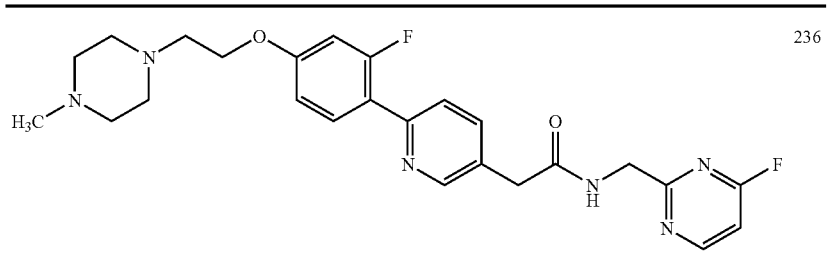
236
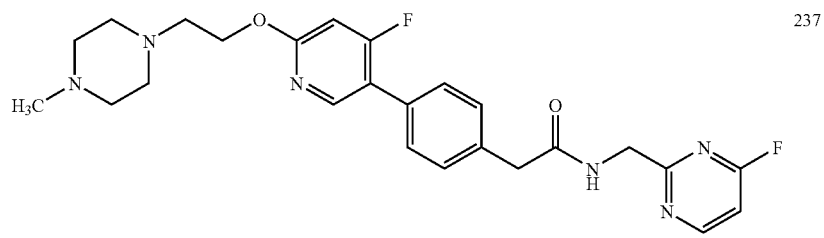
237
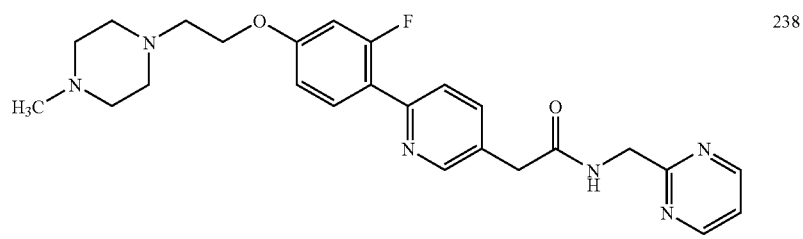
238
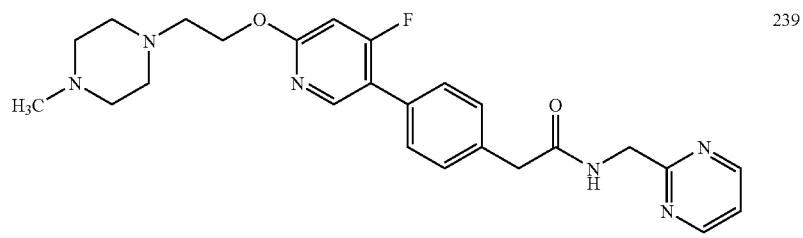
239
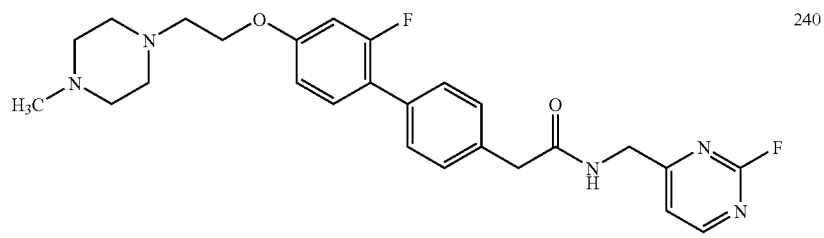
240
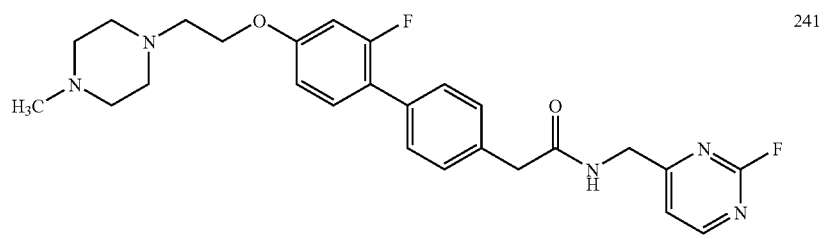
241

TABLE 2-continued
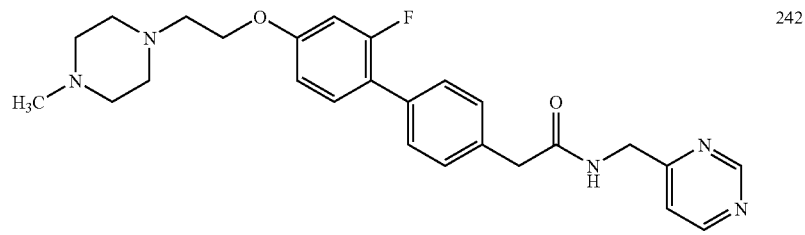 242
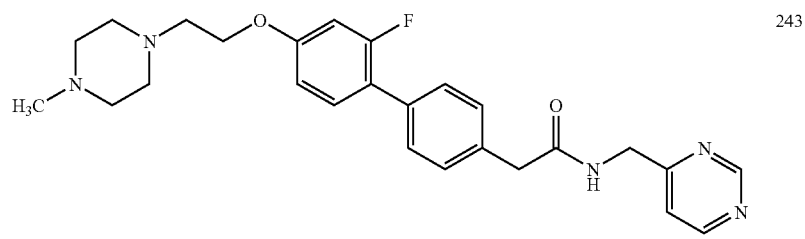 243
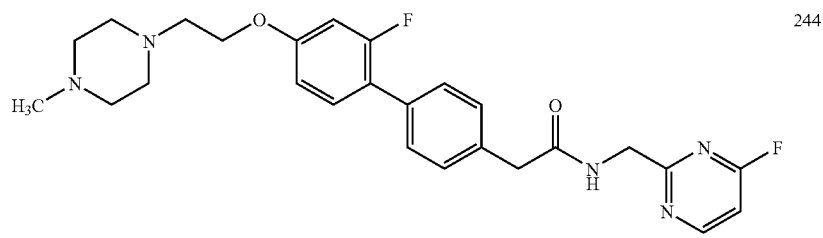 244
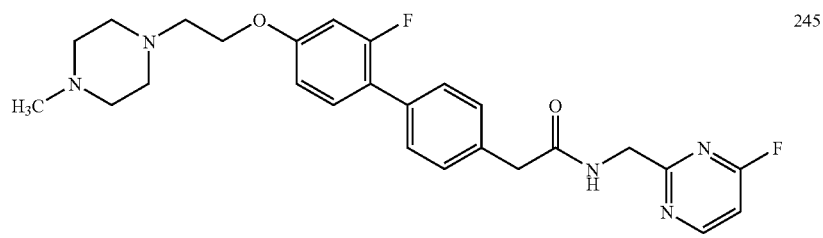 245
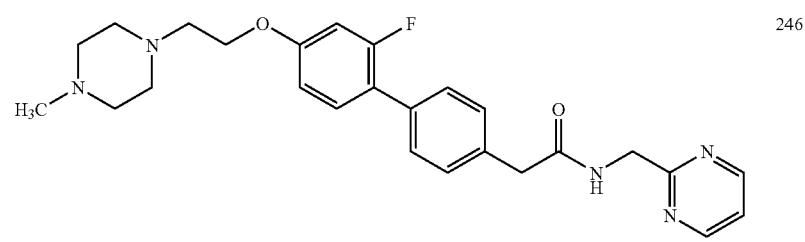 246
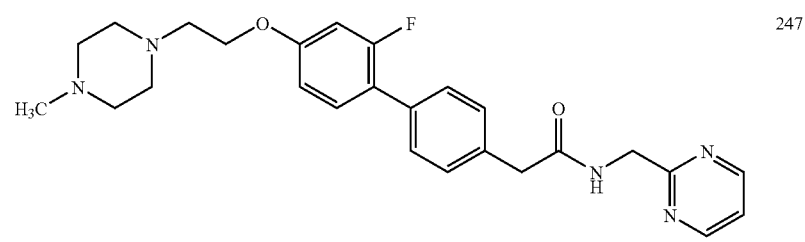 247

Compound of the invention include compounds of Formula IA, and salts, solvates, hydrates, or prodrugs thereof;

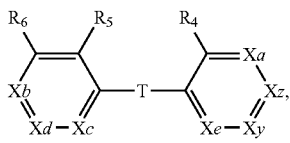

(Formula IA)

wherein: T is absent (i.e., the rings are connected by a bond), $CR_{12}R_{13}$, $C(O)$, $O$, $S$, $S(O)$, $S(O)_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$ or N, or N—O;

$X_b$ is $CR_b$, N, or N—O;

$X_c$ is $CR_c$ or N, or N—O;

$X_d$ is $CR_d$ or N, or N—O;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

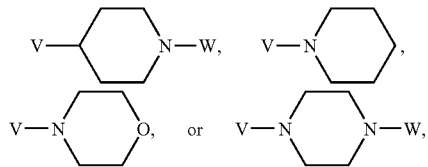

wherein W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $OPO_3H_2$, $OPO_3H_2$, $NH_2$, $NHR_{19}$, $NHR_{20}R_{21}$,

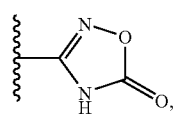

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

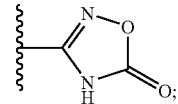

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

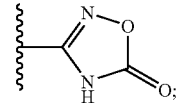

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

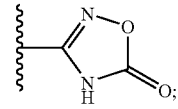

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or $R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, $-CH_2-$, $-CH_2CH_2-$, $-CH_2CH_2CH_2-$, $-O-CH_2-$, $-OCH_2CH_2-$ or $-OCH_2CH_2CH_2-$;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl; and Z is $(CHR_1)_n-C(O)-NR_2(CHR_3)_m-Ar$, where Ar is a substituted or unsubstituted aryl or nitrogen-containing heteroaryl group, $R_1$, $R_2$, and $R_3$ are independently H or $C_1$, $C_2$, $C_3$, $C_4$, $C_5$, or $C_6$ alkyl; and n and m are, independently 0, 1, or 2;

provided that at least one of $R_a$, $R_b$, $R_c$, $R_d$, $R_e$, $R_4$, $R_5$, and $R_6$ is P.

In one embodiment of the invention, at least one of $X_a$, $X_b$, $X_c$, $X_d$, $X_e$, $X_y$ and $X_z$ is N. In another embodiment, at least two of $X_a$, $X_b$, $X_c$, $X_d$, $X_e$, $X_y$ and $X_z$ are N. In another embodiment, at least one of $X_a$ and $X_y$ is N. For example, both $X_a$ and $X_y$ are N. In another embodiment, $X_a$, $X_b$, $X_c$, $X_d$, and $X_e$ are not each N or N—O. In another embodiment, $X_c$, $X_d$, and $X_e$ are not each N or N—O.

In one embodiment, T is absent. In another embodiment, $X_b$ is $CR_b$. In another embodiment, $R_b$ is P. For example, in one embodiment, P is O-lower ($C_1$, $C_2$, $C_3$, $C_4$, $C_5$, or $C_6$) alkyl-K. In one embodiment, lower ($C_1$, $C_2$, $C_3$, $C_4$, $C_5$, or $C_6$) alkyl is $CH_2CH_2CH_2$. In one embodiment, lower ($C_1$, $C_2$, $C_3$, $C_4$, $C_5$, or $C_6$) alkyl is branched alkyl. For example, branched alkyl is

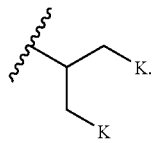

In another embodiment, K, L, M, N, or Q, if present, is lower $C_1$, $C_2$, $C_3$, $C_4$, $C_5$ or $C_6$ alkoxy. For example, K is methoxy. In one embodiment, branched alkyl is

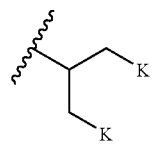

and K is methoxy. In another embodiment, K, L, M, N, or Q, if present, is COOH. For example, in one embodiment, K is COOH. In another embodiment, K, L, M, N, or Q, if present, is aryl. For example, aryl is tetrazole.

In one embodiment, $R_b$ is

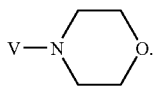

In another embodiment, $R_b$ is

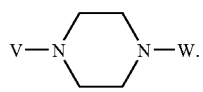

In one embodiment, V is —$OCH_2CH_2$. In another embodiment, V is a bond. In one embodiment, W is $C_1$, $C_2$, $C_3$, $C_4$, $C_5$, or $C_6$ alkyl. For example, W is methyl or ethyl.

In one embodiment, $X_z$ is CZ, further wherein Z is

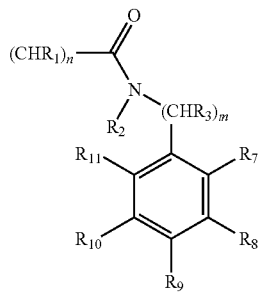

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

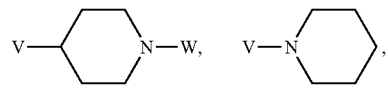

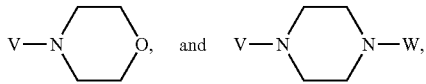

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl. In another embodiment, at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl. In another embodiment, at least one of $R_8$ or $R_{10}$ is halogen. For example, halogen is fluorine. In another embodiment, at least one of $R_7$ or $R_{11}$ is $C_1$, $C_2$, $C_3$, $C_4$, $C_5$, or $C_6$ alkoxy or O-benzyl. For example, at least one of $R_7$ or $R_{11}$ is ethoxy or at least one of $R_7$ or $R_{11}$ is O-benzyl. In one embodiment, $R_1$ is H. In one embodiment, n is 1. In one embodiment, $R_2$ is H. In one embodiment, $R_3$ is H. In one embodiment, m is 1. In another embodiment, m and n are each 1 and $R_2$ and $R_3$ are each H.

In one embodiment, $R_4$ and $R_6$ are each H. In another embodiment $R_5$ is selected from halogen and $C_1$, $C_2$, $C_3$, $C_4$, $C_5$, or $C_6$ alkyl. In one embodiment, $R_5$ is halogen. For example, $R_5$ is Cl or F. In another embodiment, $R_5$ is $C_1$, $C_2$, $C_3$, $C_4$, $C_5$, or $C_6$ alkyl. For example, $R_5$ is methyl or ethyl.

The invention includes a solvate of a compound according to Formula IA. The invention includes a hydrate of compound according to Formula IA. The invention includes an acid addition salt of a compound according to Formula IA. For example, a hydrochloride salt. In another embodiment, the invention includes a pharmaceutically acceptable salt. The invention includes a composition comprising a compound of Formula IA and at least one pharmaceutically acceptable excipient.

Certain compounds of the invention include compounds selected from Table 3.
TABLE 3
| Compound # | Structure |
| --- | --- |
| 248 | 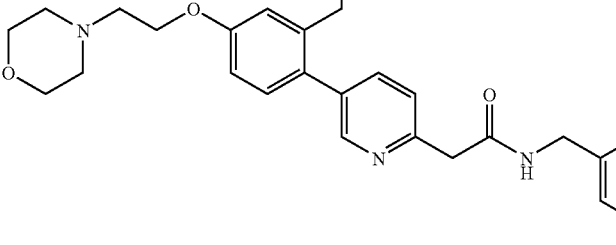 |
| 249 | 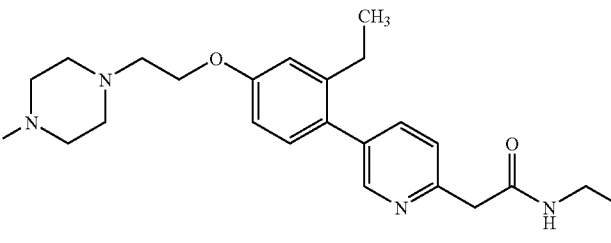 |
| 250 | 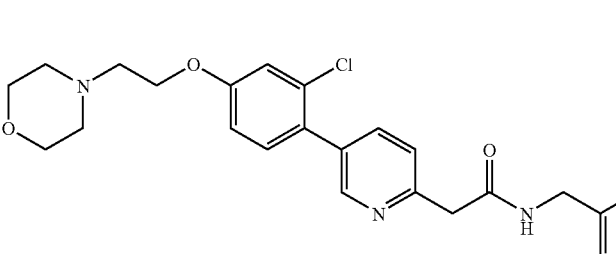 |
| 251 | 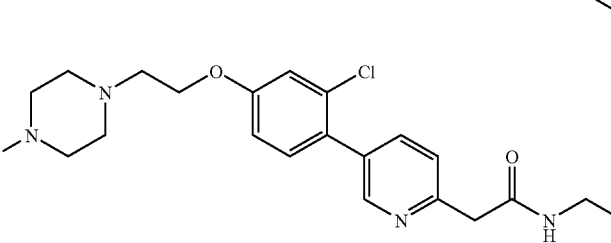 |
| 252 | 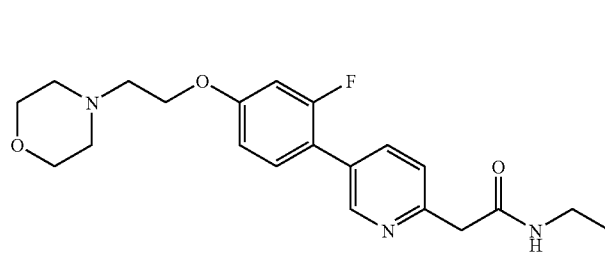 |

TABLE 3-continued

| Compound # | Structure |
|---|---|
| 253 | 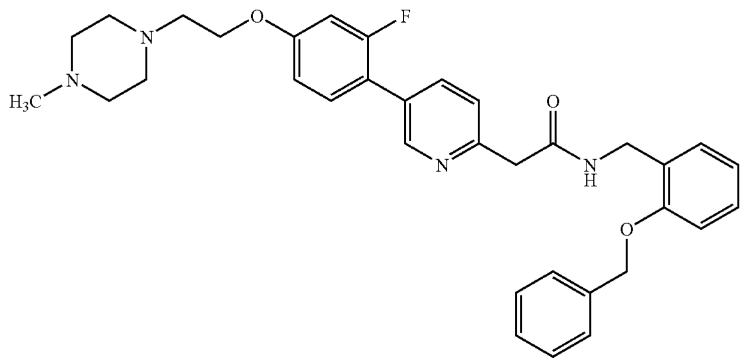 |
| 254 | 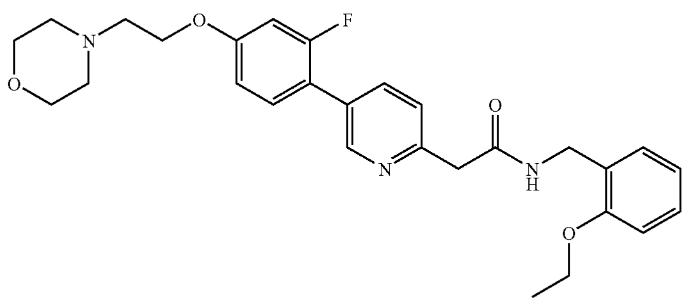 |
| 255 | 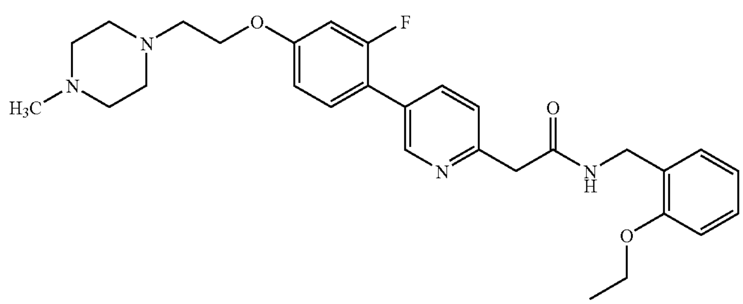 |
| 256 | 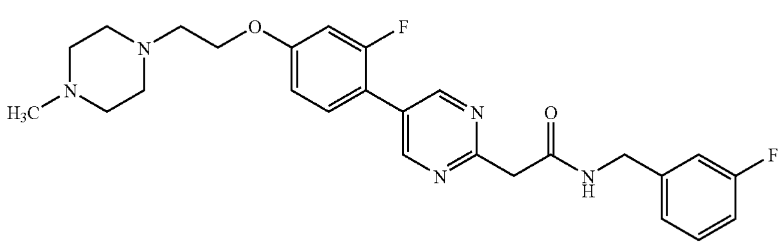 |
| 257 | 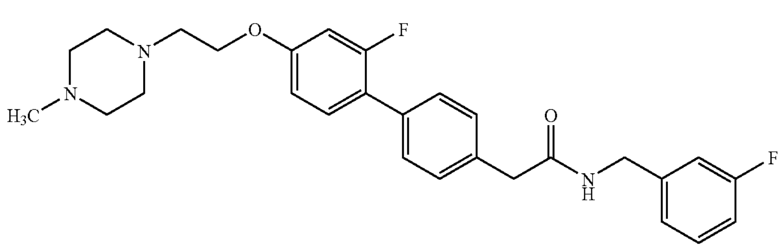 |

TABLE 3-continued
| Compound # | Structure |
|---|---|
| 258 | 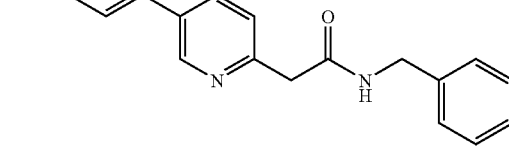 |
| 259 | 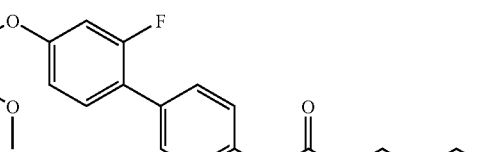 |
| 260 | 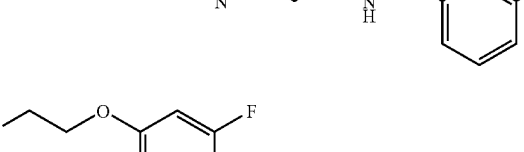 |
| 261 | 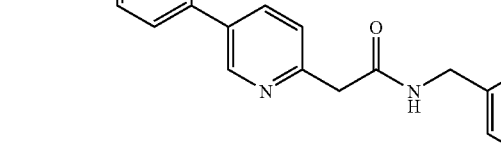 |
| 262 | 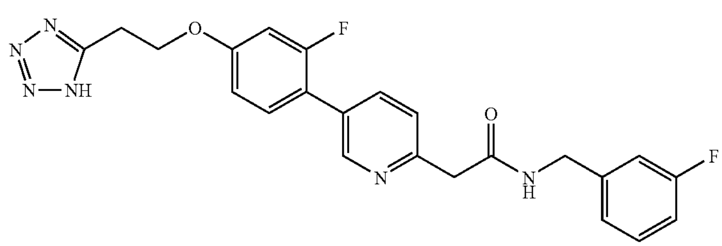 |
| 263 | 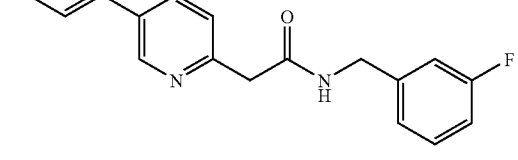 |

TABLE 3-continued

| Compound # | Structure |
|---|---|
| 264 | 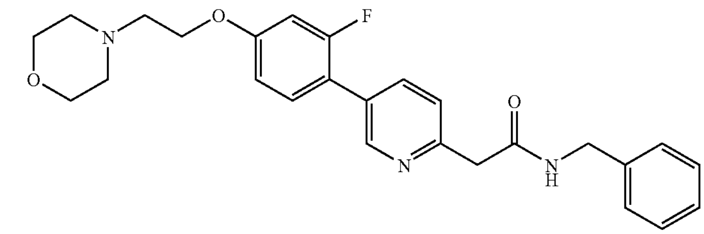 |
| 265 | 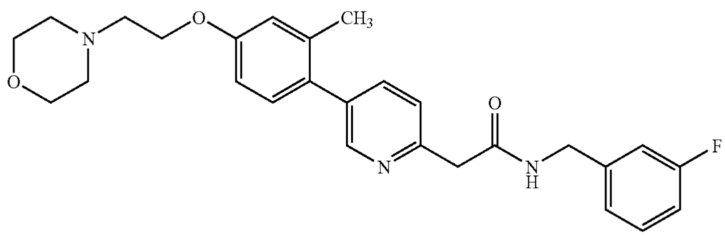 |
| 266 | 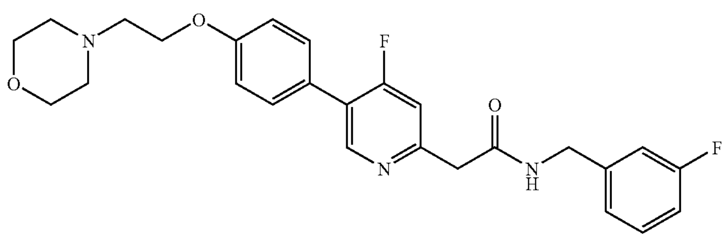 |
| 267 | 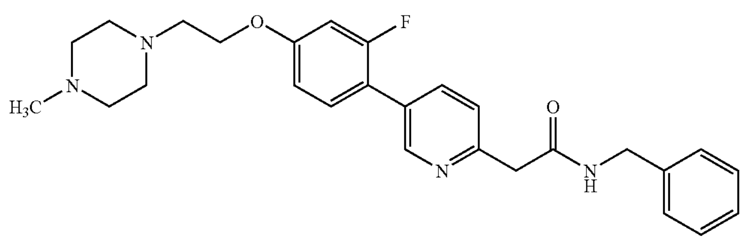 |
| 268 | 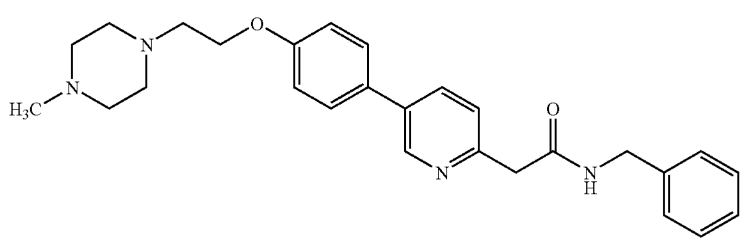 |
| 269 | 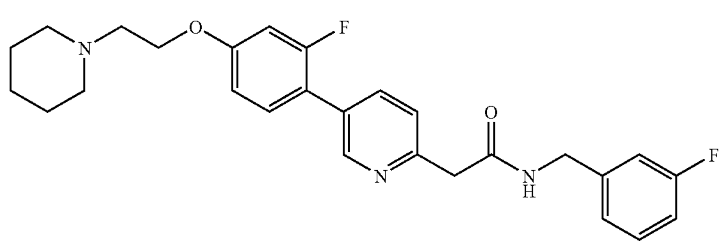 |

TABLE 3-continued
| Compound # | Structure |
|---|---|
| 270 | 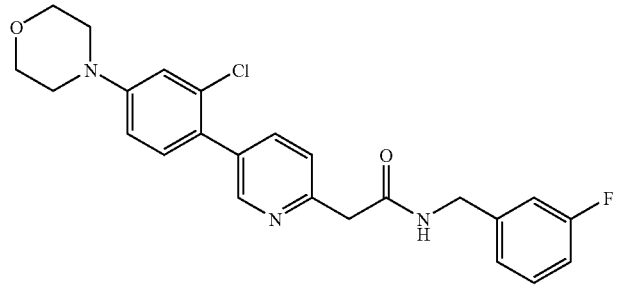 |
| 271 | 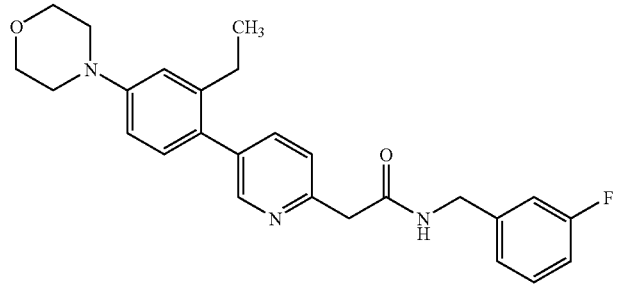 |
| 272 | 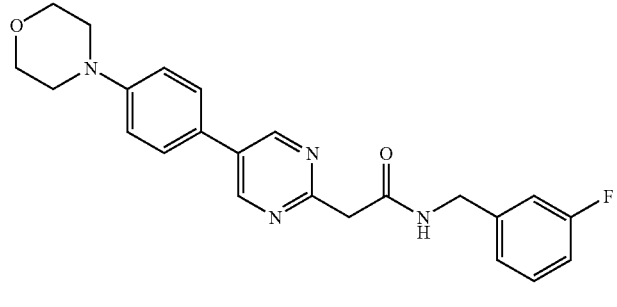 |
| 273 | 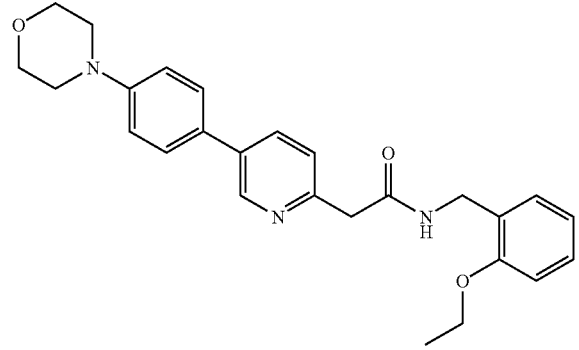 |

TABLE 3-continued

| Compound # | Structure |
|---|---|
| 274 | 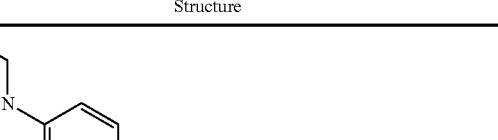 |

The invention relates to a solvate of a compound according to one of Formulae I, IA, II, III, IV, V, VI, VII, VIII, IX, X, XI, XII, or XIII. The invention also relates to a hydrate of a compound according to one of Formulae I, IA, II, III, IV, V, VI, VII, VIII, IX, X, XI, XII, or XIII.

The invention also relates to an acid addition salt of a compound according to one of Formulae I, IA, II, III, IV, V, VI, VII, VIII, IX, X, XI, XII, or XIII. For example, a hydrochloride salt.

Further, the invention relates to a prodrug of a compound according to one of Formulae I, IA, II, III, IV, V, VI, VII, VIII, IX, X, XI, XII, or XIII.

The invention also relates to a pharmaceutically acceptable salt of a compound of one of Formulae I, IA, II, III, IV, V, VI, VII, VIII, IX, X, XI, XII, or XIIII.

The invention includes compositions comprising a compound according to one of Formulae I, IA, II, III, IV, V, VI, VII, VIII, IX, X, XI, XII, or XIII and at least one pharmaceutically acceptable excipient.

Certain compounds of the invention are non-ATP competitive kinase inhibitors.

The invention also includes a method of preventing or treating a cell proliferation disorder by administering a pharmaceutical composition that includes a compound according to one of Formulae I, IA, II, III, Iv, V, VI, VII, VIII, IX, X, XI, XII, or XIII, or a salt, solvate, hydrate, or prodrug thereof, and at least one pharmaceutically acceptable excipient to a subject in need thereof.

For example, the cell proliferation disorder is pre-cancer or cancer. The cell proliferation disorder treated or prevented by the compounds of the invention may be a cancer, such as, for example, colon cancer or lung cancer.

The cell proliferation disorder treated or prevented by the compounds of the invention may be a hyperproliferative disorder The cell proliferation disorder treated or prevented by the compounds of the invention may be psoriases.

For example, the treatment or prevention of the proliferative disorder may occur through the inhibition of a tyrosine kinase. For example, the tyrosine kinase can be a Src kinase or focal adhesion kinase (FAK).

The invention relates to a method of treating or preventing a disease or disorder that is modulated by kinase inhibition, by administering a pharmaceutical composition that includes a compound according to Formula I or IA or one of Formulae II, III, IV, V, VI, VII, VIII, IX, X, XI, XII, or XIII, or a salt, solvate, hydrate, or prodrug thereof, and at least one pharmaceutically acceptable excipient. For example, the disease or disorder that is modulated by tyrosine kinase inhibition is cancer, pre-cancer, a hyperproliferative disorder, or a microbial infection. For example, the compound is a compound according to Formula I, IA or II.

The pharmaceutical composition of the invention may modulate a kinase pathway. For example, the kinase pathway is a Src kinase pathway, or focal adhesion kinase pathway.

The pharmaceutical composition of the invention may modulate a kinase directly. For example, the kinase is Src kinase, or focal adhesion kinase.

Certain pharmaceutical compositions of the invention are non-ATP competitive kinase inhibitors.

For example, the compounds of the invention are useful to treat or prevent a microbial infection, such as a bacterial, fungal, parasitic or viral infection.

Certain pharmaceutical compositions of the invention include a compound selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 93, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, and 137. For example, the pharmaceutical composition includes Compound 33, 38, 40, 76, 133, 134, 136 or 137.

Certain pharmaceutical compositions of the invention include a compound selected from Compound 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, or 247. For example, the pharmaceutical composition includes Compound 146 or 147.

Certain pharmaceutical compositions of the invention include a compound selected from Compounds 248-274. For example, the compound of the invention is Compound 248, 249, 250, 251, 252, 253, 254, 255, 256, 257, 258, 259, 260, 261, 262, 263, 264, 265, 266, 267, 268, 269, 270, 271, 272, 273, or 274.

A compound of the invention may be used as a pharmaceutical agent. For example, a compound of the invention is used as an anti-proliferative agent, for treating humans and/or animals, such as for treating humans and/or other mammals. The compounds may be used without limitation, for example, as anti-cancer, anti-angiogenesis, anti-microbial, anti-bacterial, anti-fungal, anti-parasitic and/or anti-viral agents. Additionally, the compounds may be used for other cell proliferation-related disorders such as diabetic retinopathy, macular degeneration and psoriases. Anti-cancer agents include anti-metastatic agents.

The compound of the invention used as a pharmaceutical agent may be selected from Compounds 1-136 and 137. For example, the compound of the invention used as a pharmaceutical agent is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 93, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137. For example, the compound of the invention used as a pharmaceutical agent is selected from Compounds 33, 38, 40, 76, 133, 134, 136 and 137.

Certain pharmaceutical agents include a compound selected from the Compound 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, or 247. For example, the compound of the invention used as a pharmaceutical agent is selected from Compounds 146 and 147.

Certain pharmaceutical agents include a compound selected from Compounds 248, 249, 250, 251, 252, 253, 254, 255, 256, 257, 258, 259, 260, 261, 262, 263, 264, 265, 266, 267, 268, 269, 270, 271, 272, 273, or 274.

In one aspect of the invention, a compound of the invention, for example, a compound of Formula I or IA, or one of Formulae II, III, IV, V, VI, VII, VIII, IX, X, XI, XII, or XIII, is used to treat or prevent a cell proliferation disorder in an subject. In one aspect of the embodiment, the cell proliferation disorder is pre-cancer or cancer. In another aspect of the embodiment, the cell proliferation disorder is a hyperproliferative disorder. In another embodiment, prevention or treatment of the cell proliferation disorder, cancer or hyperproliferative disorder occurs through the inhibition of a kinase. In another embodiment, prevention or treatment of the cell proliferation disorder, cancer or hyperproliferative disorder occurs through the inhibition of a tyrosine kinase. In another embodiment, prevention or treatment of the cell proliferation disorder, cancer or hyperproliferative disorder occurs through the inhibition of Src kinase or focal adhesion kinase (FAK). In another embodiment, the subject is a mammal. In one embodiment, the subject is human.

The invention is also drawn to a method of treating or preventing cancer or a proliferation disorder in a subject, comprising administering an effective amount of a compound of the invention, for example, a compound of Formula I or one of Formulae II, III, IV, V, VI, VII, VIII, IX, X, XI, XII, or XIII. For example, the compound of the invention may be a kinase inhibitor. The compound of the invention may be a non-ATP competitive kinase inhibitor. The compound of the invention may inhibit a kinase directly, or it may affect the kinase pathway.

Another aspect of the invention includes a method of protecting against or treating hearing loss in a subject comprising administering a compound having the Formulae I, IA, II, III, IV, V, VI, VII, VIII, IX, X, XI, XII, and XIII. In one embodiment, the compound inhibits one or more components of a kinase signaling cascade. In one embodiment, the compound is an allosteric inhibitor. In one embodiment, the compound is a peptide substrate inhibitor. In one embodiment, the compound does not inhibit ATP binding to the protein kinase. In one embodiment, the compound inhibits a Src family protein kinase. In one embodiment, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically e.g., by administering drops into the ear, intraarterially, intralesionally, by metering pump, or by application to mucous membranes. In another embodiment, the compound is administered with a pharmaceutically acceptable carrier.

In one embodiment, the compound is administered before initiation of hearing loss. In another embodiment, the compound is administered after initiation of hearing loss.

In one embodiment, the compound is administered in combination with a drug that causes hearing loss e.g., cis platinum or an aminoglycoside antibiotic. In another embodiment, the compound is administred in combination with a drug that targets hairy cells.

In one embodiment, at least one of $X_a$, $X_b$, $X_c$, $X_d$, $X_e$, $X_y$ and $X_z$ is N. In another embodiment, T is absent. In another embodiment, $X_z$ is CZ and Z is

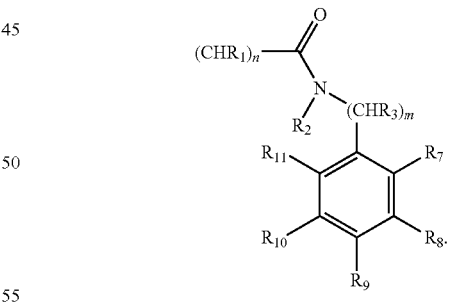

In one embodiment, m and n are each 1 and $R_2$ and $R_3$ are each H. In another embodiment, at least one of $R_7$, $R_8$, $R_9$, $R_{10}$ and $R_{11}$ is halogen, $C_1$, $C_2$, $C_3$, $C_4$, $C_5$, or $C_6$ alkyl, or O-benzyl. In one embodiment, the compound is Compound 25 (KX1-329).

Another aspect of the invention includes a method of protecting against or treating osteoporosis in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, at least one of $X_a$, $X_b$, $X_c$, $X_d$, $X_e$, $X_y$, and $X_z$ is N. In another embodiment, T is absent. In another embodiment, $X_z$ is CZ and Z is

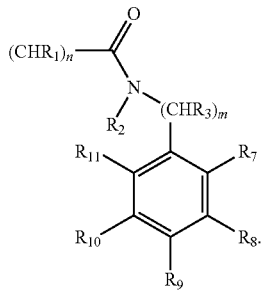

In one embodiment, m and n are each 1 and $R_2$ and $R_3$ are each H. In another embodiment, at least one of $R_7$, $R_8$, $R_9$, $R_{10}$ and $R_{11}$ is halogen, $C_1$, $C_2$, $C_3$, $C_4$, $C_5$, or $C_6$ alkyl, or O-benzyl. In one embodiment, the compound is Compound 25 (KX1-329), Compound 38 (KX2-377), Compound 76 (KX2-361), Compound 133 (KX2-392), Compound 134 (KX2-391), or Compound 137 (KX2-394).

In one embodiment, the administration of the compound is carried out orally, parentally, subcutaneously, intravenously, intramuscularly, intraperitoneally, by intranasal installation, by intracavitary or intravesical installation, topically, intraarterially, intralesionally, by metering pump, or by application to mucous membranes. In one embodiment, the compound is administered with a pharmaceutically acceptable carrier. In one embodiment, the compound is administered before initiation of osteoporosis. In another embodiment, the compound is administered after initiation of osteoporosis.

Another aspect of the invention includes a method of protecting against or treating ophthalmic diseases e.g., macular degeneration, retinopathy, macular edema, etc. in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase. In another embodiment, the compound inhibits one or more components in the VEGF pathway.

In one embodiment, the administration of the compound is carried out orally, parentally, subcutaneously, intravenously, intramuscularly, intraperitoneally, by intranasal installation, by intracavitary or intravesical installation, topically (e.g., by administering drops to the eye), intraarterially, intralesionally, by metering pump, or by application to mucous membranes. In one embodiment, the compound is administered with a pharmaceutically acceptable carrier. In one embodiment, the compound is administered before initiation of the ophthalmic disease. In another embodiment, the compound is administered after initiation of ophthalmic disease.

Another aspect of the invention includes a method of protecting against or treating diabetes in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal installation, by intracavitary or intravesical installation, topically, intraarterially, intralesionally, by metering pump, or by application to mucous membranes. In one embodiment, the compound is administered with a pharmaceutically acceptable carrier. In one embodiment, the compound is administered before initiation of the diabetes. In another embodiment, the compound is administered after initiation of disease.

Another aspect of the invention includes a method of protecting against or treating obesity in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal installation, by intracavitary or intravesical installation, topically, intraarterially, intralesionally, by metering pump, or by application to mucous membranes. In one embodiment, the compound is administered with a pharmaceutically acceptable carrier. In one embodiment, the compound is administered before the subject is obese. In another embodiment, the compound is administered after the subject is obese.

Another aspect of the invention includes a method of protecting against or treating stroke in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal installation, by intracavitary or intravesical installation, topically, intraarterially, intralesionally, by metering pump, or by application to mucous membranes. In one embodiment, the compound is administered with a pharmaceutically acceptable carrier. In one embodiment, the compound is administered before a stroke has occurred. In another embodiment, the compound is administered after a stroke has occurred.

Another aspect of the invention includes a method of protecting against or treating athrosclerosis in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of regulating immune system activity in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of protecting against or treating hepatitis B in a subject comprising administering a compound having a Formulae I, IA, II, III, IV, V, VI, VII, VIII, IX, X, XI, XII, and XIII. In one embodiment, the compound inhibits one or more components of a kinase signaling cascade. In another embodiment, the compound is an allosteric inhibitor. In one embodiment, the compound is a peptide substrate inhibitor. In one embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the subject has contracted hepatitis B. In another embodiment, the compound is administered after the subject has contracted hepatitis B.

Another aspect of the invention is a method of preventing or treating a cell proliferation disorder comprising administering to a subject in need thereof a compound having the Formula IA. In one embodiment, the compound inhibits one or more components of a protein kinase signaling cascade. In another embodiment, the compound is an allosteric inhibitor. In another embodiment, the compound is a peptide substrate inhibitor. In another embodiment, the compound does not inhibit ATP binding to a protein kinase. In one embodiment, the compound inhibits a Src family protein kinase. In another embodiment, the Src family protein kinase is pp60$^{c\text{-}src}$ tyrosine kinase.

In one embodiment, at least one of $X_a$, $X_b$, $X_c$, $X_d$, $X_e$, $X_y$ and $X_z$ is N. In another embodiment, $X_z$ is CZ, further wherein Z is

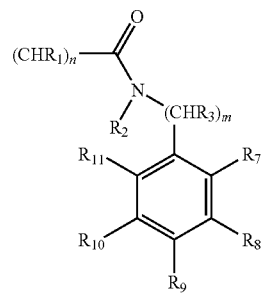

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

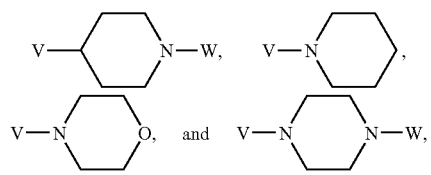

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl. In one embodiment, at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl. In another embodiment, m and n are each 1 and $R_2$ and $R_3$ are each H. In one embodiment, $R_4$ and $R_6$ are each H. In one embodiment of the invention, a compound is selected from 248, 249, 250, 251, 252, 253, 254, 255, 256, 257, 258, 259, 260, 261, 262, 263, 264, 265, 266, 267, 268, 269, 270, 271, 272, 273, or 274.

Definitions

For convenience, certain terms used in the specification, examples and appended claims are collected here.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate ATP in a highly conserved pocket. About 50% of the known oncogene products are protein tyrosine kinases (PTKs), and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products and focal adhesion kinase (FAK)). The hyperactivation of Src has been reported in a number of human cancers, including those of the colon, breast, lung, bladder, and skin, as well as in gastric cancer, hairy cell leukemia, and neuroblastoma.

"inhibits one or more components of a protein kinase signaling cascade" means that one or more components of the kinase signaling cascade are effected such that the functioning of the cell changes. Components of a protein kinase signaling cascade include any proteins involved directly or indirectly in the kinase signaling pathway including second messengers and upstream and downstream targets.

"Treating", includes any effect, e.g., lessening, reducing, modulating, or eliminating, that results in the improvement of the condition, disease, disorder, etc. "Treating" or "treatment" of a disease state includes: (1) preventing the disease state, i.e. causing the clinical symptoms of the disease state not to develop in a subject that may be exposed to or predisposed to the disease state, but does not yet experience or display symptoms of the disease state; (2) inhibiting the disease state, i.e., arresting the development of the disease state or its clinical symptoms; or (3) relieving the disease state, i.e., causing temporary or permanent regression of the disease state or its clinical symptoms.

"Disease state" means any disease, disorder, condition, symptom, or indication.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the terms "psoriatic condition" or "psoriasis" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. The proliferative diseases can include dysplasias and disorders of the like.

An "effective amount" of a compound of the disclosed invention is the quantity which, when administered to a subject having a disease or disorder, results in regression of the disease or disorder in the subject. Thus, an effective amount of a compound of the disclosed invention is the quantity which, when administered to a subject having a cell proliferation disorder, results in regression of cell growth in the subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present invention effective when administered alone or in combination as an anti-proliferative agent. For example, an effective amount refers to an amount of the compound present in a formulation or on a medical device given to a recipient patient or subject sufficient to elicit biological activity, for example, anti-proliferative activity, such as e.g., anti-cancer activity or anti-neoplastic activity. The combination of compounds optionally is a synergistic combination. Synergy, as described, for example, by Chou and Talalay, $Adv.$ $Enzyme$ $Regul.$ vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, or increased anti-proliferative effect, or some other beneficial effect of the combination compared with the individual components.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A therapeutically effective amount of one or more of the compounds can be formulated with a pharmaceutically acceptable carrier for administration to a human or an animal. Accordingly, the compounds or the formulations can be administered, for example, via oral, parenteral, or topical routes, to provide an effective amount of the compound. In alternative embodiments, the compounds prepared in accordance with the present invention can be used to coat or impregnate a medical device, e.g., a stent.

The term "prophylactically effective amount" means an effective amount of a compound or compounds, of the present invention that is administered to prevent or reduce the risk of unwanted cellular proliferation.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

With respect to the chemical compounds useful in the present invention, the following terms can be applicable:

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R^1$ at each occurrence is selected independently from the definition of $R_1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_{3-14}$ carbocycle, or 3-14-membered heterocycle) derivatives.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in another embodiment, cycloalkyls have five or six carbons in the ring structure.

Unless the number of carbons is otherwise specified, "lower alkyl" includes an alkyl group, as defined above, but having from one to ten, or in another embodiment from one to six, carbon atoms in its backbone structure. "Lower alkenyl" and "lower alkynyl" have chain lengths of, for example, 2-5 carbon atoms.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylaryl amino), acylamino (including alkylcarbonyl amino, arylcarbonyl amino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

The term "substituted alkenyls" refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "substituted alkynyls" refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

"Counterion" is used to represent a small, negatively charged species such as chloride, bromide, hydroxide, acetate, and sulfate.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "glycoside" means any molecule in which a sugar group is bonded through its anomeric carbon to another group. Examples of glycosides include, for example methyl α-D-glucopyranoside

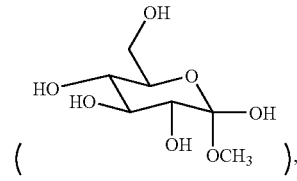

methyl β-D-glucopyranoside

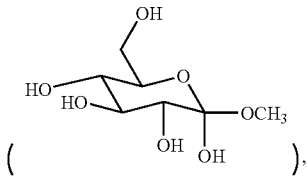

glucoside, galactoside, lactoside, lactosidoglycoside, maltoside, etc. Because a glycoside is bonded through its anomeric carbon to another group, it is also known as a non-reducing sugar (i.e., it is not subject to attack by reagents that attack carbonyl groups).

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and S(O)$_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In one embodiment, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Acyl" includes compounds and moieties that contain the acyl radical (CH$_3$CO—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "thiocarbonyl" or "thiocarboxy" includes compounds and moieties which contain a carbon connected with a double bond to a sulfur atom.

The term "ether" or "alkoxy" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). In one embodiment, an anionic group is a carboxylate.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J., Chem. Educ. 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine. Examples include:

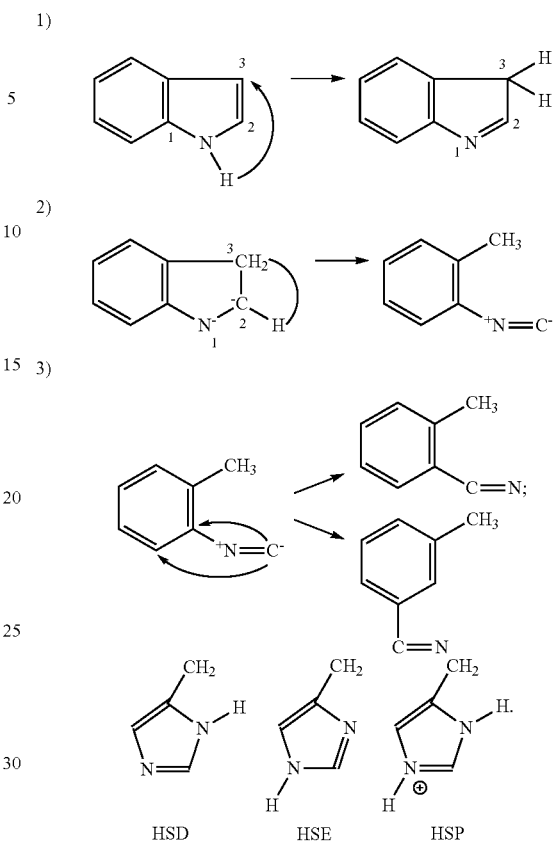

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. The compounds of this invention may exist in stereoisomeric form, therefore can be produced as individual stereoisomers or as mixtures.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein. For example, all of the compounds represented by formula I are indole derivatives, and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxylamine-containing, and imine-containing compounds of the present invention.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

"Protecting group" refers to a grouping of atoms that when attached to a reactive group in a molecule masks, reduces or prevents that reactivity. Examples of protecting groups can be found in Green and Wuts, *Protective Groups in Organic Chemistry*, (Wiley, $2^{nd}$ ed. 1991); Harrison and Harrison et al., *Compendium of Synthetic Organic Methods*, Vols. 1-8 (John Wiley and Sons, 1971-1996); and Kocienski, *Protecting Groups*, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenylmethyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other suitable amine protecting groups are straightforwardly identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Stable compound" and "stable structure" are meant to indicate a compound that is sufficiently robust to survive isolation to a useful degree of purity from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

The compounds, or pharmaceutically acceptable salts thereof, is administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in Remington: the Science and Practice of Pharmacy, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one embodiment, the compound is prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds, or salts, solvates, tautomers or polymorphs thereof, can be combined with sterile aqueous or organic media to form injectable solutions or suspensions. In one embodiment, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, the compositions contain about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the invention are also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In one embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Syntheses

Representative syntheses of compounds of the invention are described herein.

Synthesis of Compounds 1 and 2 (KX1-136 and KX1-305)

3-benzyloxybenzonitrile

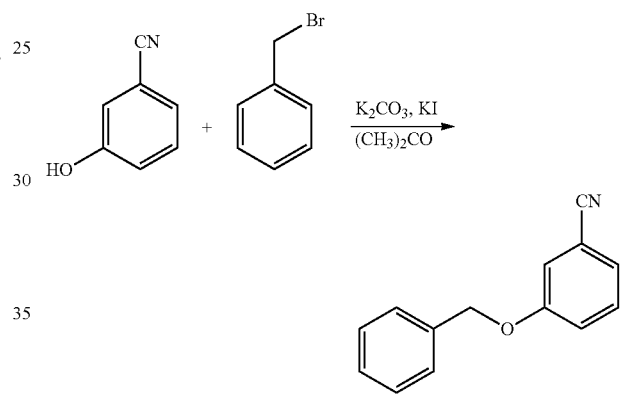

To a solution of 3-cyanophenol (5.00 g, 42.00 mmol) in acetone (100 ml), potassium carbonate (5.79 g, 42.0 mmol), potassium iodide (335 mg, 21.0 mmol) and benzyl bromide (4.20 ml, 42.00 mmol) were added and the reaction mixture refluxed for 12 hrs (TLC, ethyl acetate:hexane 1:1, $R_f$=0.6), then the solvent removed under vacuum and the residue portioned between water (50 ml) and ethyl acetate (50 ml), the organic layer was washed with water twice and dried over anhydrous sodium sulfate and evaporated under reduced pressure to give the target ether as a yellow oil (8.46 g) 96% yield; $^1$H NMR (DMSO (dimethylsulfoxide), 400 MHz): δ 7.51-7.33 (m, 9H), 5.16 (s, 2H).

3-benzyloxybenzylaminehydrochloride

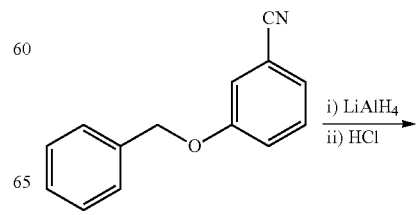

-continued

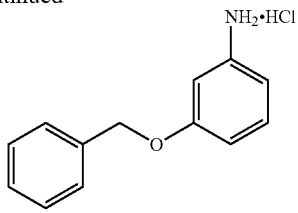

To a suspension of lithium aluminum hydride, LAH (4.314 g, 113.684 mmol) in dry ether (200 ml) a solution of the 3-benzyloxybenzonitrile in ether (7.92 g, 37.894 mmol) was added drop-wise during 10 min at room temperature, and allowed to stir for 4 hrs (TLC, ethyl acetate:hexane 1:3, $R_f$=0.5), the reaction was quenched with 10 ml ethyl acetate and 10 ml water and filtered. The organic layer was washed with water, dried over $Na_2SO_4$ and treated with 10 ml conc. HCl to form instant white precipitate (6 g) 68% yield. $^1$H NMR (DMSO, 400 MHz): δ 8.33 (s, 3H), 7.45-7.37 (m, 4H), 7.34-7.30 (m, 2H), 7.19 (s, 1H), 7.02 (t, J=10 Hz, 2H), 5.10 (s, 2H), 3.97 (s, 2H).

N(3-benzyloxy-benzyl)-4-biphenylacetamide

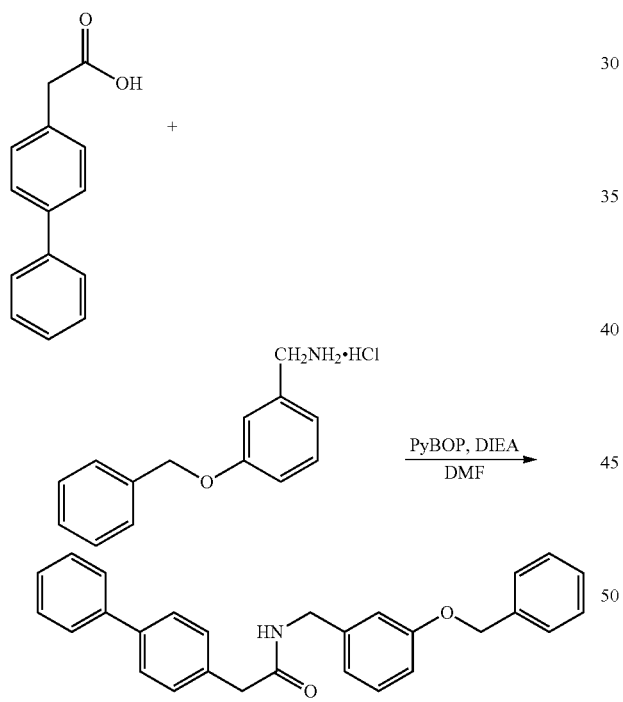

To a solution of 4-biphenyl acetic acid (2.29 g, 10.45 mmol) in dimethylformamide, DMF, (30 ml) was added diisopropylethylamine, DIEA, (5.47 ml, 31.35 mmol) and stirred at room temperature for 15 min, then benzotriazolyloxy-tris[pyrrolidino]-phosphonium hexafluorophosphate, PyBOP™, (5.43 g, 10.45 mmol) was added and the stirring was continued for further 30 min, then 3-benzyloxybenzylaminehydrochloride (2.6 g, 10.45 mmol) was added and the stirring continued for 24 hrs. The reaction mixture was then poured on to ice cooled water acidified with (10 ml) 1 N HCl and extracted with ethyl acetate (100 ml) and the organic layer washed with saturated solution of $NaHCO_3$, water and brine, dried over $Na_2SO_4$ and the solvent removed under vacuum to give a yellowish-white powder of the desired compound (2.65 g) 62% yield.

Another procedure involves use amide formation using the acid chloride as shown in the following reaction.

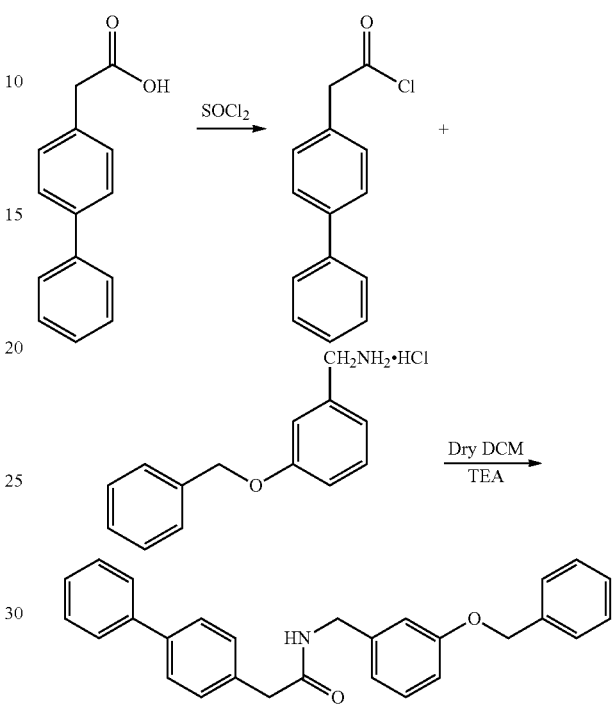

To 4-biphenylacetic acid (2.5 g) in a flask, thionylchloride (20 ml) was added and heated to reflux for 1 h, cooled, and the excess thionylchloride removed under vacuum to dryness, then the produced crude acid chloride 2.8 g, dissolved in dry DCM (dichloromethane) (30 ml), and added drop wise at 0° C. to equimolar amount of the 3-benzyloxybenzylamine solution in DCM (10 ml) with (1.5 mol) of triethylamine (TEA) and stirred for 5 hrs, then poured onto acidified cold water, the organic layer washed with water, brine and the solvent removed under reduced pressure to give the target amide in 80% yield. $^1$H NMR (DMSO, 500 MHz): δ 8.58 (t, J=12 Hz 1H), 7.60-7.57 (m, 4H), 7.44-7.29 (m, 10H), δ 7.21 (t, J=16.5 Hz, 2H), 6.85 (d, J=6.5 Hz, 2H), 6.81 (d, J=8.0 Hz, 1H), 5.00 (s, 2H), 4.24 (d, J=6 Hz, 2H), 3.51 (s, 2H).

Compound 1:
N(3-hydroxy-benzyl)-4-biphenylacetamide

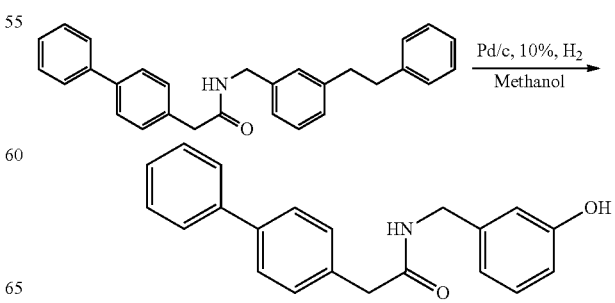

To remove the benzyl group of this ether (5.00 g, 13.35 mmol) was dissolved in methanol (20 ml), to this solution was added a catalytic amount of 10% Pd/C (355 mg, 2.21 mmol) in a Parr hydrogenator (55 psi) for 5 hrs, filtered through celite and the solvent removed under vacuum to give the target phenol as yellowish powder (3.20 g) 84% yield, which crystallized from methanol to give (1.5 g) of white crystalline material, mp=169-170° C. $^1$HNMR (DMSO, 400 MHz): δ 9.34 (s, 1H), 8.53 (s, 1H), 7.63 (d, J=8 Hz, 2H), 7.58 (d, J=8.4 Hz, 2H), 7.44 (t, J=7.6 Hz, 2H), 7.35 (d, J=8 Hz, 3H), 7.07 (t, J=8 Hz, 1H), 6.65-6.60 (m, 3H), 4.17 (d, J=5.6 Hz,2H), 3.5 (s, 2H). FAB (fast atom bombardment) HRMS m/e calcd. For (M+H) $C_{21}H_{20}NO_2$: 318.1449; found: 318.1484.

Compound 2:
N(3-fluoro-benzyl)-4-biphenylacetamide

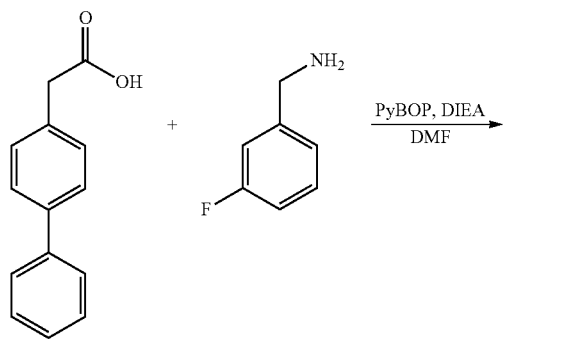

To a solution of 4-biphenyl acetic acid (2.00 g, 9.42 mmol) in DMF (20 ml) was added DIEA (3.29 ml, 18.84 mmol) and stirred at room temperature for 15 min, then PyBOP (4.90 g, 9.42 mmol) added and the stirring continued for further 30 min, then 3-fluorobenzylamine (1.18 g, 9.42 mmol) added and the stirring continued for 24 hrs, then the reaction mixture poured on to ice cooled water acidified with (10 ml) 1 N HCl and extracted with ethyl acetate (100 ml) and the organic layer washed with saturated solution of NaHCO$_3$, water and brine, dried over Na$_2$SO$_4$ and the solvent removed under vacuum to give a white powder of the desired compound (1.00 g) 33% yield. Another method involves the acid chloride coupling method described below.

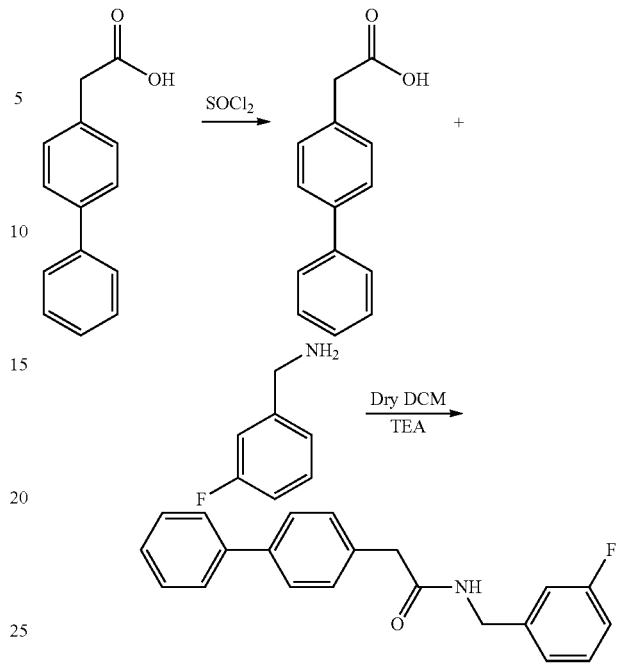

4-biphenylacetic acid (2.5 g, 11.78 mmol) charged in a flask then thionylchloride (15 ml) was added and heated to reflux for 1 h, cooled, and the excess thionylchloride removed under vacuum to dryness, then the produced crude acid chloride (2.8 g, 12.13 mmol) dissolved in dry DCM (30 ml), and added drop wise at 0° C. to (1.38 ml, 12.13 mmol) of the 3-fluorobenzylamine solution in DCM (10 ml) along with (1.69 ml, 12.13 mmol) of TEA and stirred for 5 hrs, then poured onto acidified cold water, the organic layer washed with water, brine and the solvent removed under reduced pressure to give the target amide (3.1 g) 80% yield. Recrystallized from methanol, mp=170-172° C. $^1$H NMR (DMSO, 500 MHz): δ 8.62 (t, J=11 Hz, 1H), 7.63 (d, J=8 Hz, 2H), 7.59 (d, J=8.5 Hz, 2H), 7.44 (t, J=7.5 Hz, 2H), 7.37-7.31 (m, 4H), 7.08-7.01 (m, 3H), 4.28 (d, J=5.5 Hz, 2H), 3.52 (s, 2H). FAB HRMS m/e calcd. For (M+H) $C_{21}H_{18}FNO$: 320.1406; found: 320.2, and the base peak found: 342.1262 for (M+Na); calcd. 342.1372.

Synthesis of Compound 3, KX1-306

The synthesis, outlined in Scheme 1, began with acid chloride formation of biphenylacetic acid followed by amide coupling with 3,5-dibenzyloxybenzylamine. A large number of impurities were introduced by acid chloride formation. However, other amide coupling procedures such as, for example, PyBOP or carbodiimides, can also be used in this reaction.

Cleavage of one of the benzyl groups was accomplished under high pressure hydrogen (50-60 psi) for 15 hours. The reaction was monitored by TLC. Silica gel chromatography was used to separate the product from the starting material as well as the dihydroxy side-product.

Biphenyl acetic acid (220 mg, 1.00 mmol) was dissolved in DCM, 5 eq (0.38 mL) of thionyl chloride were added and the reaction was refluxed for 4 hours. Solvents were removed in vacuo and the residue was dissolved in DCM. 3,5-Dibenzyloxybenzylamine (1.1 eq) was added followed by TEA (1 eq). The reaction was then stirred at room temperature overnight. The reaction was diluted to 45 mL (with DCM) and washed with 1 N HCl (3×20 L), saturated sodium bicarbonate (3×20 mL), and brine (3×20 mL). The Reaction was then dried with sodium sulfate and removed in vacuo to give 330 mg of crude product. Silica gel chromatography (1:1 DCM:EtOAc (ethyl acetate)) gave 220 mg pure product. TLC Rf=0.2 (single spot, 7:3 hexanes:EtOAc). LCMS 514.2 (m+H) 536.2 (m+Na). $^1$HNMR (300 MHz, CDCl$_3$) δ (ppm) 3.65 (s, 2H), 4.50 (d, 5.7 Hz, 2H), 4.96 (s, 4H), 5.71 (s, 1H), 6.43 (s, 2H), 6.49 (s, 1H), 7.58-7.26 (m, 19H).

The dibenzyloxyamide (1) was dissolved in 15 ml EtOAc (ethyl acetate) with gentle heating in a Parr bottle. This was put on the hydrogenator at 50 psi hydrogen for 15 hr. The reaction was filtered through celite and the solvent was removed in vacuo to give a crude mixture of starting material and product. Silica gel chromatography gave 50 mg 1 and 41 mg desired product KX1-306; LCMS 424.1 (m+H), 446.2 (m+Na), 847.0 (2m+H), 868.9 (2m+Na). $^1$HNMR (400 MHz, CDCl$_3$) δ (ppm) 3.66 (s, 2H), 4.38 (d, 5.6 Hz, 2H), 4.98 (s, 2H), 5.71 (s, 1H), 6.43 (s, 2H), 6.49 (s, 1H), 7.30-7.45 (m, 10H), 7.54-7.57 (m, 4H).

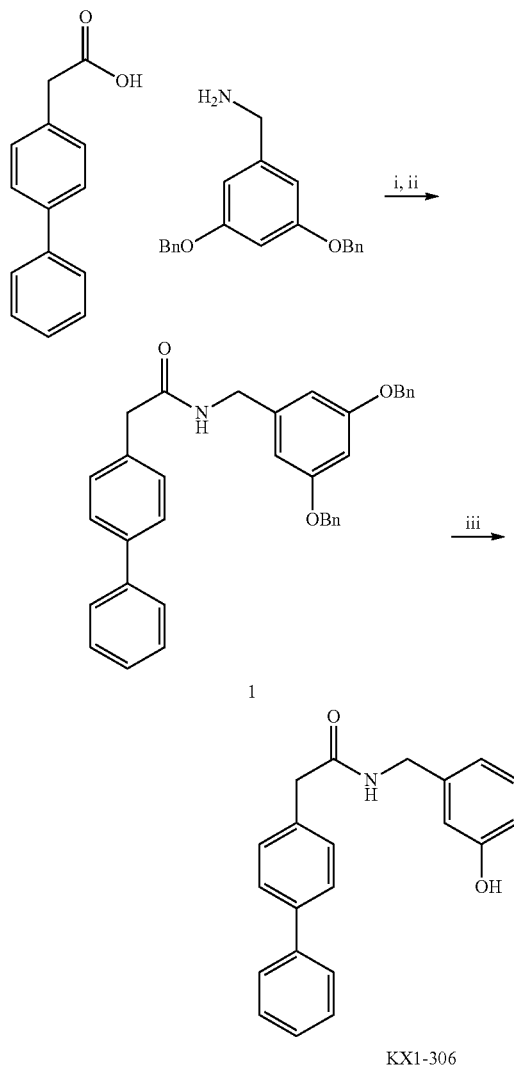

Scheme 1

Reagents:
i) SOCl$_2$, DCM.
ii) 3,5dibenzyloxybenzylamine (1.0 eq), TEA (2.0 eq) 20% yield (two steps, with chromatography).
iii) 10% Pd/C (10 mol %), H$_2$, 55 psi, EtOAc 24 hr (53%, after chromatography, BORMS.

Synthesis of Compound 4, KX1-307

The synthesis is outlined in Scheme 2. In one synthesis, the reaction commenced with amide bond formation to give 2, followed by a Suzuki coupling with phenylboronic acid to give the meta-biphenyl product Compound 4, KX1-307. In the Suzuki reaction, the biphenyl product was formed but the reaction did not go to completion (by NMR and LCMS) despite additional, time, heat, and extra catalyst. Using silica gel chromatography, the product could not be separated from the bromo starting material 2. Reversing the Suzuki and amide coupling solved the separation problem and successfully produced the metabiphenyl amide KX1-307 as well as 2'-Fluorobiphenyl-4-acetamide KX1-309 (compound 6, Scheme 3).

3-Bromophenylacetic acid (250 mg, 1.163 mmol) and 156 mg (1.1 eq) of phenylboronic acid were dissolved in 6 mL water:isopropanol (6:1). Sodium carbonate (160 mg, 1.3 eq) was dissolved in 0.5 mL distilled water and added to the reaction followed by Pd(OH)$_2$/C (74 mg, 3 mol %). This was rotated in a 65° C. water bath for 5 hours. The reaction was filtered through filter paper. Filter paper was washed with 25 mL isopropanol:water:1 N NaOH (35:5:1). Washes were combined and acidified to pH 2 with 1 N sulfuric acid. Isopropanol was removed in vacuo and water (10 mL) was added. This aqueous layer was washed with dichloromethane (3×20 mL). Organic washes were combined, dried with sodium sulfate, and removed in vacuo to give 215 mg (87% yield) of the biphenyl product 3. TLC Rf=0.7 (long streak, 1:1 EtOAc:DCM). $^1$HNMR (300 MHz, CDCl$_3$) δ (ppm) 3.72 (s, 2H), 7.26-7.60 (m, 9H).

3-Biphenylacetic acid (3) (100 mg, 0.472 mmol), 3-Fluorobenzylamine (1.1 eq), 1-(3-dimethylaminopropyl)-3-ethyl-carbodiimide hydrochloride, EDCI, (1.1 eq), and HOBT (1-hydroxyenzotriazole, 1.0 eq) were all dissolved in 10 mL anhydrous DCM. After 10 min DIEA (1.1 eq) was added and the reaction was allowed to go overnight. The reaction was diluted to 25 mL and washed with 1N HCl (3×10 L), saturated sodium bicarbonate (3×10 mL), and brine (2×20 mL). The reaction was dried with sodium sulfate and removed in vacuo to give 124 mg pure KX1-307 (83% yield). TLC Rf=0.7 (single spot, 1:1 EtOAc:DCM). $^1$HNMR (300 MHz, CDCl$_3$) δ (ppm) 3.69 (s, 2H) 4.40 (d, 6.0 Hz) 5.77 (s, 1H) 6.86-6.96 (m, 3H) 7.10-7.26 (m, 2H) 7.32 (m, 8H).

Scheme 2

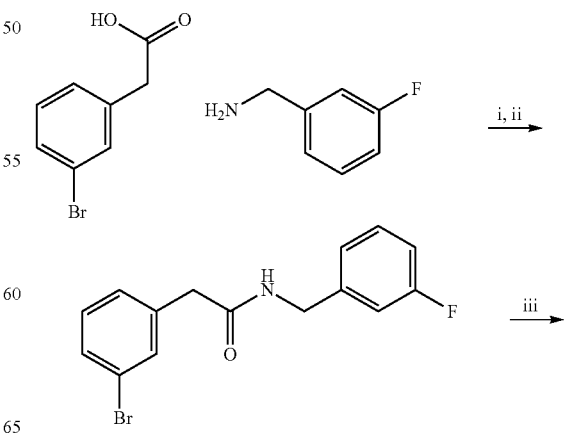

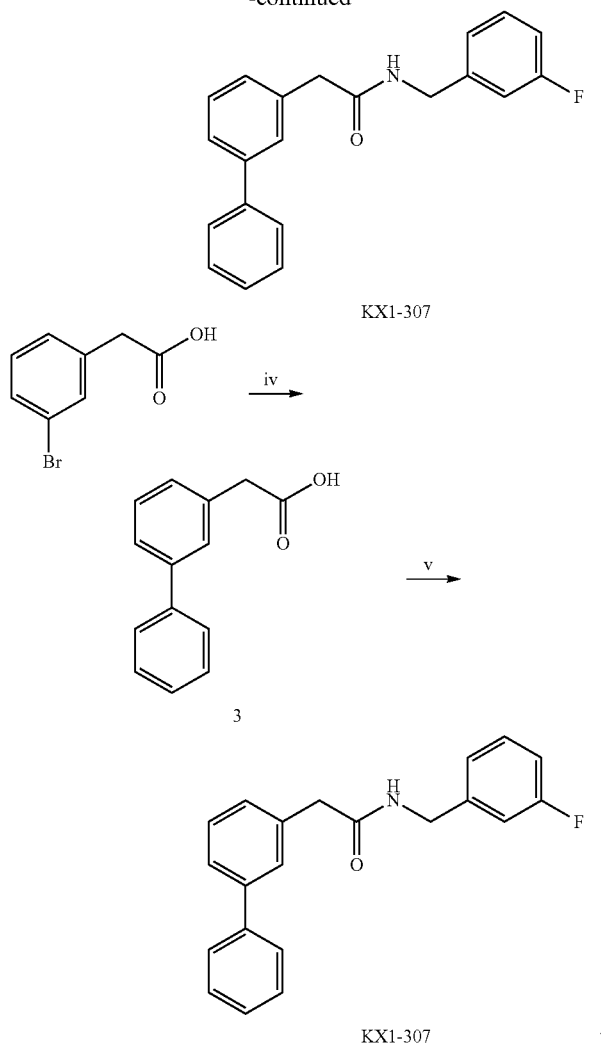

KX1-307

Reagents:
i) SOCl₂, DCM.
ii) 3-Fluorobenzylamine (1.1 eq), DIEA (2.2 eq) (20% after chromatography).
iii) Phenylboronic acid (1.2 eq), 2M sodium carbonate, Pd(PPh₃)₄ (3 mol %), Toluene (inseparable miture).
iv) Phenylboronic acid (1.1 eq), Na₂CO₃ (1.3 eq), Pd(OH)₂/C (3 mol %), 1:6 isopropanol:water (87% yield).
v) 3-Fluorobenzylamine (1.1 eq), EDCI (1.1 eq), HOBT (1.0 eq), DIEA (1.1 eq) (83% yield).

Synthesis of Compound 6, KX-309

The synthesis is outlined in Scheme 3. 4-Bromophenylacetic acid (500 mg, 2.33 mmol) and 358 mg of 2-fluorophenylboronic acid (1.1 eq) were dissolved in 12 mL, 6:1 water:isopropanol. Sodium carbonate (320 mg, 1.3 eq) was dissolved in 1 mL distilled water and added to the reaction followed by Pd(OH)₂/C (148 mg, 3 mol %). This was rotated in a 65° C. water bath for 5 hours. The reaction was filtered through filter paper. Filter paper was washed with 50 mL isopropanol:water:1 N NaOH (35:5:1). Washes were combined and acidified to pH 2 with I N sulfuric acid. Isopropanol was removed in vacuo, water (20 mL) was added and washed with dichloromethane (3×30 mL). Organic washes were combined, dried with sodium sulfate, and removed in vacuo to give 177 mg (35% yield) of the biphenyl product 4. TLC Rf=0.7 (long streak, 1:1 EtOAc:DCM). ¹HNMR (500 MHz, CDCl₃) δ (ppm) 3.73 (s, 2H), 7.16 (t, 10.5 Hz, 1H), 7.22 (t, 7.5 Hz, 1H), 7.32 (qd, 1.5 Hz, 7.5 Hz, 1H), 7.38 (d, 8.0 Hz, 2H), 7.44 (td, 1.5 Hz, 7.5 Hz, 1H), 7.54 (d, 8.0 Hz, 2H).

2'-Fluorobiphenylacetic acid (4) (103 mg, 0.448 mmol), 3-Fluorobenzylamine (1.1 eq), EDCI (1.1 eq), and HOBT (1.0 eq) were all dissolved in 6 mL anhydrous DCM. After 10 min DIEA (1.1 eq) was added and the reaction was allowed to go overnight. Reaction was diluted to 25 mL and washed with 1 N HCl (3×10 L), saturated sodium bicarbonate (3×10 mL), and brine (2×20 mL). The reaction was dried with sodium sulfate and removed in vacuo to give 126 mg pure Compound 6, KX1-309 (83% yield). LCMS 360.1 (m+Na) 696.8 (2m+Na). ¹HNMR (300 MHz, CDCl₃) δ (ppm) 3.67 (s, 2H) 4.21 (d, 6.0 Hz, 2H) 5.79 (s, 1H) 6.87-6.98 (m, 3H) 7.10-7.44 (m, 7H) 7.53 (dd, 1.5 Hz, 7.5 Hz, 2H).

Scheme 3

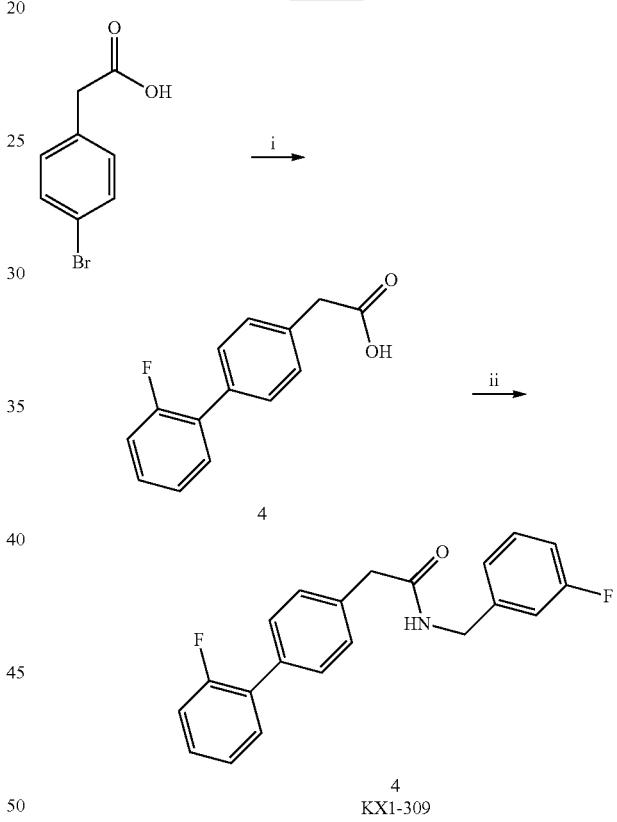

KX1-309

Reagents:
i) Phenylboronic acid (1.1 eq), Na₂CO₃ (1.3 eq), Pd(OH)₂/C (3 mol %), 1:6 isopropanol:water (35% yield).
ii) 3-Fluorobenzylamine (1.1 eq), EDCI (1.1 eq), HOBT (1.0 eq), DIEA (1.1 eq), 83% yield.

Synthesis of Compound 5: N-(3-fluorophenyl)-4-biphenylacetamide, KX1-308.

Thionyl chloride (0.38 ml, 5.0 mmole) was added to an ice water cooled solution of 4-Biphenylacetic acid (0.2 g, 0.9 mmole) in 5 ml dichloromethane, solution allowed to warm to room temperature then heated under reflux for 1 hr, the solvent and excess thionyl chloride was evaporated under vacuum, the oil formed was redissolved in 5 ml dichloromethane followed by addition of 4-Dimethylaminopyridine (0.12 gm, 1.0 mmole) and 3-Fluoroaniline (0.11 gm, 1.0 mmole), stirred at room temperature over night, then the reaction mixture was diluted with 10 ml dichloromethane and 20 ml water, the organic layer washed with 1 N HCl, saturated NaHCO$_3$ solution, and saturated NaCl solution, dried using Na$_2$SO$_4$ and evaporated dryness (0.2 gm, 72%), H$_1$-NMR INOVA-500 (CDCl$_3$) δ 3.805 (s, 2H), 6.815 (t, J=8.5 Hz, 1H), 7.068 (d, J=8.0 Hz, 1H), 7.218-7.284 (m, 2H), 7.380-7.499 (m, 6H) 7.620-7.664 (m, 4H). MS (m/z) 306.2 (M+H)$^+$.

Synthesis of Compound 7: N-(3-fluorobenzyl)-4-(3-fluorophenyl)phenylacetamide, KX1-310

Synthesis of (4'-Fluoro-biphenyl-4-yl)-acetic acid: 4-Bromo-phenylacetic acid (0.5 gm, 2.3 mmole), 3-fluorophenylboronic acid (0.36 gm, 2.4 mmole) and 50% water wet 10% Palladium carbon (0.16 gm, 0.075 mmole Pd) were added to 10 ml of 5:1 water isopropanol mixture, then Na$_2$CO$_3$ (0.32 gm, 3 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was acidified using 20% H$_2$SO$_4$, filtered and dried (3'-Fluoro-biphenyl-4-yl)-acetic acid: (0.4 gm, 75%) H$^1$-NMR INOVA-500 (DMSO d$_6$) δ 3.623 (s, 2H), 7.192 (m, 1H), 7.358 (d, J=8.0 Hz, 2H), 7.474-7.515 (m, 3H), 7.652 (d, J=8.0 Hz, 2H), 12.316 (s, 1H).

3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.22 gm, 76%); H$^1$-NMR INOVA-500 (DMSO d$_6$) δ 3.550 (s, 2H), 4.303 (d, J=6.5 Hz, 2H), 7.027-7.097 (m, 3H), 7.197 (m, 1H), 7.350 (m, 1H), 7.389 (d, J=8.0 Hz, 2H), 7.477-7.518 (m, 3H), 7.657 (d, J=8.0 Hz, 2H), 8.652 (t, J=5.5 Hz, 1H). MS (m/z) 338.1 (M+H)$^+$.

Synthesis of Compound 8, N-(3-fluorobenzyl)-4-(4-fluorophenyl)phenylacetamide, KX1-311

Synthesis of (4'-Fluoro-biphenyl-4-yl)-acetic acid: 4-Bromo-phenylacetic acid (0.5 gm, 2.3 mmole), 4-fluorophenylboronic acid (0.36 gm, 2.4 mmole) and 50% water wet 10% Palladium carbon (0.16 gm, 0.075 mmole Pd) were added to 10 ml of 5:1 water isopropanol mixture, then Na$_2$CO$_3$ (0.32 gm, 3 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was acidified using 20% H$_2$SO$_4$, filtered and dried (0.4 gm, 75%) H$^1$-NMR INOVA-500 (DMSO d$_6$) δ 3.621 (s, 2H), 7.290 (t, J=8.5 Hz, 2H), 7.351 (d, J=7.5 Hz, 2H), 7.593 (d, J=7.5 Hz, 2H), 7.695 (t, J=7 Hz, 2H), 12.386 (s, 1H).

(4'-Fluoro-biphenyl-4-yl)-acetic acid (0.2 gm, 0.9 mmole), 3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.26 gm, 90%); H$^1$-NMR INOVA-500 (DMSO d$_6$) δ 3.541 (s, 2H), 4.304 (d, J=5.5 Hz, 2H), 7.027-7.098 (m, 3H), 7.273-7.382 (m, 5H), 7.582 (d, J=8.0, 2H), 7.694 (m, 2H), 8.641 (t, J=5.5 Hz, 2H) MS (m/z) 338.1 (M+H)$^+$.

Synthesis of Compound 9, N-(3-fluorobenzyl)-N-methyl-4-biphenylacetamide, KX1-312

4-biphenylacetic acid (0.25 gm, 1.2 mmole), N-methyl-3-fluorobenzylamine (0.16 gm, 1.2 mmole), EDCI (0.23 gm, 1.2 mmole), and DIEA (0.42 ml, 2.4 mmole) was dissolved in 10 ml DCM and stirred overnight. The reaction mixture was diluted with 10 ml of DCM washed with 10% HCl, saturated NaHCO$_3$ solution, and saturated NaCl solution, dried using Na$_2$SO$_4$ and evaporated to produce viscous clear oil (160 mg, 43%), H$^1$-NMR INOVA-500 (DMSO d$_6$) indicated the presence of a mixture of cis and trans isomers in a ratio of 1:2, running the NMR experiment was run at 50° C. slightly change the value for the chemical shift, but had almost no effect on the ratio. Protons are labeled H$_a$ or H$_b$ to indicate it belongs to one isomer or the other. H$^1$-NMR INOVA-500 (DMSO d$_6$) 2.813 (s, 3H$_a$), 3.000 (s, 3H$_b$), 3.784 (s, 2H$_a$), 3.841 (s, 2H$_b$), 4.543 (s, 2H$_b$), 4.681 (s, 2H$_a$), 6.931-7.649 (m, 13H$_a$+13 H$_b$). MS (m/z) 334.2 (M+H)$^+$.

Synthesis of Compound 10, N-(3-fluorobenzyl)-4-phenyl-2-fluorophenylacetamide, KX1-313

Synthesis of 4-Bromo-2-fluoro-phenylacetamide: 4-Bromo-2-fluorobenzylbromide (5 gm, 18.7 mmole) was dissolved in 30 ml ethanol, to which water solution (10 ml) of KCN (2.43 gm, 37.4 mmole) was added, refluxed overnight, then it was cooled to room temperature, poured into 200 ml of crushed ice, filtered, chromatographed using 1:1 ethyl acetate followed by ethyl acetate (the cyano compound was hydrolyzed on the silica gel to produce the carboxamide), which was evaporated to produce white solid, (1.3 gm, 32%) H$^1$-NMR INOVA-500 (DMSO d$_6$) δ 3.436 (s, 2H), 7.005 (s, 1H), 7.289 (t, J=8.0 Hz, 1H), 7.361 (d, J=8.0 Hz, 1H), 7.478 (m, 1H), 7.517 (s, 1H).

Synthesis of 4-Bromo-2-fluoro-phenylacetic acid: 4-Bromo-2-fluoro-phenylacetamide (1.3 gm) was suspended in 100 ml of 30% NaOH, heating at reflux temperature for 24 hrs, cooled to room temperature, washed with DCM and ethyl acetate. The aqueous layer was acidified with conc. HCl, extracted with ethyl acetate, evaporated; the residue was crystallized from isopropanol-water to give needle crystals (0.5 gm, 38%) H$^1$-NMR INOVA-500 (DMSO d$_6$) δ 3.619 (s, 2H), 7.316 (t, J=8.0 Hz, 1H), 7.379 (dd, J=8.0, 1.5 Hz, 1H), 7.516 (dd, J=8.0, 1.5 Hz, 1H), 12.555 (s, 1H).

Synthesis of 4-phenyl-2-fluorophenylacetic acid: 4-Bromo-2-fluoro-phenylacetic acid (0.25 gm, 1.1 mmole), phenylboronic acid (0.15 gm, 1.2 mmole) and 50% water wet 10% Palladium carbon (0.07 gm, 0.033 mmole Pd) were added to 10 ml of 5:1 water isopropanol mixture, then Na$_2$CO$_3$ (0.14 gm, 1.3 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was acidified using 20% H$_2$SO$_4$, filtered and dried (0.2 gm, 83%) H$^1$-NMR INOVA-500 (DMSO d$_6$) δ 3.675 (s, 2H), 7.382-7.518 (m, 6H), 7.707 (d, J=7.5 Hz, 2H), 12.498 (s, 1H).

Synthesis of N-(3-fluorobenzyl)-4-phenyl-2-fluorophenylacetamide: 4-phenyl-2-fluorophenylacetic acid (0.2 gm, 0.9 mmole), 3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.20 gm, 70%);

H'-NMR INOVA-500 (DMSO d$_6$) δ 3.612 (s, 2H), 4.318 (d, J=6 Hz, 2H), 7.064-7.117 (m, 3H), 7.345-7.503 (m, 7H), 7.695 (d, J=7.5 Hz, 2H), 8.660 (t, J=6 Hz, 1H). MS (m/z) 338.1 (M+H)$^+$.

Synthesis of Compound 11,
N(3-fluorobenzyl)-2-phenylpyridine-5-acetamide,
KX1-314

Synthesis of 2-phenylpyridine-5-acetic acid: 2-chloropyridine-5-acetic acid (0.2 gm, 1.21 mmole), phenylboronic acid (0.16 gm, 1.3 mmole) and 50% water wet 10% Palladium carbon (0.08 gm, 0.036 mmole Pd) were added to 10 ml of 5:1 water isopropanol mixture, then Na$_2$CO$_3$ (0.15 gm, 1.4 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was dried under vacuum and crude mixture was used without any purification in the next step.

Synthesis of N(3-fluorobenzyl)-2-phenylpyridine-5-acetamide: To the crude from the above reaction, 3-fluorobenzylamine (0.15 gm, 1.2 mmole), PyBOP (0.67 gm, 1.3 mmole), and DIEA (0.32 gm, 2.6 mmole) and was stirred in DMF overnight. The reaction mixture was then poured into water; solid was collected by filtration, re-crystallized using water-methanol (0.06 gm, 18% in two steps). H$^1$-NMR INOVA-500 (CDCl$_3$) δ3.645 (s, 2H), 4.438 (d, J=5.5 Hz, 2H), 5.867 (s, 1H), 6.925-7.009 (m, 3H), 7.268 (m, 1H), 7.408-7.493 (m, 3H), 7.735 (m, 2H), 7.965-7.982 (m, 2H), 8.582 (s, 1H). MS (m/z) 321.2 (M+H)$^+$.

Synthesis of Compound 12, N-(3-Fluoro-benzyl)-2-(4-pyridin-2-yl-phenyl)-acetamide, KX1-315

Synthesis of 4-(2-Pyridinyl)benzylalcohol: 4-(2-Pyridinyl)benzaldehyde (2 gm, 11 mmole), and NaBH$_4$ (0.42 gm, 11 mmole) were stirred at room temperature for 2 hr, ethanol was evaporated, residue dissolved in ethyl acetate washed with saturated NaHCO$_3$ solution, and saturated NaCl solution, dried using Na$_2$SO$_4$ and evaporated to produce white solid (1.5 gm, 75%).

Synthesis of (4-Pyridin-2-yl-phenyl)-acetic acid: The crude of 4-(2-Pyridinyl)benzylalcohol was dissolved in 20 ml DCM, cooled using ice/methanol, triethylamine (1.25 ml, 8.9 mmole) was added followed by methanesulfonylchloride (0.7 ml, 8.9 mmole) added drop wise over 5 minutes. The reaction was allowed to stir at room temperature till the TLC indicated consumption of the starting material (3 hrs), after completion of the reaction, the reaction mixture was washed with water, saturated NaHCO$_3$ solution, and saturated NaCl solution, dried using Na$_2$SO$_4$ and evaporated to produce yellow oil, the oil produced was dissolved in 25 ml of 90% ethanol, KCN (1.05 gm, 16.2 mmole) was then added and it was heated under reflux overnight. Ethanol was evaporated; solid was washed with 50 ml water and filtered. The solid was dissolved in 30 ml of conc. HCl, refluxed for 48 hr; charcoal was added refluxed for 1 hr, filtered. The HCl was evaporated, the solid formed was dissolved in 5 ml of water, NaOH 1 N was added drop wise while extracting with ethyl acetate, the ethyl acetate extract was dried with Na$_2$SO$_4$ and evaporated to produce white solid (0.6 gm, 35% in 3 steps) H$^1$-NMR INOVA-500 (DMSO d$_6$) δ 3.641 (s, 2H), 7.345 (t, J=6.0 Hz, 1H), 7.381 (d, J=8.5 Hz, 2H), 7.879 (t, J=8.0 Hz, 1H), 7.951 (d, J=8.0 Hz, 1H), 8.034 (d, J=8.0 Hz, 2H), 8.662 (d, J=4.0 Hz, 1H), 12.390 (s, 1H).

Synthesis of N-(3-Fluoro-benzyl)-2-(4-pyridin-2-yl-phenyl)-acetamide: (4-Pyridin-2-yl-phenyl)-acetic acid (0.2 gm, 0.9 mmole), 3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.13 gm, 45%); H$^1$-NMR INOVA-500 (DMSO d$_6$) δ 3.563 (s, 2H), 4.305 (d, J=6.0 Hz, 2H), 7.032-7.095 (m, 3H), 7.332-7.360 (m, 2H), 7.404 (d, J=8.0 Hz, 2H), 7.874 (t, J=7.0 Hz, 1H), 7.948 (d, J=8.0 Hz, 1H), 8.034 (d, J=8.0 Hz, 2H), 8.659 (d, J=4 Hz, 2H). MS (m/z) 321.2 (M+H)$^+$.

Synthesis of Compounds 13 and 24

Syntheses of the pyridyl derivatives, Compound 13, KX1-316, and Compound 24, KX1-327, are shown in Scheme 4. The amide was made first with an EDCI coupling to give amide 5. The Suzuki with 3- or 4-pyridylboronic acids was then performed. The basic nature of the pyridine ring was exploited to purify the product from and remaining starting material. The product was pulled into the aqueous phase away from the starting material using 1 N HCl. After several organic washes the aqueous layer was basified and the product extracted with ethyl acetate. This purification procedure worked well and eliminated the need for chromatography.

KX1-316 (Compound 13)

A flame dried 50 mL round bottom flask with two condensers was charged with argon. Dimethoxyethane, 15 mL and 1 mL 2 M potassium carbonate was heated to 45° C. while argon was bubbled through the solution. After 1 hour the bromo amide (240 mg, 0.7475 mmol) and 3-pyridylboronic acid (92 mg, 1.1 eq) were added. After one hour, Pd(PPh$_3$)$_4$ (43 mg, 5 mol %) was added neat. Reaction was heated at 65-75° C. for 48 hours. The solvent was poured into a round bottom flask, the remaining residue was washed with ethyl acetate. Solvents were combined and removed in vacuo. The residue was taken up in 20 mL 1 N HCl and washed with ethyl acetate (3×10 mL). The acid layer was then basified with a combination of 2 N NaOH and saturated sodium bicarbonate to pH 8-9. The aqueous layer was then washed with ethyl acetate (3×20 mL). Solvent extracts were combined, dried with sodium sulfate and removed in vacuo. Residue was purified on silica gel column (1:1 DCM:EtOAc) to give 90 mg of the desired product (38% yield). TLC, R$_f$ 0.2 (1:1 DCM:EtOAc). LCMS 321.3 (m+H) 640.8 (2m+Na) 662.9 (2M+Na). $^1$HNMR (500 MHz, DMSO) 3.54 (s, 2H) 4.29 (d, 6.0 Hz, 2H) 7.00-7.08 (m, 3H) 7.34 (q, 8.0 Hz, 1H) 7.40 (d, 10.0 Hz, 2H) 7.47 (dd, 6.0 Hz, 10.0 Hz, 1H) 7.66 (d, 10.0 Hz, 2H) 8.05 (dt, 2.5 Hz, 10.0 Hz, 1H) 8.55 (dd, 2.0 Hz, 6.0 Hz, 1H) 6.40 (t, 7.0 Hz, 1H) 8.78 (d, 2.5 Hz, 1H).

KX1-327 (Compound 24)

A flame dried 50 mL round bottom flask with two condensers was charged with argon. Dimethoxyethane, 15 mL and 1 mL 2 M potassium carbonate was heated to 45° C. while argon was bubbled through the solution. After 1 hour the bromo amide (150 mg, 0.4672 mmol) and 4-pyridylboronic acid (57 mg, 1 eq) were added. After one hour Pd(PPh$_3$)$_4$ (27 mg, 5 mol %) was added neat. Reaction was heated at 65-75° C. for 72 hours. The solvent was poured into a round bottom flask, the remaining residue was washed with ethyl acetate. Solvents were combined and removed in vacuo. The residue was taken up in 20 mL 1 N HCl and washed with ethyl acetate (3×10 mL). The acid layer was then basified with a combination of 2 N NaOH and saturated sodium bicarbonate to pH 8-9. The aqueous layer was then washed with ethyl acetate (3×20 mL). Solvent extracts were combined, dried with sodium sulfate and removed in vacuo to give 71 mg of the desired product (48% yield). TLC, Rf 0.2 (1:1 DCM:EtOAc). LCMS 321.3 (m+H). $^1$HNMR (500 MHz, DMSO) 3.56 (s, 2H) 4.29 (d, 6.0 Hz, 2H) 7.04 (m, 3H) 7.34 (q, 6.5 Hz, 1H) 7.42 (d, 8.0 Hz, 2H) 7.69 (d, 6.0 Hz, 2H) 7.75 (d, 8.5 Hz, 2H) 8.61 (d, 6.0 Hz, 2H) 8.64 (t, 5.5 Hz, 1H).

Scheme 4

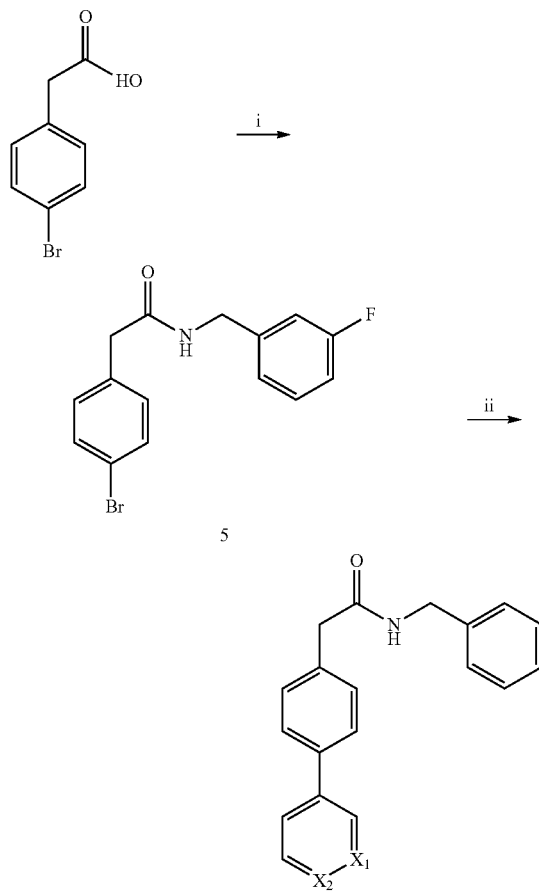

Reagents:
i) 3-Fluorobenzylamine (1.1 eq), EDCl (1.1 eq), HOBT (1.0 eq), DIEA (1.1 eq), 88% yield.
ii) 3(or 4)-Pyridylboronic acid (1.1 eq), Na$_2$CO$_3$ (1.3 eq), Pd(PPh$_3$)$_4$ (5 mol %), Dimethoxyethane, 2M Na$_2$CO$_3$ (2 eq). KX1-316 ($X_1$ = N, $X_2$ = C) 38%, KX1-327 ($X_1$ = C, $X_2$ = N) 47%.

Synthesis of Compound 14, 2-[6-(3-Chloro-phenyl)-pyridin-3-yl]-N-(3-fluoro-benzyl)-acetamide, KX1-317

Synthesis of 2-(3-Chloro-phenyl)-pyridine-5-acetic acid: 2-chloropyridine-5-acetic acid (0.2 gm, 1.21 mmole), 3-chlorophenylboronic acid (0.2 gm, 1.3 mmole) and 50% water wet 10% Palladium carbon (0.08 gm, 0.036 mmole Pd) were added to 10 ml of 5:1 water isopropanol mixture, then Na$_2$CO$_3$ (0.15 gm, 1.4 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was dried under vacuum and crude mixture was used without any purification in the next step.

Synthesis of 2-[6-(3-Chloro-phenyl)-pyridin-3-yl]-N-(3-fluoro-benzyl)-acetamide: To the crude from the above reaction, 3-fluorobenzylamine (0.15 gm, 1.2 mmole), PyBOP (0.67 gm, 1.3 mmole), and DIEA (0.32 μm, 2.6 mmole) and was stirred in DMF overnight. The reaction mixture was then poured into water; solid was collected by filtration, re-crystallized using water-methanol (0.02 gm, 6% in two steps). H$^1$-NMR INOVA-500 (DMSO d$_6$) δ 3.611 (s, 2H), 4.314 (d, J=6.0 Hz, 2H), 7.048-7.106 (m, 3H), 7.364 (m, 1H), 7.500-7.545 (m, 2H), 7.808 (dd, J=8.0, 2.0 Hz, 1H), 7.997 (d, J=8.0 Hz, 1H), 8.046 (d, J=8.0 Hz, 1H), 8.126 (d, J=2.0 Hz, 1H), 8.578 (s, 1H), 8.699 (bs, 1H). MS (m/z) 355.2 (M+H)$^+$.

Synthesis of Compound 14, 2-[6-(4-Ethyl-phenyl)-pyridin-3-yl]-N-(3-fluoro-benzyl)-acetamide, KX1-318

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(4-ethyl-phenyl)-pyridin-3-yl]-N-(3-fluoro-benzyl)-acetamide: 2-(6-Chloro-pyridin-3-yl)-N-(3-fluoro-benzyl)-acetamide and (0.125 gm, 0.5 mmole), 4-ethylbenzeneboronic acid (0.083 gm, 0.55 mmole) was dissolved in dimethoxymethane (DME), Na$_2$CO$_3$ (0.11 gm, 1 mmole) in 5 ml of water was added to the DME solution, the solution was then degassed for 30 min (Ar through the solution and vacuum applied for the first 5 min), Palladiumtetrakistriphenylphosphine (0.029 gm, 0.025 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2. The product is white solid (0.08 gm, 47%). H$^1$-NMR INOVA-500 (DMSO d$_6$) δ 1.228 (t, J=7.5 Hz, 3H), 2.669 (q, J=7.5 Hz, 2H), 3.590 (s, 2H), 4.321 (d, J=6 Hz, 2H), 7.053-7.113 (m, 3H), 7.324-7.375 (m, 3H), 7.766 (dd, J=9.0, 2.0 Hz, 1H), 7.887 (d, J=8.5 Hz, 1H), 7.994 (d, J=8.0 Hz, 2H), 8.548 (s, 1H), 8.696 (t, J=5.5 Hz, 1H). MS (m/z) 349.3 (M+H)$^+$.

Synthesis of Compound 16, N-(3-Fluoro-benzyl)-2-(2-fluoro-biphenyl-4-yl)-acetamide, KX1-319

Synthesis of 2-Fluoro-biphenyl-4-carbaldehyde: 4-Bromo-2-fluoro-biphenyl (2 gm, 8 mmole) was dissolved in 20 ml of anhydrous tetrahydrofuran, THF, cooled to −78° C. under argon (Ar), n-Butyl lithium 2.5 M (3.5 ml, 8.8 mmole) was added drop wise over 10 min, and was stirred for additional 1 hr, DMF anhydrous (0.68 ml, 8.8 mmole) was then added, stirred for additional 1 hr, then warmed to room temperature over 4 hr, It was then quenched with water, extracted with ether, ether was dried, evaporated, the produced compound was purified using 9:1 hexane/ethyl acetate, to produce white solid (1 gm, 62.5%); H$^1$-NMR INOVA-500 (CDCl$_3$) δ 7.416-7.495 (m, 3H), 7.581-7.661 (m, 4H), 7.723 (d, J=8.0 Hz, 1H), 9.991 (s, 1H).

Synthesis of (2-Fluoro-biphenyl-4-yl)-methanol: 2-Fluoro-biphenyl-4-carbaldehyde (1 gm, 5 mmole), $NaBH_4$ were dissolved in ethanol stirred for 2 hrs, NaOH 10% was added, ethanol was evaporated, the reaction mixture was extracted with ethyl acetate, the ethyl acetate extract was dried with $Na_2SO_4$ and evaporated to produce white solid (0.8 gm, 80%). $H^1$-NMR INOVA-500 ($CDCl_3$) δ 2.266 (s, 1H), 4.683 (s, 2H), 7.142-7.168 (m, 2H), 7.339-7.442 (m, 4H), 7.519-7.535 (m, 2H).

Synthesis of (2-Fluoro-biphenyl-4-yl)-acetic acid: (2-Fluoro-biphenyl-4-yl)-methanol (0.75 gm, 3.7 mmole) was dissolved in 20 ml DCM, cooled using ice/methanol, triethylamine (0.55 ml, 4.0 mmole) was added followed by methanesulfonylchloride (0.3 ml, 4.0 mmole) added drop wise over 5 minutes. The reaction was allowed to stir at room temperature till the TLC indicated consumption of the starting material (2 hrs), after completion of the reaction, the reaction mixture was washed with water, saturated $NaHCO_3$ solution, and saturated NaCl solution, dried using $Na_2SO_4$ and evaporated to produce yellow oil, the oil produced was dissolved in 25 ml of 70% ethanol, KCN (0.4 gm, 6 mmole) was then added and it was heated under reflux overnight. Ethanol was evaporated; solid was washed with 50 ml water and filtered. The solid was dissolved in 20 ml of ethanol, then 20 ml of conc. $H_2SO_4$ was added, and was refluxed overnight; the solution was allowed to cool to room temperature, poured to 200 ml of crushed ice, the solid was collected by vacuum filtration, suspended in 25 ml of NaOH 30%, heated at reflux temperature for 24 hrs, cooled to room temperature, washed with DCM and ethyl acetate. The aqueous layer was acidified with conc. HCl, extracted with ethyl acetate, evaporated; the residue was crystallized from isopropanol-water to give white solid (0.15 gm, 18% in 3 steps) $H^1$-NMR INOVA-500 (DMSO $d_6$) δ 3.672 (s, 2H), 7.191-7.254 (m, 2H), 7.389-7.560 (m, 6H), 12.494 (s, 1H).

Synthesis of N-(3-Fluoro-benzyl)-2-(2-fluoro-biphenyl-4-yl)-acetamide: (2-Fluoro-biphenyl-4-yl)-acetic acid (0.12 gm, 0.5 mmole), 3-fluorobenzylamine (0.0 8 ml, 0.6 mmole), PyBOP (0.34 gm, 0.6 mmole), and DIEA (0.22 ml, 1.3 mmole) was dissolved in DMF stirred overnight, the reaction mixture was then poured into water, solid was collected by filtration, re-crystallized using water-methanol. (0.140 gm, 83%); HL-NMR INOVA-500 (DMSO $d_6$) δ 3.580 (s, 2H), 4.316 (d, J=5.5 Hz, 2H), 7.037-7.110 (m, 3H), 7.210-7.247 (m, 2H), 7.343-7.372 (m, 2H), 7.457-7.501 (m, 3H), 7.544 (d, J=8.0 Hz, 2H), 8.660 (t, J=6.0 Hz, 1H). MS (m/z) 338.1 $(M+H)^+$.

Synthesis of Compound 17, N-(3-Fluoro-benzyl)-2-[6-(4-fluoro-phenyl)-pyridin-3-yl]-acetamide, KX1-320

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); $H^1$-NMR INOVA-500 ($CDCl_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(4-fluoro-phenyl)-pyridin-3-yl]-acetamide: 2-(6-Chloro-pyridin-3-yl)-N-(3-fluoro-benzyl)-acetamide and (0.093 gm, 0.33 mmole), 4-fluorobenzeneboronic acid (0.052 gm, 0.37 mmole) was dissolved in DME, $Na_2CO_3$ (0.07 gm, 0.66 mmole) in 5 ml of water was added to the DME solution, the solution was then degassed for 30 min (Ar through the solution and vacuum applied for the first 5 min), Palladiumtetrkestriphenylphosphine (0.016 gm, 0.015 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2. then it crystallized from methanol-water to produce white solid (0.013 gm, 12%). $H^1$-NMR INOVA-500 (DMSO $d_6$) δ 3.587 (s, 2H), 4.306 (d, J=5.0 Hz, 2H), 7.041-7.099 (m, 3H), 7.295-7.363 (m, 3H), 7.777 (d, J=7.5, 1H), 7.913 (d, J=8.0 Hz, 1H), 8.119 (s, 2H), 8.546 (s, 1H), 8.702 (s, 1H). MS (m/z) 339.2 $(M+H)^+$.

Synthesis of Compound 18, N-(3-Fluoro-benzyl)-2-[6-(3-fluoro-phenyl)-pyridin-3-yl]-acetamide, KX1-321

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); $H^1$-NMR INOVA-500 ($CDCl_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(3-fluoro-phenyl)-pyridin-3-yl]-acetamide: 2-(6-Chloro-pyridin-3-yl)-N-(3-fluoro-benzyl)-acetamide and (0.125 gm, 0.5 mmole), 3-fluorobenzeneboronic acid (0.08 gm, 0.55 mmole) was dissolved in DME, $Na_2CO_3$ (0.11 gm, 1.0 mmole) in 5 ml of water was added to the DME solution, the solution was then degassed for 30 min (Ar through the solution and vacuum applied for the first 5 min), Palladiumtetrkestriphenylphosphine (0.029 gm, 0.025 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2, then it crystallized from methanol-water to produce white solid (0.075 gm, 45%). $H^1$-NMR INOVA-500 (DMSO $d_6$) δ 3.614 (s, 2H), 4.318 (d, J=6.0 Hz, 2H), 7.053-7.099 (m, 3H), 7.273 (t, J=9.0 Hz, 1H), 7.367 (q, J=7.0 Hz, 1H), 7.542 (q, J=7.0 Hz, 1H), 7.812 (d, J=8.0 Hz, 1H), 7.891 (d, J=10.0 Hz, 1H), 7.942 (d, J=7.5 Hz, 1H), 7.992 (d, J=8.0 Hz, 1H), 8.583 (s, 1H), 8.717 (s, 1H). MS 339.2 $(M+H)^+$.

Synthesis of Compound 19, 2-[6-(3-Ethoxy-phenyl)-pyridin-3-yl]-N-(3-fluoro-benzyl)-acetamide, KX1-322

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); $H^1$-NMR INOVA-500 ($CDCl_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(3-fluoro-phenyl)-pyridin-3-yl]-acetamide: 2-(6-Chloro-pyridin-3-yl)-N-(3-fluoro-benzyl)-acetamide and (0.15 gm, 0.54 mmole), 3-ethoxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrkestriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2. then it crystallized from methanol-water to produce white solid (0.03 gm, 17%). H$^1$-NMR INOVA-500 (DMSO d$_6$) δ 1.366 (t, J=7.0 Hz, 3H), 3.591 (s, 2H), 4.110 (q, J=7.0 Hz, 2H), 4.312 (d, J=5.5 Hz, 2H), 6.985 (d, J=7.5 Hz, 1H), 7.048-7.105 (m, 3H), 7.342-7.402 (m, 2H), 7.621 (m, 2H), 7.770 (d, J=7.0 Hz, 1H), 7.826 (d, J=8.0 Hz, 1H), 7.942 (d, J=7.5 Hz, 1H), 8.550 (s, 1H), 8.701 (s, 1H). MS (m/z) 365.2 (M+H)$^+$.

Synthesis of Compound 20, 4-{5-[(3-Fluoro-benzyl-carbamoyl)-methyl]-pyridin-2-yl}-benzoic acid, KX1-323

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(3-fluoro-phenyl)-pyridin-3-yl]-acetamide: 2-(6-Chloro-pyridin-3-yl)-N-(3-fluoro-benzyl)-acetamide and (0.15 gm, 0.54 mmole), 4-carboxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrkestriphenylphosphine (0.031 gm, 0.027 mmole) was added, degassed for additional 15 min, refluxed for 24 hr. The reaction was allowed to cool to room temperature, filtered, solid washed with ethyl acetate, NaOH 10%, the aqueous layer was washed several times with ethyl acetate, neutralized by drop wise addition of HCl 1% having ethyl acetate in the medium with shaking after each addition of the HCl, ethyl acetate was evaporated and the solid formed was crystallized from methanol-water to produce a white solid (0.07 gm, 40%). H$^1$-NMR INOVA-500 (DMSO d$_6$) δ 3.625 (s, 2H), 4.318 (d, J=5.5 Hz, 2H), 7.053-7.111 (m, 3H), 7.376 (q, J=7.0 Hz, 1H), 7.8341 (d,J=8.0, 1H), 8.015-8.063 (m, 3H), 8.206 (d, J=8.0 Hz, 1H), 8.613 (s, 1H), 8.724 (t, J=5.5, 1H). MS (m/z) 365.3 (M+H)$^+$.

Synthesis of Compound 21, 2-[6-(2-Ethoxy-phenyl)-pyridin-3-yl]-N-(3-fluoro-benzyl)-acetamide KX1-324

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(2-Ethoxy-phenyl)-pyridin-3-yl]-N-(3-fluoro-benzyl)-acetamide: 2-(6-Chloro-pyridin-3-yl)-N-(3-fluoro-benzyl)-acetamide and (0.15 gm, 0.54 mmole), 2-ethoxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrkestriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 2:1, then it crystallized from methanol-water to produce a white solid (0.075 gm, 40%). H$^1$-NMR INOVA-500 (DMSO d$_6$) δ 1.339 (t, J=7.0 Hz, 3H), 3.581 (s, 2H), 4.112 (q, J=7.0 Hz, 2H), 4.322 (d, J=5.5 Hz, 2H), 7.032-7.135 (m, 5H), 7.358-7.387 (m, 2H), 7.703 (d, J=7.0, 1H), 7.748 (d, J=7.0 Hz, 1H), 7.871 (d, J=7.0 Hz, 1H), 8.548 (s, 1H), 8.725 (s, 1H). MS (m/z) 365.2 (M+H)$^+$.

Synthesis of Compound 22, 2-[6-(4-Ethoxy-phenyl)-pyridin-3-yl]-N-(3-fluoro-benzyl)-acetamide KX1-325

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(4-Ethoxy-phenyl)-pyridin-3-yl]-N-(3-fluoro-benzyl)-acetamide: 2-(6-Chloro-pyridin-3-yl)-N-(3-fluoro-benzyl)-acetamide and (0.15 gm, 0.54 mmole), 4-ethoxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrkestriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 2:1, then it crystallized from methanol-water to produce a white solid (0.08 gm, 42%). H$^1$-NMR INOVA-500 (DMSO d$_6$) δ 1.357 (t, J=7.0 Hz, 3H), 3.564 (s, 2H), 4.090 (q, J=7.0 Hz, 2H), 4.309 (d, J=6.0 Hz, 2H), 7.012-7.103 (m, 5H), 7.361 (q, J=7.0 Hz, 1H), 7.726 (d, J=8.0 Hz, 1H), 7.842 (d, J=8.0 Hz, 1H), 8.012 (d, J=8.5 Hz, 2H), 8.503 (s, 1H), 8.686 (s, 1H). MS (m/z) 365.2 (M+H)$^+$.

Scale-Up Synthesis of Compound 22 HCl 2-[6-(4-Ethoxy-phenyl)-pyridin-3-yl]-N-(3-fluorobenzyl)-acetamide HCl, KX1-325 HCl Synthesis of 2-(6-Chloro-pyridin-3-yl)-N-(3-fluoro-benzyl)-acetamide HCl: 2-chloropyridine-5-acetic acid (6.0 gm, 34 mmole), 3-fluorobenzylamine (4.5 ml, 34 mmole), PyBOP (18 gm, 36 mmole), and DIEA (12.5 ml, 75 mmole) was dissolved in DMF stirred overnight, the reaction mixture was then poured into water, solid was collected by filtration, recrystallized using water-methanol (6.3 gm, 70%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(4-Ethoxy-phenyl)-pyridin-3-yl]-N-(3-fluoro-benzyl)-acetamide: 2-(6-Chloro-pyridin-3-yl)-N-(3-fluoro-benzyl)-acetamide and (4.8 gm, 17.2 mmole), 4-ethoxybenzeneboronic acid (3.14 gm, 18.9 mmole) was suspended in DME (100 ml), Na$_2$CO$_3$ (3.6 gm, 34.4 mmole) in 15 ml of water was added to the DME solution, the solution was then degassed for 30 min (Ar through the solution and vacuum applied for the first 5 min), Palladiumtetrkestriphenylphosphine (0.99 gm, 0.86 mmole) was added, degassed for additional 15 min, refluxed overnight. The reaction was allowed to cool to room temperature, filtered, the solid washed with cold ethyl acetate and saturated NaHCO$_3$ solution, the solid was then recrystallized from methanol to produce white solid (4.8 gm).

4.6 gm of the free amine was dissolved in 50 ml ethanol with gentle heating, then 25 ml of 4 N HCl in ethyl acetate was added, the solution was concentrated to 20 ml, then diluted with 100 ml of cold ethyl acetate, the solid formed was filtered washed with more ethyl acetate (50×2) and dried (4.3 gm, 65%); H$^1$-NMR INOVA-500 (DMSO d$_6$) δ 1.386 (t, J=7.0 Hz, 3H), 3.822 (s, 2H), 4.179 (q, J=7.0 Hz, 2H), 4.339 (d, J=6.0 Hz, 2H), 7.074-7.182 (m, 5H), 7.374 (m, 1H), 8.106 (d, J=8.0 Hz, 1H), 8.263 (d, J=8.0 Hz, 1H), 8.312 (s, 2H), 8.718 (s, 1H), 8.981 (s, 1H). MS (m/z) 365.2 (M+H)$^+$.

Melting Point of the free base: 0.1 gm of the HCl salt was stirred in 10 ml of 20% NaOH for 10 min, filtered; the solid was crystallized from ethanol water, dried in the oven at 100° C. for 2 hrs. Melting point was found to be 173-176° C.

Synthesis of Compound 23, N-(3-Fluoro-benzyl)-2-[6-(4-methanesulfonyl-phenyl)-pyridin-3-yl]-acetamide, KX1-326

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, recrystallized using water-methanol (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(4-methanesulfonyl-phenyl)-pyridin-3-yl]-acetamide: 2-(6-Chloro-pyridin-3-yl)-N-(3-fluoro-benzyl)-acetamide and (0.15 gm, 0.54 mmole), 4-methanesulfonyl benzeneboronic acid (0.12 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrkestriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 2:1, then it crystallized from methanol-water to produce a white solid (0.02 gm, 10%); H$^1$-NMR INOVA-500 (DMSO d$_6$) δ 3.341 (s, 3H), 3.635 (s, 2H), 4.315 (d, J=7.0 Hz, 2H), 7.047-7.110 (m, 3H), 7.366 (q, J=9.0 Hz, 1H), 7.857 (d, J=8.5 Hz, 1H), 8.027-8.081 (m, 3H), 8.343 (d, J=10.5 Hz, 2H), 8.631 (s, 1H), 8.731 (s, 1H). MS (m/z) 399.2 (M+H)$^+$.

Synthesis of Compound 24, KX1-327, and Compound 26, KX1-357

The syntheses are shown in Scheme 5.

Compound 24, KX1-327 HCl

A solution of 75 mL 1,2-Dimethoxyethane and 16 mL 2 M sodium carbonate was thoroughly degassed by heating at 50° C. with an argon stream through the solvent. 5.00 g of the 4-bromophenyl acetamide (5, 15.6 mmol) and 1.95 grams of 4-pyridylboronic acid (1.00 eq) were added to and degassing continued for 1 hour. Tetrakis(triphenylphosphine)palladium (5 mol %) was added neat and the reaction was refluxed for 24 hours. The reaction was cooled and poured into 300 mL distilled water and filtered to give 5.014 g crude product. This crude product was taken up in 1 L of a 1 to 1 mix of 1 N HCl and ethyl acetate. The organic layer was discarded and the aqueous layer was washed two more times with EtOAc. The aqueous layer was the basified with solid sodium bicarbonate to pH 7.5. This was then extracted 3×300 mL EtOAc to give about 3.25 g of semi-pure product. Pure crystals of the free base were made by dissolving 200 mg in a minimum amount of ethyl acetate with gentle heating and sonication. Hexanes was added to this solution until it became cloudy. This was heated until clear. Addition of more hexanes followed by heating was repeated two more times. This clear solution was allowed to stand overnight in a sealed vessel. White crystals formed which were washed with hexanes and dried to give about 50 mg (mp 145-146° C.). The rest of the product was dissolved in ethanol and two equivalents of hydrochloric acid (1.1 M in EtOAc) were added. After 1 hour the ethanol was removed and redissolved in the least amount of ethanol at 40° C. EtOAc was added until the solution became cloudy. The solution was allowed to stand and the desired product crystallized as pure white crystals. The crystals were filtered off, washed with EtOAc and dried to give 2.4 grams (48% overall yield); LCMS 321.3 (m+H). $^1$HNMR (500 MHz, DMSO) 3.61 (s, 2H) 4.29 (d, 7.5 Hz, 2H) 7.04 (m, 3H) 7.34 (q, 9.5 Hz, 1H) 7.50 (d, 10.5 Hz, 2H) 7.95 (d, 10.5 Hz, 2H) 8.24 (d, 8.0 Hz, 2H) 8.70 (s. 1H) 8.87 (d, 8.0 Hz, 2H).

Compound 26, KX1-357

47.0 mg of KX1-327 were dissolved in 5 mL DCM. Meta-chloroperoxybenzoic acid (35.0 mg, 1.4 eq) were added and the reaction was allowed to stir for 13 hours. The reaction was washed 3×5 mL saturated sodium bicarbonate, dried with sodium sulfate and concentrated to give 45 mg of a yellow solid. NMR revealed the product contained about 15% impurity, which may have been m-chlorobenzoic acid (or the peroxide). The solid was redissolved in 5 mL DCM and washed 3×5 mL saturated sodium bicarbonate, dried with sodium sulfate and concentrated to give 26 mg of the desired product as a yellow solid; LCMS 337.2 (M+H), 672.9 (2M+H), 694.8 (2M+Na). $^1$HNMR (400 MHz, DMSO) 3.54 (s, 2H), 4.28 (d, 6.0 Hz, 2H), 7.00-7.08 (m, 3H), 7.34 (q, 8.0 Hz, 1H), 7.40 (d, 8.4 Hz, 2H), 7.72 (d, 8.4 Hz, 2H), 7.75 (d, 7.2 Hz, 2H), 8.24 (d, 8.4 Hz, 2H), 8.63 (t, 5.6 Hz, 1H).

Scheme 5

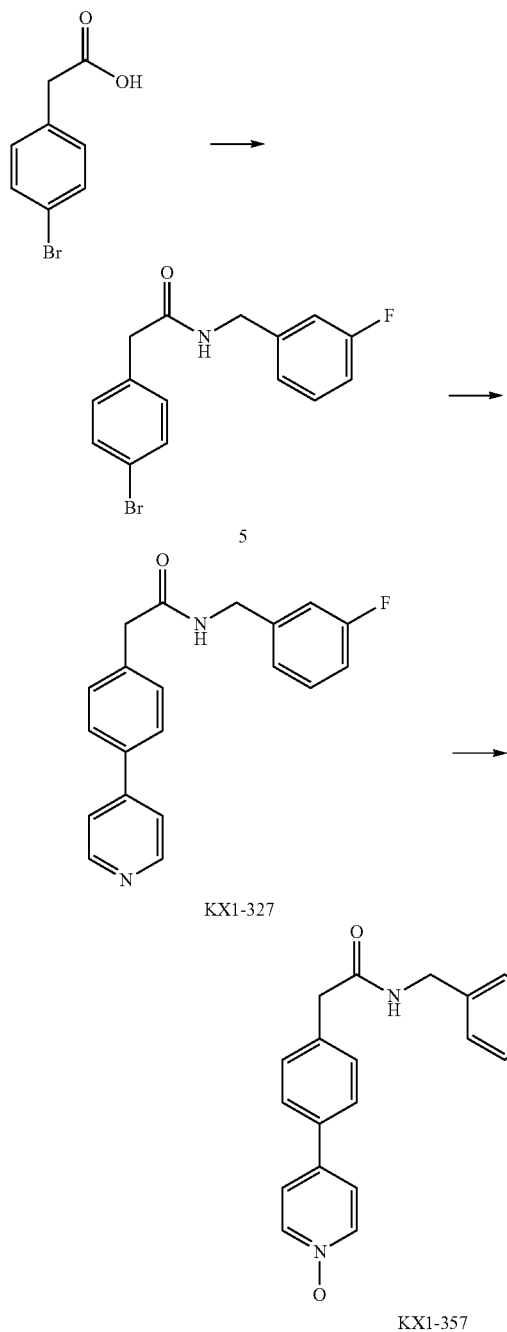

KX1-327

KX1-357

4-Bromophenylacetic acid (6.00 g, 47.9 mmol) was dissolved in 40 mL of anhydrous dichloromethane under an argon atmosphere and cooled in an ice bath. 3-Fluorobenzylamine (1.00 eq) was added and unintended precipitation of the acetic acid/benzylamine salt occurred. More dichloromethane (20 mL) was added followed by DIEA (2.2 eq), HOBT (1.0 eq), and EDCI (1.1 eq). After about 2 hours the solid broke up, 4 hours after that the reaction was finished by TLC. The reaction was diluted with 200 mL of dichloromethane and 200 mL of 1 N hydrochloric acid. Upon shaking in a separatory funnel an emulsion formed. This emulsion was divided in half and dichloromethane was removed. 500 mL ethyl acetate and another 300 mL 1 N HCl was added to each half. The organic layer was washed 2 more times with 1 N HCl, 3×300 mL saturated sodium bicarbonate, and 3×200 mL with saturated sodium chloride. Organic layers from each extraction were combined and dried with sodium sulfate, and solvent was removed to give 13.12 g (85% yield) desired product; $^1$HNMR (500 MHz, CDCl$_3$) δ (ppm) 3.58 (s, 2H), 4.45 (d, 6.0 Hz, 2H), 5.70 (bs, 1H) 6.93 (m, 3H), 7.16 (d, 8.1 Hz, 2H), 7.26 (m, 1H) 7.48 (d, 8.1 Hz, 2H).

Synthesis of Compound 25, KX1-329

As shown in Scheme 6,5-Hydroxy-2-methylpyridine was converted to the triflate, 6, followed by Suzuki reaction to give the 5-phenyl-2-methylpyridine. The methylpyridine, 7, was deprotonated with n-butyllithum and added to a solution of ethyl carbonate. Saponification followed by amide coupling with PyBOP gave the desired product.

5-Hydroxy-2-methylpyridine (3.00 g, 27.5 mmol) was dissolved in 15 mL anhydrous pyridine and cooled to 0° C. Triflic anhydride (7.76 g, 1.1 eq) was added drop wise over 3 minutes. Following the addition the reaction was removed from the ice bath and allowed to stir for 6 hr. The volume was then reduced to 8 mL in vacuo, diluted with 50 mL distilled water, and then extracted with 75 mL EtOAc. The organic layer was then washed with 1 N HCl (3×50 mL), dried with sodium sulfate, and removed in vacuo to give 2.78 g (42%) of an amber oil (6); LCMS 242.1 (m+H). $^1$HNMR (400 MHz, CDCl$_3$) 2.58 (s, 3H) 7.26 (d, 8.4 Hz, 1H) 7.52 (dd, 2.8 Hz, 8.4 Hz, 1H) 8.47 (d, 2.8 Hz, 1H).

A flame dried 50 mL round bottom flask with two condensers was charged with argon. Dimethoxyethane, 25 mL and 6 mL 2 M sodium carbonate was heated to 45° C. while argon was bubbled through the solution. After 1 hour, the pyridyl triflate (6) (1.538 g, 6.382 mmol) and phenylboronic acid (856 mg, 1.1 eq) were added. After one hour Pd(PPh$_3$)$_4$ (370 mg, 5 mol %) was added, the reaction was heated at 65-75° C. for 48 hours. The solvent was poured into a round bottom flask, the remaining residue was washed with ethyl acetate. Solvents were combined and removed in vacuo. The residue was purified by silica gel chromatography (hexanes:EtOAc) to give 702 mg of the desired product 7 (65% yield); LCMS 170.2 (m+H). $^1$HNMR (400 MHz, CDCl$_3$) 3.60 (s, 3H) 7.22 (d, 8.0 Hz, 1H) 7.38 (t, 7.2 Hz, 1H) 7.46 (t, 7.2 Hz, 2H) 7.56 (d, 8.0 Hz, 2H) 7.77 (dd, 2.4 Hz, 8.0 Hz, 1H) 8.73 (d, 2.4 Hz, 1H).

5-Phenyl-2-methylpyridine (7, 205 mg, 1.223 mmol) was dissolved in freshly distilled THF in flame dried glassware under argon. Cooled to −78° C. in a dry ice/acetone bath for 20 minutes. N-Butyllithium (0.485 mL, 1.0 eq) was added drop wise over 5 minutes. This solution was added to a THF solution of ethyl carbonate (1.5 eq) via a cannula. The solution was stirred for 2 hours before being quenched with methanol added drop wise. 1 N sodium hydroxide (1 mL) was added before removing the organic solvents in vacuo. The remaining aqueous solution was extracted with ether (3×15 mL). Organic layers were combined and dried with sodium sulfate and removed in vacuo to give 208 mg 8 (71% yield) $^1$HNMR (500 MHz, CDCl$_3$) 1.30 (m, 3H) 2.61 (s, 2H) 4.20 (m, 3H) 7.22 (d, 8.0 Hz, 1H) 7.38 (t, 7.5 Hz, 1H) 7.48 (t, 7.5 Hz, 2H) 7.58 (m, 2H) 7.78 (dd, 2.5 Hz, 8.0 Hz, 1H) 8.73 (d, 2.5 Hz, 1H).

Ethyl ester 8 (208 mg, 0.86 mmol) was dissolved in 5 mL THF. 1 N NaOH (about 1 mL) was added and the reaction was put in a 35° C. water bath overnight. The volume of the reaction was reduced to about 1 mL and then acidified with 1 N HCl to precipitate the desired product. The precipitate was isolated by decanting and drying in vacuo to give 54 mg (30% yield) of 9; LCMS 214.1 (m+H) 236.0 (m+Na). $^1$HNMR (400 MHz, CD$_3$OD) 3.64 (s, 2H) 7.24-7.28 (m, 4H) 7.25 (t, 8.4 Hz, 2H) 7.52 (d, 8.4 Hz, 2H) 7.87 (dd, 2.0 Hz, 8.0 Hz, 1H) 8.53 (d, 2.0 Hz, 1H).

Carboxylic acid 9 (54 mg, 0.232 mmol), 3-Fluorobenzylamine (1.1 eq), and PyBOP (1.1 eq) were dissolved in 3 ml anhydrous DMF. After 10 minutes DIEA (1.1 eq) was added and the reaction was allowed to stir overnight. The DMF was removed in vacuo and the residue was taken up with methanol and crystallized from methanol/water to give 44 mg Compound 25, KX1-329 (55%) as clear, needle crystals; TLC, Rf 0.2 (1:1 DCM:EtOAc). LCMS 321.2 (m+H), 343.1 (m+Na), 662.9 (2 m+Na). $^1$HNMR (400 MHz, CDCl$_3$) 3.82 (s, 2H), 4.46 (d, 8.8 Hz, 2H), 6.91 (t, 9.2 Hz, 2H) 6.99 (d, 7.6 Hz, 1H), 7.25 (t, 8.4 Hz, 2H), 7.34 (d, 8.0 Hz, 2H) 7.40 (tt, 1.2 Hz, 7.2 Hz, 2H) 7.55 (d, 7.6 Hz, 2H) 7.80 (b, 1H) 7.86 (dd, 2.0 Hz, 7.6 Hz, 1H) 8.73 (d, 2.0 Hz, 1H).

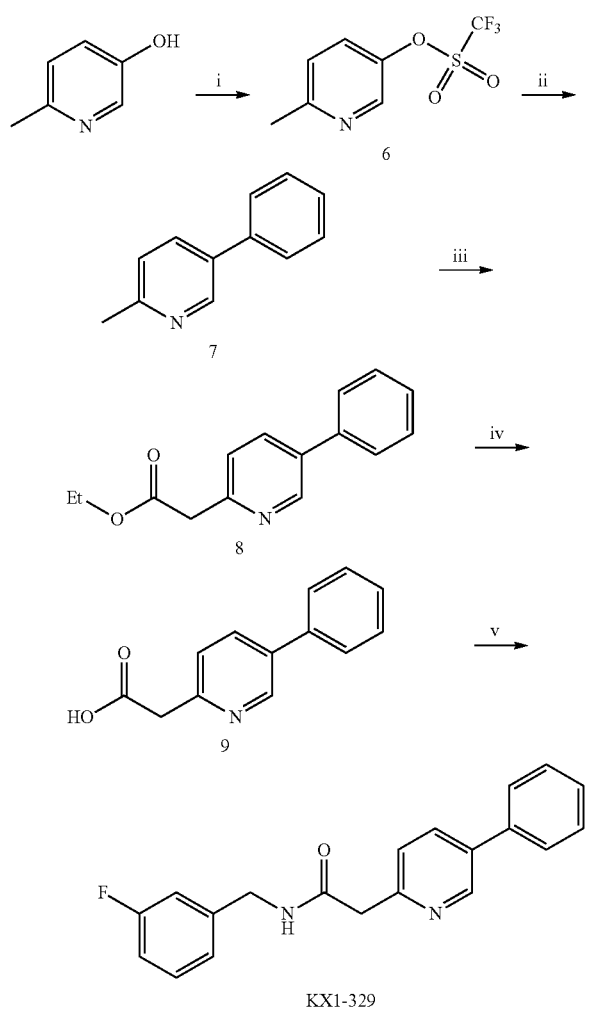

Scheme 6

KX1-329

Reagents:
i) Tf$_2$O, pyridine (43%).
ii) Phenylboronic acid (1.1 eq), Na$_2$CO$_3$ (1.3 eq), Pd(PPh$_3$)$_4$ (5 mol %), Dimethoxyethane, 2M Na$_2$CO$_3$ (2 eq) (65% after chromatography).
iii) n-Butyl lithium (1.0 eq), diethylcarbonate (1.5 eq), anhydrous THF.
iv) LiOH, THF 30C (18% after crystallization).
v) 3-fluorobenzylamine (1.1 eq), PyBOP (1.1 eq), DIEA (1.1 eq), DMF (55% yield).

Synthesis of Compound 27, 2-[6-(4-Ethoxy-phenyl)-1-oxo-pyridin-3-yl]-N-(3-fluoro-benzyl)-acetamide, KX1-358

To an ice cooled solution of 0.2 gm of 2-[6-(4-Ethoxy-phenyl)pyridin-3-yl]-N-(3-fluoro-benzyl)-acetamide in 80 ml DCM, 0.13 gm of m-chloroperbenzoic acid was added as solid. After stirring overnight, the reaction was washed with saturated sodium bicarbonate solution, dried with sodium sulfate, evaporated to dryness under vacuum, then chromatographed (silica gel) using ethyl acetate followed by 10% methanol in ethyl acetate to produce 0.16 gm (78%); H$^1$-NMR INOVA-400 (DMSO d$_6$) δ 1.357 (t, J=7.0 Hz, 3H), 3.564 (s, 2H), 4.090 (q, J=6.8 Hz, 2H), 4.309 (d, J=5.60 Hz, 2H), 7.012-7.103 (m, 5H), 7.245 (d, J=8.0 Hz, 1H), 7.729 (m, 1H), 7.529 (d, J=8.0 Hz, 1H), 7.800 (d, J=8.5 Hz, 2H), 8.225 (s, 1H), 8.663 (t, J=5.6 Hz, 1H). MS (m/z) 380 (M+H)$^+$.

For the following syntheses, unless otherwise noted, reagents and solvents were used as received from commercial suppliers. Proton and carbon nuclear magnetic resonance spectra were obtained on a Bruker AC 300 or a Bruker AV 300 spectrometer at 300 MHz for proton and 75 MHz for carbon. Spectra are given in ppm (δ) and coupling constants, J, are reported in Hertz. Tetramethylsilane was used as an internal standard for proton spectra and the solvent peak was used as the reference peak for carbon spectra. Mass spectra and LC-MS mass data were obtained on a Perkin Elmer Sciex 100 atmospheric pressure ionization (APCI) mass spectrometer. LC-MS analyses were obtained using a Luna C8(2) Column (100×4.6 mm, Phenomenex) with UV detection at 254 nm using a standard solvent gradient program (Method B). Thin-layer chromatography (TLC) was performed using Analtech silica gel plates and visualized by ultraviolet (UV) light, iodine, or 20 wt % phosphomolybdic acid in ethanol. HPLC analyses were obtained using a Prevail C18 column (53×7 mm, Alltech) with UV detection at 254 nm using a standard solvent gradient program (Method A).

| Method A: | | | |
|---|---|---|---|
| Time (min) | Flow (mL/min) | % A | % B |
| 0.0 | 3.0 | 95.0 | 5.0 |
| 10.0 | 3.0 | 0.0 | 100.0 |
| 11.0 | 3.0 | 0.0 | 100.0 |

A = Water with 0.1 v/v Trifluoroacetic Acid
B = Acetonitrile with 0.1 v/v Trifluoroacetic Acid

| Method B: | | | |
|---|---|---|---|
| Time (min) | Flow (mL/min) | % A | % B |
| 0.0 | 2.0 | 95.0 | 5.0 |
| 4.0 | 2.0 | 5.0 | 95.0 |

A = Water with 0.02 v/v Trifluoroacetic Acid
B = Acetonitrile with 0.02 v/v Trifluoroacetic Acid

Synthesis of N-benzyl-2-(5-bromopyridin-2-yl)acetamide

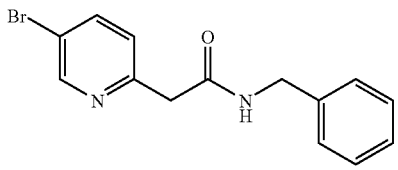

A flask was charged with 5-(5-bromopyridin-2(1H)-ylidene)-2,2-dimethyl-1,3-dioxane-4,6-dione (1.039 g, 3.46 mmol), benzylamine (0.50 mL, 4.58 mmol), and toluene (20 mL). The reaction was brought to reflux under nitrogen for 18 hours, then cooled and placed in a freezer until cold. The product was collected by filtration and washed with hexanes to yield a mass of bright white crystals (1.018 g, 96%).

Synthesis of 4-(2-(4-(4,4,5,5-tetramethyl[1,3,2]dioxaborolan-2-yl)-phenoxy)ethyl)morpholine

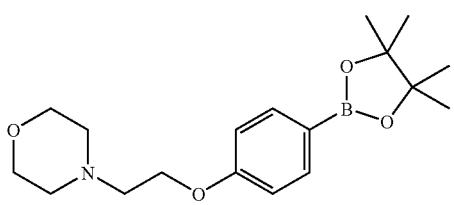

To a stirring solution of 4-(4,4,5,5-tetramethyl[1,3,2]dioxaborolan-2-yl)-phenol (2.55 g, 11.58 mmol), 2-morpholin-4-ylethanol (1.60 mL, 1.73 g, 13.2 mmol) and triphenyl phosphine (3.64 g, 13.9 mmol) in methylene chloride (60 mL) at 0° C. was added dropwise DIAD (2.82 g, 13.9 mmol). The reaction was allowed to warm to room temperature and stir overnight. After 18 hours, additional portions of triphenyl phosphine (1.51 g, 5.8 mmol), 2-morpholin-4-ylethanol (0.70 mL, 5.8 mmol), and DIAD (1.17 g, 5.8 mmol) were added. After stirring an additional 2 hours at room temperature the reaction was concentrated and the residue purified by flash chromatography (5% to 25% EtOAc in CHCl$_3$) to provide the product as a white solid (2.855 g, 74%).

Synthesis of Compound 134, KX2-391

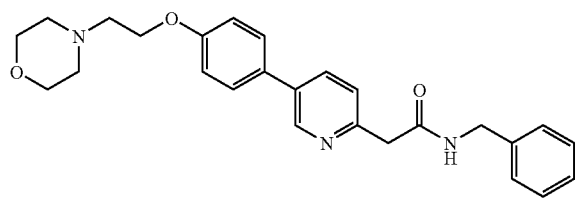

A 10 mL reaction tube with a septum closure and stir bar was charged with N-benzyl-2-(5-bromopyridin-2-yl)acetamide (123 mg, 0.403 mmol), 4-(2-(4-(4,4,5,5-tetramethyl[1,3,2]dioxaborolan-2-yl)-phenoxy)ethyl)morpholine (171 mg, 0.513 mmol), and FibreCat 1007[1] (30 mg, 0.015 mmol). Ethanol (3 mL) was added, followed by aqueous potassium carbonate solution (0.60 mL, 1.0 M, 0.60 mmol). The tube was sealed and heated under microwave conditions at 150° C. for 10 minutes. The reaction was cooled and concentrated to remove the majority of the ethanol, and then taken up in 10 mL of ethyl acetate and washed successively with water and saturated sodium chloride solution. The organic layer was dried with MgSO$_4$, filtered and concentrated to a white solid. This white solid was triturated with ethyl ether to give ALB 30349 as a white solid (137 mg, 79%): mp 135-137° C.; $^1$H NMR (300 MHz, CDCl$_3$) δ 8.70 (d, 1H, J=2.0 Hz), 7.81 (dd, 1H, J=2.4 Hz, J=8.0 Hz), 7.65 (br s, 1H), 7.49 (d, 2H, J=8.8 Hz), 7.37-7.20 (m, 6H), 7.01 (d, 2H, J=8.8 Hz), 4.49 (d, 2H, J=5.8 Hz), 4.16 (t, 2H, J=5.7 Hz, 3.82 (s, 2H), 3.78-3.72 (m, 4H), 2.84 (t, 2H, J=5.7 Hz), 2.62-2.58 (m, 4H); HPLC (Method B) 98.0% (AUC), t$_R$=1.834 min.; APCI MS m/z 432 [M+H]$^+$.

[1] Polymer bound di(acetato)dicyclohexylphenylphosphinepalladium(II), manufactured by Johnson Matthey, Inc. and available from Aldrich (catalog # 590231).

(4-bromo-3-fluorophenyl) (morpholino)methanone

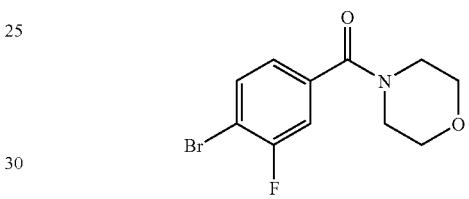

A 500 mL flask was charged with 4-bromo-3-fluorobenzoic acid (5.00 g, 22.83 mmol), 100 mL DMF, morpholine (2.4 ml, 27.5 mmol), and 4-Ethylmorpholine (8.6 ml, 67.9 mmol). HOBt (4.32 g, 32.0 mmol) was added followed by EDC (5.25 g, 27.4 mmol) and the reaction allowed to stir at room temperature for 18 hours. The reaction was concentrated and the resulting orange syrup taken up in 100 mL EtOAc and 100 mL water. The organic layer was washed with 100 mL 2N HCl, 100 mL saturated sodium bicarbonate, and 100 mL saturated sodium chloride. The organic was then dried with MgSO$_4$, filtered, and concentrated to give 6.476 g (98%) of a viscous yellow oil. This material was used without further purification.

4-(4-bromo-3-fluorobenzyl)morpholine

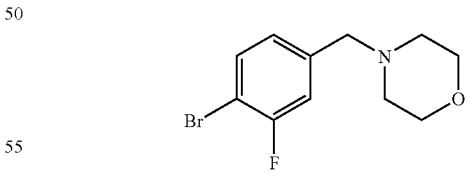

A 250 ml flask was charged with (4-bromo-3-fluorophenyl)(morpholino)methanone (4.569 g, 15.86 mmol) and dissolved in 16 mL of THF. Diphenylsilane (6.2 ml, 33.4 mmol) was added followed by carbonyltris(triphenylphosphine)rhodium(I)hydride (100 mg, 0.109 mmol) and the reaction stirred at room temperature for 20 hours.

The reaction was diluted with 200 mL of ether and extracted with 1N HCl (2×150 mL). This resulted in the formation of a white precipitate in the separatory funnel. The acid layer and the resulting white precipitate were washed with ether (2×100 mL), and then basified with solid NaOH pellets (23 g). The aqueous layer was then extracted with ether (3×125 mL), dried over MgSO$_4$, filtered, and concentrated to give 1.35 g (31%) of a colorless oil. This material was used without further purification.

4-(3-fluoro-4-(4,4,5,5-tetramethyl-1,3,2-dioxaborolan-2-yl)benzyl)morpholine

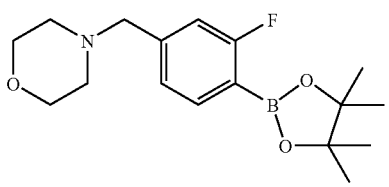

A 10 mL microwave reaction tube with septum closure was charged with 4-(4-bromo-3-fluorobenzyl)morpholine (405 mg, 1.48 mmol), Bis(pinacolato)diboron (516 mg, 2.03 mmol), Pd(dppf)Cl$_2$·CH$_2$Cl$_2$ (62 mg, 0.076 mmol), potassium acetate (659 mg, 6.72 mmol), and DMF (3.6 mL). The vial was placed under nitrogen by evacuation/backfilling (5 cycles) and stirred at 80° C. for 8 hours. The reaction was cooled, diluted with ethyl acetate (25 mL) and filtered. The organics were washed with water (25 mL) and saturated sodium chloride (25 mL). The organic layer was then dried over MgSO$_4$ and concentrated to a dark oil. The product was purified by silica gel chromatography eluting with 2% MeOH in CHCl$_3$ to give 310 mg (65%) of an off-white solid.

Synthesis of Compound 136, KX2-393

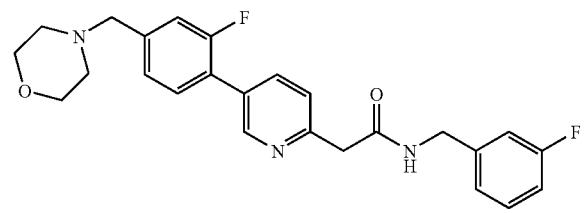

A 10 mL microwave reaction tube with septum closure was charged with 4-(3-fluoro-4-(4,4,5,5-tetramethyl-1,3,2-dioxaborolan-2-yl)benzyl)morpholine (307 mg, 0.96 mmol), 2-(5-bromopyridin-2-yl)-N-(3-fluorobenzyl)acetamide (247 mg, 0.77 mmol), and FibreCat 1007 (60 mg, 0.03 mmol). Ethanol (3 mL) was added followed by aqueous potassium carbonate solution (1.2 mL, 1.0 M, 1.2 mmol). The tube was sealed and heated under microwave conditions at 150° C. for 10 minutes. The reaction was cooled and concentrated to remove the majority of the ethanol, and then taken up in 10 mL of ethyl acetate and washed successively with water and saturated sodium chloride solution. The organic layer was dried with MgSO$_4$, filtered, and concentrated. The material was purified by column chromatography (silica gel, 100:0 CHCl$_3$/MeOH to 95:5 CHCl$_3$/MeOH) to provide ALB 30351 as a white solid (240 mg, 74%): mp 91-92° C.; $^1$H NMR (300 MHz, CDCl$_3$) δ 8.71 (br s, 1H), 7.86-7.84 (m, 1H), 7.78 (br s, 1H), 7.37 (t, 2H, J=7.5 Hz), 7.28-7.21 (m, 3H), 7.02 (dd, 1H, J=0.6 Hz, J=7.7 Hz), 6.98-6.90 (m, 2H), 4.49 (d, 2H, J=5.9 Hz), 3.84 (s, 2H), 372-3.75 (m, 4H), 3.52 (s, 2H), 2.47-2.50 (m, 4H); HPLC (Method A) 98.7% (AUC), t$_R$=3.866 min.; APCI MS m/z 438 [M+H]$^+$.

4-(2-(4-bromo-3-fluorophenoxy)ethyl)morpholine

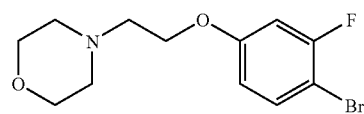

A flask was charged with 4-bromo-3-fluorophenol (4.999 g, 26.2 mmol) and triphenylphosphine (10.298 g, 39.3 mmol). Methylene chloride (120 mL) was added followed by 2-morpholinoethanol (4 mL, 33.0 mmol) and the solution was stirred on an ice water bath to cool. After 5 minutes, diisopropyl azodicarboxylate (7.6 ml, 39.1 mmol) was added over 6 to 8 minutes. The reaction was left stirring on the cold bath to slowly warm to room temperature overnight. The reaction was concentrated and the residue purified by flash chromatography (25% to 100% EtOAc in hexanes) to provide the product as a colorless oil (2.621 g, 33%).

4-(2-(3-fluoro-4-(4,4,5,5-tetramethyl-1,3,2-dioxaborolan-2-yl)phenoxy)ethyl)morpholine

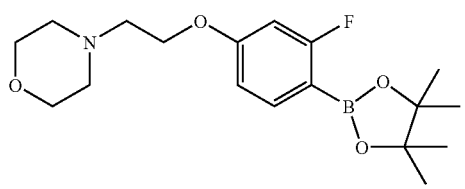

A 40 mL microwave reaction tube with a septum closure and stir bar was charged with 4-(2-(4-bromo-3-fluorophenoxy)ethyl)morpholine (307 mg, 1.0 mmol), Bis(pinacolato)diboron (318 mg, 1.25 mmol), Pd(dppf)Cl$_2$—CH$_2$Cl$_2$ (68 mg, 83 µmol), and Potassium acetate (316 mg, 3.22 mmol). DME (20 ml) was added and the tube sealed. The tube was evacuated/backfilled w. N$_2$ (5 cycles) and microwaved at 125° C. for 30 minutes. The reaction was cooled to room temperature, concentrated and the residue purified by column chromatography (silica gel, 2% MeOH in CHCl$_3$) to provide the product as a colorless oil (356 mg, >99%). The $^1$H NMR spectrum shows the product to contain a small amount of pinacol-like impurity. The material was used as-is.

Synthesis of Compound 133, KX2-392

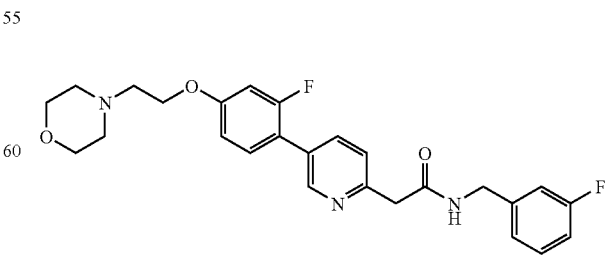

A 10 mL microwave reaction tube with septum closure was charged with 4-(2-(3-fluoro-4-(4,4,5,5-tetramethyl-1,3,2-dioxaborolan-2-yl)phenoxy)ethyl)morpholine (175 mg, 0.50 mmol), 2-(5-bromopyridin-2-yl)-N-(3-fluorobenzyl)acetamide (121 mg, 0.37 mmol), and FibreCat 1007 (30 mg, 0.03 mmol). Ethanol (3 mL) was added followed by aqueous potassium carbonate solution (0.600 mL, 1.0 M, 0.60 mmol). The tube was sealed and heated under microwave conditions at 150° C. for 10 minutes. The reaction was cooled, filtered, and concentrated to remove the majority of the ethanol. The residue was then taken up in 10 mL of ethyl acetate and washed successively with water and saturated sodium chloride solution. The organic layer was dried with $MgSO_4$, filtered, and concentrated. The material was purified by column chromatography (silica gel, 100:0 $CHCl_3$/MeOH to 95:5 $CHCl_3$/MeOH) to provide ALB 30350 as a white solid (70 mg, 40%): mp 126-127° C.; $^1H$ NMR (500 MHz, $CDCl_3$) δ 8.67 (br s, 1H), 7.77-7.85 (m, 2H), 7.21-7.37 (m, 3H), 7.02 (d, 1H, J=7.7 Hz), 6.90-6.97 (m, 2H), 6.82 (dd, 1H, J=2.5 Hz, J=8.6 Hz), 6.76 (dd, 1H, J=2.4 Hz, J=12.4 Hz), 4.49 (d, 2H, J=5.9 Hz), 4.15 (t, 2H, J=5.7 Hz), 3.83 (s, 2H), 3.71-3.78 (m, 4H), 2.83 (t, 2H, J=5.7 Hz), 2.56-2.63 (m, 4H); HPLC (Method A)>99% (AUC), $t_R$=4.026 min.; APCI MS m/z 468 $[M+H]^+$.

was stirred on an ice water bath to cool. After 5 minutes, diisopropyl azodicarboxylate (7.6 ml, 39.1 mmol) was added over 6 to 8 minutes. The reaction was left stirring on the cold bath to slowly warm to room temperature overnight. The reaction was concentrated and the residue purified by flash chromatography (25% to 100% EtOAc in hexanes) to provide the product as a colorless oil (2.62 g, 33%).

1-(2-(3-fluoro-4-(4, 4,5,5-tetramethyl-1,3,2-dioxaborolan-2-yl)phenoxy)ethyl)-4-methylpiperazine

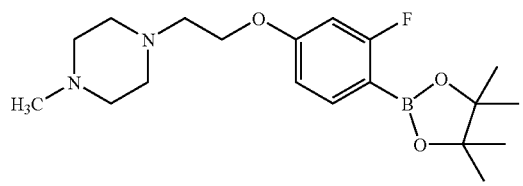

1-(2-(4-bromo-3-fluorophenoxy)ethyl)-4-methylpiperazine

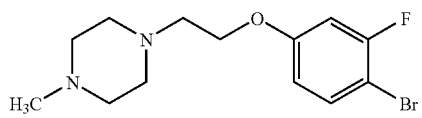

A flask was charged with 4-bromo-3-fluorophenol (5.00 g, 26 mmol) and triphenylphosphine (10.30 g, 39 mmol). Methylene chloride (120 mL) was added followed by 2-(4-methylpiperazin-1-yl)ethanol (4.61 g, 32 mmol) and the solution A 40 mL microwave reaction tube with a septum closure and stir bar was charged with 1-(2-(4-bromo-3-fluorophenoxy)ethyl)-4-methylpiperazine (428 mg, 1.35 mmol), Bis (pinacolato)diboron (375 mg, 1.48 mmol), $Pd(dppf)Cl_2$—$CH_2Cl_2$ (63 mg, 77 μmol), and Potassium acetate (410 mg, 4.18 mmol). DME (10 ml) was added and the tube sealed. The tube was evacuated/backfilled w. $N_2$ (5 cycles) and microwaved at 100° C. for 30 minutes. Additional $Pd(dppf)Cl_2$—$CH_2Cl_2$ (63 mg, 77 μmol) was added and the reaction microwaved at 100° C. for 60 minutes. The reaction was cooled to room temperature, concentrated and the residue purified by column chromatography (silica gel, 1% to 2% MeOH in $CHCl_3$) to provide the product as a dark oil (354 mg, 72%).

Synthesis of Compound 137, KX2-394

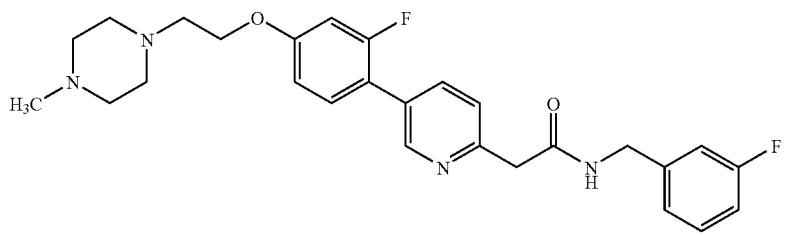

A 10 mL microwave reaction tube with septum closure was charged with 1-(2-(3-fluoro-4-(4,4,5,5-tetramethyl-1,3,2-dioxaborolan-2-yl)phenoxy)ethyl)-4-methylpiperazine (340 mg, 0.93 mmol), 2-(5-bromopyridin-2-yl)-N-(3-fluorobenzyl)acetamide (201 mg, 0.62 mmol), and FibreCat 1007 (125 mg, 0.06 mmol). Ethanol (3 mL) was added followed by aqueous potassium carbonate solution (1.00 mL, 1.0 M, 1.00 mmol). The tube was sealed and heated under microwave conditions at 150° C. for 10 minutes. The reaction was cooled, filtered, and concentrated to remove the majority of the ethanol. The residue was then taken up in 10 mL of ethyl acetate and washed successively with water and saturated sodium chloride solution. The organic layer was dried with $MgSO_4$, filtered, and concentrated. The material was purified by column chromatography (silica gel, 98:2 $CHCl_3$/MeOH to 90:10 $CHCl_3$/MeOH) to provide ALB 30352-2 as a tan gum (28 mg, 9%): $^1$H NMR (300 MHz, $CDCl_3$) δ 8.66 (br s, 1H), 7.78-7.94 (m, 2H), 7.20-7.40 (m, 3H), 6.88-7.06 (m, 3H), 6.70-6.85 (m, 2H), 4.47 (d, 2H, J=5.9 Hz), 4.14 (t, 2H, J=5.7 Hz), 3.83 (s, 2H), 2.85 (t, 2H, J=5.7 Hz), 2.41-2.77 (m, 8H), 2.34 (s, 3H); HPLC (Method A)>99% (AUC), $t_R$=3.778 min.; APCI MS m/z 481 $[M+H]^+$.

Example 2

Cell Growth Inhibition

The drug concentration required to block net cell growth by 50% relative to a control sample is measured as the $GI_{50}$. The $GI_{50}$s for several of the compounds of the invention were assayed as described herein.

The HT29 cell line is a NCI standard human colon carcinoma cell line. HT-29 cells were obtained from ATCC at passage 125 and were used for inhibition studies between passage 126-151. HT29 cells were routinely cultured in McCoy's 5A medium supplemented with Fetal Bovine Serum (1.5% v/v) and L-glutamine (2 mM).

The c-Src 3T3 is a mouse fibroblast NIH 3T3 normal cell line that has been transfected with a point-mutant of human c-Src wherein tyrosine 527 has been converted to a phenylalanine. This mutation results in "constitutively active" c-Src because phosphorylation on tyrosine 527 results in auto-inhibition of Src by having it fold back on its own SH2 domain. With a Phe there, this phosphorylation can't occur and therefore auto-inhibition can't occur. Thus, the always fully active mutant Src then converts the normal mouse fibroblasts into rapidly growing tumor cells. Since the hyperactive Src is the main factor driving growth in these cells (particularly when cultured under low growth serum conditions), compounds active in blocking this growth are thought to work by blocking Src signaling (e.g. as a direct Src kinase inhibitor or as an inhibitor acting somewhere else in the Src signaling cascade). The cells were routinely cultured in DMEM supplemented with Fetal Bovine Serum (2.0% v/V), L-glutamine (2 mM) and Sodium Pyruvate (1 mM).

In the BrdU Assay for cell growth inhibition, quantitation of cell proliferation was based on the measurement of BrdU incorporation during DNA synthesis. The Cell Proliferation ELISA BrdU assay kit (colorimetric) was obtained from Roche Applied Science and performed as per vendor instructions.

Growth inhibition was expressed as a $GI_{50}$ where the $GI_{50}$ is the sample dose that inhibits 50% of cell growth. The growth inhibition (GI) is determined from the formula GI=$(T_0-T_N \times 100/T_0-CON_n)$ where $T_0$ is the BrdU growth of untreated cells at time "0", $T_n$ is the BrdU growth of treated cells at day "n" and $CON_n$ is the control BrdU growth of control cells at day "n". The $GI_{50}$ was extrapolated and the data plotted using XL-Fit 4.0 software.

Actively growing cultures were trypsinized and cells were resuspended in 190 µL of appropriate culture medium supplemented with 1.05% FBS in each well of a 96-well culture plate (1000 HT-29 cells; 2500 c-Src 3T3 cells). For 96 well culture plate experiments, c-Src 3T3 medium was supplemented with 10 mM HEPES buffer. HT-29 cells were seeded in standard tissue culture 96-well plates and c-Src 3T3 cells were seeded in 96-well plates coated with Poly-D-lysine (BIOCOAT™). To increase $CO_2$ diffusion, c-Src 3T3 96-well plates were incubated with their lids raised by ~2 mm using sterile rubber caps.

Seeded 96 well plates were allowed to attach overnight for 18-24 hours, either at 37° C. and 5% $CO_2$ for HT-29 or at 37° C. and 10% $CO_2$ for c-Src 3T3. Approx 18-24 hours after seeding, the initial growth of cells ($T_0$) was determined for untreated cells using the BrdU assay. Samples were reconstituted in DMSO at 20 mM and intermediate dilutions made using DMEM containing 10% FBS. The final assay concentrations were 1.5% for FBS and 0.05% for DMSO. Samples were added as 10 µL aliquots in triplicate and plates were incubated as above for ~72 hours. Negative (vehicle) and positive controls (e.g., AZ (KX-328)) were included. Plates were assayed for BrdU and the data analyzed as above for $GI_{50}$.

The results are shown in Table 4. In this table, the data is listed as Growth % of Control, such that a lower number at an indicated concentration indicates a greater potency of the compound in blocking growth of that tumor cell line. All compounds were initially prepared as 20 mM DMSO stock solutions and then diluted into buffer for the in vitro tumor growth assays. NG means no cell growth beyond the control and T means the number of cells in the drug treated wells was less than in the control (i.e. net cell loss). NT indicates that the test was not performed. Compound AZ (KX-328) is an ATP-competitive tyrosine kinase inhibitor, as described in Plé et al., J. Med. Chem, 47:871-887 (2004).

As shown in Table 4, $GI_{50}$s were obtained for a number of the compounds in other cell lines. These GI50's were determined using the standard tumor growth inhibition assays, similar to that described in detail for the HT29 cell line above, and the following cell lines: colon tumor cell lines KM12, lung cancer cell line H460 and lung cancer cell line A549 (all are NCI standard tumor cell lines).

TABLE 4

| | | HT-29 Growth, % of Control Mean, n = 3 | | | | c-Src 3T3 Growth, % of Control Mean, n = 3 | | |
|---|---|---|---|---|---|---|---|---|
| KX-# | CMPD | 5 uM | 500 nM | 50 nM | $GI_{50}$ | 10 uM | 1.0 uM | 100 nM |
| KX2-328 | AZ | T | 10.0 | 73.0 | 99 nM (c-Src 3T3), 794 nM (HT29) | T | T | 13.0 |
| KX1-136 | 1 | T | T | 83.1 | 53 nM (c-Src 3T3), 484 nM (HT29) 105 nM (KM12) 280 nM (H460) 330 nM (A549) | T | T | 46.3 |
| KX1-305 | 2 | T | T | 107.7 | 349 nM (c-Src 3T3), 877 nM (HT29), 410 nM (KM12) | T | T | 35.0 |

TABLE 4-continued

| | | HT-29 Growth, % of Control Mean, n = 3 | | | | c-Src 3T3 Growth, % of Control Mean, n = 3 | | |
|---|---|---|---|---|---|---|---|---|
| KX-# | CMPD | 5 uM | 500 nM | 50 nM | GI$_{50}$ | 10 uM | 1.0 uM | 100 nM |
| | | | | | 890 nM (H460) 1.03 uM (A549) | | | |
| KX1-307 | 4 | 39.4 | 93.8 | 85.9 | | 4.2 | 45.3 | 65.7 |
| KX1-308 | 5 | 32.3 | 76.1 | 87.9 | | 67.1 | 77.7 | 94.5 |
| KX1-312 | 9 | 33.7 | 67.6 | 93.7 | | 12.1 | 94.5 | 98.5 |
| KX1-306 | 3 | T | T | 124.4 | | T | T | 47.0 |
| KX1-313 | 10 | T | T | 80.2 | | T | T | 91.6 |
| KX1-319 | 16 | T | T | 101.2 | | T | T | 88.2 |
| KX1-309 | 6 | T | T | 29.5 | | T | T | T |
| KX1-310 | 7 | T | T | 93.3 | | T | T | 101.8 |
| KX1-311 | 8 | T | T | 60.4 | | T | T | 81.3 |
| KX1-327 | 24 | T | T | 31.6 | >200 nM (c-Src 3T3), 680 nM (HT29) | T | T | 81.3 |
| KX1-316 | 13 | T | 45.1 | 77.8 | >200 nM (c-Src 3T3) | T | T | 88.2 |
| KX1-315 | 12 | T | 50.3 | 66.0 | | T | 88.1 | 89.3 |
| KX1-314 | 11 | 14.4 | 83.7 | 53.21 | | 39.3 | 88.4 | 93.6 |
| KX1-317 | 14 | T | 64.0 | 83.5 | | T | 85.6 | 94.2 |
| KX1-318 | 15 | T | 93.2 | 164.7 | | T | 71.0 | 91.4 |
| KX1-320 | 17 | 86.2 | 132.0 | 111.2 | | 73.1 | 86.5 | 90.4 |
| KX1-321 | 18 | 23.7 | 118.1 | 127.2 | | 55.8 | 96.2 | 95.5 |
| KX1-322 | 19 | T | 87.2 | 114.1 | 3,730 nM (Src 3T3) | T | T | 94.6 |
| KX1-323 | 20 | 60.8 | 106.9 | 105.6 | | 93.2 | 97.3 | 96.6 |
| KX1-324 | 21 | NG | 95.7 | 91.0 | | T | 90.0 | 96.0 |
| KX1-325 | 22 | T | T | 85.0 | 207 nM (c-Src 3T3), 215 nM (HT29) | T | 54.2 | 97.6 |
| KX1-326 | 23 | 43.7 | 73.2 | 65.4 | | 55.7 | 87.3 | 92.2 |
| KX1-329, | 25 | T | T | 101 | 269 nM (c-Src 3T3), 338 nM (HT29) | T | T | 96.0 |
| KX1-357 | 26 | NT | NT | NT | | 9.0 | 95.4 | 101.3 |
| KX1-358 | 27 | NT | NT | NT | | 82.7 | 91.4 | 92.2 |
| KX2-359 | 28 | T | T | T | 34 nM (c-Src 3T3), 45 nM (HT29) | T | T | T |
| KX2-360 | 54 | T | T | 91 | | T | T | 106.0 |
| KX2-361 | 76 | T | T | T | 11 nM (c-Src 3T3), 10 nM (HT29) | T | T | T |
| KX2-362 | 78 | T | T | 86 | 56 nM (c-Src 3T3), 56 nM (HT29) | T | T | 101 |
| KX2-363 | 79 | T | 67 | 92 | | 100 | 70 | 92 |
| KX2-364 | 82 | T | 80 | 105 | | T | 81 | 92 |
| KX2-365 | 40 | T | T | 88 | 133 nM (c-Src 3T3), 93 nM (HT29) | T | T | 88 |
| KX2-366 | 75 | T | 54 | 89 | | T | 83 | 103 |
| KX2-367 | 41 | T | 6 | 64 | | T | T | 102 |
| KX2-368, slightly insoluble | 29 | T | 70 | 107 | | 27 | 101 | 99 |
| KX2-369 | 55 | T | 72 | 87 | | T | 101 | 100 |
| KX2-370 | 77 | 81 | 93 | 112 | | 106 | 105 | 104 |
| KX2-371 | 81 | 16 | 33 | 98 | | 16 | 72 | 75 |
| KX2-372 | 80 | T | T | T | 58 nM (c-Src 3T3); 67 nM (HT-29) | T | T | T |
| KX2-373 | 72 | T | T | 64 | 96 nM (c-Src 3T3); 639 nM (HT-29) | T | T | 97 |
| KX2-374 | 115 | T | 57 | 74 | | T | 84 | 110 |
| KX2-375 | 36 | T | T | 99 | 206 nM (c-Src 3T3); 354 nM (HT-29) | T | T | T |
| KX2-376 | 74 | T | 93 | 96 | >1,600 nM (c-Src 3T3); >400 nM (HT-29) | T | T | T |
| KX2-377 | 38 | T | T | T | 118 nM (c-Src 3T3); 111 nM (HT-29) | T | T | T |
| KX2-378 | 31 | T | 61 | 88 | | 48 | 107 | 122 |
| KX2-379 | 70 | T | 88 | 89 | | T | 104 | 106 |
| KX2-380 | 30 | T | 50 | 100 | | T | 119 | 124 |
| KX2-381 | 33 | T | T | 58 | 914 nM (c-Src 3T3); 375 nM (HT-29) | T | T | 116 |
| KX2-382 | 68 | 50 | 97 | 80 | | 103 | 114 | 117 |
| KX2-383 | 116 | | | | 327 nM (c-Src 3T3); 248 nM (HT-29) | | | |
| KX2-384 | 64 | | | | 1,430 nM (c-Src 3T3); inactive (HT-29) | | | |
| KX2-385 | 83 | | | | 232 nM (c-Src 3T3) | | | |
| KX2-386 | 37 | | | | 897 nM (c-Src 3T3); inactive (HT-29) | | | |
| KX2-387 | 38 | | | | inactive (c-Src 3T3); 1,860 nM (HT-29) | | | |
| KX2-388 | 66 | | | | >1,600 nM (c-Src 3T3); 906 nM (HT-29) | | | |
| KX2-389 | 60 | | | | Inactive (c-Src 3T3); inactive (HT-29) | | | |
| KX1-329 N-oxide | 135 | | | | inactive (c-Src 3T3); inactive (HT-29) | | | |
| KX2-390 | 114 | | | | 797 nM (c-Src 3T3); 868 nM (HT-29) | | | |
| KX2-391 | 133 | | | | 13 nM (c-Src 3T3); 23 nM (HT-29) | | | |
| KX2-392 | 134 | | | | 13 nM (c-Src 3T3); 21 nM (HT-29) | | | |
| KX2-393 | 136 | | | | 24 nM (c-Src 3T3); 52 nM (HT-29) | | | |
| KX2-394 | 137 | | | | 13 nM (c-Src 3T3); 26 nM (HT-29) | | | |

NG = No growth, total growth inhibition;
T = Cytotoxic Effect on Cells, negative growth;
NT = Not tested

Example 3

Inhibition of Isolated Kinases

It is believed that the conformation of Src outside cells vs. inside cells is markedly different, because inside cells, Src is embedded in multiprotein signaling complexes. Thus, because the peptide substrate binding site is not well formed in isolated Src (as shown by Src x-ray structures), it is believed that the activity against isolated Src for a peptide substrate binding inhibitor would be weak. Binding to this site will require the inhibitor to capture the very small percentage of total Src protein in the isolated enzyme assay that is in the same conformation that exists inside cells. This requires a large excess of the inhibitor to drain significant amounts of the enzyme from the catalytic cycle in the assay.

However, inside cells this large inhibitor excess is not needed because the SH2 & SH3 domain binding proteins have already shifted the Src conformation so that the peptide substrate binding site is fully formed. Now, low concentrations of the inhibitor can remove the enzyme from the catalytic cycle since all of the enzyme is in the tight binding conformation.

KX2-328 is AstraZeneca's published ATP-competitive Src inhibitor (AZ28) and is used as a postive control in many of the experiments described herein. Note that KX2-391 has weak activity against isolated kinases because the peptide binding site is not well formed outside of cells (a close analog, KX2-394 is a little more potent against isolated Src), but have very potent activity inside whole cells. Without wishing to be bound by theory, it is thought that the difference in activity is attributed to the fact that the peptide binding site is now fully formed in cells due to the allosteric effects of the binding protein partners in the multi-protein signaling complexes, relative to isolated kinase assays.

Table 5 illustrates percent activity of isolated kinases in the presence of the AstraZeneca ATP-competitive inhibitor (KX-328, AZ-28) or KX2-391 relative to control (untreated) isolated kinases.

TABLE 5

| Target | AZ28 @ 10 μM | KX2-391 @ 10 μM |
|---|---|---|
| Abl(h) | 1 | 120 |
| CHK1(h) | NT | 105 |
| EGFR(h) | 3 | 134 |
| FGFR2(h) | 94 | 94 |
| Fyn(h) | 2 | 85 |
| IGF-1R(h) | 110 | 101 |
| IR(h) | 125 | 112 |
| Lck(h) | 1 | 109 |
| Lyn(h) | 0 | 113 |
| MAPK2(h) | 105 | 112 |
| PDGFRβ(h) | 98 | 110 |
| PKCα(h) | 111 | 111 |
| Pyk2(h) | 43 | 97 |
| Yes(h) | 1 | 92 |
| ZAP-70(h) | 97 | 108 |
| PI3 kinase | 99 | 100 |

The AstraZeneca ATP competitive inhibitor shows the typical off target kinase inhibition activity for ATP-competitive inhibitors, poor selectivity as evidenced by strong inhibition of Abl, EGFRTK, Fyn, Lck, Lyn & Yes. In contrast, poor inhibition of these off-target kinases is seen with KX2-391.

However, KX2-391 is a more potent inhibitor of Src-driven cell growth, assayed as described in Example 2. In the c-Src/NIH-3T3 engineered cell line, the $GI_{50}$ for AZ28 is 99 nM, vs. 13 nm for KX2-391, and in the NCI human colon cancer cell line HT29, the $GI_{50}$ for AZ28 is 794 nM, vs. 23 nm for KX2-391. Similar to KX2-391, the $GI_{50}$ for KX2-394 in the c-Src/NIH-3T3 engineered cell line is 13 nM, and in the NCI human colon cancer cell line HT29, the $GI_{50}$ for KX2-394 is 794 nM, vs. 33 nm.

In separate examples, titration data indicate that AZ28 is a potent inhibitor of isolated Src (IC50=8 nM). The titration data with FAK shows that AZ28 is at least ca. 100× less potent against isolated FAK (IC50>500 nM). Whereas, titration data indicate that KX2-391 and KX2-394 are less potent inhibitors of isolated Src (IC50=46 μM and 5 μM, respectively). The titration data with FAK shows that KX2-391 and KX2-394 are similarly potent against isolated FAK (IC50>48 μM).

Note that AZ28 is 10-100× less potent against cell growth than against isolated Src. This is typical of ATP competitive inhibitors since the concentration of competing ATP is much higher in whole cells than in the isolated enzyme assays

Example 4

Effect of Compounds on Intracellular Phosphorylation Levels

HT29 (colon cancer) and c-Src527F/NIH-3T3 (Src transformed) cell lines were treated with KX2-391 or with AstraZeneca's ATP competitive Src inhibitor AZ28. AZ28 serves as a positive comparator to show what a validated Src inhibitor should do in these assays. After treatment with compound, cells were lysed, subjected to PAGE and probed with a battery of antibodies. The antibodies were selected to determine whether compounds caused changes in phosphorylation of known Src substrates. In addition, off-target protein phosphorylation was also investigated. Further, induction of apoptosis was evaluated via Caspase 3 cleavage. Multiple doses of each compound were tested because the trends in response to increasing drug concentration are the most reliable indicator of activity.

A dose response curve for KX2-391 was generated using the GI50 for this compound in each of the two cell lines as the 1× concentration. Three additional doses 0.2×, 5×& 25×multiples the GI50's were also tested in addition to a no drug control "C". The same range of multiples of the GI50 for AZ28 in these two cell lines was run as a comparison. As shown in FIG. 1, the expected dose response for Src-Y416 autophosphorylation was obtained in both cell lines, and for both compounds. This data indicates that KX2-391 is a Src inhibitor inside cells.

Figure 2:
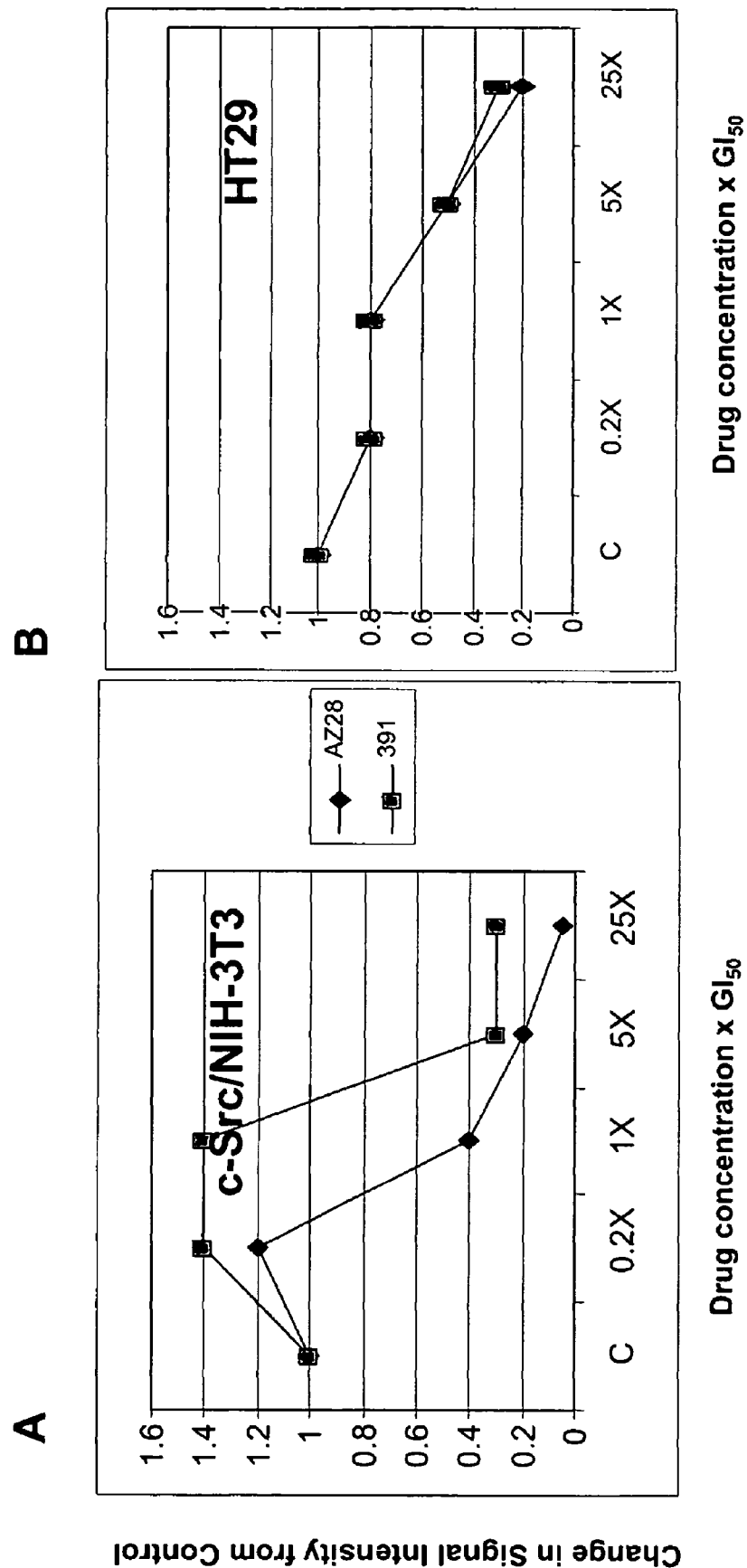
FIG. 2A is a graph indicating the effect of AZ28 and KX2-391 on FAK phosphorylation in c-Src/NIH-3T3 cells.
FIG. 2B is a graph indicating the effect of AZ28 and KX2-391 on FAK phosphorylation in HT-29 cells.

FIG. 2 shows phosphorylation of FAK Tyr 925, a known Src transphorylation substrate within cells. KX2-391 and AZ28 inhibited Src trans-phosphorylation. This data indicates that KX2-391 is a Src inhibitor inside cells.

Figure 3:
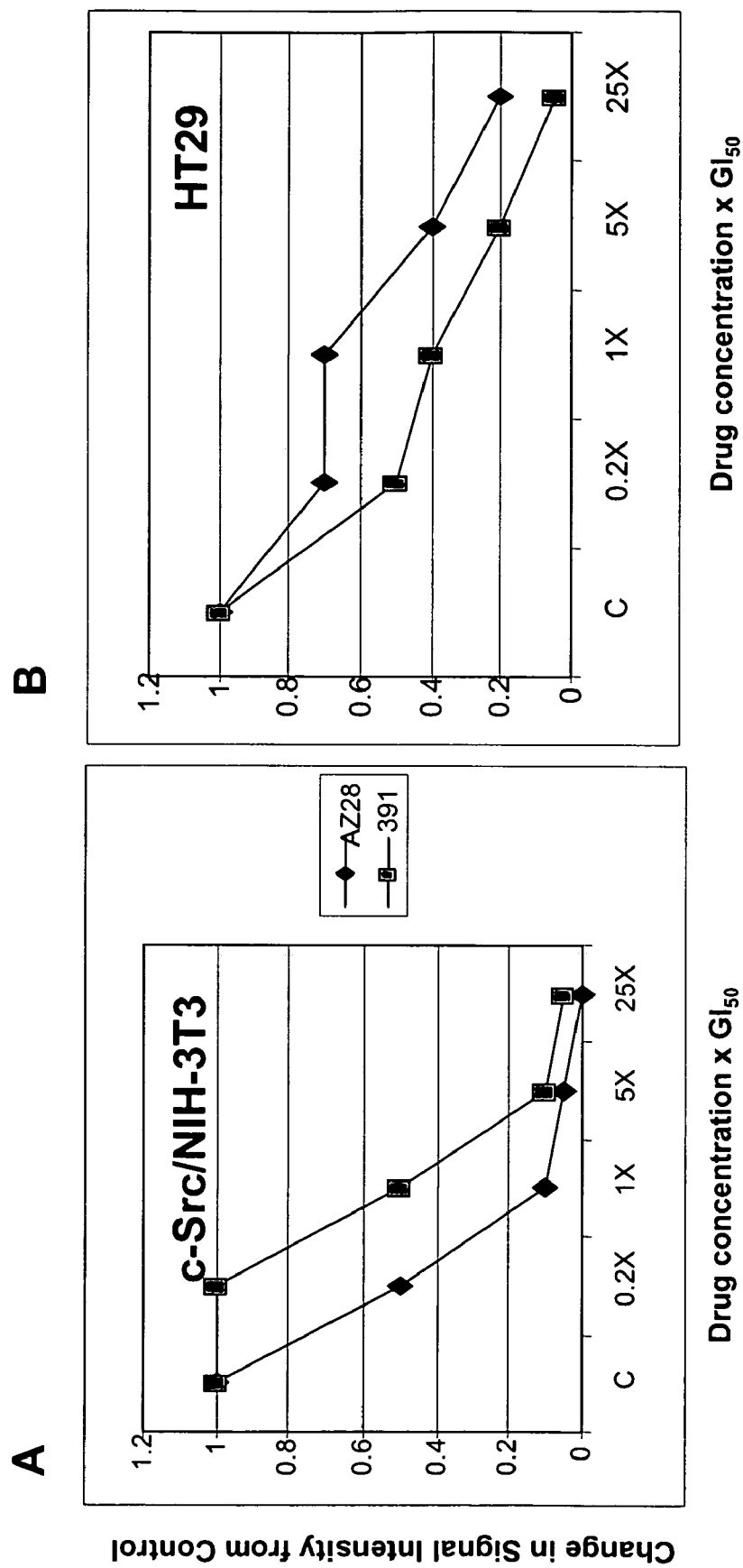
FIG. 3A is a graph indicating the effect of AZ28 and KX2-391 on Shc phosphorylation in c-Src/NIH-3T3 cells.
FIG. 3B is a graph indicating the effect of AZ28 and KX2-391 on Shc phosphorylation in HT-29 cells.

FIG. 3 shows phosphorylation of Shc Y239/240, a known Src transphorylation substrate within cells. KX2-391 and AZ28 inhibited Src trans-phosphorylation. This data indicates that KX2-391 is a Src inhibitor inside cells.

Figure 4:
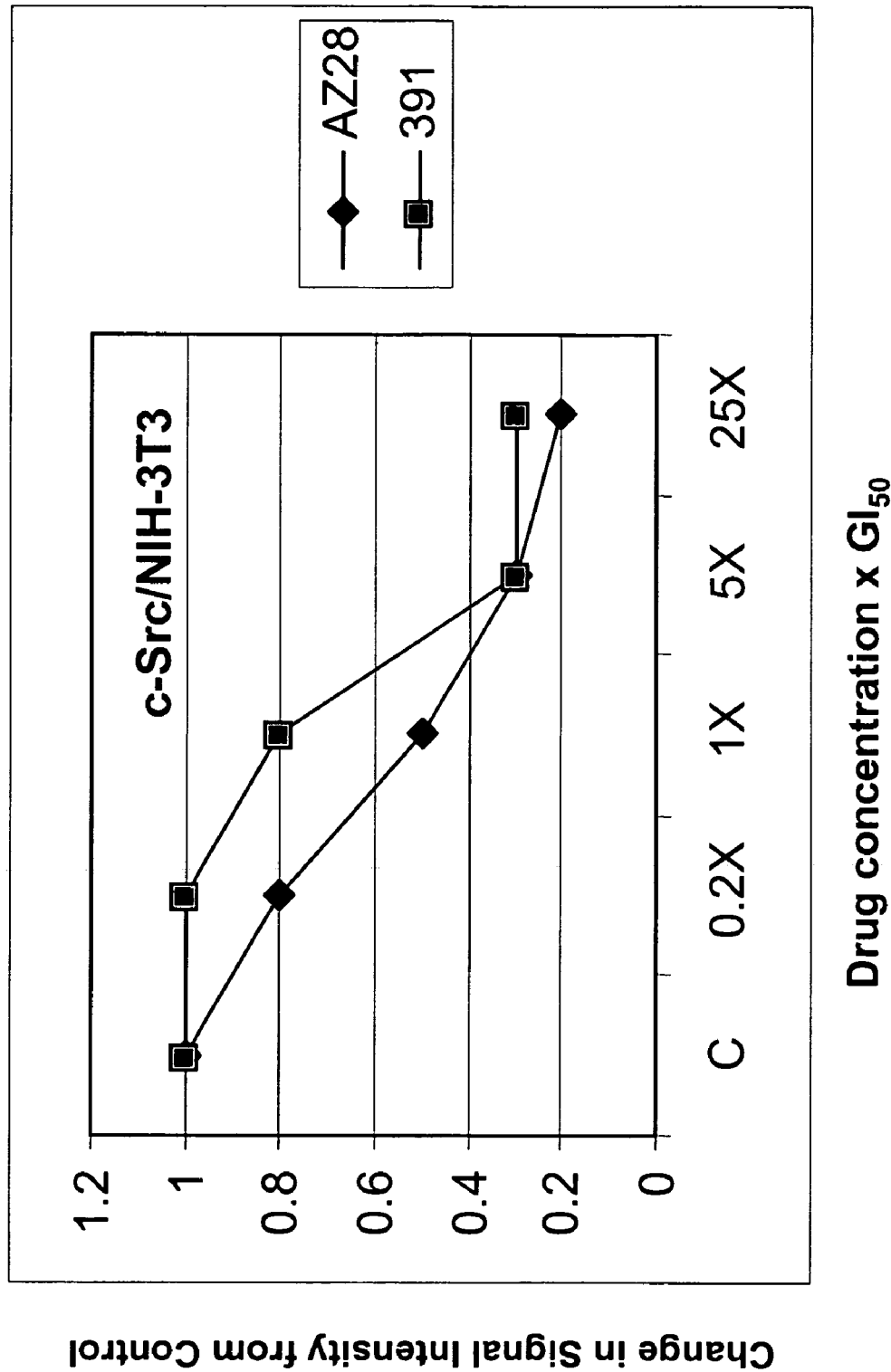
FIG. 4 is a graph indicating the effect of AZ28 and KX2-391 on paxillin phosphorylation in c-Src/NIH-3T3 cells.

FIG. 4 shows phosphorylation of Paxillin Y-31, a known Src transphorylation substrate within cells. KX2-391 and AZ28 inhibited Src trans-phosphorylation. This data indicates that KX2-391 is a Src inhibitor inside cells. Note: paxillin Y-31 was not detected in HT29 cells with or without added drug.

Figure 5:
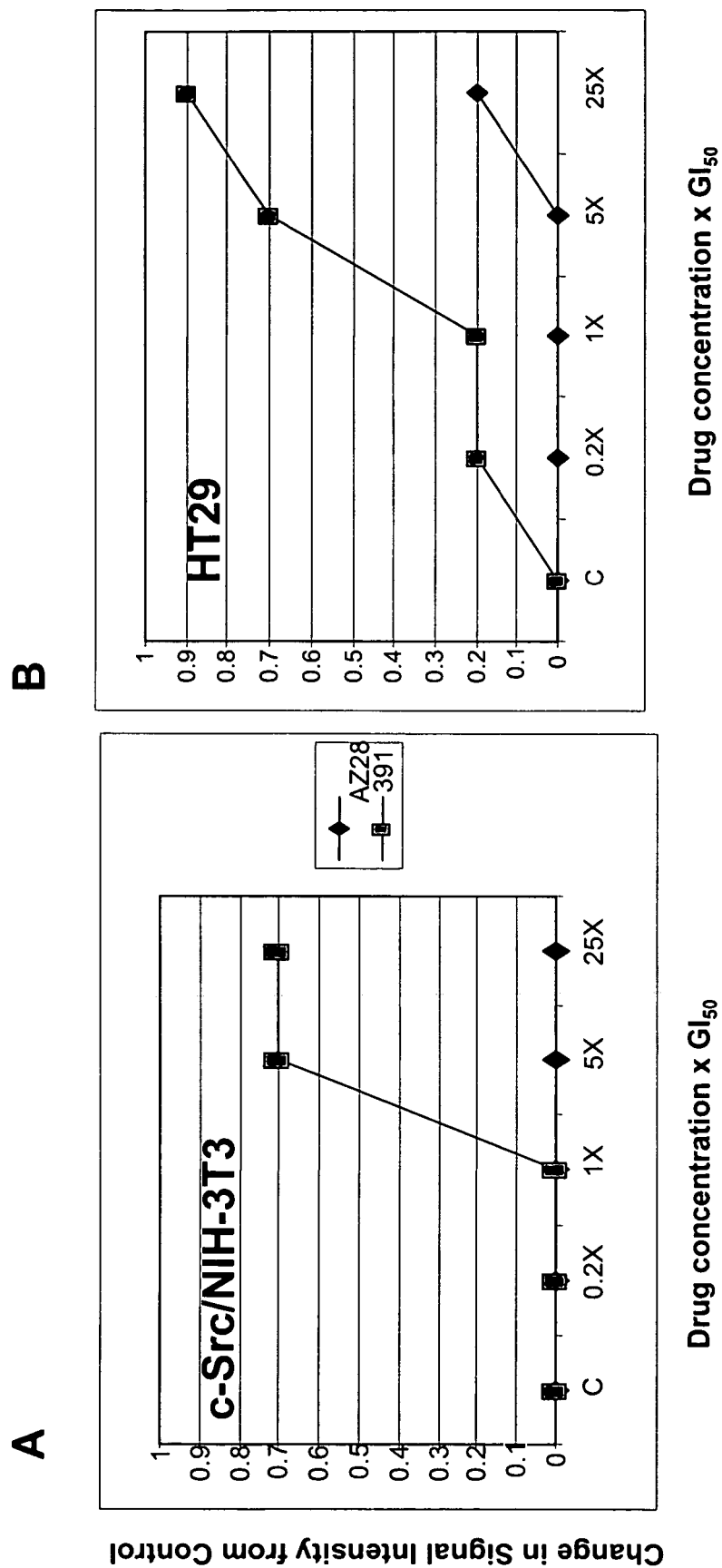
FIG. 5A is a graph indicating the effect of AZ28 and KX2-391 on caspase-3 cleavage in c-Src/NIH-3T3 cells.
FIG. 5B is a graph indicating the effect of AZ28 and KX2-391 on caspase-3 cleavage in HT-29 cells.

Cleavage of Caspase-3 is a good measure of induction of apoptosis. It is known that AZ28 is not effective in inducing apoptosis in HT29 (colon cancer) and c-Src527F/NIH-3T3 (Src transformed) cell lines. In contrast, as shown in FIG. 5, KX2-391 is very effective in inducing apoptosis.

Figure 6:
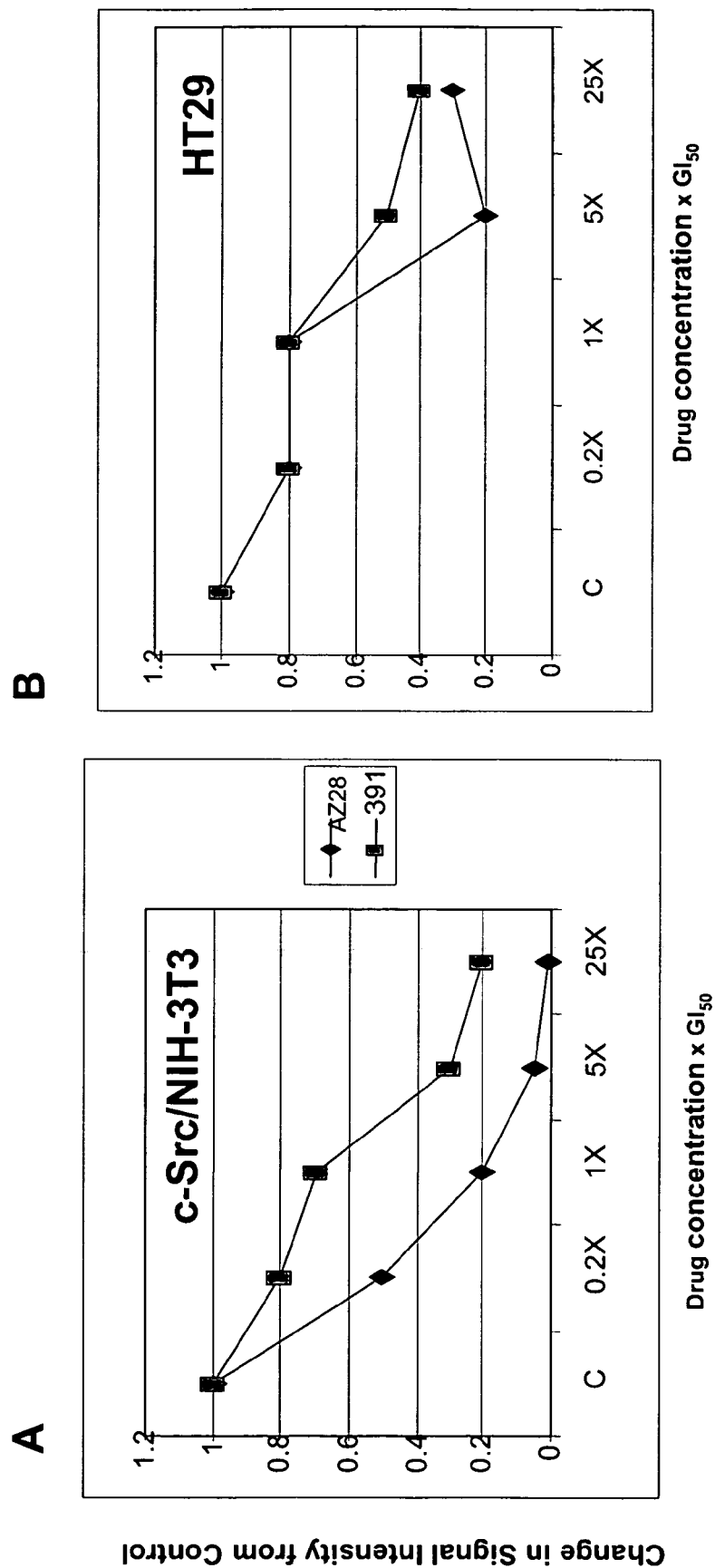
FIG. 6A is a graph indicating the effect of AZ28 and KX2-391 on total phosphotyrosine levels in c-Src/NIH-3T3 cells.
FIG. 6B is a graph indicating the effect of AZ28 and KX2-391 on total phosphotyrosine levels in HT-29 cells.

Since Src activity is very high in both HT29 (colon cancer) and c-Src527F/NIH-3T3 (Src transformed) cell lines, one would expect to see a reduction in the total phosphotyrosine levels when Src activity is inhibited. FIG. 6 indicates that this is true for both AZ28 and KX2-391. This data indicates that KX2-391 is a Src inhibitor inside cells.

Figure 7:
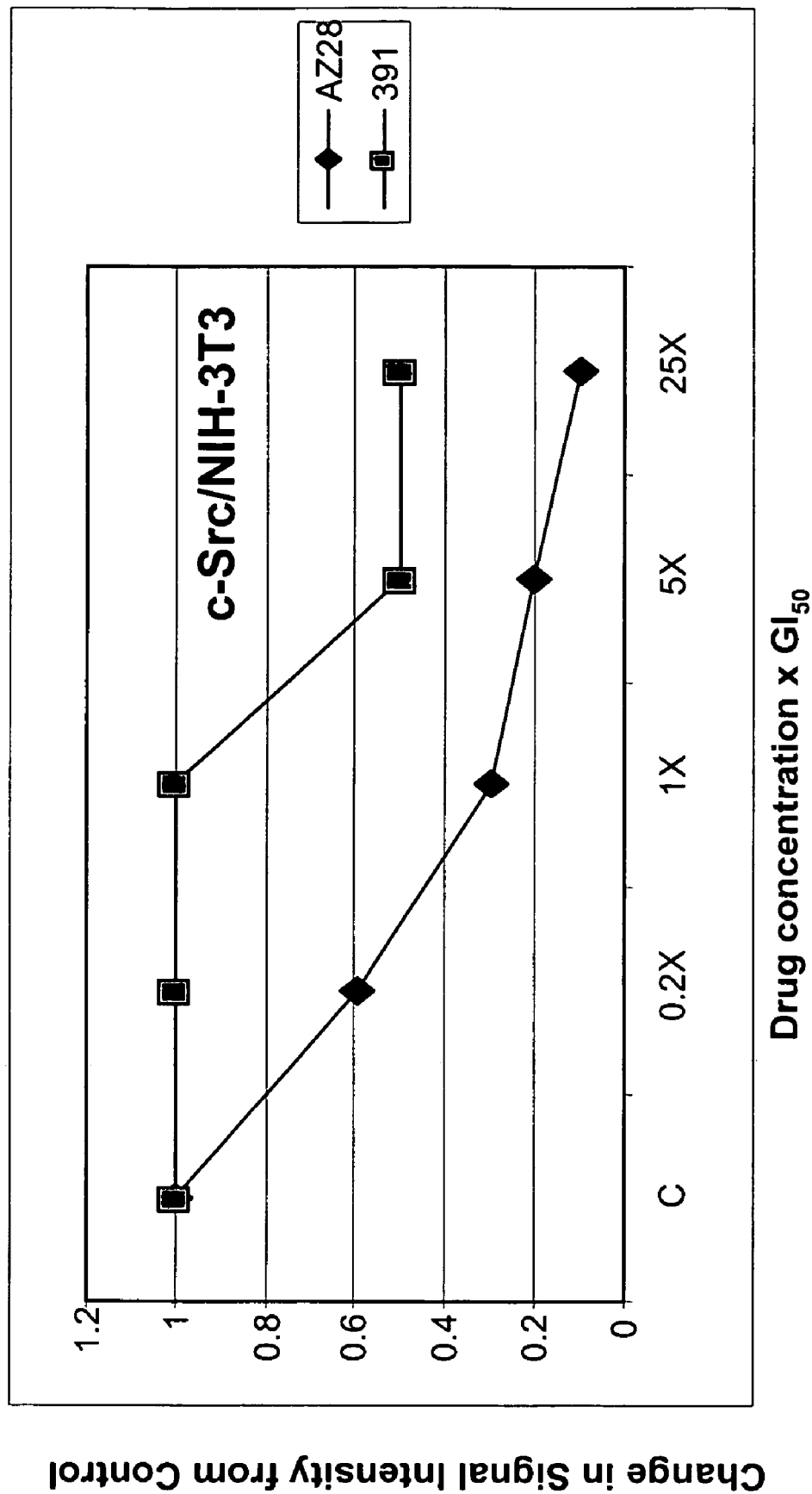
FIG. 7 is a graph indicating the effect of AZ28 and KX2-391 on autophosphorylation of PDGFR in c-Src/NIH-3T3 cells.

PDGF receptor tyrosine kinase autophosphorylates on Y572/574. This is thought not to be a direct Src substrate in cells. It is known that AZ28 is not a potent inhibitor of isolated PDGF receptor tyrosine kinase (see Table 5). Nevertheless, a dose response reduction in PDGF receptor autophosphorylation is seen with AZ28, as shown in FIG. 7. This suggests that this is an indirect effect. Some effect is seen with KX2-391, however it is somewhat less potent. Thus, KX2-391 is less active than AZ28 against indirect PDGF autophoshorylation inhibition. PDGF receptor tyrosine kinase Y572/574 was not detected in HT29 cells with no drug added (as well as with drug added).

FAK Y397 is mainly a FAK autophosphorylation site and only a poor Src transphorylation site. AZ28 is not a potent FAK inhibitor (see isolated enzyme data in Table 5). Nevertheless, some inhibition of FAK autophosphorylation in c-Src527F/NIH3T3 cells with AZ28 is shown in FIG. 8. However, no inhibition of FAK autophosphorylation in c-Src527F/NIH3T3 cells is seen with KX-391. The opposite is true in the NCI human colon cancer cell line HT29.

Figure 9:
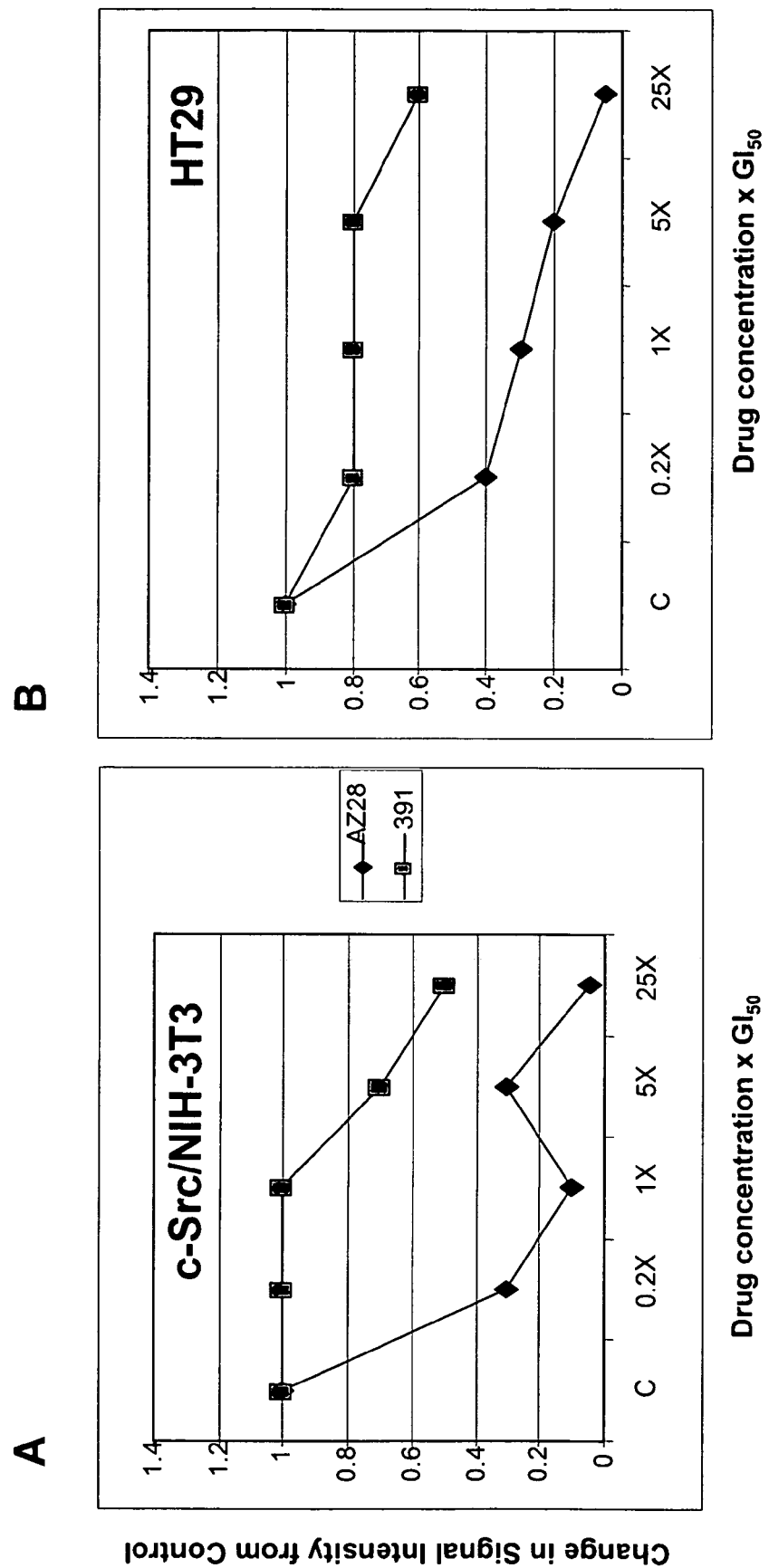
FIG. 9A is a graph indicating the effect of AZ28 and KX2-391 on autophosphorylation of EGFR in c-Src/NIH-3T3 cells.
FIG. 9B is a graph indicating the effect of AZ28 and KX2-391 on autophosphorylation of EGFR in HT-29 cells.

The isolated enzyme data shown in Table 5 demonstrated that AZ28 is a potent EGFR tyrosine kinase inhibitor. In agreement with this the tumor cell data in FIG. 9 shows that AZ28 potently inhibits EGFR tyrosine kinase autophosphorylation. This site is not a direct Src phosphorylation site. The tumor cell data in FIG. 9 also shows that KX-391 is less active against the off target autophosphorylation of EGFRTK.

Example 5

Protection Against Noise-Induced Hearing Loss Using PTK Inhibitors

Chinchillas (N=6) were used in studies of noise-induced hearing loss. The animals' hearing sensitivity was measured using standard electrophysical techniques before the experimental manipulation. In particular, hearing thresholds were measured through evoked potentials from recording electrodes chronically implanted in the inferior colliculus, following standard laboratory procedures. Animals were anesthetized, the auditory bullae were opened, and the left and right cochleas were visualized. The round window leading to the scala tympani of the cochlea was used as the access point for drug application. Animals were treated with KX1-004, KX1-141, KX1-329 or KX2-328 (a non-ATP competitive inhibitor from Astrazeneca), emulsified in DMSO, in 1000 mM of saline solution, which was placed on the round window of one ear. A control solution of 3 mM DMSO in 1000 mM of saline solution was placed on the round window of the other ear. The solution was allowed to set on the round window for 30 minutes, then the auditory bullae were closed. Subsequently, the animals were exposed to 4 kHz band noise at 105 dB SPL for four hours. Following the noise exposure, the animals' hearing was tested at day 1, day 7, and day 21 to determine evoked potential threshold shifts. Permanent threshold shift was assessed at day 21.

Figure 10:
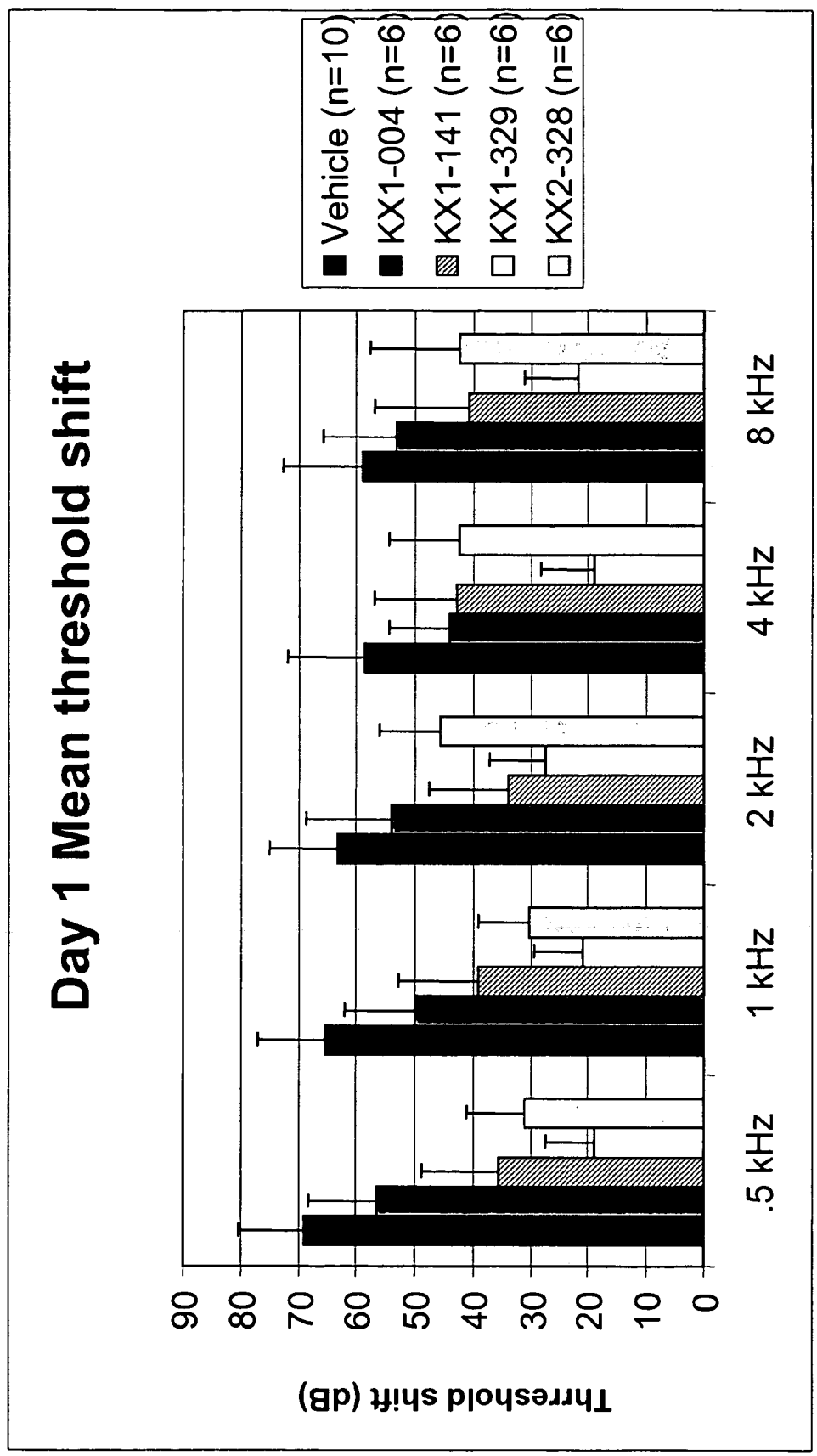
FIG. 10 is a bar chart showing the average threshold shifts (dB) in chinchilla cochleas after exposure to 0.5 kHz, 1 kHz, 2 kHz, 4 kHz, and 8 kHz band noise on day 1 after experimental manipulation.
Figure 11:
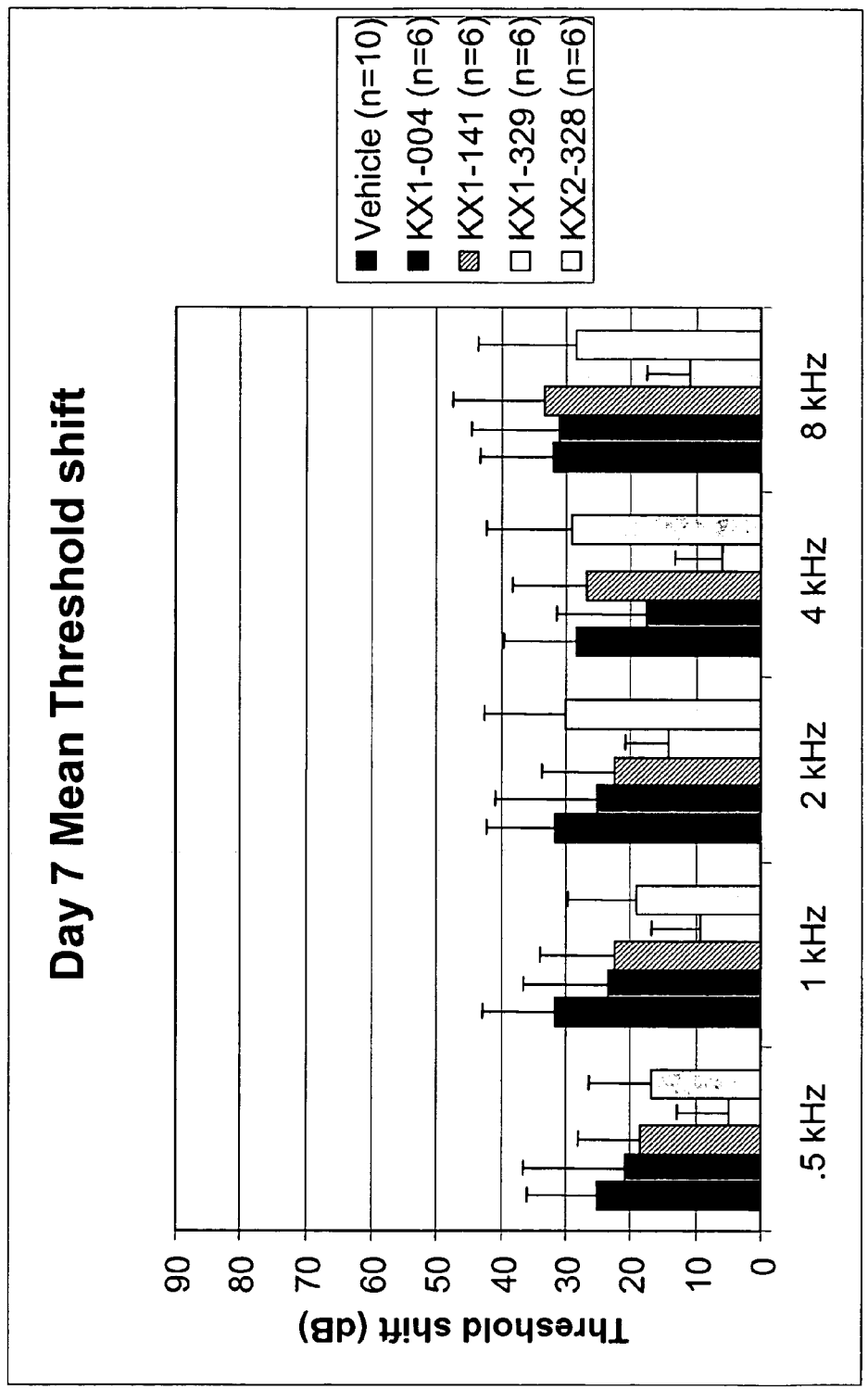
FIG. 11 is a graph showing the average threshold shifts (dB) in chinchilla cochleas after exposure to 0.5 kHz, 1 kHz, 2 kHz, 4 kHz, and 8 kHz band noise on day 7 after experimental manipulation.
Figure 12:
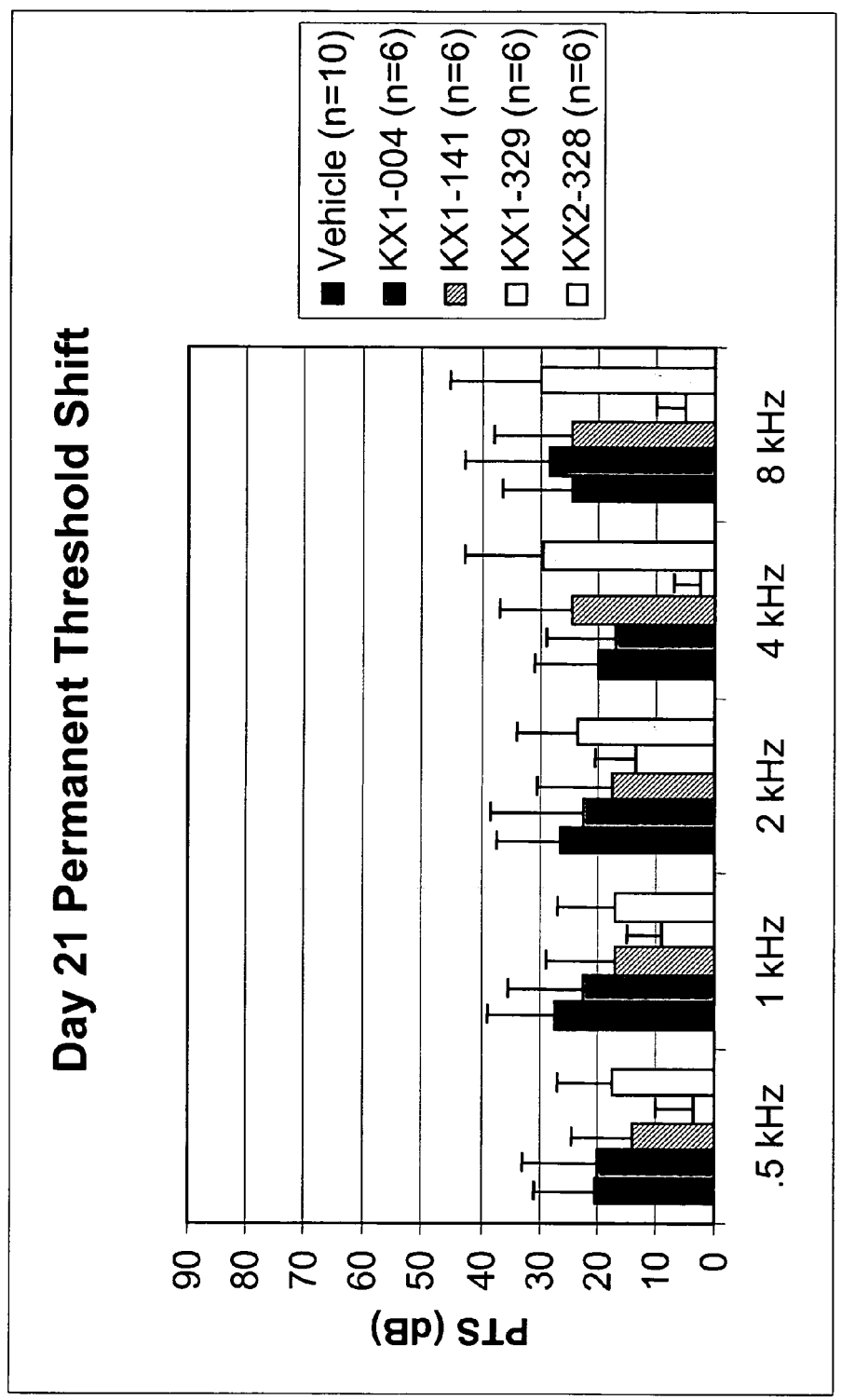
FIG. 12 is a graph showing the average threshold shifts (dB) in chinchilla cochleas after exposure to 0.5 kHz, 1 kHz, 2 kHz, 4 kHz, and 8 kHz band noise on day 21 after experimental manipulation.

FIGS. 10-12 show the average threshold shifts for animals treated with KX1-004, KX1-141, KX1-329 or KX2-328. In particular, FIG. 10 shows average threshold shifts after exposure to 0.5 kHz, 1 kHz, 2 kHz, 4 kHz, and 8 kHz band noise on day I after experimental manipulation. FIG. 11 shows average threshold shifts after exposure to 0.5 kHz, 1 kHz, 2 kHz, 4 kHz, and 8 kHz band noise on day 7 after experimental manipulation. FIG. 12 shows average threshold shifts after exposure to 0.5 kHz, I kHz, 2 kHz, 4 kHz, and 8 kHz band noise on day 21 after experimental manipulation. As shown in FIGS. 10-12, in most cases, the average dB threshold shifts for ears treated with KX1-004, KX1-141, KX1-329 or KX2-328 were lower, indicating that the compounds reduced the level of hearing loss in treated animals relative to the untreated control animals.

Example 6

Protection Against Cisplatin-Induced Hearing Loss Using PTK Inhibitors

The effects of high level noise and ototoxic drugs, such as cisplatin or the class of aminoglycosides, share several common features in the inner ear. First, the noise and/or drugs alter the free radical/antioxidant levels in the cochlea (inner ear). The increase in free radicals has been shown to be a causative factor in the apoptotic death of the sensory cells. Guinea pigs (N=7) were used in studies of cisplatin-induced hearing loss. The animals' hearing sensitivity was measured using standard electrophysical techniques before the experimental manipulation. In particular, hearing thresholds were measured through evoked potentials from recording electrodes chronically implanted in the inferior colliculus, following standard laboratory procedures. Animals were anesthetized and treated with cisplatin. Subsequently, the animals' hearing was tested to determine evoked potential threshold shifts.

Figure 13:
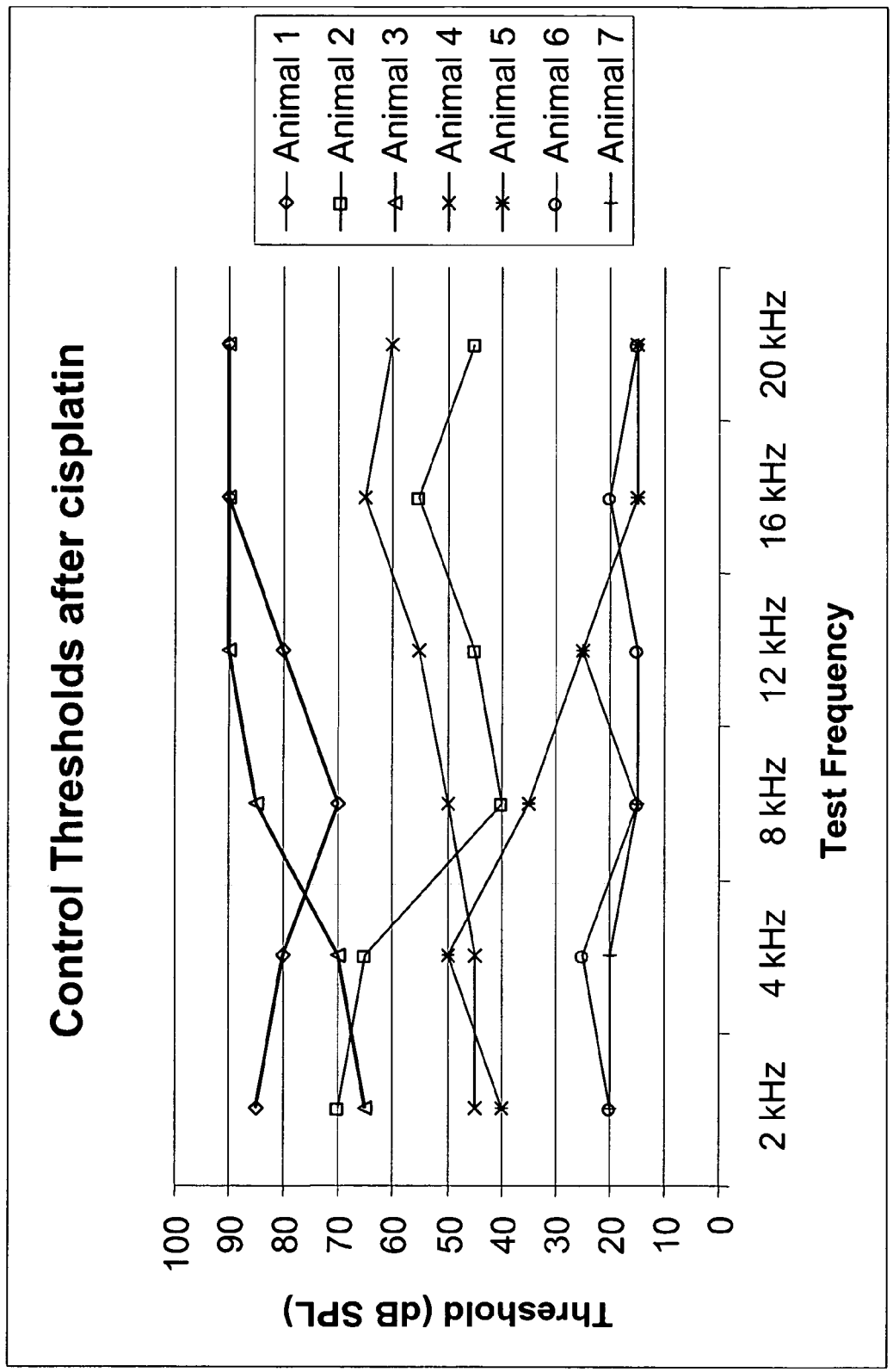
FIG. 13 is a line graph showing the threshold shifts (dB) in guinea pig cochleas after exposure to 2 kHz, 4 kHz, 8 kHz, 12 kHz, 16 kHz and 20 kHz band noise after treatment with cisplatin.
Figure 14:
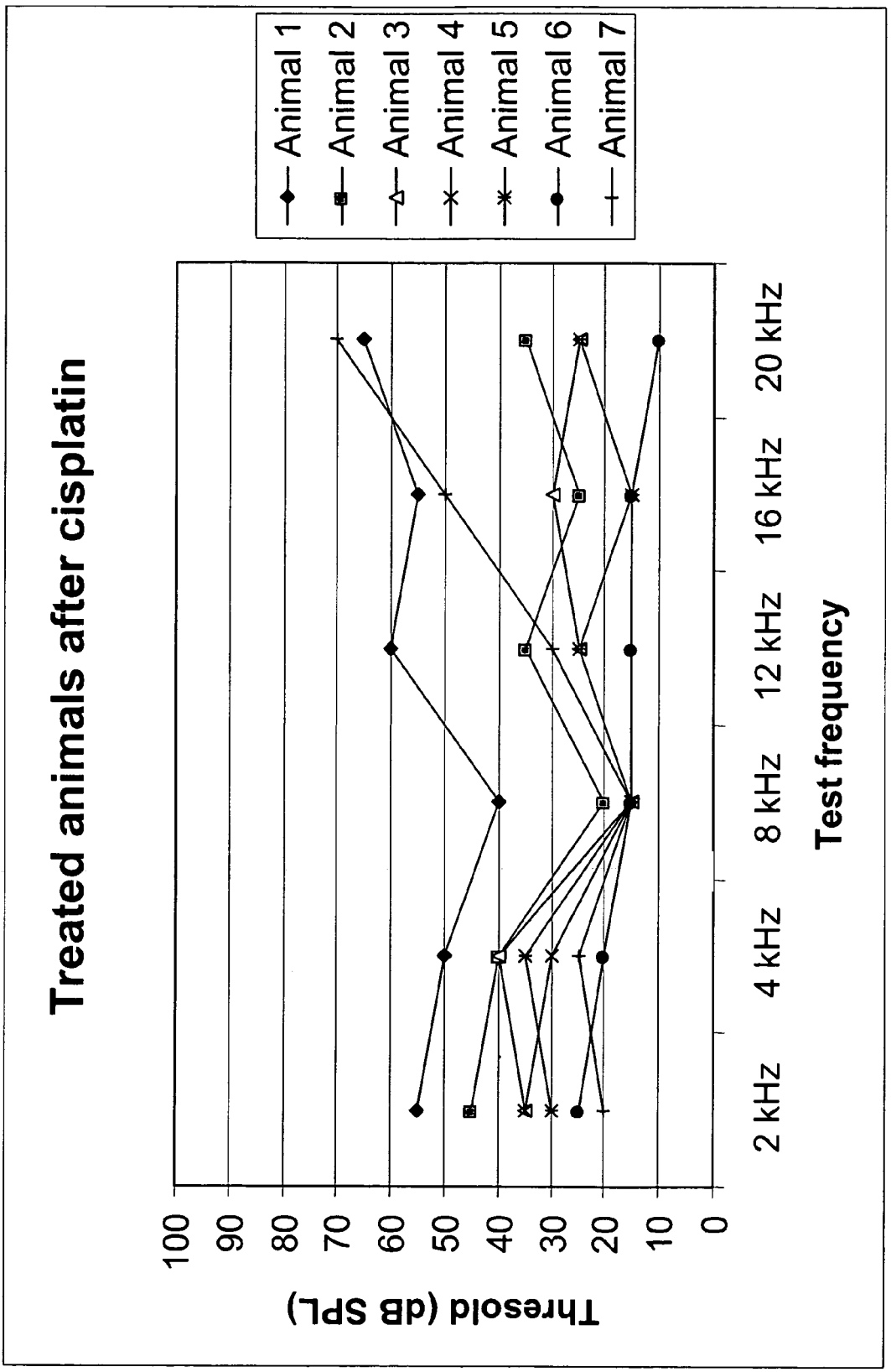
FIG. 14 is a line graph showing the threshold shifts (dB) in KX1-004-treated guinea pig cochleas after exposure to 2 kHz, 4 kHz, 8 kHz, 12 kHz, 16 kHz and 20 kHz band noise after treatment with cisplatin.
Figure 15:
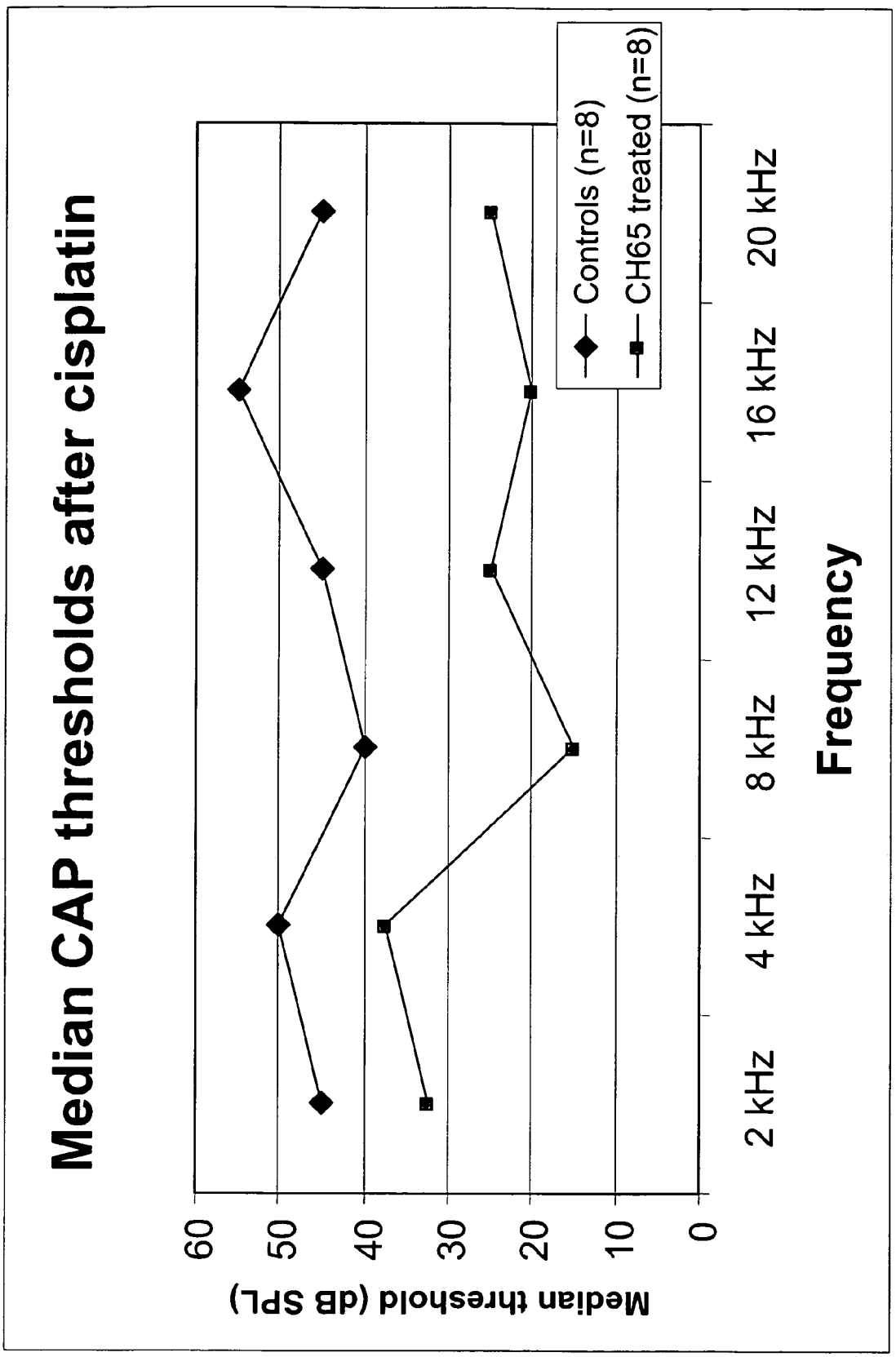
FIG. 15 is a line graph showing the average threshold shifts (dB) in KX1-004-treated guinea pig cochleas and untreated control guinea pig cochleas after exposure to 2 kHz, 4 kHz, 8 kHz, 12 kHz, 16 kHz and 20 kHz band noise after treatment with cisplatin.

FIG. 13 shows threshold shifts for a number of guinea pigs after exposure to 2 kHz, 4 kHz, 8 kHz, 12 kHz, 16 kHz and 20 kHz band noise after treatment with cisplatin. FIG. 14 shows the threshold shifts for animals treated with KX1-004 (CH65). Animals were treated subcutaneously with KX1-004 prior to the cisplatin-induced hearing loss. FIG. 15 shows the median CAP thresholds after cisplatin-induced hearing loss for both the untreated control animals and the KX1-004 (CH65)-treated animals. As shown in FIG. 15, KX1-004 treatment protected against ciplatin-induced hearing loss.

Example 7

Effect of Compounds on Osteoclast Formation

Figure 16:
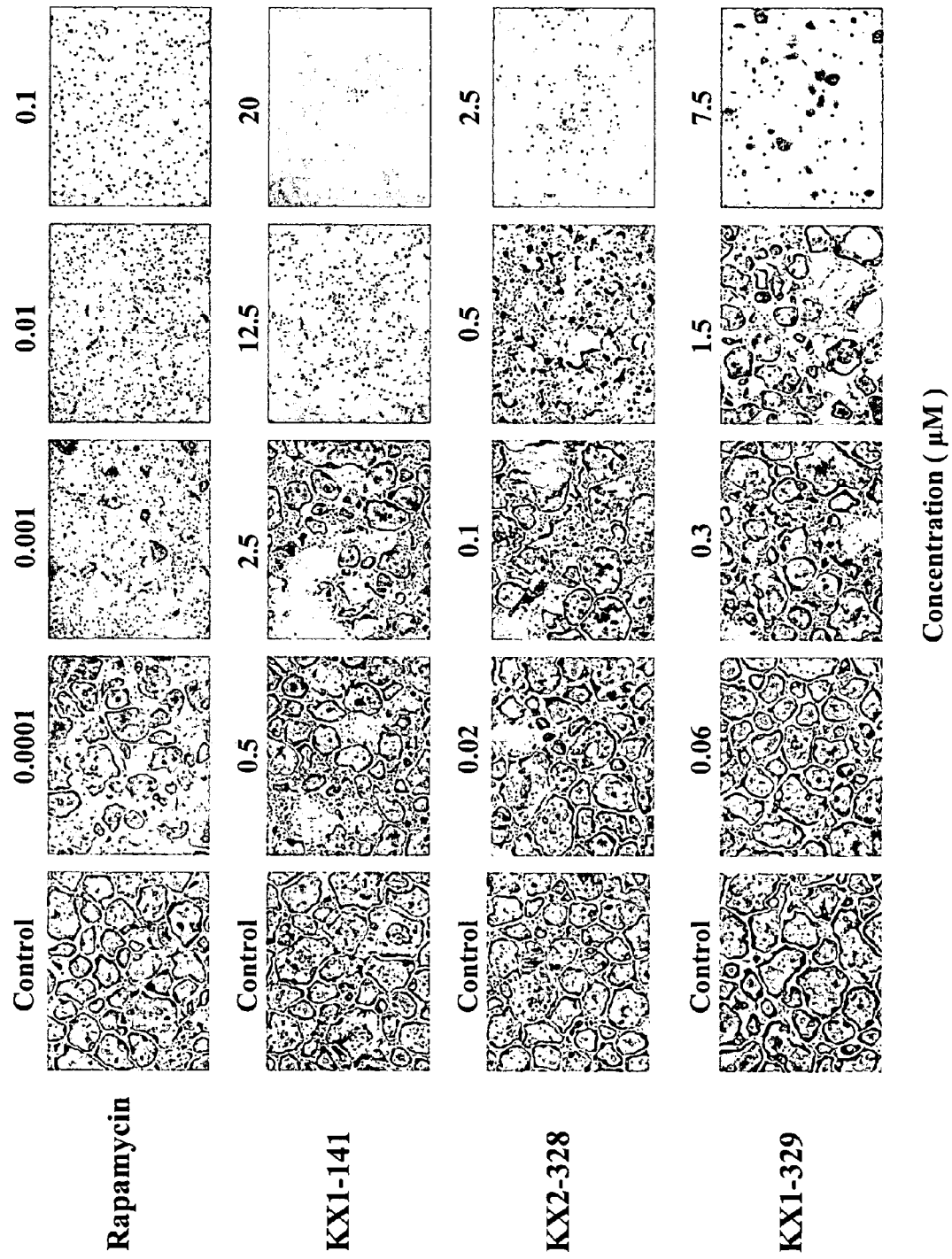
FIG. 16 is a series of illustrations depicting the effect of compounds on osteoclast formation.

To determine the effect of the compounds on osteoclast formation, the compounds were added to osteoclast precursors derived from spleen cells. For the generation of spleen-derived osteoclasts, spleen cells comprising osteoclast precursors were treated with Rapamycin, KX1-141, KX2-328 (Astrazeneca compound), or KX1-329 for 5 days in the presence of receptor activator of nuclear factor-κB ligand (RANKL) and macrophage colony-stimulating factor (M-CSF). In in vitro murine or human osteoclast models, soluble RANKL enables osteoclast precursors to differentiate in the presence of M-CSF (Quinn, et al.; 1998, *Endocrinology*, 139, 4424-4427; Jimi, et al.; 1999, *J. Immunol.*, 163, 434-442). The untreated control cells were incubated in the presence of RANKL and M-CSF alone. Rapamycin was used as a positive control for the inhibition of osteoclast formation. FIG. 16 shows that increasing concentrations of Rapamycin (0.0001 µM, 0.001 µM, 0.01 µM, or 0.1 µM), KX1-141 (0.5 µM, 2.5 µM, 12.5 µM, or 20 µM), KX2-328 (0.02 µM, 0.1 µM, 0.5 µM, or 2.5 µM), or KX1-329 (0.06 µM, 0.3 µM, 1.5 µM or 7.5 µM) were added to the spleen cells. The cells were stained as shown in FIG. 16. All four compounds, including the positive control Rapamycin, inhibited the formation of osteoclasts compared to the untreated control.

Figure 17:
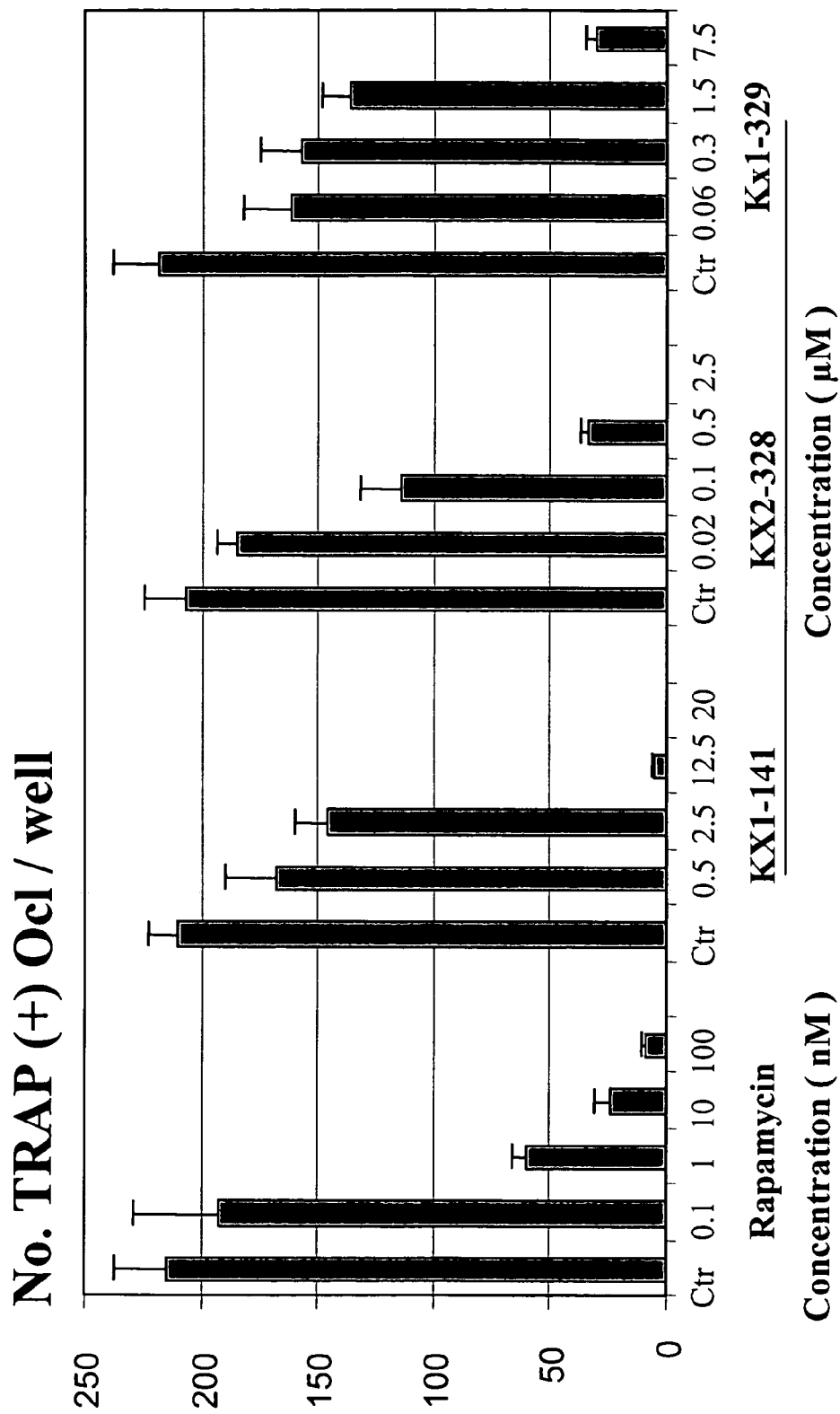
FIG. 17 is a bar chart demonstrating the effect of compounds on osteoclast formation.

For generating spleen-derived osteoclasts, spleen cells were treated as described above. FIG. 17 shows that increasing concentrations of Rapamycin (0.1 nM, 1 nM, 10 nM, or 100 nM), KX1-141 (0.5 µM, 2.5 µM, 12.5 µM, or 20 µM), KX2-328 (0.02 µM, 0.1 µM, 0.5 µM, or 2.5 µM), or KX1-329 (0.06 µM, 0.3 µM, 1.5 µM or 7.5 µM) were added to the spleen cells. Cells were then stained with the osteoclast marker, tartrate-resistant acid phosphatase (TRAP) to visualize differentiated cells. The numbers of TRAP-positive osteoclasts were counted. All four compounds, including the positive control Rapamycin, reduced the number of TRAP-positive osteoclasts compared to the untreated control (Ctr).

Example 8

Effect of Compounds on Osteoclast Survival

Figure 18:
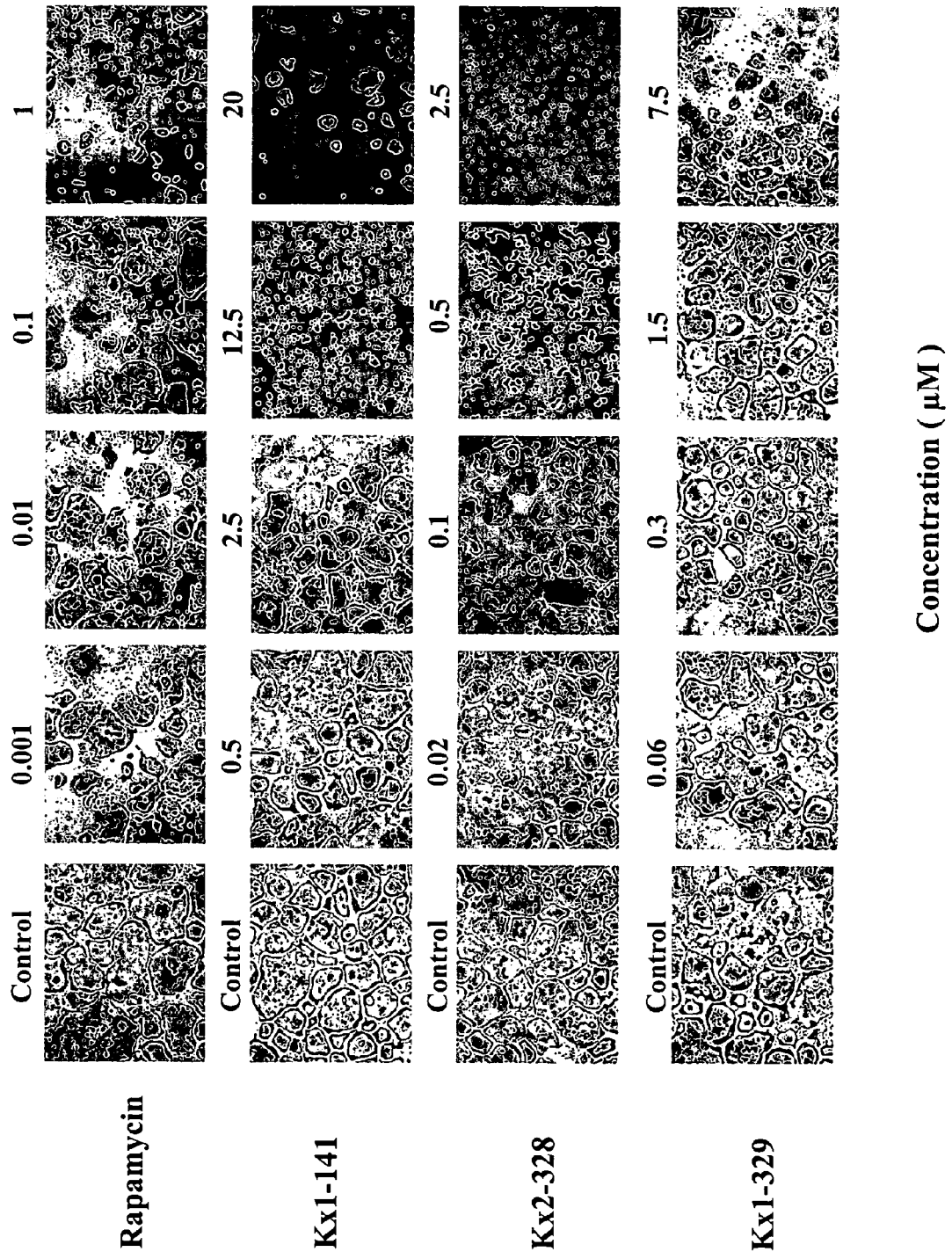
FIG. 18 is a series of illustrations showing the effect of compounds on osteoclast survival.

To determine the effect of the compounds on osteoclast survival, osteoclasts were treated with Rapamycin, KX1-141, KX2-328, or KX1-329 for 48 hours in the presence of RANKL and M-CSF. The untreated, control cells were incubated in the presence of RANKL and M-CSF alone. Rapamycin was used as a positive control for the inhibition of osteoclast survival. FIG. 18 shows that increasing concentrations of Rapamycin (0.001 µM, 0.01 µM, 0.1 µM, or 1 µM), KX1-141 (0.5 µM, 2.5 µM, 12.5 µM, or 20 µM), KX2-328 (0.02 µM, 0.1 µM, 0.5 µM, or 2.5 µM), or KX1-329 (0.06 µM, 0.3 µM, 1.5 µM or 7.5 µM) were added to the osteoclasts. The cells were stained as shown in FIG. 18. All four compounds, including the positive control Rapamycin, inhibited the survival of osteoclasts compared to the untreated control.

Figure 19:
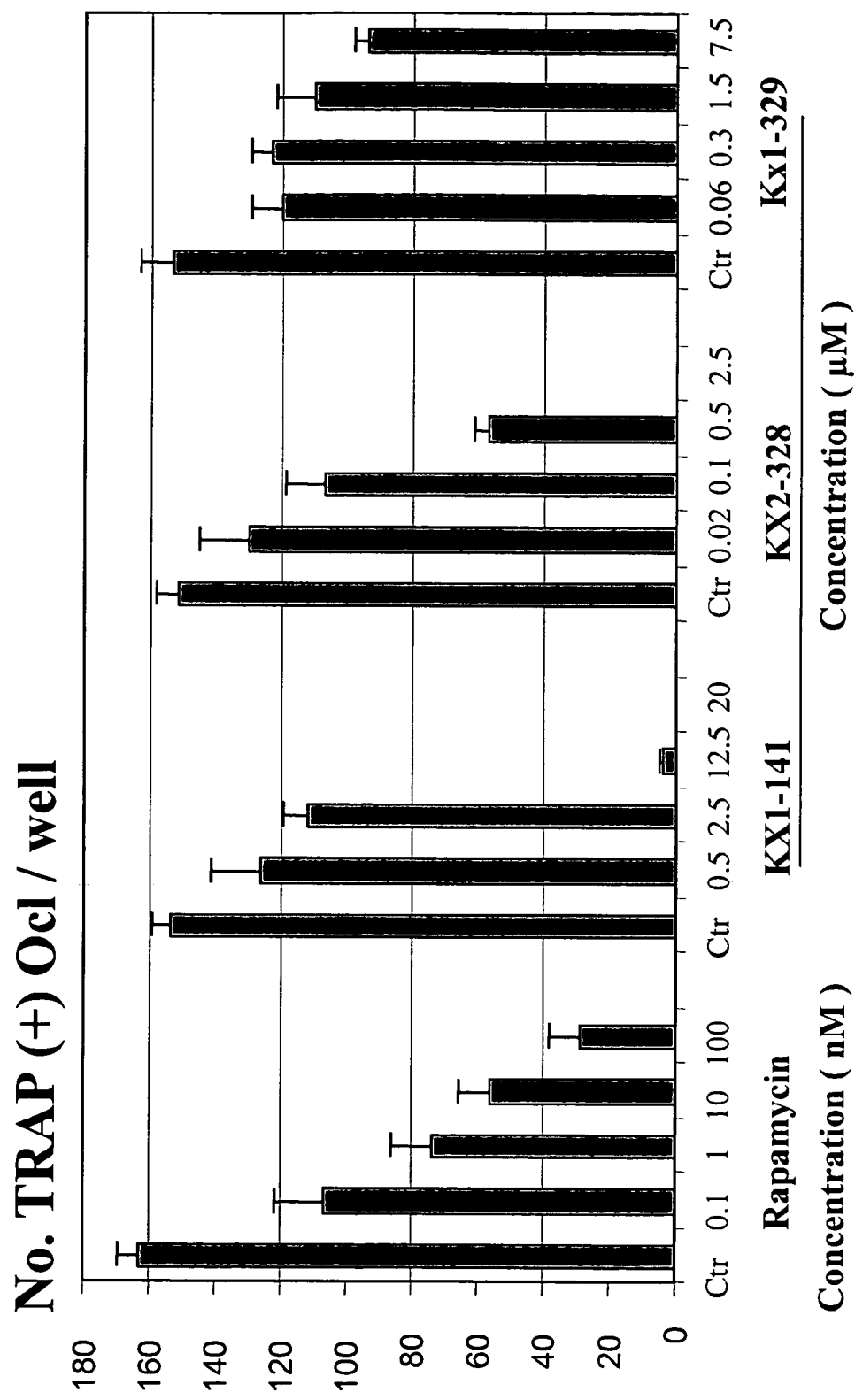
FIG. 19 is a bar chart depicting the effect of compounds on osteoclast survival.

As described above, osteoclasts were treated with Rapamycin, KX1-141, KX2-328, or KX1-329 for 48 hours in the presence of RANKL and M-CSF. FIG. 19 shows that increasing concentrations of Rapamycin (0.1 nM, 1 nM, 10 nM, or 100 nM), KX1-141 (0.5 µM, 2.5 µM, 12.5 µM, or 20 µM), KX2-328 (0.02 µM, 0.1 µM, 0.5 µM, or 2.5 µM), or KX1-329 (0.06 µM, 0.3 µM, 1.5 µM or 7.5 µM) were added to the osteoclasts. Cells were then stained with TRAP and the number of TRAP-positive osteoclasts were counted. All four compounds, including the positive control Rapamycin, reduced the number of TRAP-positive osteoclasts compared to the untreated control.

Example 9

Effect of Compounds on Bone Resorption In Vitro

Figure 20A:
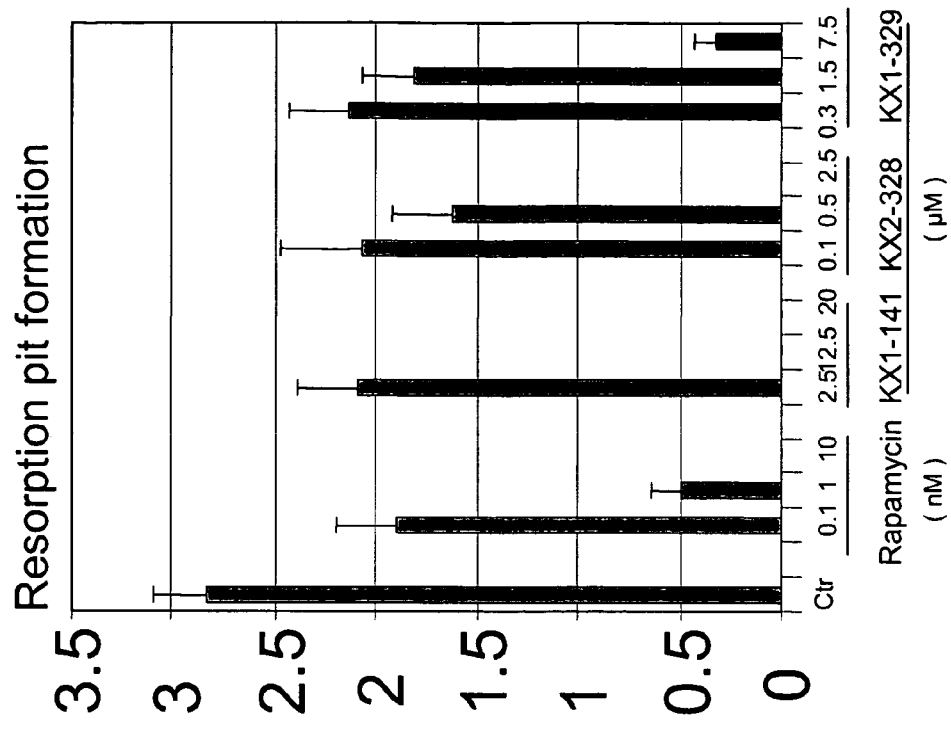
FIG. 20A is a bar chart demonstrating the effect of compounds on bone resorption in vitro.

To determine the effects of the compounds on osteoclast formation on bone slices, the bone slices were treated with Rapamycin, KX1-141, KX2-328, or KX1-329. FIG. 20A shows that increasing concentrations of Rapamycin (0.1 nM, 1 nM, or 10 nM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The number of osteoclasts on the bone slices were counted. All four compounds, including the positive control Rapamycin, reduced the number of osteoclasts on the bone slices compared to the untreated control (Ctr).

Figure 20B:
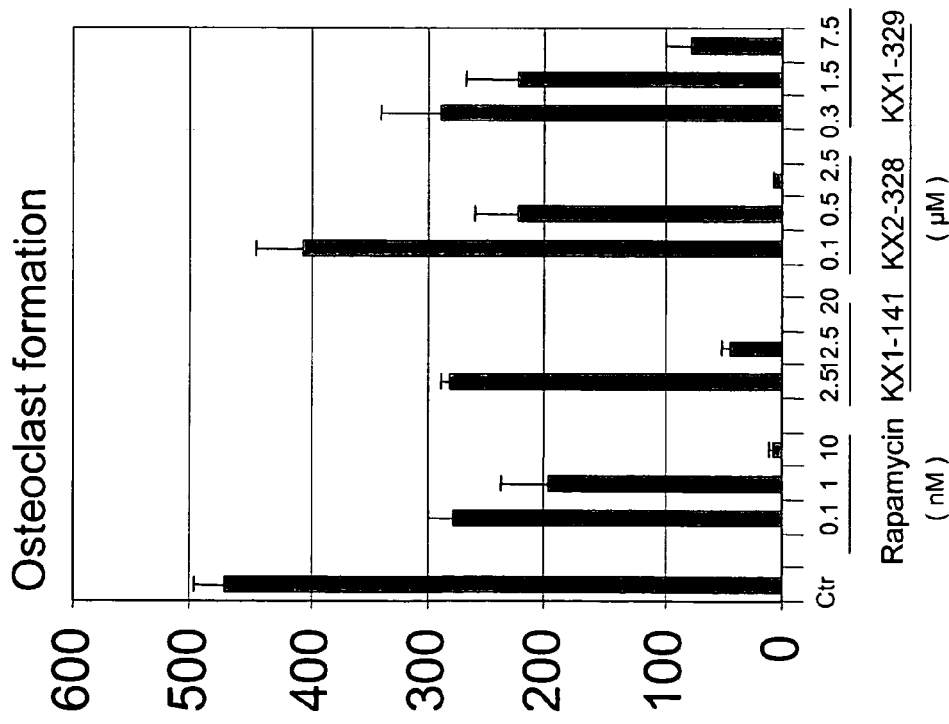
FIG. 20B is a bar chart showing the effect of compounds on resorption pit formation.

During the resorption of bone, osteoclasts form resorption pits. To determine the effects of the compounds on resorption pit formation on bone slices, the bone slices were treated with Rapamycin, KX1-141, KX2-328, or KX1-329, as described above. FIG. 20B shows that increasing concentrations of Rapamycin (0.1 nM, 1 nM, or 10 nM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The number of resorption pits on the bone slices was determined. The compounds reduced the number of resorption pits on the bone slices compared to the untreated control (Ctr).

Bone slices were treated as indicated above. FIG. 21A shows that increasing concentrations of Rapamycin (0.001 µM, 0.01 µM, or 0.1 µM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The bone slices were then stained with TRAP. All four compounds, including the positive control Rapamycin, reduced the number of TRAP-positive osteoclasts on the bone slices compared to the untreated control. Notably, 12.5 µM KX1-141 significantly reduced the number of TRAP-positive osteoclasts on the bone slices compared to the untreated control.

Bone slices were treated as indicated above. FIG. 21B shows that increasing concentrations of Rapamycin (0.001 µM, 0.01 µM, or 0.1 µM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The bone slices were stained with Toluidine Blue to reveal resorption pits, which are indicators of osteoclast-mediated resorption of bone. All four compounds, including the positive control Rapamycin, reduced the number of resorption pits on the bone slices compared to the untreated control.

Example 10

Effect of Compounds on Osteoblasts

Figure 22:
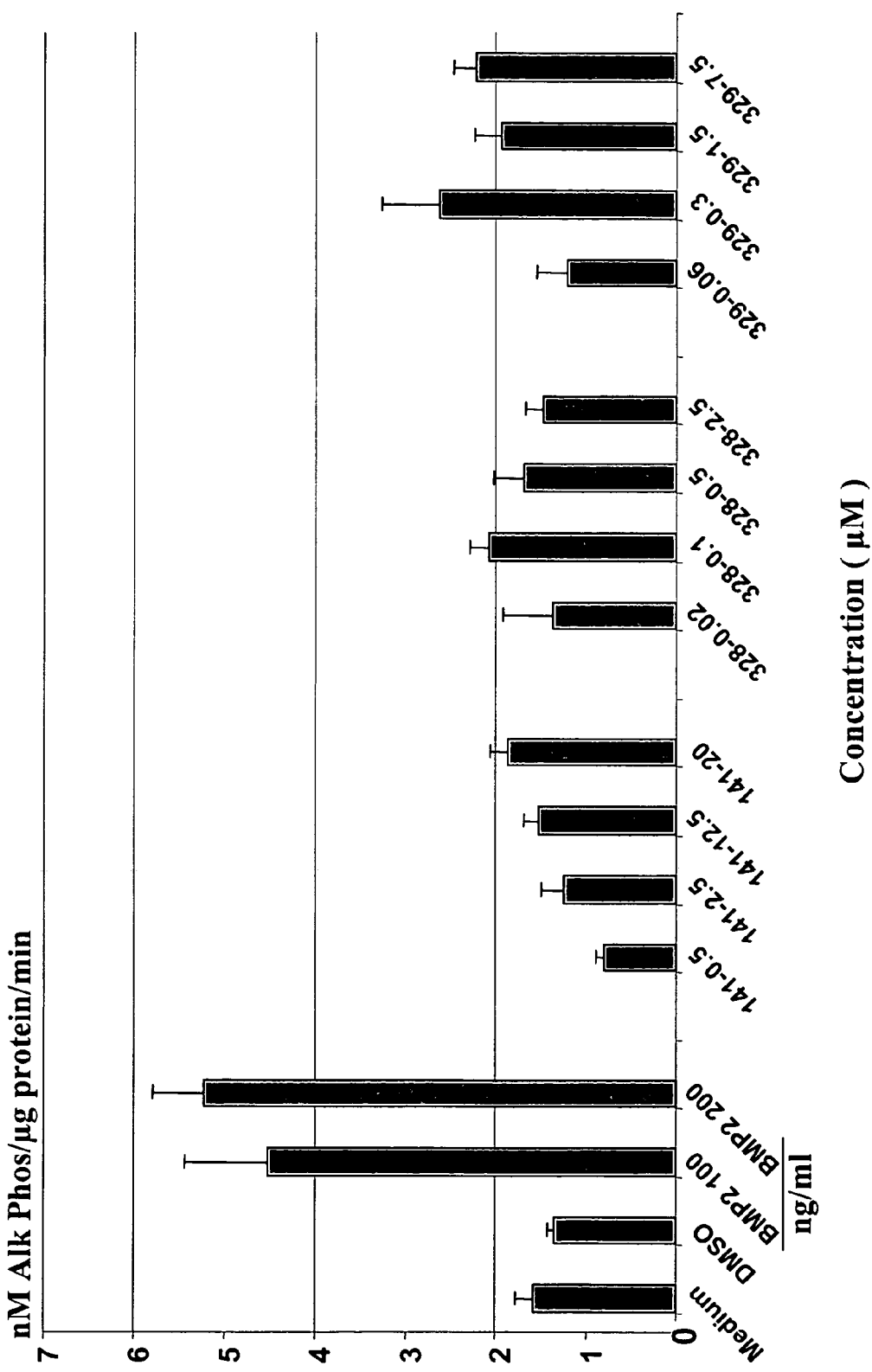
FIG. 22 is a bar chart showing the effect of compounds on alkaline phosphatase expression by osteoblasts.

The enzyme alkaline phosphatase has been used as an indicator of osteoblast activity, as it is involved in making phosphate available for calcification of bone. To determine the effects of the compounds on osteoblast activity, osteoblasts were treated with KX1-141 (0.5 µM, 2.5 µM, 12.5 µM, or 20 µM), KX2-328 (0.02 µM, 0.1 µM, 0.5 µM, or 2.5 µM), or KX1-329 (0.06 µM, 0.3 µM, 1.5 µM or 7.5 µM) and alkaline phosphatase expression was determined (nM alkaline phosphatase/µg protein/min (FIG. 22). As controls, osteoblasts were treated with medium alone, dimethyl sulfoxide (DMSO), or bone morphogenic protein-2 (BMP2). BMPs, defined as osteoinductive by their ability to induce osteogenesis when implanted in extraskeletal sites, are thought to mediate the transformation of undifferentiated mesenchymal cells into bone-producing osteoblasts.

Figure 23:
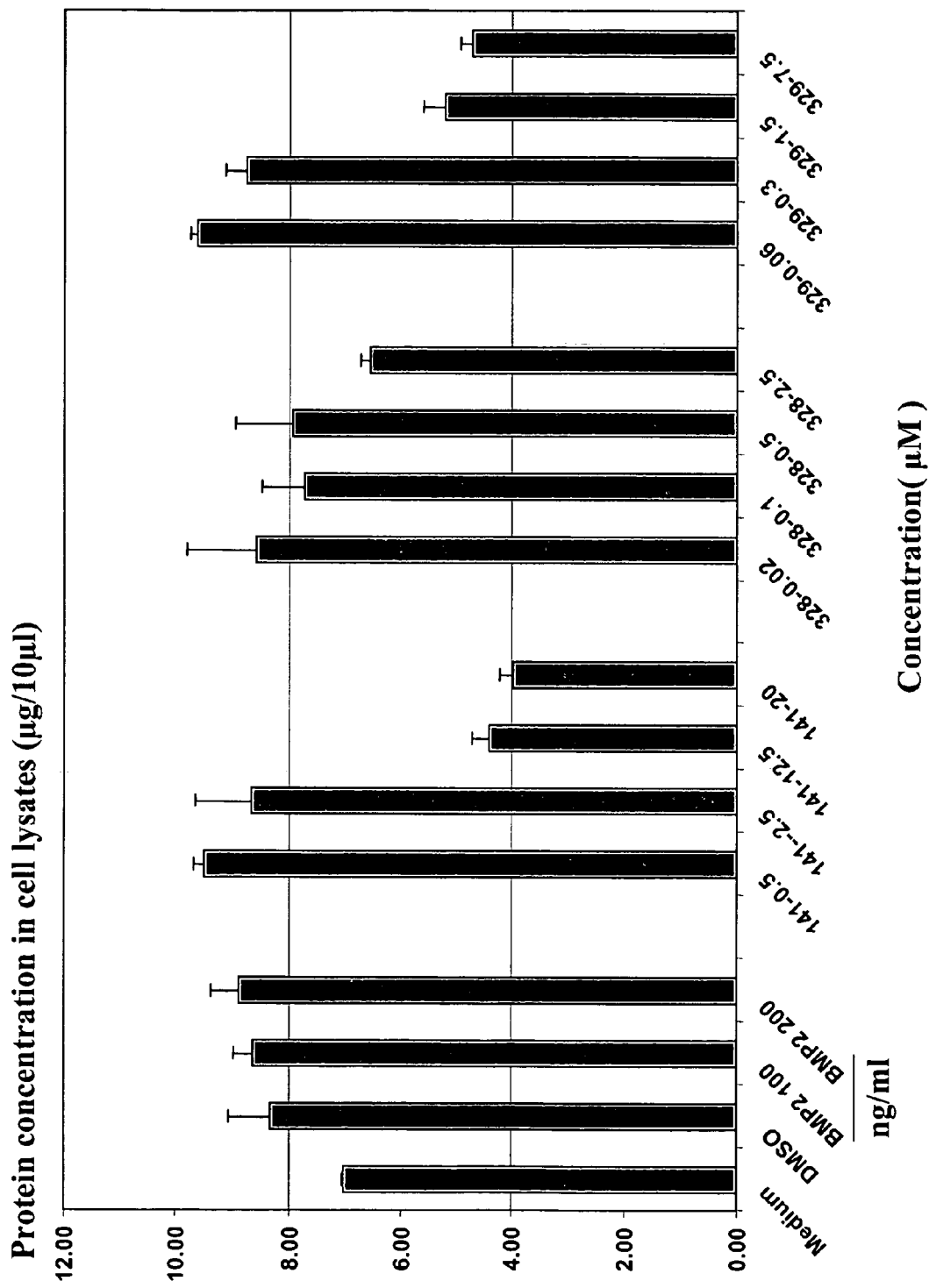
FIG. 23 is a bar chart depicting the effect of compounds on protein expression by osteoblasts.

To determine the effects of the compounds on osteoblast activity and protein expression, osteoblasts were treated with medium, DMSO, BMP2, KX1-141, KX2-328, or KX1-329 as indicated above. The protein concentration in cell lysates was determined (µg/10 µl) (FIG. 23). Notably, KX1-141 increased protein concentration when administered at 0.5 µM and 2.5 µM, but reduced protein concentration in cell lysates when administered at 12.5 µM and 20 µM. Additionally, KX1-329 increased protein concentration when administered at 0.06 µM and 0.3 µM, but reduced protein concentration when administered at 1.5 µM and 7.5 µM.

Example 11

Effect of Compounds on Obesity

The following example illustrates that the compounds of the present invention could be used to treat obesity. The compounds are tested using a method described previously (Minet-Ringuet, et al.; 2006, *Psychopharmacology*, Epub ahead of print, incorporated herein by reference). Thirty male Sprague-Dawley rats initially weighing 175-200 g are housed in individual Plexiglas cages with an artificial 12:12-h light-dark cycle (lights on at 08:00 h) in a room maintained at 24±1° C. and 55±5% humidity. Food and water are available ad libitum throughout. All rats are fed with a medium fat diet (metabolizable energy 17.50 kJ/g) composed of 140 g/kg of whole milk protein, 538.1 g/kg of cornstarch, 87.6 g/kg of sucrose, and 137 g/kg of soya bean oil, and this diet is supplemented with minerals and vitamins (mineral salts 35 g/kg, vitamins 10 g/kg, cellulose 50 g/kg, and choline 2.3 g/kg). This food, named P14-L, which resembles the usual human diet (14% proteins, 31% lipids, and 54% carbohydrates) is prepared in the laboratory in the form of a powder.

Several doses of the compound of the instant invention are tested: 0.01, 0.1, 0.5, and 2 mg/kg, in addition to the control solution. The compound is solubilized in water and then incorporated into the diet. The basal food intake is recorded during the adaptation period and used to determine the daily quantity of the compound of the instant invention incorporated into food. The compound is mixed into the food in the laboratory. After 1 week of adaptation to the laboratory conditions, the rats are separated into five groups (n=6 per group) with homogenous weight and receive the compound of the instant invention in their food for 6 weeks. Weight is recorded three times per week. Body composition is measured at the end of the study by dissection and by weighing the main organs and tissues. Briefly, rats are deeply anesthetized by an intraperitoneal injection of an overdose of anesthetic (sodium pentobarbital 48 mg/kg) and heparinized (100 U heparin/100 g body weight). They are bled (to avoid coagulation in tissues) by sectioning the vena cava and abdominal aorta before removal and weighing of the main fresh organs (liver, spleen, kidneys, and pancreas) and tissues (perirenal and scapular brown adipose tissue, epididymal, retroperitoneal, visceral, and subcutaneous white adipose tissues (WATs), and carcass defined by muscles and skeleton). The compound of the instant invention could reduce the body weight of the animals, indicating that the compound may be used to treat obesity in a subject.

Example 12

Effect of Compounds on Insulin-Induced GLUT4 Translocation in 3T3-L1 Adipocytes

The following example illustrates that the compounds of the present invention could be used to treat diabetes. The compounds are tested using a method described previously (Nakashima, et al.; 2000, *J. Biol. Chem.*, 275, 12889-12895). Either control IgG, or the compound of the instant invention is injected into the nucleus of differentiated 3T3-L1 adipocytes on coverslips. Glutathione S-transferase fusion proteins are each coinjected with 5 mg/ml sheep IgG for detection purposes. Prior to staining, the cells are allowed to recover for a period of 1 h. Cells are starved for 2 hr in serum-free medium, stimulated with or without insulin (0.5 nM or 17 nM) for 20 min and fixed.

Immunostaining is performed using rabbit polyclonal anti-GLUT4 (F349) (1 µg/ml). Each fluorescein isothiocyanate-positive microinjected cell is evaluated for the presence of plasma membrane-associated GLUT4 staining. Control cells are injected with preimmune sheep IgG and then processed in the same way as experimentally injected cells. As quantitated by immunofluorescent GLUT4 staining, insulin leads to an increase in GLUT4 translocation to the plasma membrane. Cells are incubated with wortmannin as a control to block basal and insulin-induced GLUT4 translocation. The compounds of the instant invention could stimulate insulin-induced GLUT4 translocation, which could indicate that administration of the compounds of the invention inhibited kinase activity, e.g., PTEN function, resulting in an increase in intracellular phosphatidylinositol 3,4,5-triphosphate levels, which stimulates GLUT4 translocation.

Example 13

Effect of Compounds on Retinal Neovascularization

The following example illustrates that the compounds of the present invention could be used to treat eye diseases, e.g., macular degeneration, retinopathy and macular edema. The effect of compounds on retinal neovascularization is determined using a model of retinal neovascularization as previously described (Aiello, et al.; 1995, *Proc. Natl. Acad. Sci.*, 92, 10457-10461). Briefly, C57B1/6J mice are exposed to 75% $O_2$ from postnatal day 7 (P7) to P12 along with nursing mothers. At P12, the mice are returned to room air. Intraocular injections are performed at P12 and sometimes P14 as described below. At P17 the mice are sacrificed by cardiac perfusion of 4% paraformaldehyde in phosphate-buffered saline and the eyes are enucleated and fixed in 4% paraformaldehyde overnight at 4° C. before paraffin embedding.

Mice are deeply anesthetized with tribromoethanol for all procedures. The lid fissure is opened (e.g., using a no. 11 scalpel blade) and the eye is proptosed. Intravitreal injections are performed by first entering the left eye with an Ethicon TG140-8 suture needle at the posterior limbus. A 32-gauge Hamilton needle and syringe are used to deliver the compound of the instant invention diluted in Alcon balanced salt solution through the existing entrance site. The eye is then repositioned and the lids are approximated over the cornea. Repeat injections are performed through a previously unmanipulated section of limbus 2 days later. As a control, equal amounts of saline are injected to the right eye.

Over 50 serial 6-µm paraffin-embedded axial sections are obtained starting at the optic nerve head. After staining with periodic acid/Schiff reagent and hematoxylin (Pierce, et al.; 1995, *Proc. Natl. Acad. Sci. USA.*, 92, 905-909; Smith et al.; 1994, *Invest. Ophthal. Vis. Sci.*, 35, 101-111), 10 intact sections of equal length, each 30 µm apart, are evaluated for a span of 300 µm. Eyes exhibiting retinal detachment or endophthalmitis are excluded from evaluation. All retinal vascular cell nuclei anterior to the internal limiting membrane are counted in each section by a fully masked protocol. The mean of all 10 counted sections yield average neovascular cell nuclei per 6-µm section per eye. No vascular cell nuclei anterior to the internal limiting membrane are observed in normal, unmanipulated animals (Smith et al.; 1994, *Invest. Ophthal. Vis. Sci.*, 35, 101-111). Reduced neovascularization could be observed in the eyes treated with the compounds of the instant invention as compared to the eyes in the saline control group.

Example 14

Identification of Compounds that Modulate Kinase Signaling Cascade Associated with Stroke Many animal models for stroke have been developed and characterized, see e.g., Andaluz, et al., Neurosurg. Clin. North Am., vol. 13:385-393 (2002); Ashwal, S. and W. J.

Pearce., Curr. Opin. Pediatr., vol 13:506-516 (2001); De Lecinana, et al., Cerebrovasc. Dis., vol. 11(Suppl. 1):20-30 (2001); Ginsberg and Busto, Stroke, vol. 20:1627-1642 (1989); Lin, et al., J. Neurosci. Methods, vol. 123:89-97 (2003); Macrae, I. M., Br. J. Clin. Pharmacol., vol. 34:302-308 (1992); McAuley, M. A., Cerebrovasc. Brain Metab. Rev., vol. 7:153-180 (1995); Megyesi, et al., Neurosurgery, vol. 46:448-460 (2000); Stefanovich, V. (ed.), Stroke: animal models. Pergamon Press, Oxford (1983); and Traystman, R. J., ILAR J. 44:85-95 (2003), each of which is hereby incorporated by reference in its entirety. For a review of animal models of focal (stroke) and global (cardiac arrest) cerebral ischemia, see e.g., Traystman, ILAR J., vol. 44(2):85-95 (2003) and Carmichael, NeuroRx®: The Journal of the American Society for Experimental NeuroTherapeutics, vol. 2:396-409 (2005, each of which is hereby incorporated by reference in its entirety.

Compounds that modulate cell death in stroke are identified using any of the art-recognized models for stroke. In the studies described herein, intra-arterial suture occlusion of the middle cerebral artery (MCA), a procedure known as MCAo, through the internal carotid artery is used as a model for cell death in stroke. In the control and test group of rats, the external carotid artery is transected, the common carotid artery is tied off, and the external carotid artery is then used as a pathway to pass a suture through the internal carotid artery, wherein the suture lodges in the junction of the anterior and middle cerebral arteries. To reduce subarachnoid hemorrhage and premature reperfusion, the suture is preferably coated with an agent such as silicone. The suture is used to occlude the MCA, e.g., for a duration of 60, 90, or 120 minutes and to permanently occlude the MCA.

In the test group, rats are administered a compound of the invention at a variety of times prior to, during and after occlusion of the MCA with the suture. The effects of the compound on the test group is compared to the effects observed in the control group, for example, by measuring the extent of cell death in each MCAo group. Typically, in the control group, the pattern of cell death follows a progression from early infarction in the striatum to delayed infarction in the dorsolateral cortex overlying the striatum. Striatal is mostly necrotic and occurs rapidly. The pattern of cell-death in the test group is compared to that of the control group to identify compounds that modulate cell death in stroke.

Example 15

Identification of Compounds that Modulate Kinase Signaling Cascade Associated with Atherosclerosis Many animal models for atherosclerosis have been developed and characterized. For a review of animal models of atherosclerosis, restenosis and endovascular graft research, see e.g., Narayanaswamy et al., JVIR, vol. 11(1): 5-17 (2000), which is hereby incorporated by reference in its entirety. Atherosclerosis is induced in a suitable animal model using a high fat/high cholesterol (HFHC) diet. The test animal is an animal that contains cholesterol ester transferase, such as the rabbit or the swine. The HFHC diet is produced, e.g., using commercial chow supplemented with fat. Cholesterol intake is between 0.5-2.0% of the diet. A test group of animals, e.g., rabbits or swine, receives a compound of the invention. The effect of the test compound is compared to the effects of atherosclerosis in the untreated, control group of animals. Effects that are compared include, for example, the degree of plaque formation, the number and/or frequency of myocardial infarctions observed in each group of animals, and the extent of tissue damage secondary to myocardial infarction exhibited in coronary tissue.

Myocardial infarction is studied using a variety of animal models such as rats and mice. The majority of myocardial infarctions result from acute transbotic occlusion of pre-existing atherosclerotic plaques of coronary arteries, which is mimicked in animal models by ligation of the left coronary artery in e.g., rats and mice. Myocardial infarction induces global changes in the ventricular architecture, a process called ventricular remodeling. The infarcted heart progressively dilates and accelerates the deterioration of ventricular dysfunction that eventually results in heart failure.

Myocardial ischemia is induced in test and control groups of animals, e.g., mice or rats, by ligating the left anterior descending coronary artery. The affected heart tissue is contacted with a compound of the invention, for example, by intraperitoneal (i.p.) injections, after the induction of ischemia. High resolution magnetic resonance imaging (MRI), dry weight measurements, infarct size, heart volume, and area at risk are determined 24 hours postoperatively. Survival rates and echocardiography are determined at various times postoperatively in the rats receiving injections of the compound of the invention. Other effects of the test compound are compared to the control group of rats. For example, changes in left ventricular geometry and function are characterized using echocardiography to compare end-diastolic diameters, relative wall thickness, and the percentage of fractional shortening. In excised hearts, the infarct size calculated and expressed as a percentage of left ventricular surface area.

Example 16

Identification of Compounds that Modulate Kinase Signaling Cascade Associated with Neuropathic Pain Many animal models for neuropathic pain, such as chronic neuropathic pain, have been developed and characterized, see e.g., Bennett & Xie, Pain, vol. 33, 87-107 (1988); Seltzer et al., Pain, vol. 43, 205-18 (1990); Kim & Chung, Pain, vol. 50, 355-63 (1992); Malmberg & Basbaum, Pain, vol. 76, 215-22 (1998); Sung et al., Neurosci Lett., vol. 246, 117-9 (1998); Lee et al., Neuroreport, vol. 11, 657-61 (2000); Decosterd & Woolf, Pain, vol. 87, 149-58 (2000); Vadakkan et al., J Pain, vol. 6, 747-56 (2005), each of which is hereby incorporated by reference in its entirety. For a review of animal models used for neuropathic pain, see e.g., Eaton, J. Rehabilitation Research and Development, vol. 40(4 Supplement):41-54 (2003), the contents of which are hereby incorporated by reference in their entirety.

Compounds that modulate neuropathic pain are identified using any of the art-recognized models for neuropathic pain. For example, the models for neuropathic pain generally involve injury to the sciatic nerve, although the method used to induce injury varies. For example, the sciatic nerve is injured due to partial constriction, complete transection, freezing of the nerve, and metabolic, chemical, or immune insults to the nerve. Animals with these types of nerve injury have been shown to develop abnormal pain sensations similar to those reported by neuropathic pain patients. In the studies described herein, the sciatic nerve of test and control groups of subjects, such as mice, are injured. In the test group, subjects are administered a compound of the invention at a variety of times prior to, during and after injury to the sciatic nerve. The effects of the compound on the test group are compared to the effects observed in the control group, e.g., through physical observation and examination of the subjects. For example, in mice, the subject's hindpaw is used to test the response to non-noxious stimuli, such as tactile stimulation, or to test the subject's response to stimuli that would be noxious in the course of ordinary events, for example, radiant heat delivered to the hindpaw. Evidence of allodynia, a condition in which ordinarily nonpainful stimuli evoke pain, or a hyperalgesia, the excessive sensitiveness or sensibility to pain, in the test subjects indicates that test compound is not effectively modulating neuropathic pain in the test subjects.

Example 17

Identification of Compounds that Modulate Kinase Signaling Cascade Associated with Hepatitis B Many animal models for hepatitis B have been developed and characterized. For a review of animal models of hepatitis B, see e.g., Guha et al., Lab Animal, vol. 33(7):37-46 (2004), which is hereby incorporated by reference in its entirety. Suitable animal models include, for example, the chimpanzee, tree shrews (non-rodent small animals that are phylogenetically close to primates, see Walter et al., Hepatology, vol. 24(1):1-5 (1996), which is hereby incorporated by reference in its entirety), and surrogate models such as the woodchuck, duck and ground squirrel. (See e.g., Tennant and Gerin, ILAR Journal, vol. 42(2):89-102 (2001), which is hereby incorporated by reference in its entirety).

For example, primary hepatocytes are isolated from livers of the tree shrew species tupaia belangeri and are infected with HBV. In vitro infection results in viral DNA and RNA synthesis in hepatocytes and secretion hepatitis B surface antigen (HBsAg) and hepatitis B e antigen (HBeAg) into culture medium. Tupaias can also be infected with HBV in vivo, resulting in viral DNA replication and gene expression in tupaia livers. Similar to acute, self-limited hepatitis B in humans HBsAg is rapidly cleared from serum, followed by seroconversion to anti-HBe and anti-HBs.

Compounds that modulate hepatitis B are identified using any of the art-recognized models for hepatitis B. In the studies described herein, test and control groups of animals, e.g., chimpanzees or tree shrews, are infected with HBV. In the test group, subjects are administered a compound of the invention at a variety of times prior to, during and after exposure to HBV. The effects of the compound on the test group are compared to the effects observed in the control group, e.g., through physical observation and examination of the subjects and through blood or serum analysis to determine at what point in time the infection is cleared from the subject. For example, assays are run to detect the presence and/or amount of hepatitis B virus called surface antigens and fragments thereof. Alternatively or in addition, the subject's liver is analyzed. Liver function tests analyze levels of certain proteins and enzymes, such as, for example, aspartate aminotransferase (AST, formerly serum glutamic-oxaloacetic transaminase (SGOT)) and alanine aminotransferase (ALT, formerly serum glutamate-pyruvate transaminase (SGPT)).

Example 18

The Effect of Compounds on Tyrosine Kinase Inhibition

The following example illustrates that the compounds of the present invention could be used to treat autoimmune diseases. The compounds are tested using a method described previously (Goldberg, et al.; 2003, *J. Med. Chem.*, 46, 1337-1349). The kinase activity is measured using DELFIA (dissociation enhanced lanthanide fluoroimmunoassay), which utilizes europium chelate-labeled anti-phosphotyrosine antibodies to detect phosphate transfer to a random polymer, poly-Glu4-Tyr1 (PGTYR). The kinase assay is performed in a neutravidin-coated 96-well white plate in kinase assay buffer (50 mM HEPES, pH 7.0, 25 mM MgCl2, 5 mM MnCl2, 50 mM KCl, 100 μM Na3VO4, 0.2% BSA, 0.01% CHAPS). Test samples (compounds of the instant invention) initially dissolved in DMSO at 1 mg/mL are prediluted for dose response (10 doses with starting final concentration of 1 μg/mL, 1-3.5 serial dilutions) with the assay buffer. A 25 μL aliquot of this diluted sample and a 25 μL aliquot of diluted enzyme (lck) (0.8 nM final concentration) are sequentially added to each well. The reaction is started with a 50 μL/well of a mixture of substrates containing 2 μM ATP (final ATP concentration is 1 μM) and 7.2 ng/μL PGTYR-biotin in kinase buffer. Background wells are incubated with buffer and substrates only. Following 45 min of incubation at room temperature, the assay plate is washed three times with 300 μL/well DELFIA wash buffer. A 100 μL/well aliquot of europium-labeled anti-phosphotyrosine (Eu$^{3+}$-PT66, 1 nM, Wallac CR04-100) diluted in DELFIA assay buffer is added to each well and incubated for 30 min at room temperature. Upon completion of the incubation, the plate is washed four times with 300 μL/well of wash buffer and 100 μL/well of DELFIA wash buffer. Enhancement solution (Wallac) is added to each well. After 15 min, timeresolved fluorescence is measured on the LJL's analyst (excitation at 360 nm, emission at 620 nm, EU 400 dichroic mirror) after a delay time of 250 μs. The compound of the instant invention could inhibit the kinase activity of lck, indicating that the compound may be used to treat autoimmune disease in a subject.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:
1. A compound according to Formula IA

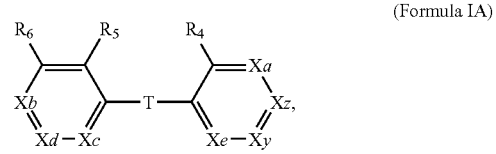

(Formula IA)

or a pharmaceutically acceptable salt thereof,
wherein: T is a bond;
$X_y$ is CY, N, or N—O;
$X_z$ is CZ;
Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;
$X_a$ is $CR_a$ or N, or N—O;
$X_b$ is $CR_b$;
$X_c$ is $CR_c$;

$X_d$ is $CR_d$;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

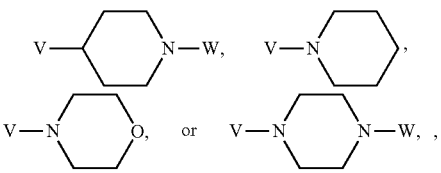

wherein W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $OPO_3H_2$, $OPO_3H_2$, $NH_2$, $NHR_{19}$, $NHR_{20}R_{21}$,

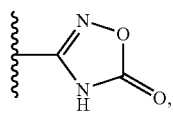

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

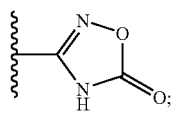

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

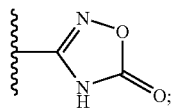

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

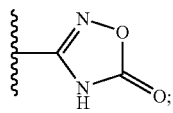

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

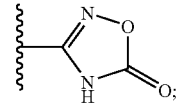

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, —$CH_2$—, —$CH_2CH_2$—, —$CH_2CH_2CH_2$—, —O—$CH_2$—, —$OCH_2CH_2$— or —$OCH_2CH_2CH_2$—;

Z is $(CHR_1)_n$—C(O)—$NR_2(CHR_3)_m$—Ar, where Ar is a substituted or unsubstituted aryl or nitrogen-containing heteroaryl group, $R_1$, $R_2$, and $R_3$ are independently H or $C_1$, $C_2$, $C_3$, $C_4$, $C_5$, or $C_6$ alkyl; and n is 1, or 2;

and m is 0, 1, or 2;

provided that at least one of $R_a$, $R_b$, $R_c$, $R_d$, $R_e$, $R_4$, $R_5$, and $R_6$ is P and wherein only one of $X_a$, $X_e$, and $X_y$ is N or N—O.

2. The compound of claim 1, wherein $X_y$ is N.

3. The compound of claim 1, wherein Z is

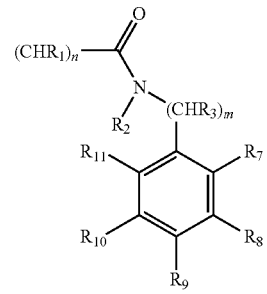

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

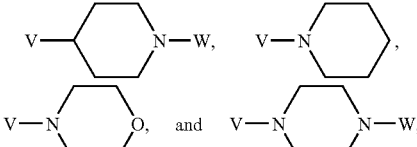

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl.

4. The compound of claim 3, wherein at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl.

5. The compound of claim 3, wherein m is 1.

6. The compound of claim 1, wherein $R_4$ and $R_6$ are each H.

7. The compound of claim 1, wherein the compound is selected from

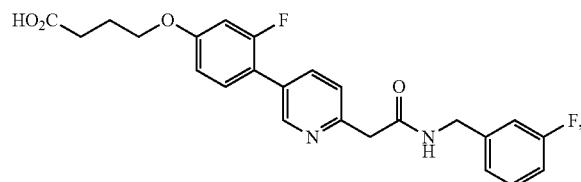

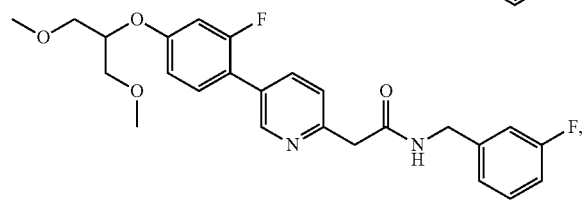

and

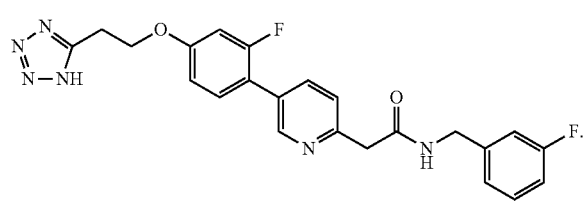

8. The compound of claim 2, wherein $X_a$, $X_c$, $X_d$, and $X_e$ are each C—H.

9. The compound of claim 3, wherein n is 1.

10. The compound of claim 3, wherein $R_2$ is H.

11. The compound of claim 3, wherein $R_1$ and $R_3$ are each H.

12. The compound of claim 1, wherein $R_5$ is halogen.

13. The compound of claim 12, wherein $R_5$ is fluorine.

14. The compound of claim 1, wherein P is O-lower ($C_1$, $C_2$, $C_3$, $C_4$, $C_5$, or $C_6$) alkyl-K.

15. The compound of claim 3, wherein P is O-lower ($C_1$, $C_2$, $C_3$, $C_4$, $C_5$, or $C_6$) alkyl-K, $X_y$ is N and $X_a$, $X_c$, $X_d$, and $X_e$ are each C—H.

16. The compound of claim 14, wherein P is O-lower ($C_1$, $C_2$, $C_3$, $C_4$, $C_5$, or $C_6$) linear alkyl-K.

17. The compound of claim 14, wherein P is O-lower ($C_1$, $C_2$, $C_3$, $C_4$, $C_5$, or $C_6$) branched alkyl-K.

18. The compound of claim 14, wherein P is O-lower ($C_2$ or $C_3$) alkyl-K.

19. The compound of claim 14, wherein K is selected from lower $C_1$, $C_2$, $C_3$, $C_4$, $C_5$, $C_6$ alkoxy, COOH, and tetrazole.

20. The compound of claim 15, wherein K is selected from lower $C_1$, $C_2$, $C_3$, $C_4$, $C_5$, $C_6$ alkoxy, COOH, and tetrazole.

21. The compound of claim 20, wherein n and m are each 1; $R_1$, $R_2$, $R_3$ are each H; $R_8$ is halogen, and $R_7$, $R_9$, $R_{10}$ and $R_{11}$ are hydrogen.

22. The compound of claim 21, wherein $R_5$ is halogen and $R_6$ is hydrogen.

23. A pharmaceutical composition comprising a compound of claim 1 or a pharmaceutically acceptable salt thereof and at least one pharmaceutically acceptable excipient.

24. A pharmaceutical composition comprising a compound selected from

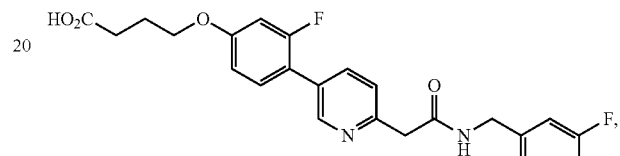

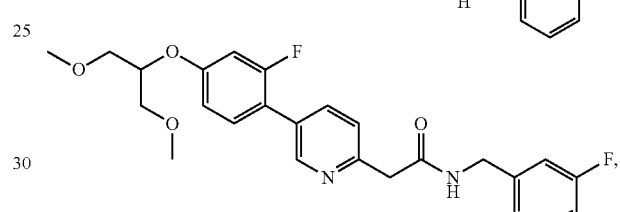

and

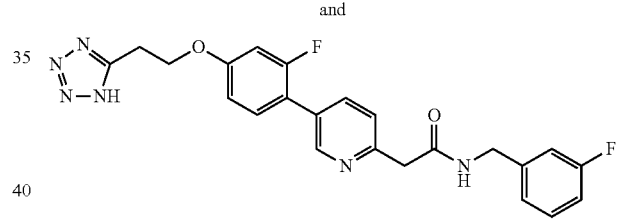

or a pharmaceutically acceptable salt thereof and at least one pharmaceutically acceptable excipient.

* * * * *

UNITED STATES PATENT AND TRADEMARK OFFICE
CERTIFICATE OF CORRECTION

PATENT NO.        : 7,968,574 B2
APPLICATION NO.   : 11/480174
DATED             : June 28, 2011
INVENTOR(S)       : David G. Hangauer, Jr.

It is certified that error appears in the above-identified patent and that said Letters Patent is hereby corrected as shown below:

On the Title page, Item [56] under the section Foreign Patent Documents, please remove the text "WO WO 2004/056774 A2 7/2004".

On the Title page, Item [56] under the Other Publications, the text "Zhng" should read --Zhang--.

Column 235, claim 1, line 22, please remove the text "$OPO_3H_2$,".

Signed and Sealed this
Fourteenth Day of August, 2012

David J. Kappos
*Director of the United States Patent and Trademark Office*